(12) United States Patent
Hartmann et al.

(10) Patent No.: US 9,381,208 B2
(45) Date of Patent: Jul. 5, 2016

(54) STRUCTURE AND USE OF 5' PHOSPHATE OLIGONUCLEOTIDES

(75) Inventors: Gunther Hartmann, Bonn (DE); Veit Hornung, Pullach (DE)

(73) Assignee: Rheinische Friedrich-Wilhelms-Universität, Bonn (DE)

( * ) Notice: Subject to any disclaimer, the term of this patent is extended or adjusted under 35 U.S.C. 154(b) by 0 days.

(21) Appl. No.: 13/466,747

(22) Filed: May 8, 2012

(65) Prior Publication Data

US 2012/0288476 A1    Nov. 15, 2012

Related U.S. Application Data

(62) Division of application No. 12/376,812, filed as application No. PCT/EP2007/007024 on Aug. 8, 2007, now abandoned.

(30) Foreign Application Priority Data

Aug. 8, 2006   (EP) .................................. 06016578
Oct. 10, 2006  (EP) .................................. 06021271

(51) Int. Cl.
| | | |
|---|---|---|
| C07H 21/02 | (2006.01) | |
| C07H 21/04 | (2006.01) | |
| A61K 48/00 | (2006.01) | |
| A61K 31/7115 | (2006.01) | |
| A61K 31/7105 | (2006.01) | |
| C07H 21/00 | (2006.01) | |

(52) U.S. Cl.
CPC .......... *A61K 31/7115* (2013.01); *A61K 31/7105* (2013.01); *C07H 21/00* (2013.01)

(58) Field of Classification Search
CPC ..... C12N 15/111; C12N 15/113; A61K 48/00
See application file for complete search history.

(56) References Cited

U.S. PATENT DOCUMENTS

| | | | |
|---|---|---|---|
| 3,534,017 A | 10/1970 | Fujimoto et al. | |
| 4,210,746 A | 7/1980 | Kerr et al. | |
| 4,522,811 A | 6/1985 | Eppstein et al. | |
| 5,166,195 A | 11/1992 | Ecker | |
| 5,194,428 A | 3/1993 | Agrawal et al. | |
| 5,264,423 A | 11/1993 | Cohen et al. | |
| 5,271,941 A | 12/1993 | Cho-Chung | |
| 5,292,875 A | 3/1994 | Stec et al. | |
| 5,366,878 A | 11/1994 | Pederson et al. | |
| 5,606,049 A | 2/1997 | Vaghefi | |
| 5,635,377 A | 6/1997 | Pederson et al. | |
| 5,644,048 A | 7/1997 | Yau | |
| 5,646,267 A | 7/1997 | Stec et al. | |
| 5,652,355 A | 7/1997 | Metelev et al. | |
| 5,736,294 A | 4/1998 | Ecker et al. | |
| 5,770,713 A | 6/1998 | Imbach et al. | |
| 6,143,881 A | 11/2000 | Metelev et al. | |
| 6,344,323 B1 | 2/2002 | Seifert | |
| 6,346,614 B1 | 2/2002 | Metelev et al. | |
| 6,369,209 B1 | 4/2002 | Manoharan et al. | |
| 6,737,520 B2 | 5/2004 | Manoharan et al. | |
| 6,900,308 B2 | 5/2005 | Wyrzykiewicz et al. | |
| 7,119,184 B2 | 10/2006 | Manoharan et al. | |
| 7,217,807 B2 | 5/2007 | Bentwich | |
| 7,285,658 B2 | 10/2007 | Cook et al. | |
| 7,371,735 B2 | 5/2008 | Harel-Bellan et al. | |
| 7,598,230 B2 | 10/2009 | Cook et al. | |
| 7,696,334 B1 | 4/2010 | Bentwich | |
| 7,696,342 B1 | 4/2010 | Bentwich | |
| 7,759,478 B1 | 7/2010 | Bentwich | |
| 7,790,867 B2 | 9/2010 | Bentwich | |
| 7,807,653 B2 | 10/2010 | Cook et al. | |
| 7,862,816 B2 | 1/2011 | Krasnoperov et al. | |
| 8,563,709 B2 | 10/2013 | Iba et al. | |
| 8,912,158 B2 | 12/2014 | Dimmeler et al. | |
| 2008/0664786 | 6/1996 | Agrawal | |
| 2003/0129615 A1 | 7/2003 | Wyrzykiewicz et al. | |
| 2003/0171570 A1 | 9/2003 | Schweitzer | |
| 2003/0203868 A1 | 10/2003 | Bushman | |

(Continued)

FOREIGN PATENT DOCUMENTS

| | | |
|---|---|---|
| CA | 2589406 | 6/2006 |
| CN | 1434054 A | 8/2003 |

(Continued)

OTHER PUBLICATIONS

Bowie et al., *Trends in Immunology*, 28 (4), 147-150 (2007).
Elbashir et al., The EMBO Journal, 20 (23), 6877-6888 (2001).
Hornung et al., *Science*, 314, 994-997 (2006).
Kim et al., *Nature Biotechnology*, 22 (3), 321-325 (2004).
Pichlmair et al., *Science*, 314, 997-1001 (2006).
Schlee et al., *Molecular Therapy*, 14 (4), 463-470 (2006).
Genbank, "Japanese encephalitis virus isolate CH2195LA, complete genome," GenBank Accession No. AF221499.1 (downloaded Jul. 25, 2013).
Genbank, "Influenza A virus (A/Puerto Rico/8/34/Mount Sinai(H1N1)) segment 1, complete sequence," GenBank Accession No. AF389115.1 (downloaded Aug. 28, 2013).
Genbank, "Influenza A virus (A/Puerto Rico/8/34/Mount Sinai(H1N1)) segment 2, complete sequence," GenBank Accession No. AF389116.1 (downloaded Aug. 28, 2013).
Genbank, "Influenza A virus (A/Puerto Rico/8/34/Mount Sinai(H1N1)) segment 3, complete sequence," GenBank Accession No. AF389117.1 (downloaded Aug. 28, 2013).
Genbank, "Influenza A virus (A/Puerto Rico/8/34/Mount Sinai(H1N1)) segment 4, complete sequence," GenBank Accession No. AF389118.1 (downloaded Aug. 28, 2013).
Genbank, "Influenza A virus (A/Puerto Rico/8/34/Mount Sinai(H1N1)) segment 5, complete sequence," GenBank Accession No. AF389119.1 (downloaded Aug. 28, 2013).

(Continued)

*Primary Examiner* — Amy Bowman
(74) *Attorney, Agent, or Firm* — Leydig, Voit & Mayer, Ltd.

(57) ABSTRACT

Oligonucleotides bearing free, uncapped 5' phosphate group(s) are recognized by RIG-I, leading to the induction of type I IFN, IL-18 and IL-1β production. Bacterial RNA also induces type I IFN production. 5' phosphate oligonucleotides and bacterial RNA can be used for inducing an anti-viral response or an anti-bacterial response, in particular, type I IFN and/or IL-18 and/or IL-1β production, in vitro and in vivo and for treating various disorders and diseases such as viral infections, bacterial infections, parasitic infections, tumors, allergies, autoimmune diseases, immunodeficiencies and immunosuppression. Single-stranded 5' triphosphate RNA can be used for inducing an anti-viral response, an anti-bacterial response, or an anti-tumor response, in particular, type I IFN and/or IL-18 and/or IL-1β production, in a target cell-specific manner.

4 Claims, 38 Drawing Sheets

(56) References Cited

U.S. PATENT DOCUMENTS

| | | |
|---|---|---|
| 2004/0059104 A1 | 3/2004 | Cook et al. |
| 2004/0234999 A1 | 11/2004 | Farrar et al. |
| 2004/0261149 A1 | 12/2004 | Fauquet et al. |
| 2005/0026861 A1 | 2/2005 | Kandimalla et al. |
| 2005/0182005 A1 | 8/2005 | Tuschl et al. |
| 2005/0222060 A1 | 10/2005 | Bot et al. |
| 2005/0249736 A1 | 11/2005 | Krasnoperov et al. |
| 2006/0035815 A1 | 2/2006 | Chen et al. |
| 2006/0178334 A1 | 8/2006 | Rossi et al. |
| 2007/0066521 A1 | 3/2007 | Fauquet |
| 2007/0259832 A1 | 11/2007 | Cook et al. |
| 2007/0265220 A1 | 11/2007 | Rossi et al. |
| 2007/0265224 A1 | 11/2007 | Cook et al. |
| 2007/0287681 A1 | 12/2007 | Jeong et al. |
| 2008/0171712 A1 | 7/2008 | Kandimalla et al. |
| 2008/0188428 A1 | 8/2008 | Bentwich |
| 2008/0250521 A1 | 10/2008 | Abdullah et al. |
| 2009/0143327 A1 | 6/2009 | Smolke et al. |
| 2009/0203121 A1 | 8/2009 | Hochberg et al. |
| 2009/0203894 A1 | 8/2009 | Liu et al. |
| 2010/0178272 A1 | 7/2010 | Hartmann |
| 2010/0260788 A1 | 10/2010 | Debelak et al. |
| 2010/0303859 A1 | 12/2010 | Williams |
| 2011/0130738 A1 | 6/2011 | Schmidt |
| 2011/0165133 A1 | 7/2011 | Rabinovich et al. |
| 2011/0245481 A1 | 10/2011 | Iba et al. |
| 2011/0247091 A1 | 10/2011 | Magor et al. |
| 2012/0225924 A1 | 9/2012 | Lin et al. |
| 2013/0121989 A1 | 5/2013 | Gaertig et al. |
| 2013/0189367 A1 | 7/2013 | Zhang et al. |
| 2013/0302252 A1 | 11/2013 | Zhang et al. |
| 2014/0171368 A1 | 6/2014 | Goepferich et al. |
| 2015/0018407 A1 | 1/2015 | Dimmeler et al. |

FOREIGN PATENT DOCUMENTS

| | | |
|---|---|---|
| CN | 101088565 A | 12/2007 |
| CN | 101190944 A | 6/2008 |
| CN | 101632833 A | 1/2010 |
| CN | 101974529 A | 2/2011 |
| CN | 102475892 A | 5/2012 |
| DE | 1 695 303 A1 | 4/1972 |
| DE | 41 10 085 A1 | 10/1992 |
| DE | 10 2007 052 114 A1 | 5/2009 |
| EP | 0 021 099 A1 | 1/1981 |
| EP | 0 031 285 A2 | 7/1981 |
| EP | 81104827.1 A2 | 1/1982 |
| EP | 0 081 099 A2 | 6/1983 |
| EP | 0 339 842 A2 | 11/1989 |
| EP | 0 386 563 A1 | 9/1990 |
| EP | 0 415 901 A2 | 3/1991 |
| EP | 0 698 034 B1 | 2/1996 |
| EP | 0 754 188 B1 | 11/1997 |
| EP | 0 788 366 B1 | 12/1999 |
| EP | 0 739 899 B1 | 6/2001 |
| EP | 1 247 815 A2 | 10/2002 |
| EP | 1 493 818 A2 | 1/2005 |
| EP | 1 505 152 A1 | 2/2005 |
| EP | 1 626 086 A2 | 2/2006 |
| EP | 1 637 597 A1 | 3/2006 |
| EP | 1 657 306 A1 | 5/2006 |
| EP | 1 743 901 A2 | 1/2007 |
| EP | 05020019.5 A1 | 3/2007 |
| EP | 05020020.3 A1 | 3/2007 |
| EP | 06016578.4 A1 | 2/2008 |
| EP | 1920775 A1 | 5/2008 |
| EP | 1 939 291 A2 | 7/2008 |
| EP | 2 113 565 A1 | 11/2009 |
| EP | 2 141 234 A1 | 1/2010 |
| EP | 2 207 797 A1 | 7/2010 |
| EP | 1 453 962 B1 | 8/2010 |
| EP | 2 213 738 A2 | 8/2010 |
| EP | 2 284 266 A2 | 2/2011 |
| EP | 2 327 783 A1 | 6/2011 |
| EP | 2 338 449 A1 | 6/2011 |
| EP | 2 388 499 A1 | 6/2011 |
| EP | 1 857 119 B1 | 11/2011 |
| EP | 2 277 508 B1 | 4/2012 |
| EP | 1 969 125 B1 | 6/2012 |
| EP | 2 497 827 A1 | 9/2012 |
| EP | 2 123 757 B1 | 10/2012 |
| EP | 2 508 530 A1 | 10/2012 |
| EP | 2 514 758 A1 | 10/2012 |
| EP | 2 518 150 A2 | 10/2012 |
| EP | 2 551 354 A1 | 1/2013 |
| EP | 1 915 448 B1 | 9/2013 |
| EP | 2 671 949 A1 | 12/2013 |
| EP | 1 957 648 B1 | 4/2014 |
| EP | 1 973 574 B1 | 4/2014 |
| EP | 2 712 870 A1 | 4/2014 |
| EP | 2 069 500 B1 | 9/2014 |
| EP | 2 207 787 B1 | 11/2014 |
| EP | 2 492 355 B1 | 8/2015 |
| JP | 0H6-501843 A | 3/1994 |
| JP | 07-099976 A | 4/1995 |
| JP | 08-154687 A | 6/1996 |
| JP | 2003-535043 A | 11/2003 |
| JP | 2005-526778 A | 9/2005 |
| JP | 2006-238795 A | 9/2006 |
| WO | 84/00688 A1 | 3/1984 |
| WO | 89/08146 A1 | 9/1989 |
| WO | 90/14353 A1 | 11/1990 |
| WO | 91/06309 A1 | 5/1991 |
| WO | 92/02641 A1 | 2/1992 |
| WO | 92/03454 A1 | 3/1992 |
| WO | 92/17484 A1 | 10/1992 |
| WO | 93/07882 A1 | 4/1993 |
| WO | 93/08296 A1 | 4/1993 |
| WO | 93/23569 A1 | 11/1993 |
| WO | 94/02501 A1 | 2/1994 |
| WO | 94/15619 A1 | 7/1994 |
| WO | 94/17093 A1 | 8/1994 |
| WO | 94/24144 A2 | 10/1994 |
| WO | 94/26764 A1 | 11/1994 |
| WO | 95/03406 A2 | 2/1995 |
| WO | 95/32719 A1 | 12/1995 |
| WO | 96/02556 A2 | 2/1996 |
| WO | 96/07392 A2 | 3/1996 |
| WO | 96/18736 A2 | 6/1996 |
| WO | 96/19572 A1 | 6/1996 |
| WO | WO 96/08394 | 6/1996 |
| WO | 96/40159 A1 | 12/1996 |
| WO | 96/41812 A1 | 12/1996 |
| WO | WO 96/40159 A1 | 12/1996 |
| WO | WO 96/41812 A1 | 12/1996 |
| WO | 99/55857 A2 | 11/1999 |
| WO | 00/66609 A1 | 11/2000 |
| WO | 01/16312 A2 | 3/2001 |
| WO | 01/22990 A2 | 5/2001 |
| WO | 01/70751 A1 | 9/2001 |
| WO | WO 01/68077 A2 | 9/2001 |
| WO | 02/10432 A2 | 2/2002 |
| WO | 03/008432 A1 | 1/2003 |
| WO | 03/012052 A2 | 2/2003 |
| WO | 03/072757 A2 | 9/2003 |
| WO | WO 03/078595 A2 | 9/2003 |
| WO | 03/086280 A2 | 10/2003 |
| WO | 03/087367 A2 | 10/2003 |
| WO | 03/087368 A2 | 10/2003 |
| WO | 03/101375 A2 | 12/2003 |
| WO | 2004/015062 A2 | 2/2004 |
| WO | 2004/020631 A2 | 3/2004 |
| WO | 2004/022777 A1 | 3/2004 |
| WO | 2004/024063 A2 | 3/2004 |
| WO | 2004/044123 A2 | 5/2004 |
| WO | 2004/045543 A2 | 6/2004 |
| WO | 2004/048511 A2 | 6/2004 |
| WO | 2004/061423 A2 | 7/2004 |
| WO | 2004/074441 A2 | 9/2004 |
| WO | 2004/080418 A2 | 9/2004 |
| WO | 2004/080425 A2 | 9/2004 |
| WO | 2004/083430 A2 | 9/2004 |
| WO | 2004/085623 A2 | 10/2004 |

(56) References Cited

FOREIGN PATENT DOCUMENTS

| WO | 2004/106517 A1 | 12/2004 |
|---|---|---|
| WO | 2004/111190 A2 | 12/2004 |
| WO | WO 2005/005632 A2 | 1/2005 |
| WO | 2005/076979 A1 | 8/2005 |
| WO | 2005/089287 A2 | 9/2005 |
| WO | 2005/108573 A2 | 11/2005 |
| WO | 2005/117991 A2 | 12/2005 |
| WO | 2006/016574 A1 | 2/2006 |
| WO | WO 2006/063252 A2 | 6/2006 |
| WO | 2006/074400 A2 | 7/2006 |
| WO | 2006/078646 A2 | 7/2006 |
| WO | 2006/105361 A2 | 10/2006 |
| WO | 2006/110813 A2 | 10/2006 |
| WO | 2006/119643 A1 | 11/2006 |
| WO | 2006/122409 A1 | 11/2006 |
| WO | 2006/130949 A1 | 12/2006 |
| WO | WO 2006/128739 A1 | 12/2006 |
| WO | 2007/021142 A1 | 2/2007 |
| WO | 2007/030619 A2 | 3/2007 |
| WO | 2007/031319 A1 | 3/2007 |
| WO | 2007/031322 | 3/2007 |
| WO | 2007/038788 A2 | 4/2007 |
| WO | 2007/051303 A1 | 5/2007 |
| WO | 2007/107304 A2 | 9/2007 |
| WO | 2008/017473 A2 | 2/2008 |
| WO | WO 2008/017473 A2 | 2/2008 |
| WO | 2008/045576 A2 | 4/2008 |
| WO | 2008/076127 A1 | 6/2008 |
| WO | 2008/080091 A2 | 7/2008 |
| WO | 2008/087641 A2 | 7/2008 |
| WO | 2008/087642 A2 | 7/2008 |
| WO | 2008/099396 A1 | 8/2008 |
| WO | 2008/124165 A2 | 10/2008 |
| WO | 2008/131807 A2 | 11/2008 |
| WO | 2008/134593 A1 | 11/2008 |
| WO | 2009/018500 A1 | 2/2009 |
| WO | 2009/038707 A2 | 3/2009 |
| WO | 2009/046541 A1 | 4/2009 |
| WO | 2009/051659 A2 | 4/2009 |
| WO | 2009/056116 A1 | 5/2009 |
| WO | 2009/060124 A2 | 5/2009 |
| WO | 2009/060281 A2 | 5/2009 |
| WO | 2009/061417 A1 | 5/2009 |
| WO | 2009/064590 A2 | 5/2009 |
| WO | 2009/068677 A1 | 6/2009 |
| WO | 2009/083738 A2 | 7/2009 |
| WO | 2009/141146 A1 | 11/2009 |
| WO | 2009/146556 A1 | 12/2009 |
| WO | 2009/151600 A2 | 12/2009 |
| WO | 2010/028079 A2 | 3/2010 |
| WO | 2010/042742 A2 | 4/2010 |
| WO | 2010/042749 A2 | 4/2010 |
| WO | 2010/042751 A2 | 4/2010 |
| WO | 2010/042755 A2 | 4/2010 |
| WO | 2010/047216 A1 | 4/2010 |
| WO | 2010/062502 A1 | 6/2010 |
| WO | 2010/099161 A1 | 9/2010 |
| WO | 2010/118263 A1 | 10/2010 |
| WO | 2010/120874 A2 | 10/2010 |
| WO | 2010/136192 A1 | 12/2010 |
| WO | 2010/147655 A2 | 12/2010 |
| WO | 2011/008857 A1 | 1/2011 |
| WO | 2011/011716 A1 | 1/2011 |
| WO | 2011/028218 A1 | 3/2011 |
| WO | 2011/064130 A1 | 6/2011 |
| WO | 2011/133559 A2 | 10/2011 |
| WO | 2011/138328 A2 | 11/2011 |
| WO | 2011/140285 A2 | 11/2011 |
| WO | 2012/056449 A2 | 5/2012 |
| WO | 2012/056457 A2 | 5/2012 |
| WO | 2012/091523 A2 | 7/2012 |
| WO | 2012/125987 A2 | 9/2012 |
| WO | 2012/130886 A1 | 10/2012 |
| WO | 2013/003887 A1 | 1/2013 |
| WO | 2013/013820 A1 | 1/2013 |
| WO | 2013/020986 A1 | 2/2013 |
| WO | 2013/053480 A1 | 4/2013 |
| WO | 2013/053481 A1 | 4/2013 |
| WO | 2013/075140 A1 | 5/2013 |
| WO | 2013/153082 A1 | 10/2013 |
| WO | 2014/049079 A1 | 4/2014 |
| WO | 2014/124433 A1 | 4/2014 |

OTHER PUBLICATIONS

Genbank, "Influenza A virus (A/Puerto Rico/8/34/Mount Sinai(H1N1)) segment 6, complete sequence," GenBank Accession No. AF389120.1 (downloaded Aug. 28, 2013).
Genbank, "Influenza A virus (A/Puerto Rico/8/34/Mount Sinai(H1N1)) segment 7, complete sequence," GenBank Accession No. AF389121.1 (downloaded Aug. 28, 2013).
Genbank, "Influenza A virus (A/Puerto Rico/8/34/Mount Sinai(H1N1)) segment 8, complete sequence," GenBank Accession No. AF389122.1 (downloaded Aug. 28, 2013).
Genbank, "Vesticular stomatitis Indiana virus, complete genome," GenBank Accession No. J02428.1 (downloaded Jul. 25, 2013).
Huang et al., *Biochemistry*, 39: 15548-15555 (2000).
Kato et al., *Immunity*, 23: 19-28 (Jul. 2005).
Kato et al., *Nature Letters*, 441: 101-105 (May 4, 2006).
Kao et al., *Virology*, 287: 251-260 (2001).
Rosa et al., *Molec. Cell. Biol.*, 1: 785-796 (Sep. 1981).
Samanta et al., *EMBO J.*, 25: 4207-4214 (2006).
Schlee et al., *Immunity*, 31: 25-34 (Jul. 17, 2009).
Schlee et al., *Molec. Therapy*, 18: 1254-1262 (Jul. 2010).
Tschopp et al., *Nature Reviews*, 4: 95-104 (Feb. 2003).
Van Holten et al., *Arthritis Research*, 4: 346-352 (2002).
Wagner et al., "Lipofektion," RÖMPP Online, Version 3.36 (Sep. 9, 2013) partial English translation.
Walther et al., *Drugs*, 60: 249-271 (Aug. 2000).
Yoneyama et al., *J. Immunol.*, 175: 2851-2858 (2005).
Yoneyama et al., *Nature Immunol.*, 5: 730-737 (Jul. 2004).
Singh et al, *PNAS*, 86: 8280-8283 (1989).
Absher, et al., *Nature*, 223: 715-717 (Aug. 16, 1969).
Aigner, et al., *J. Biomed. Biotechnol.*, 2006(4):71659 (2006).
Akira, et al., *C. R. Biol.*, 327(6):581-9 (2004).
Alexopoulou, et al., *Nature*, 413: 732-8 (Oct. 18, 2001).
Andrejeva et al., *PNAS USA*, 101:17264-9 (Dec. 7, 2004).
Barton et al., *Nat. Immunol* 7: 49-56 (Jan. 2006).
Bass, et al., *Cell* 55(6): 1089-98 (1988).
Bekeredjian-Ding, et al., *J Immunol.*, 174: 4043-50 (Apr. 1, 2005).
Blumberg, et al., *Cell*, 23(3): 837-45 (Mar. 1981).
Blumberg, et al., *J. Virol.*, 40(2):568-76 (Nov 1981).
Brzózka, et al., *J. Virol.*, 79: 7673-81 (Jun. 2005).
Brzózka, et al., *J. Virol.*, 80: 2675-83 (Mar. 2006).
Chang, et al., *Microbes and infection*, 8: 157-71 (2006).
Chiocca, *Nat. Rev. Cancer*, 2:938-950 (2002).
Colonno, et al., *Cell*, 15(1): 93-101 (1978).
Cuesta, *J Immunol.*, 178(6): 3602-11 (2007).
Cullen, *Mol Cell* 16(6): 861-5 (Dec. 22, 2004).
Decatur, et al., *J. Biol. Chem.*, 278: 695-8 (Jan. 3, 2003).
Delale et al., *J Immunol*, 175(10): 6723-32 (Nov. 15, 2005).
Der, of al., *PNAS USA*, 92(19): 8841-5 (Sep. 12, 1995).
Diebold, et al., *Nature*, 424: 324-8 (Jul. 17, 2003).
Diebold et al., *Science*, 303: 1529-31 (Mar. 5, 2004).
Dunn, et al., *J. Mol. Biol.*, 166(4): 477-535 (Jun. 5, 1983).
Elbashir, et al., *Nature*, 411: 494-8 (May 24, 2001).
Fromont-Racine et al., *Gene*, 313: 17-42 (Aug. 14, 2003).
Furuichi, *Adv. Virus Res.*, 55: 135-84 (2000).
Gerber, et al. *Trends Biochem. Sci.* 26(6): 376-84 (2001).
Gitlin, et al., *PNAS USA*, 103(22):8459-8464 (2006).
Grzelinski, et al., *Hum. Gene Ther.*, 17(7): 751-66 (2006).
Heil et al., *Science*, 303: 1526-9 (Mar. 5, 2004).
Hemmi et al., *Nature*, 408: 740-5 (Dec. 7, 2000).
Henry, et al., *J. Exp. Med.*, 204(5): 987-94 (2007).
Honda, et al., *Virus Res.*, 55(2): 199-206 (Jun. 1998).
Hornung et al., *Nat. Med.* 11(3): 263-70 (Mar. 2005).
Hornung, et al., *J. Immunol.*, 168(9): 4531-7 (May 1, 2002).
Ishii et al., *Nat. Immunol.*, 7: 40-8 (Jan. 2006).
Judge, et al., *Nat. Biotechnol.* 23(4):457-462 (2005).

(56) References Cited

OTHER PUBLICATIONS

Kanneganti, et al., *Nature*, 440(7081):233-6 (2006).
Kariko, et al. *Immunity* 23(2): 165-75 (Aug. 2005).
Kawai et al., *Nat. Immunol*, 6(10): 981-988 (Oct. 2005).
Krieg et al., *Nature*, 374: 546-9 (Apr. 6, 1995).
Krieg, *Annu. Rev. Immunol.*, 20: 709-60 (2002).
Krug et al., *Immunity*, 21: 107-19 (Jul. 2004).
Krug, et al., *Eur. J. Immunol.*, 31(7): 2154-63 (Jul. 2001).
Lee, et al., *PNAS USA* 74(1): 59-63 (Jan. 1977).
Limbach, et al., *Nucleic Acids Res.*, 22(12): 2183-2196 (1994).
Ludwig, *Acta Biochim Biophys Acad Sci Hung.*, 16:131-3 (1981).
Maitra, et al., *PNAS USA*, 77(7): 3908-3911 (1980).
Marques, et al., *Nat. Biotechnol.* 24(5): 559-65 (May, 2006).
Meylan et al., *Nature*, 437: 1167-72 (Oct. 20, 2005).
Neumann, et al., *Curr. Top. Microbiol. Immunol.*, 283: 121-43 (2004).
Palladino, et al., *Cell*, 102(4): 437-49 (2000).
Radecke, et al., *EMBO J.*, 14(23): 5773-84 (Dec. 1, 1995).
Rothenfusser et al., *J. Immunol.* 175(8): 5260-8 (Oct. 15, 2005).
Rozenski et al., *Nucleic Acids Res.* 27(1): 196-7 (Jan. 1, 1999).
Rudd, et al., *J. Immunol.*, 176(3): 1937-42 (Feb. 1, 2006).
Russell, *Cancer Gene Ther.*, 9(12): 961-6 (2002).
Schnell, et al., *EMBO J.*, 13(18): 4195-4203 (1994).
Seth et al., *Cell*, 122(5): 669-82 (Sep. 9, 2005).
Shatkin, et al., *Nat. Struct. Biol.* 7(10): 838-42 (Oct. 2000).
Singh, et al., *PNAS USA*, 86: 8280-3 (Nov. 1989).
Sioud, et al., *J. Mol. Biol.*, 348: 1079-1090 (2005).
Strahle, et al., *Virology*, 351(1): 101-11 (2006).
Stump, et al., *Nucleic Acids Res.*, 21(23): 5480-5484 (1993).
Sugiyama, et al., *J. Immunol.*, 174(4): 2273-2279 (2005).
Sumpter, Jr. et al, *J. Viro.* 79(5): 2689-99 (Mar. 2005).
Tabeta et al., *PNAS USA*, 101(10): 3516-21 (Mar. 9, 2004).
Urban-Klein, et al., *Gene Ther.*, 12(5): 461-6 (2005).
Vollmer et al., *Antisense Nucleic Acid Drug Dev.*, 12(3): 165-75 (Jun. 2002).
Weber, et al., *J. Virol.*, 80(10): 5059-64 (May 2006).
Whelan, et al., *Curr. Top. Microbiol. Immunol.*, 283: 61-119 (2004).
Xiao et al., *Annu. Rev. Biochem.*, 71: 165-89 (2002).
Xu et al., *Mol. Cell*, 19: 727-740 (Sep. 16, 2005).
Yang et al., *EMBO J.*, 14(24): 6095-6106 (Dec. 15, 1995).
Yang et al., *Immunity*, 23(5): 465-78 (Nov. 2005).
Zeh, et al., *Cancer Gene Ther.*, 9: 1001-1012 (2002).
Chaperot et al., "Virus or TLR Agonists Induce TRAIL-Mediated Cytotoxic Activity of Plasmacytoid Dendritic Cells," *The Journal of Immunology*, 176: 248-255 (2006).
Chemicool, "Definition of Homogeneous," in *Chemicool* (2014). Retrieved on Aug. 28, 2015 from http://www.chemicool.com/definition/homogeneous.html.
Römpp, "Sequence homology," in Römpp (Aug. 2008). Retrieved on Aug. 28, 2015 from https://roempp.thieme.de/roempp4.0/do/data/RD-19-01964.
Adam, et al., *Blood*, 106(1):338-344 (2005).
Adelfinskaya, et al., *Angew. Chem. Int. Ed.*, 46:4356-4358 (2007).
Adelfinskaya, et al., *Nucleic Acids Research*, 35(15);5060-5072 (2007).
Aleman, et al., *RNA* 13(3):385-395 (Mar. 2007).
Ambion, Life Technologies Corporation, Catalog Nos. AM 1330, AM1333, AM1334, AM1338, Publ. No. 1330M, Revision G. (2012).
Arnold, et al., *J. Biol. Chem.*, 274(5):1706-2716 (1999).
Bartenschlager, et al., *J. Gen. Virol.*, 81:1631-1648 (2000).
Baudin, et al., *EMBO J.*, 13(13):3158-3166 (1994).
Behlke, et al., *Mol. Ther*, 13(4):644-670 (Apr. 2006).
Besch, et al., *Cell Death Differ*, 14:818-29 (2007).
Blackburn, et al., *J.C.S. Chem. Commun.*, 1188-1190 (1981).
Bonin, et al., *RNA*, 6:563-570 (2000).
Brownlee, et al., *Nucleic Acids Research*, 23(14):2641-2647 (1995).
Bui, et al., *Curr. Opin. Immunol.*, 19:203-8 (2007).
Carroll, et al. *Methods in Enzymology*, 275:365-382 (1996).
Cazenave, et al., *Proc. Natl. Acad. Sci. USA*, 91:6672-6676 (1994).
Chawla-Sarkar, et al., *Cell Death and Differentiation*, 11:915-923 (2004).
Chen, et al., *J Virol.*, 81(2):964-76 (2007).
Cheong, et al., *Nucleic Acids Res* 24(21):4197-421 (1996).
Chien, et al., *Cancer Gene Therapy*, 12(3):321-328 (2005).
Coe, et al., *J. Chem. Soc., Chem. Commun.*, 312-314 (1991).
Coffey, et al., *Science*, 282:1332-1334 (1998).
Cui, et al. *Molecular Cell*, 29:169-179 (2008).
Curiel, *J. Clin. Invest.*, 117:1167-74 (2007).
Danial, et al., *Cell*, 116:205-19 (2004).
Davis, et al., *PNAS*, 101(29):10697-10702 (Jul. 20, 2004).
De Fougerolles, et al., *J. Nat.Rev.Drug Discov.*, 6:443-53 (2007).
De Jonge, et al., *Gene Therapy*, 13:400-411 (2006)).
Duan, et al., *Antiviral Therapy*, 13(1):109-114 (2008).
Entry „influence A virus in Wikipedia.
Entry „Oligonucleotide synthesis in Wikipedia.
Gaur, et al., *Tetrahedron Letters*, 33:3301-3304 (1992).
Gerrits, digital disseration, FU Berlin, 2001, English Abstract.
Goldeck, et al., *Angew. Chem.*, 126(4):782-786 (2014).
Gondai, et al., *Nucleic Acids Res*, 36(3):e18 (2008).
Haas, et al., *Immunity*, 28:315-232 (2008).
Hanahan, et al., *Cell*, 100:57-70 (2000).
Hartmann, et al., *Handbook of RNA Biochemistry*, pp. 6, 39, 43 (2005).
Helm, et al., *RNA*, 5:618-621 (1999).
Hemmi, et al., *Nat Immunol*, 3:196 (Feb. 2002).
Hofacker, et al., *Bioinformatics*, 20:1495-1499 (2004).
Holy, et al., *Collect. Czech. Commun.*, 47:3447-3463 (1982).
Hsu, et al., *Croc,Natl.Acad.Sci.U.S.A.*, 84:8140-8141 (1987).
Jiang, et al., *Genes & Dev*, 17:832-837 (2003).
Kamphuis, et al., *Blood*, 108:3253-61 (2006).
Kariko, et al., *Biochem. Biophys. Res. Commun.*, 128(2):695-698 (1985).
Kawai, et al., *Nat Immunol*, 7(2):131-7 (2006).
Kennedy, et al., *J.Mol.Biol.*, 370:256-268 (2007).
Khan, et al., *J Drug Target*, 12(6):393-404 (2004).
Knorre, et al., *FEBS Letters*, 70(1):105-108 (1976).
Koh, et al., J. Med. Chem., 48:2867-2875 (2005).
Kossen, et al., *Chemistry and Biology*, 11:807-815 (2004).
Krupp, *Gene*, 72:75-89 (1988).
Kuzmine, et al., *The Journal of Biol. Chem.*, 278(5):2819-2823 (2003).
Latz, et al., *Nat Immunol*, 5(2):190-8 (2004).
Latz, et al., *Nat, Immunol*, 8:772-779 (2007).
Lau, et al., *J Exp Med*, 202 (9):1171-7 (2005).
Lebedev, et al., *Nucleosides, Nucleotides and Nucleic Acids*, 20(4-7):1403-1409 (2001).
Loo, et al., *J Virol*, 82:335-345 (2008).
Lu, et al., *Nucleic Acids Res*, 39(4):1565-1575 (Mar. 2011).
Ludwig, et al., *J. Org. Chem.*, 54:631-635 (1989).
Ludwig, et al., *J. Org. Chem.*, 56:1777-1783 (1991).
Ma, et al., *Molecular Therapy—Nucleic Acids*, 3(e161);1-11 (2014).
Matsumoto, et al., *J Immunol*, 171(6):3154-62 (2003).
McGill, et al., *Cell*, 109:707-18 (2002).
Meister, et al., *Mol Cell*, 15:185 (Jul. 23, 2004).
Melchjorsen, et al., *J Virol*, 79:12944-51 (2005).
Meyer, et al., *Methods in Molecular Biol.*, 1086:21-40 (2014).
Miller, et al., *N.Engl.J.Med.* 355:51-65 (2006).
Milligan, et al., *Dep. of Chem. and Biochem.*, 15(21)8783-98 (1987).
Milligan, et al., *Methods in Enzymology, RNA Processing, Part A General Methods*, pp. 51-62 (1989).
Minakuchi, et al., *Nucleic Acids Research*, 32(13):e109 (2004).
Mocikat, et al., *Immunity*, 19:516-569 (Oct. 2003).
Muller, et al., *Science*, 264:1918-21 (1994).
Nishiya, et al., *J Biol Chem*, 279(18):19008-17 (2004).
Obeid, et al., *Nat.Med.*, 13:54-61 (2007).
Olsen, et al., *Journal of Biological Chemistry*, 271(13):7435-7439 (1996).
Paul, et al., *Chemistry and Biology*, 13:329-338 (2006).
Pearse, et al., *Adv Drug Deliv Rev*, 57(3):465-474 (Jan. 10, 2005).
Pei et al., *Nat. Methods*, 3:670-6 (2006).
Peterli, et al., *Helvetica Chimica Acta*, 75:696-706 (1992).
Phuangsab, et al., *Cancer Lett*, 172:27-36 (2001).
Pichlmair, et al., *Science*, 314:997-1001 (2006).
Plumet, et al., *PLoS ONE*, 3(e279):1-10 (2007).

(56) References Cited

OTHER PUBLICATIONS

Poeck, et al., *Blood*, 103(8):3058-3064 (Apr. 2004) (www.bloodjournal.org/cgi/content/full/103/8/3058#REF4).
Poeck, et al., *Nature Medicine*, 14(11):1256-1262 (2008).
Portela, et al., *J. Gen. Virol.*, 2992(83):723-734 (2002).
Ranjith-Kumar, et al., *J. Virol.*, 76(24):12526-12536 (2002).
Ranjith-Kumar, et al., *RNA*, 12:303-312 (2006).
Reynolds, et al., *Nat Biotechnol*, 22:326-30 (2004).
Rohayem, et al., *Journal of Virology*, 80(14):7060-7069 (2006).
Rosa, et al., *Molecular and Cellular Biology*, 1(9):785-796 (Sep. 1981).
Rossi, *Gene Therapy*, 13:583-584 (2006).
Rubin, et al., *Lancet*, 369:1731-41 (2007).
Schlee, et al., *CTMI*, 316:207-230 (2007).
Schmidt, et al., *PNAS*, 106(29):12067-12072 (2009).
Schoatzau, et al., *Chem. Commun.*, 3:387-388 (1996).
Selisko, et al., *Virology*, 351(1):145-158 (2006).
Sioud, *Advanced Drug Delivery Reviews*, 59(2-3):153-163 (2007).
Sioud, et al., *Biochem Biophys Res Commun*, 315(4):1220-1225 (2003).
Sioud, *Eur J Immunol*, 36(5):1222-30 (2006).
Soutschek, et al., *Nature*, 432(7014):173-178 (Nov. 2004).
Sproat, et al., *Nucleic acids research*, 27(8):1950-1955 (1999).
Stetson, et al., *J.Exp.Med.* 203:1837-41 (2006).
Stojdl, et al., *Nat Med*, 6:821-825 (2000).
Takahasi, et al., *Molecular Cell*, 29:428-440 (Feb. 29, 2008).
Tormo, et al., *Am J Pathol*, 169:665-72 (2006).
Tormo, et al., *Cancer Res.*, 66:5427-35 (2006).
Tschoep, et al., *J Mol Med*, 79:306-13 (2001).
Uno, et al., *Nat.Med.*, 12:693-8 (2006).
Van Dijk, et al., *J. Gen. Virol.*, 85:1077-1093 (2004).
Van Dijk, et al., *Virology*, 211:320-323 (1995).
Wang, et al., *J Med Chem.* 47:6902-6913 (2004).
Wang, et al., *Nat Struct & Mol Biol*, 17(7):781-787 (Jul. 2010).
Wu, et al., *Brain Research*, 1008(2):284-287 (May 22, 2004).
Yoneyama, et al., *J. Biol. Chem.*, 282:15315-8 (2007).
Yount, et al., *Archives Of Biochemistry And Biophysics*, 113:288-295 (1966).
Zimmermann, et al., *Nature*, 441(7089):111-114 (May 2006).
Zlatev, et al., *ORG LETT.* 12(10):2190-2193 (2010).

C

| ORN length [nt] | Sequence |
|---|---|
| 27 | 5'-pppGGGGCUGACCCUGAAGUUCAUCUUCCC-3' |
| 24 | 5'-pppGGGGCUGACCCUGAAGUUCAUCCC-3' |
| 21 | 5'-pppGGGGCUGACCCUGAAGUUCCC-3' |
| 18 | 5'-pppGGGGCUGACCCUGAACCC-3' |
| 15 | 5'-pppGGGGCUGACCCUCCC-3' |
| 12 | 5'-pppGGGGCUGACCCC-3' |
| 9 | 5'-pppGGGGCUCCC-3' |

D

| | |
|---|---|
| tri-GFPs | 5`-pppGGGGCUGACCCUGAAGUUCAUCUU-3` |
| tri-Poly G | 5`-pppGGGAGACAGGGGGGGGGGGGGGGGGGGG-3` |
| tri-Poly A | 5`-pppGGGAGACAGGAAAAAAAAAAAAAAAAAAAA-3` |
| tri-Poly C | 5`-pppGGGAGACAGGCCCCCCCCCCCCCCCCCCCC-3` |
| tri-Poly U | 5`-pppGGGAGACAGGUUUUUUUUUUUUUUUUUUUU-3` |

| | |
|---|---|
| tri-GFPs | 5`-pppGGGCUGACCCUGAAGUUCAUCUU-3` |
| tri-GFPa | 5`-pppGGGAUGAACUUCAGGGUCAGCUU-3` |
| tri-GFPds | 5`-pppGGGCUGACCCUGAAGUUCAUCUU-3`<br>3`-UUCGACUGGGACUUCAAGUAGGGppp-5` |
| tri-GFPds<br>+ RNase T1 | 5`-pppG GGGCUGACCCUGAAGUUCAUCUU-3`<br>3`-UUCGACUGGGACUUCAAGUAGGG Gppp-5` | tri-G-AC-U-Bio
    5'-pppGGGAGACAGGCACCACACACACACACUUU-3' tri-G-AC-U
    5'-pppGGGAGACAGGCACCACACACACACACUUU-3' tri-G-AC-U-Bio /T1
5'-pppG·G·G·AG·ACAG·G·CACCACACACACACACUUU-3' tri-G-AC-U /T1
5'-pppG·G·G·AG·ACAG·G·CACCACACACACACACUUU-3'

| | |
|---|---|
| G | 5´-OH GACACACACACACACACACUUU -3´ |
| GMP | 5´-p GACACACACACACACACACUUU -3´ |
| GDP | 5´-pp GACACACACACACACACACUUU -3´ |
| GTP | 5´-ppp GACACACACACACACACACUUU -3´ |

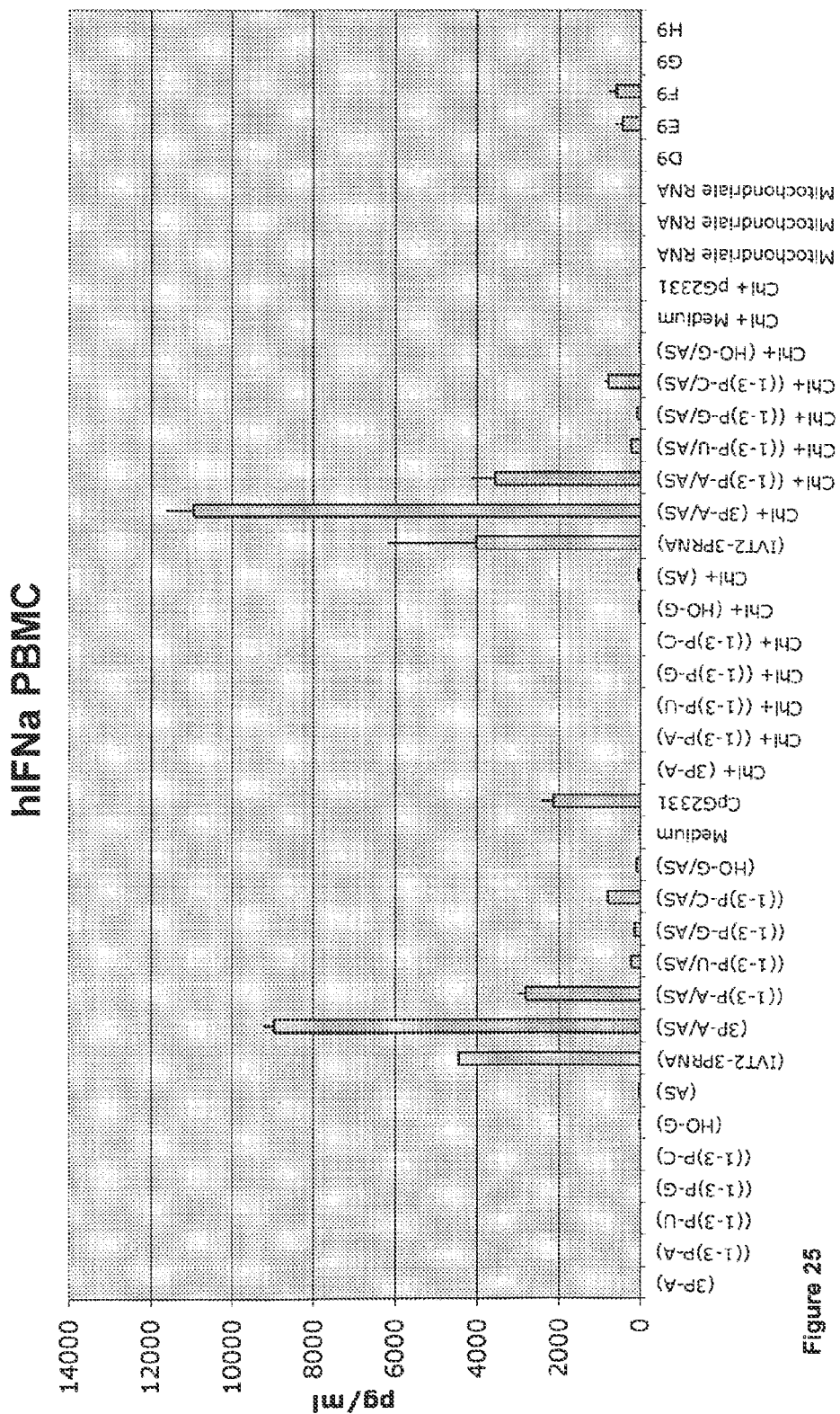

STRUCTURE AND USE OF 5' PHOSPHATE OLIGONUCLEOTIDES

CROSS REFERENCE TO RELATED APPLICATIONS

This patent application is a divisional of copending U.S. patent application Ser. No. 12/376,812, filed Apr. 20, 2009, which is the U.S. national phase of International Patent Application No. PCT/EP07/07024, filed Aug. 8, 2007, which claims the benefit of European Patent Application No. 06016578.4, filed Aug. 8, 2006, and European Patent Application No. 06021271.9, filed Oct. 10, 2006, all of which are incorporated in their entirities by reference.

SEQUENCE LISTING

Incorporated by reference in its entirety herein is a computer-readable nucleotide/amino acid sequence listing submitted concurrently herewith and identified as follows: 77,405 byte ASCII (text) file named "710373-SequenceListingReplacement.txt" created on Jul. 31, 2012.

FIELD OF THE INVENTION

The present invention relates to the field of immunotherapy and drug discovery. The present invention provides oligonucleotides which are capable of inducing an anti-viral or an anti-bacterial response, in particular, the production of type I IFN, IL-18 and/or IL-1β, and their in vitro as well as therapeutic uses.

BACKGROUND OF THE INVENTION

The vertebrate immune system established different ways to detect invading pathogens based on certain characteristics of their microbial nucleic acids. Detection of microbial nucleic acids alerts the immune system to mount the appropriate type of immune response that is required for the defense against the respective type of pathogen detected. Detection of viral nucleic acids leads to the production of type I interferon (IFN) including IFN-α and IFN-β, the key cytokines for anti-viral defense.

IFN-α was the first type of interferon to be identified and commercialized; it is widely used clinically in the treatment of a variety of tumors (e.g., hairy cell leukemia, cutaneous T cell leukemia, chronic myeloid leukemia, non-Hodgkin's lymphoma, AIDS-related Kaposi's sarcoma, malignant melanoma, multiple myeloma, renal cell carcinoma, bladder cell carcinoma, colon carcinoma, cervical dysplasia) and viral diseases (e.g., chronic hepatitis B, chronic hepatitis C). IFN-α products that are currently in clinical use include the recombinant protein and the highly purified natural protein, both of which have high production costs. Therefore, there is a need for more economical ways of providing IFN-α to patients in need. Furthermore, IFN-α is currently administrated systematically and causes a broad spectrum of side effects (e.g. fatigue, flu-like symptoms, diarrhea). Most alarmingly, IFN-α causes a decrease in bone marrow function which leads to increased susceptibility to life-threatening infections, anemia and bleeding problems. Therefore, there is a need for ways of providing IFN-α in a more localized (i.e., target-specific) matter to reduce the occurrence of side effects.

Receptor-mediated detection of pathogen-derived nucleic acids assists in protecting the host genome from invading foreign genetic material. A new picture is evolving in which the ability of biological systems to detect viral nucleic acids via protein receptor-nucleic acid ligand interactions is crucial for maintaining the integrity of the genome and for survival.

A number of receptor proteins have evolved that take part in nucleic acid recognition. Recent studies indicate that one of the most important protein receptors for antiviral defense is the retinoic-acid-inducible protein I (RIG-I), a member of the helicase family containing two caspase-recruitment domains (CARDs) and a DExD/H-box helicase domain (M. Yoneyama et al., Nat Immunol 5, 730 (July 2004)). RIG-I-mediated recognition of a specific set of RNA viruses (flaviviridae, paramyxoviridae, orthomyxoviridae and rhabdoviridae) (M. Yoneyama et al., Nat Immunol 5, 730 (July, 2004); R. Sumpter, Jr. et al., J Virol 79, 2689 (March 2005); H. Kato et al., Nature 441, 101 (Apr. 9, 2006)) has a critical role in antiviral host defense in vitro and in vivo. A second member of the the helicase family, MDA-5, is responsible for the antiviral defense against a reciprocal set of RNA viruses (picornaviridae)(H. Kato et al., Nature 441(7089):101-105, Apr. 9, 2006).

In addition to RIG-I and MDA-5, the four members of the Toll-like receptor (TLR) family, TLR3, TLR7, TLR9 and TLR9, are also known to be involved in viral nucleic acid recognition. RIG-I and MDA-5 differ from the TLRs in their subcellular localization, expression pattern, signal transduction pathways and ligands.

While RIG-I and MDA-5 are cytosolic receptors, TLR3, TLR7, TLR8 and TLR9 are located in the endosomal membrane.

While TLRs are mainly expressed on certain defined immune cell subsets (i.e. TLR9 restricted to PDC and B cells), RIG-I and MDA-5 are expressed in both immune and non-immune cells (H. Kato et al., Immunity 23, 19 (July 2005)).

Besides distinct expression profiles and cellular localization, signalling of endosomal TLRs and the two cytoplasmic receptors RIG-I and MDA-5 differs. While TLR3 signals via TRIF and TLR7, TLR8 and TLR9 signal via MyD88, RIG-I recruits a CARD-containing adaptor, IPS-1 (T. Kawai et al., Nat Immunol 6, 981 (October 2005)) (also known as MAVS (R. B. Seth et al., Cell 122, 669 (Sep. 9, 2005)), VISA (L. G. Xu et al., Mol Cell 19, 727 (Sep. 16, 2005)) or Cardif (E. Meylan et al., Nature 437, 1167 (Oct. 20, 2005))). IPS-1 relays the signal to the kinases TBK1 and IKK-i, which phosphorylate interferon-regulatory factor-3 (IRF-3) and IRF-7, transcription factors essential for the expression of type-I interferons. As a consequence, in vivo, endosomal and cytoplasmic nucleic acid receptors induce different cytokine patterns. For example, both TLR3 and MDA-5 contribute to IL-12 production in response to poly(I:C), while MDA-5 but not TLR3 is responsible for IFN-α induction (H. Kato et al., Nature 441, 101 (Apr. 9, 2006)).

The ligand for TLR3 is long dsRNA such as poly(I:C) (L. Alexopoulou, et al., Nature 413, 732 (Oct. 18, 2001)), for TLR7 ssRNA (S. S. Diebold et al., Science 303, 1529 (Mar. 5, 2004); F. Heil et al., Science 303, 1526 (Mar. 5, 2004)) and short dsRNA with certain sequence motifs (i.e., the immunostimulatory RNA, isRNA) (V. Hornung et al., Nat Med 11, 263 (March 2005)), and for TLR9 CpG DNA (A. M. Krieg et al., Nature 374, 546 (Apr. 6, 1995); H. Hemmi et al., Nature 408, 740 (Dec. 7, 2000)).

In several studies, long double-stranded RNA was proposed to be the ligand for MDA-5 and RIG-I (M. Yoneyama et al., Nat Immunol 5, 730 (July 2004); H. Kato et al., Nature 441, 101 (Apr. 9, 2006); S. Rothenfusser et al., J Immunol 175, 5260 (Oct. 15, 2005)). A synthetic mimic of long dsRNA is poly(I:C). Recent data showed that poly(I:C) is a ligand for MDA-5, while it is not recognized by RIG-I (H. Kato et al., *Nature* 441, 101 (Apr. 9, 2006)). On the other hand, long dsRNA was found to activate RIG-I but not MDA-5 (H. Kato et al., *Nature* 441, 101 (Apr. 9, 2006)). This discrepancy of long dsRNA and poly(I:C) activity suggests that there is more to cytoplasmic RNA recognition than long dsRNA.

In general, compartimentalization and different molecular structure are believed to contribute to the detection of foreign nucleic acids. DNA (G. M. Barton et al., *Nat Immunol* 7, 49 (January 2006)) and RNA (F. Heil et al., *Science* 303, 1526 (Mar. 5, 2004)) localized in the endosome or DNA localized in the cytoplasm (K. J. Ishii et al., *Nat Immunol* 7, 40 (January, 2006)) are recognized and thus interpreted as foreign. The frequency of so-called CpG motifs in microbial DNA serves as a molecular feature further improving distinction of self and non-self DNA in the endosome. Although RNA recognition in the endosome is sequence dependent (F. Heil et al., *Science* 303, 1526 (Mar. 5, 2004); V. Hornung et al., *Nat Med* 11, 263 (March 2005)), no sequence motifs have been defined so far that serve as a molecular basis to improve distinction of self and non-self RNA (i.e. motifs that are more frequent in viral than in self RNA) in the cytoplasm. Instead, the molecular characteristic of double-strandedness seems to allow distinction of self and non-self RNA. In fact, in the endosome, long double-stranded RNA and its mimic poly(I:C), but not single-stranded RNA, are recognized via TLR3 (L. Alexopoulou, et al., *Nature* 413, 732 (Oct. 18, 2001)). In the cytoplasm, abundant self RNA complicates our understanding of the recognition of non-self RNA. Nevertheless, the concept that long dsRNA in the cytoplasm is detected as non-self has never been questioned since the discovery of type I IFN.

Unlike in the absence of RIG-I and MDA-5, antiviral defense is largely maintained in the absence of TLRs (A. Krug et al., *Immunity* 21, 107 (July, 2004); K. Tabeta et al., *Proc Natl Acad Sci USA* 101, 3516 (Mar. 9, 2004); T. Delale et al., *J Immunol* 175, 6723 (Nov. 15, 2005); K. Yang et al., *Immunity* 23, 465 (November 2005)), underscoring the critical role of RIG-I and MDA-5 in antiviral responses.

It is therefore an object of the present invention to provide polynucleotides/oligonucleotides which are capable of stimulating an anti-viral response, in particular, a type I IFN response. It is another object of the present invention to provide a pharmaceutical composition capable of inducing an anti-viral response, in particular, type I IFN production, in a patient for the prevention and treatment of diseases and disorders such as viral infection. It is also an object of the present invention to provide a pharmaceutical composition for treating tumor.

A recent study demonstrated that in vitro transcribed siRNAs (small-interfering RNA), but not synthetic siRNAs, stimulated the production of type I IFN from selected cell lines (D. H. Kim et al., *Nat Biotechnol* 22, 321 (March 2004); US 2006/0178334). However, the structural requirements and the physiological relevance of this induction and the mechanism of detection remain unclear. Furthermore, in the work by Kim et al., the in vitro transcribed siRNAs, regardless of their nucleotide sequence, induced type I IFN production in both virally infected and non-infected cells, regardless of whether the target mRNAs were present or not, leading to cell death. In other words, the in vitro transcribed siRNAs induced IFN production and consequently, cell death, in a non-sequence-dependent and non-target cell-specific manner. The lack of sequence- and cell-specificity severely limits, if not precludes, the use of such in vitro transcribed siRNAs for therapeutic purposes.

It is therefore a further object of the present invention to provide polynucleotides/oligonucleotides which are capable of inducing an anti-viral response, in particular, a type I IFN response, in a nucleotide sequence-dependent and target cell-specific manner. Such polynucleotides/oligonucleotides can be advantageously used for the treatment of diseases and disorders such as viral infection and tumor without harming bystander (i.e., healthy, non-infected or non-diseased) cells.

SUMMARY OF THE INVENTION

The present invention provides an oligonucleotide or a precursor thereof which is capable of inducing an anti-viral, anti-bacterial, and/or anti-tumor response in a vertebrate cell and their in vitro and in vivo, in particular, medical, uses.

The present invention further provides a method for preparing an oligonucleotide which is capable of inducing an anti-viral, anti-bacterial, and/or anti-tumor response in a vertebrate cell.

The present invention also provides a method for preparing an oligonucleotide which lacks the capability of inducing an anti-viral, anti-bacterial, and/or anti-tumor response in a vertebrate cell.

(B) pBluescript KS was used to generate DNA templates of various lengths for in vitro transcription (lower panel). In vitro transcribed RNAs were analyzed on a 4% denaturing agarose gel prior to transfection. Subsequently in vitro generated RNAs were transfected in purified PDC and monocytes plated in 96-well plate. 24 hours after transfection supernatants were analyzed for IFN-α production. Data of two independent donors were summarized and are depicted as mean values±SEM.

(C) A set of RNA oligonucleotides was generated ranging from 27 to 9 nucleotides by gradually shortening a 27-mer oligonucleotide from the 3' end in steps of three nucleotides. Purified monocytes were transfected with the respective oligonucleotides and IFN-α production was analyzes 24 hours after stimulation. Data of five independent donors were normalized to the IFN-α induction level of the 27 nucleotides oligonucleotide (5876±1785 pg/ml) and summarized as mean values±SEM.

Sequences shown are:

```
27-mer:
                                (SEQ ID NO: 334)
5'-pppGGGGCUGACCCUGAAGUUCAUCUUCCC-3';

24-mer:
                                (SEQ ID NO: 335)
5'-pppGGGGCUGACCCUGAAGUUCAUCCC-3';

21-mer:
                                (SEQ ID NO: 336)
5'-pppGGGGCUGACCCUGAAGUUCCC-3';

18-mer:
                                (SEQ ID NO: 337)
5'-pppGGGGCUGACCCUGAACCC-3';

15-mer:
                                (SEQ ID NO: 338)
5'-pppGGGGCUGACCCUCCC-3';

12-mer:
                                (SEQ ID NO: 339)
5'-pppGGGGCUGACCCC-3';
and 9-mer:
                                (SEQ ID NO: 340)
5'-pppGGGGCUCCC-3'.
```

(D) Purified monocytes were transfected with 200 ng in vitro transcribed RNA with different homopolymeric 3' tails. Tri-GFPs was included as a positive control. 24 hours after transfection, supernatants were collected and IFN-α production was assessed via ELISA. Data of four independent donors were summarized and are depicted as mean values±SEM.

Sequences shown are:

```
tri-GFPs:
                                (SEQ ID NO: 341)
5'-pppGGGGCUGACCCUGAAGUUCAUCUU-3';

tri-Pdy G:
                                (SEQ ID NO: 342)
5'-pppGGGAGACAGGGGGGGGGGGGGGGGGGGGGG-3';

tri-Pdy A:
                                (SEQ ID NO: 343)
5'-PPPGGGAGACAGGAAAAAAAAAAAAAAAAAAAAA-3';

tri-Pdy C:
                                (SEQ ID NO: 344)
5'-PPPGGGAGACAGGCCCCCCCCCCCCCCCCCCCCC-3';
and tri-Pdy U:
                                (SEQ ID NO: 345)
5'-PPPGGG AGACAGGUUUUUUUUUUUUUUUUUUUU-3'.
```

Figure 2:
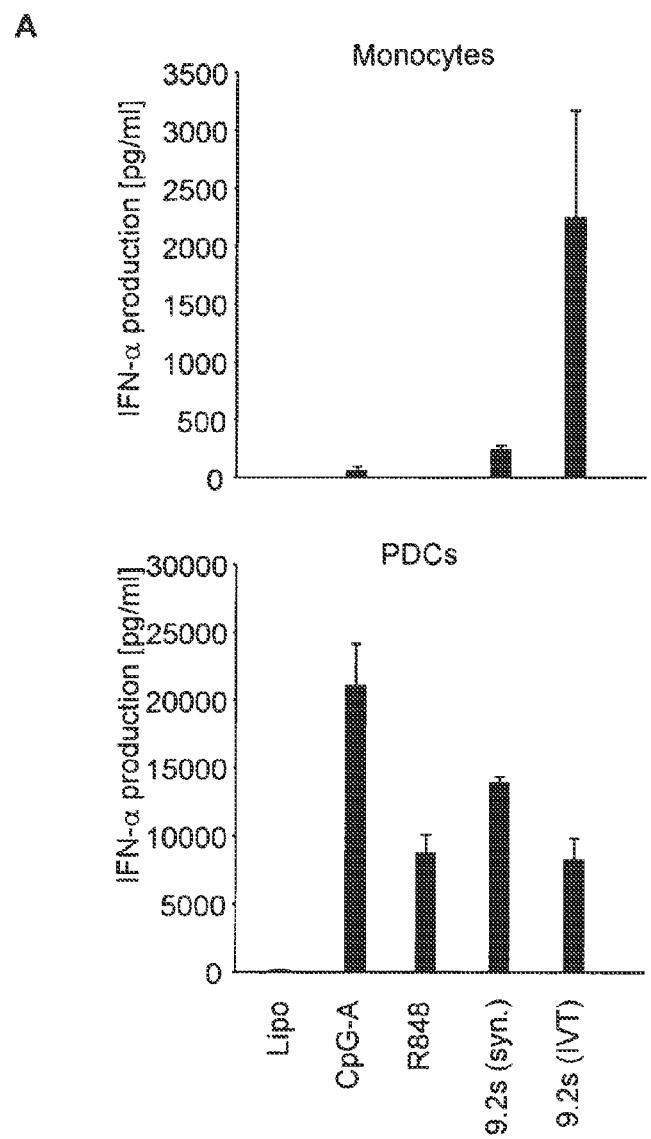
Figure 2:
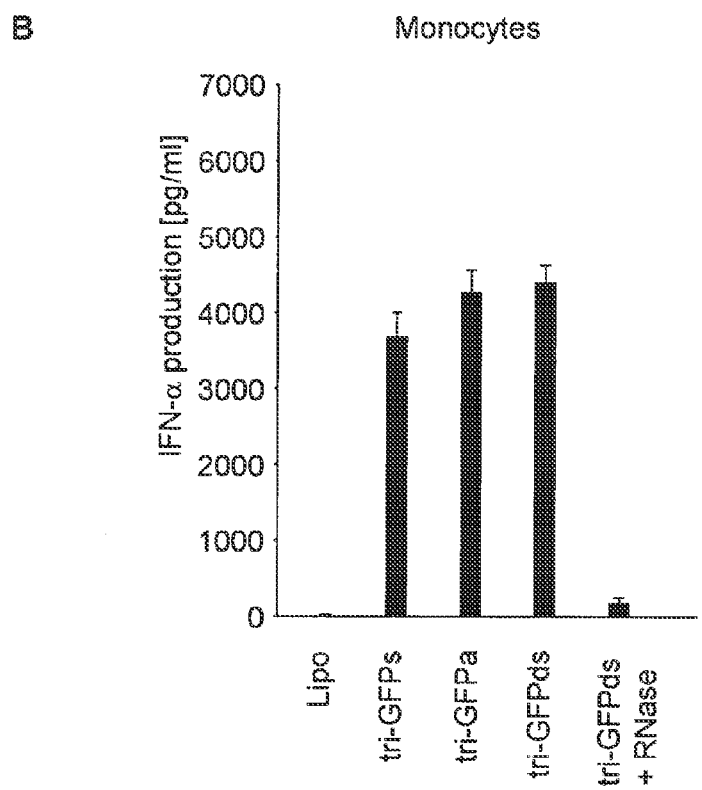
Figure 2:
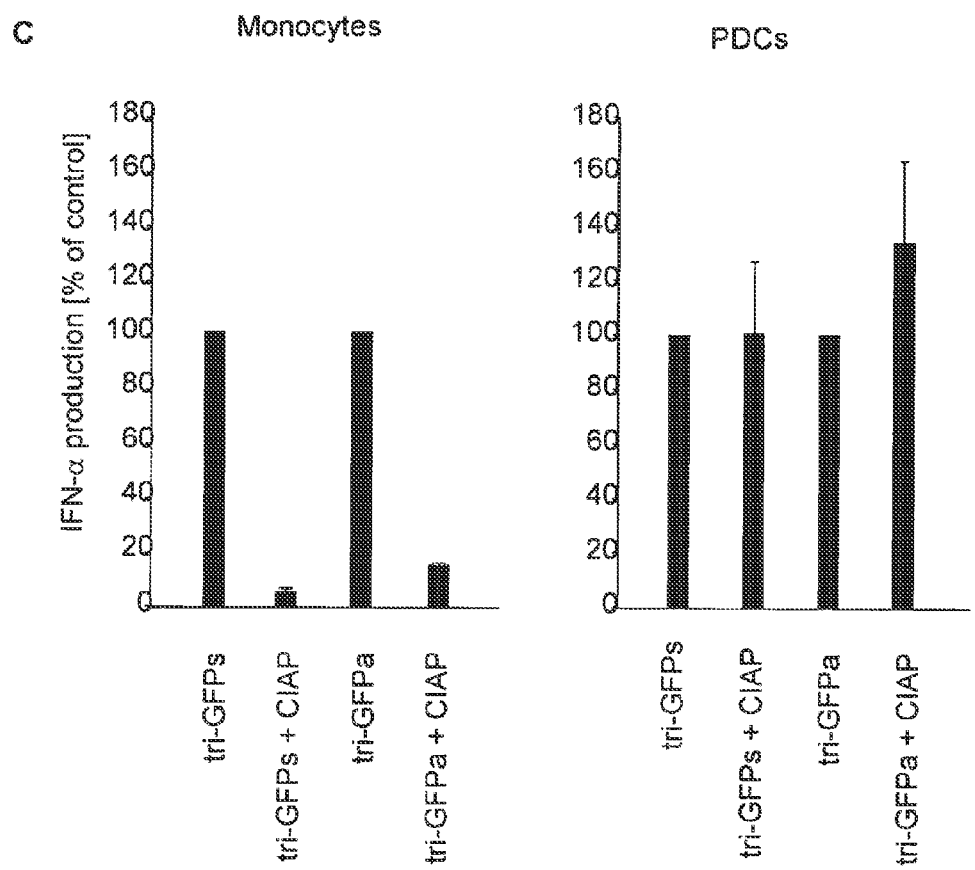

FIG. 2: 5' phosphorylated, but not synthetic RNA oligonucleotides are potent inducers of IFN-α in human monocytes (A) Synthetically synthesized or enzymatically transcribed RNA9.2s (200 ng) was transfected into purified monocytes or PDCs. CpG-A (3 μg/ml) and R848 (10 μM) were included as positive control stimuli for TLR9- or TLR7-mediated IFN-α induction in PDC. Data of two (monocytes) or three (PDCs) independent donors were summarized and are depicted as mean values±SEM.

Sequences shown are:

```
9.2s (syn):
                                (SEQ ID NO: 346)
5'-OHAGCUUAACCUGUCCUUCAA-3'
and 9.2s (IVT):
                                (SEQ ID NO: 347)
5'-pppAGCUUAACCUGUCCUUCAA-3'.
```

(B) The sense (tri-GFPs) and the antisense (tri-GFPa) strand of an established anti-GFP siRNA were transcribed using in vitro transcription. Both the single stranded components and the annealed dsRNA molecule (all 200 ng) were transfected into purified monocytes. In addition the dsRNA molecule was incubated with RNase T1 to remove the overhanging 5' ends from both strands. Data from two independent donors are depicted as mean values±SEM.

Sequences shown are:

```
tri-GFPs:
                                (SEQ ID NO: 341)
5'-pppGGGGCUGACCCUGAAGUUCAUCUU-3';

tri-GFPa:
                                (SEQ ID NO: 348)
5'-pppGGGGAUGAACUUCAGGGUCAGCUU-3';

tri-GFPds: upper strand is
                                (SEQ ID NO: 341)
5'-pppGGGGCUGACCCUGAAGUUCAUCUU-3'
and lower strand is
                                (SEQ ID NO: 348)
5'-pppGGGGAUGAACUUCAGGGUCAGCUU-3';
and tri-GFPds + RNAse T1: upper strand is
                                (SEQ ID NO: 341)
5'-pppGGGGCUGACCCUGAAGUUCAUCUU-3'
and lower strand is
                                (SEQ ID NO: 348)
5'-pppGGGGAUGAACUUCAGGGUCAGCUU-3'.
```

(C) Calf intestine alkaline phosphatase (CIAP) was used to dephosphorylate tri-GFPs and tri-GFPa. Untreated or dephosphorylated RNA oligonucleotides were subsequently transfected into monocytes and PDC. Data from two independent donors were normalized to the respective untreated control oligonucleotide and are depicted as mean values±SEM.

Figure 3:
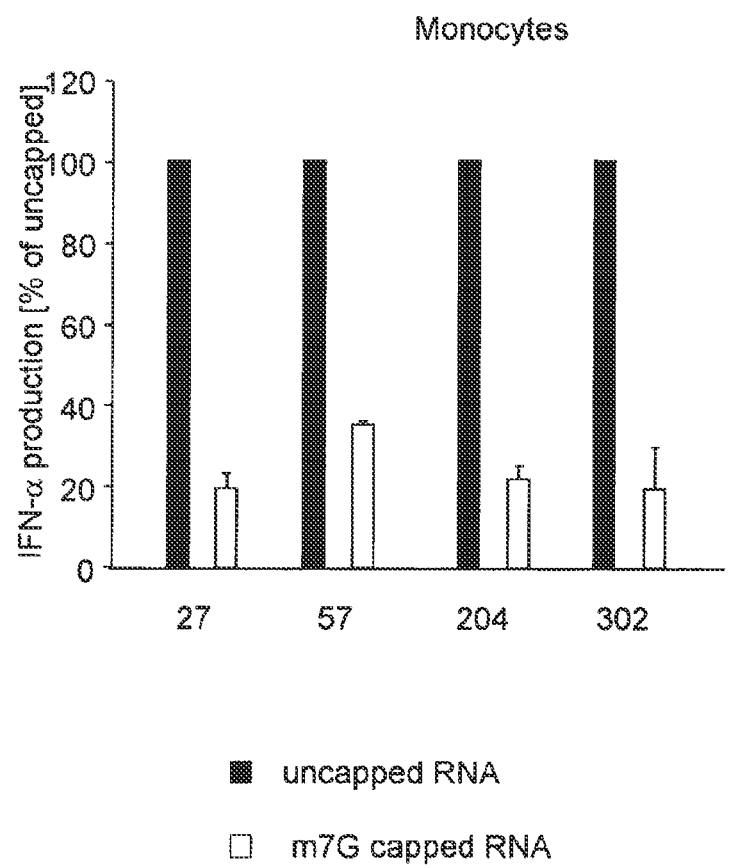
Figure 3:
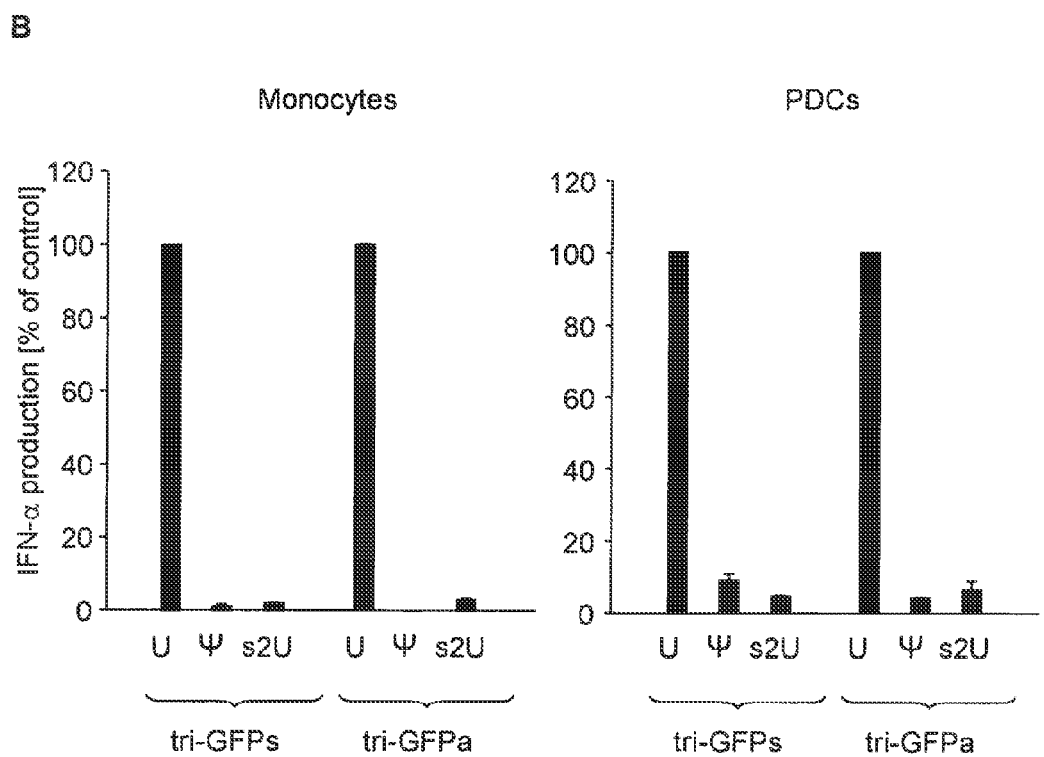
Figure 3:
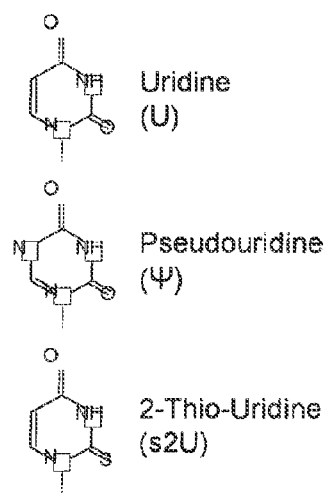
Figure 3:
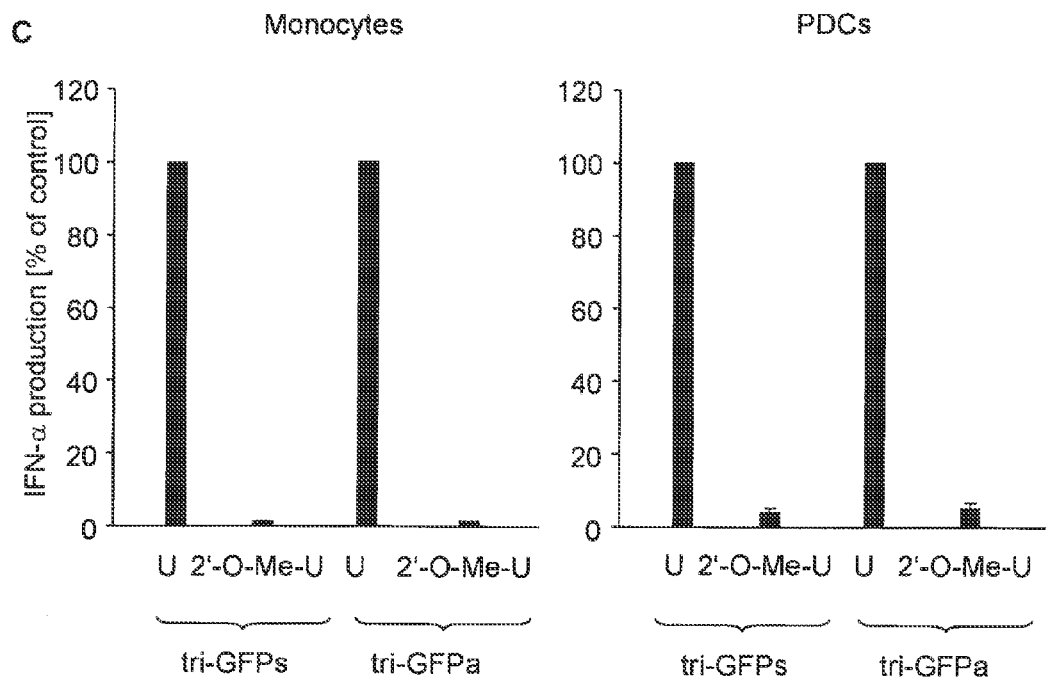
Figure 3:
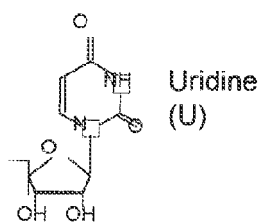
Figure 3:
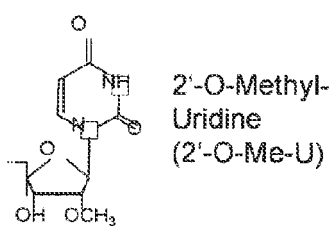

FIG. 3: 7-methyl-guanosine capping and eukaryotic-specific base modifications abolish IFN-α induction via 5"triphosphate RNA (A) RNA molecules of various length (27 nucleotides-302 nucleotides) derived from pBKS as a template (see Table 1B) were transcribed in the presence of the cap analogue N-7 methyl GpppG (m7G capped RNA) or using standard NTPs (uncapped RNA). Purified monocytes were transfected with either m7G capped or uncapped RNAs (200 ng each) and IFN-α production was assessed 24 hours after stimulation. For each RNA transcript, data of two independent donors were normalized to the uncapped RNA value and summarized as mean values±SEM. The absolute values for the respective RNA transcripts were 1401, 2351, 91, 797 and 2590 μg/ml, respectively.

(B) & (C) Tri-GFPs and tri-GFPa were synthesized via in vitro transcription in the presence of either uridine-5'-triphosphate, pseudouridine-5'-triphosphate (ψ), 2-thiouridine- 5'-triphosphate (s2U) (all B) or 2'-O-methyluridine-5'-triphosphate (C). Subsequently purified monocytes and PDCs were transfected with the respective oligonucleotides and IFN-a production was assessed 24 hours after stimulation. For each RNA transcript, data of two (B) or three (C) independent donors were normalized to the value of the RNA oligonucleotide transcribed in the presence of uridine-5'-triphosphate and summarized as mean values±SEM.

Figure 4:
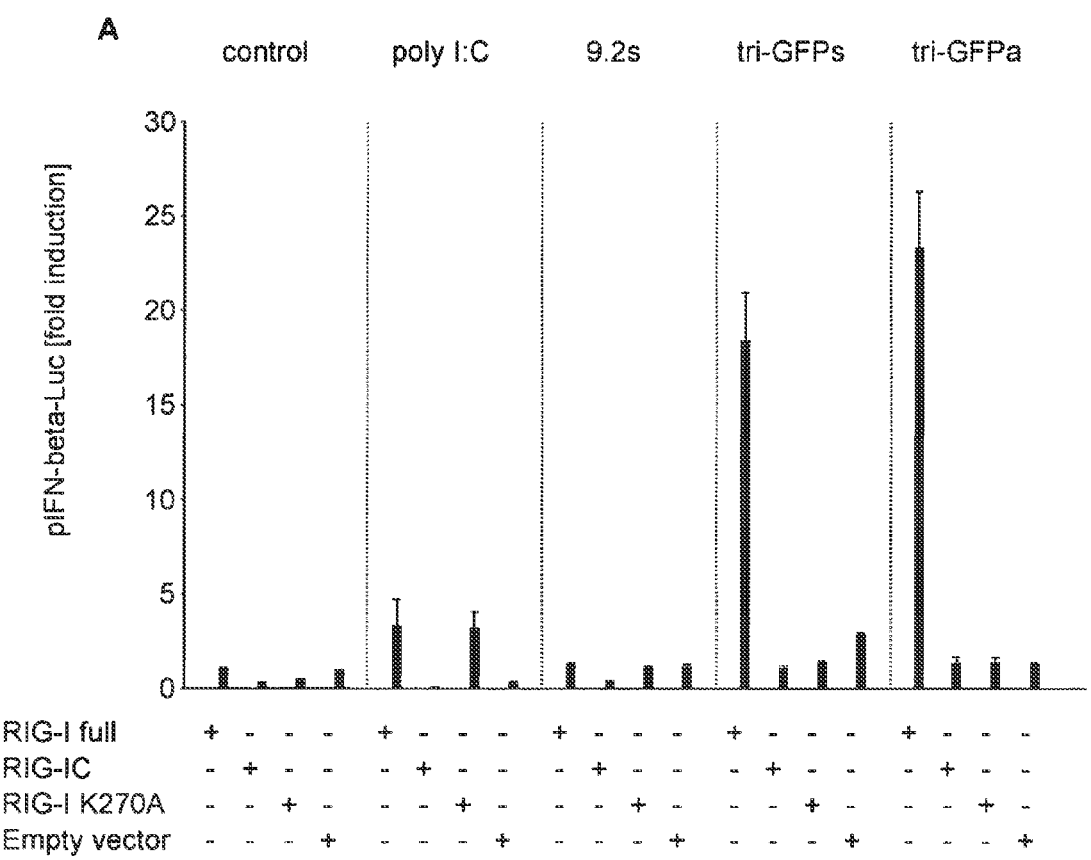
Figure 4:
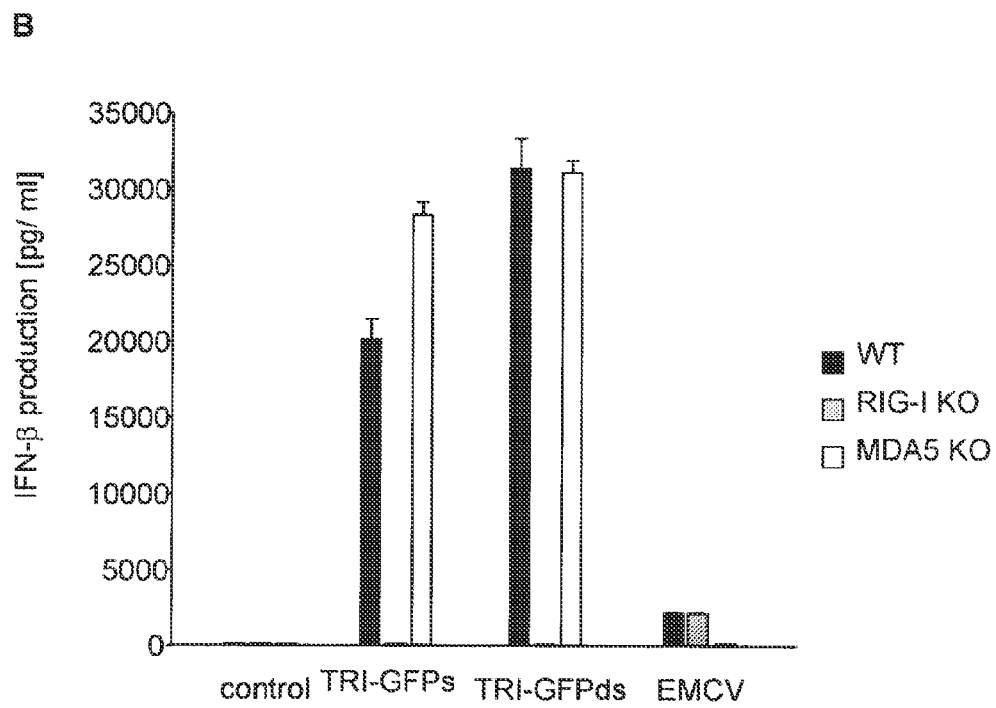
Figure 4:
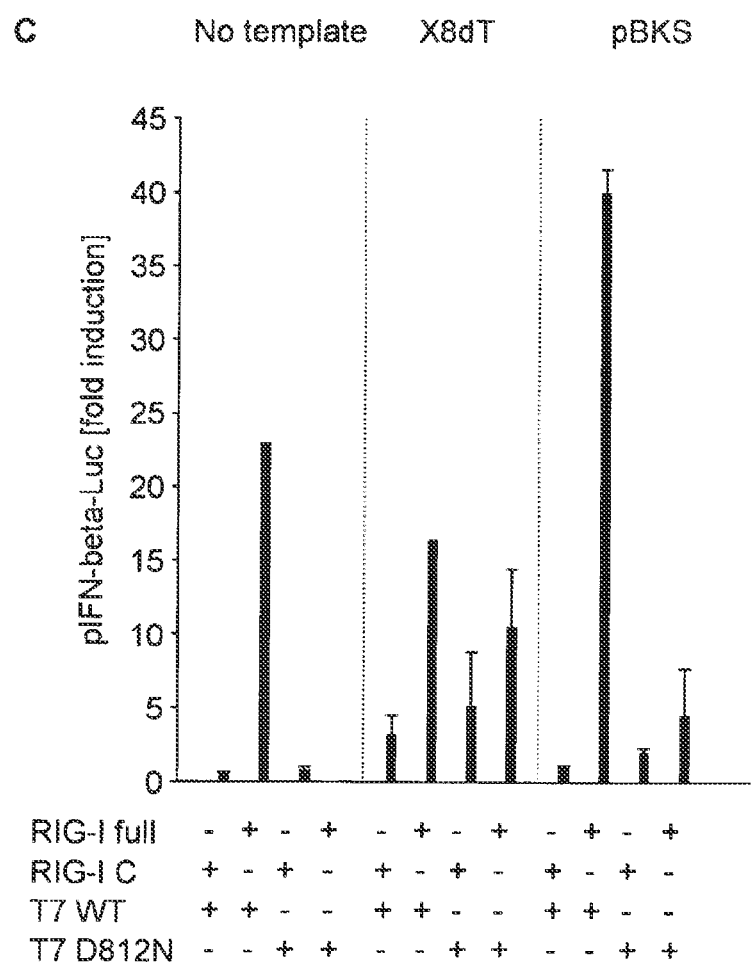
Figure 4:
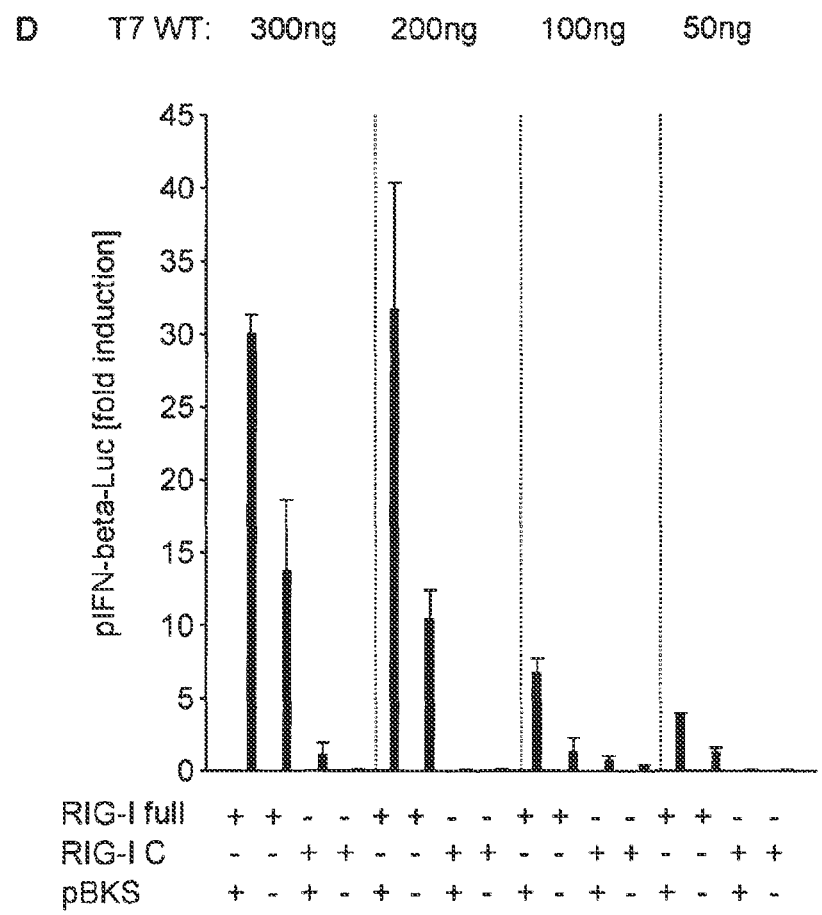

FIG. 4: Triphosphate-mediated IFN-α induction requires RIG-I but not MDA5 (A) HEK 293 cells were transfected with either RIG-I full, RIG-IC, RIG-I K270A or the corresponding empty vector (all 200 ng each) in the presence of pIFN-beta-Luc (300 ng) and pSV-beta Galactosidase (400 ng). In addition either nothing, poly I:C, synthetic RNA9.2s, tri-GFPs or tri-GFPa (all 200 ng) were included. 24 hours after transfection pIFN-beta-Luc reporter activity was assessed. Data from one representative experiment out of three were normalized to the empty vector condition and are depicted as mean values of duplicates±SEM.

(B) MEFs from mice devoid of either RIG-I or MDA5 or respective wild type MEFs were transfected with tri-GFPs or tri-GFPds. In addition MEFs were infected with EMCV at a M.O.I. of 1. 24 hours after stimulation supernatants were collected and assayed for IFN-β production. Data from one representative experiment out of three are depicted.

(C) In addition, HEK 293 cells were transfected with either RIG-I full or RIG-IC (200 ng each) and T7 RNA polymerase or the transcriptionally defective point mutant T7 RNA polymerase D812N (300 ng each) in the presence of pIFN-beta-Luc (300 ng) and pSV-beta Galactosidase (400 ng). In addition either nothing, X8dt (vector based on the pBKS backbone without T7 RNA polymerase promoter) or pBKS (all 300 ng) were included. 24 hours after transfection pIFN-beta-Luc reporter activity was assessed.

(D) In addition HEK 293 cells were transfected with decreasing doses of T7 RNA polymerase in the presence of either RIG-I full or RIG-IC (200 ng) with nothing or pBKS (300 ng), while pIFN-beta-Luc (300 ng) and pSV-beta Galactosidase (400 ng) were included. 24 hours after transfection pIFN-beta-Luc reporter activity was assessed. Data from one representative experiment out of three were normalized to the RIG-IC/pBKS/T7 RNA polymerase (300 ng) condition and are depicted as mean values of duplicates±SEM.

Figure 5:
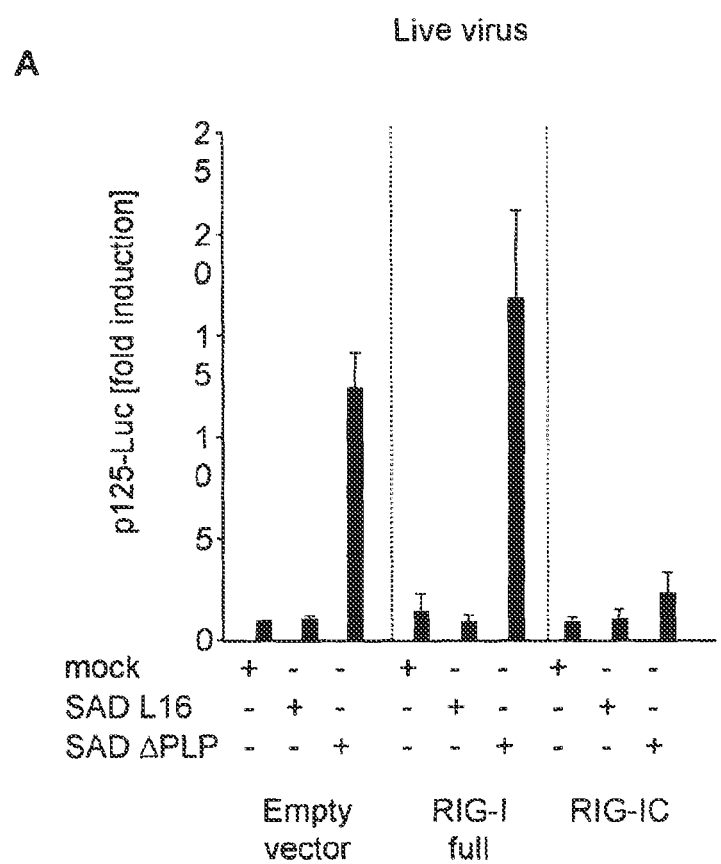
Figure 5:
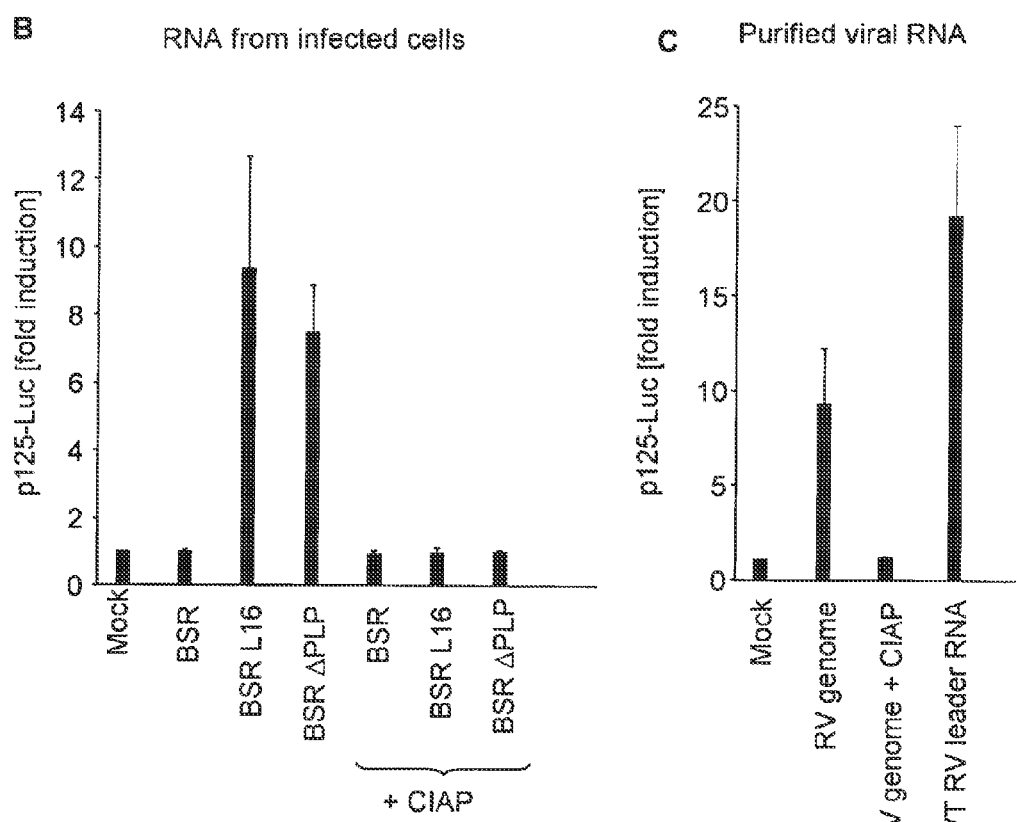

FIG. 5: Viral RNA induces IFN-induction via RIG-I depending on its 5' end phosphorylation status (A) Vero cells were transfected with either empty vector, RIG-I full or RIG-IC in the presence of the reporter plasmid p125-Luc. 6 hours later, the cells were either mock-infected or infected with RV SAD L16 or RV SAD LPLP at a MOI of 3. p125-Luc reporter activity was assessed 48 h after DNA transfection. Average data from two experiments done in duplicates are shown as mean fold values (mock=1)±SEM.

(B) HEK 293T cells were either mock-transfected with PEI, or with 1 µg total RNA isolated from non-infected BSR cells or total RNA isolated from BSR cells infected with RV L16 or RV □PLP. RNA isolates of non-infected BSR-cells, BSR cells infected with SAD L16 (BSR L16) and SAD ΔPLP (BSR dPLP) were additionally treated with CIAP and transfected accordingly. 48 h after transfection p125-Luc reporter activity was assessed. Data are shown as mean fold values (mock=1) of triplicates±SEM.

(C) Either mock, RNA isolated from gradient-purified virions (RV L16) or CIAP-treated RNA from purified virions was used to stimulate HEK 293T cells. As a positive control, an in vitro transcribed RNA oligonucleotide corresponding to the 5' terminal leader sequence (58 nt) of the RV SAD L16 cRNA was used to stimulate HEK 293T cells. 48 h after stimulation p125-Luc reporter activity was assessed. Data from the experiment are shown as mean fold values (mock=1) of triplicates±SEM.

Figure 6:
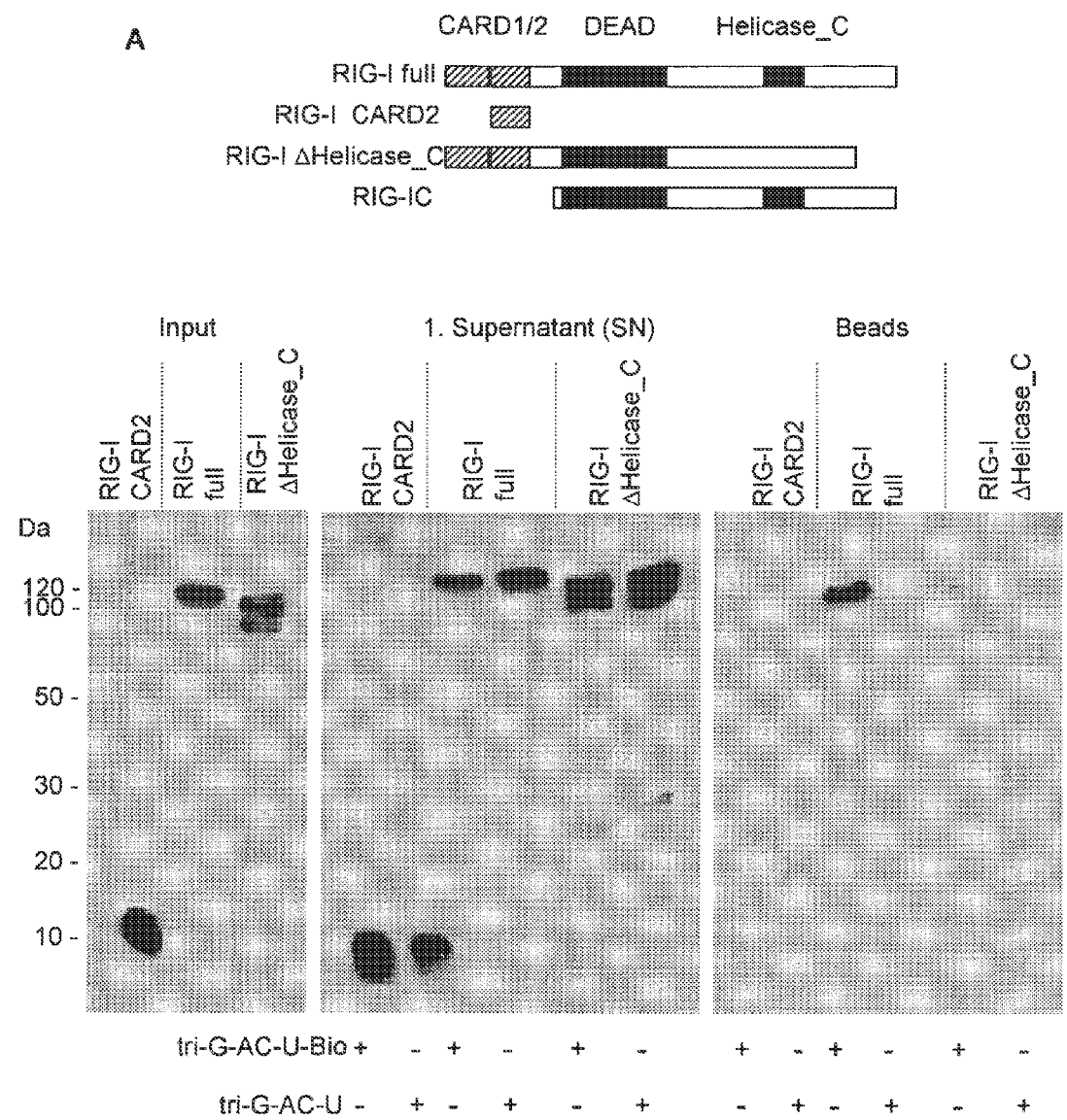
Figure 6:
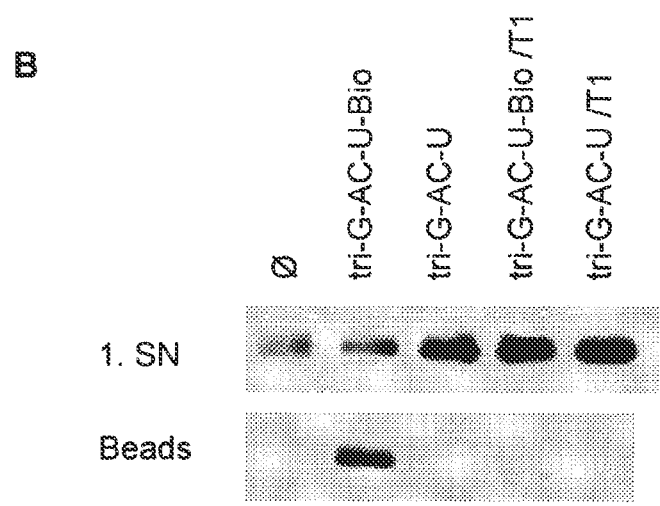

FIG. 6: Triphosphate RNA directly binds to RIG-I (A) HEK 293 cells were transiently transfected with full length RIG-I, RIG-I CARD2 or RIG-I ΔHELIc. 36 hours after transfection cells were lysed and co-incubated with the indicated RNA oligonucleotides (0.375 µg; lower right panel) for two hours at 4° C. Next, streptavidin-agarose-beads were added for an additional period of one hour. Beads were collected by centrifugation and washed four consecutive times. After all washing steps, supernatants were collected and after four washes streptavidin-agarose beads were collected by centrifugation and boiled in Laemmli buffer. For one representative experiment out of two, the input (A, left panel), the supernatants of the first wash (1. SN) (A, middle panel) and the bead-bound fraction (A, right panel) are depicted (no or little signal was seen in the supernatant of the second, third and fourth wash; data not shown). All preparations were run on the same gel and the membranes were exposed for the same time period. FIG. 6A discloses "DEAD" as SEQ ID NO: 365.

(B) RIG-IC was immunoprecipitated using Flag-agarose-beads and subsequently eluted via Flag-peptide. In analogy to above experiments, the depicted RNA oligonucleotides were added to purified RIG-IC and subsequently co-incubated with streptavidin-agarose beads. If indicated, RNase T1 was used to remove the 5' portion of the oligonucleotide containing the triphosphate group. Beads were washed four consecutive times and the first supernatant and the bead-bound fraction were analyzed by western blotting. One representative experiment out of three is shown.

Sequences shown are:

```
tri-G-AC-U-Bio:
                                        (SEQ ID NO: 349)
5'-pppGGGAGACAGGCACCACACACACACACACŬŬŬ-3',
Ŭ s biotinylated U;

tri-G-AC-U-Bio:
                                        (SEQ ID NO: 350)
5'-pppGGGAGACAGGCACCACACACACACACACUUU-3';

tri-G-AC-U-Bio/T1:
                                        (SEQ ID NO: 349)
5'-pppGGGAGACAGGCACCACACACACACACACŬŬŬ-3',
Ŭ is biotinylated U;
and tri-G-AC-U-Bio/T1:
                                        (SEQ ID NO: 350)
5'-pppGGGAGACAGGCACCACACACACACACACUUU-3'.
```

Figure 7:
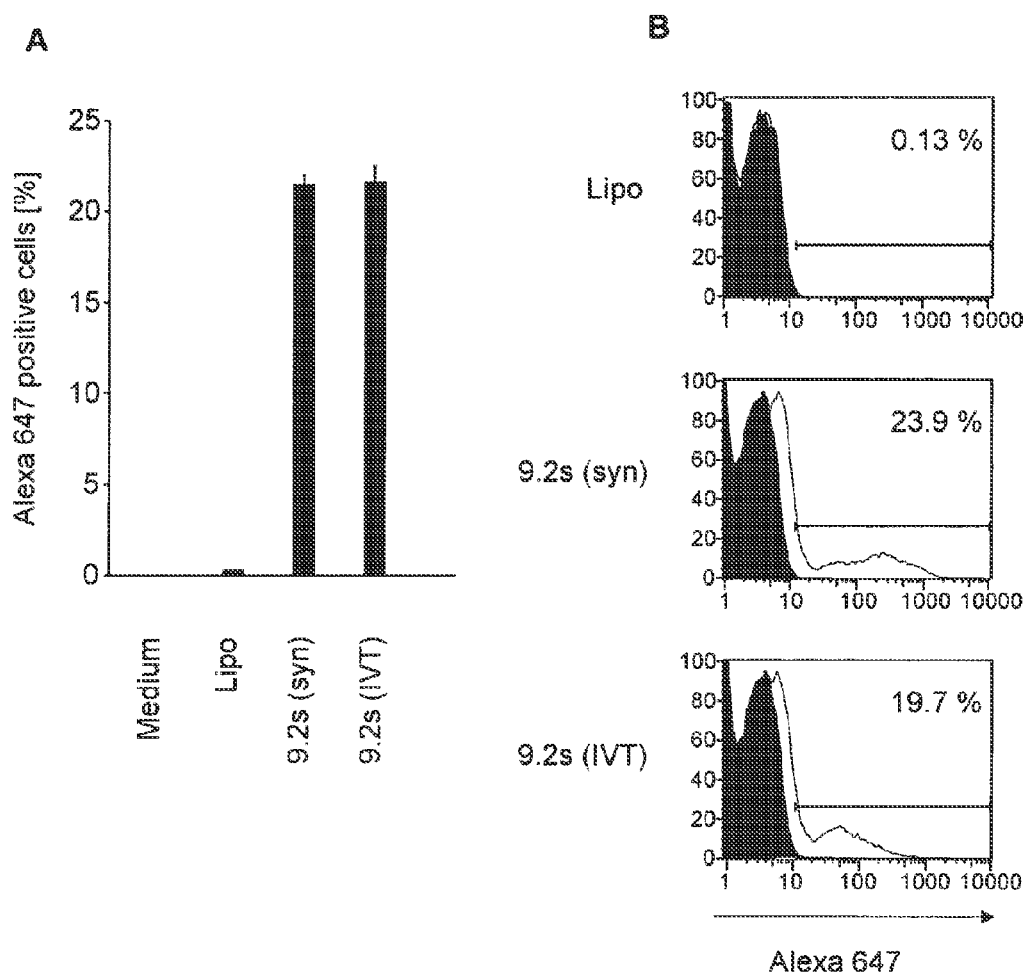

FIG. 7: No difference in uptake of synthetic and triphosphate RNA oligonucleotides in monocytes (A) Synthetic or in vitro transcribed RNA oligonucleotides of the sequence 9.2s were chemically labeled with Alexa 647 fluorophores, resulting in a base:dye ratio of 81 and 71 respectively. Subsequently purified monocytes were transfected with labeled RNA oligonucleotides (all 50 ng). Two hours after transfection cells were harvested and vigorously washed with 10 mM EDTA in PBS twice. Uptake of the fluorescently labeled oligonucleotides were assessed by flow cytometry. Untreated monocytes were used to set the threshold level for positive cells. Data from two independent donors were summarized and are depicted as mean values±SEM.

(B) Histogram plots from one representative donor are depicted.

Figure 8:
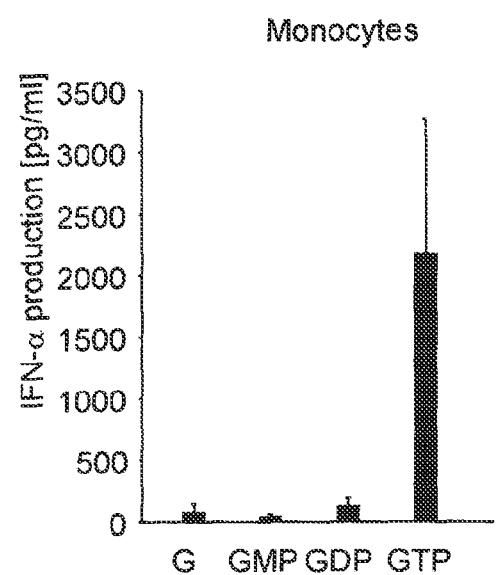

FIG. 8: Only guanosine triphosphate, but not guanosine diphosphate, guanosine monophosphate or guanosine initiated RNA oligonucleotides induce a potent IFN-α response in human monocytes Using a T7 RNA polymerase template coding for a 24-mer RNA oligonucleotide with only one initial guanosine, RNA oligonucleotides were generated via in vitro transcription in the presence of ATP, CTP and UTP and either only guanosine, guanosine-5'-monophosphate, guanosine-5'-diphosphate or guanosine-5'-triphosphate. Subsequently purified monocytes were transfected with the respective RNA oligonucleotides (all 200 ng) and IFN-α production was analyzed 24 hours after stimulation. Data from two independent donors were summarized and are depicted as mean values±SEM.

Sequences shown are:

```
G:
                                    (SEQ ID NO: 351)
5'-OHGACACACACACACACACACACUUU-3';

GMP:
                                    (SEQ ID NO: 352)
5'-pGACACACACACACACACACACUUU-3';

GDP:
                                    (SEQ ID NO: 353)
5'-ppGACACACACACACACACACACUUU-3';
and GTP:
                                    (SEQ ID NO: 354)
5'-pppGACACACACACACACACACACUUU-3'.
```

Figure 9:
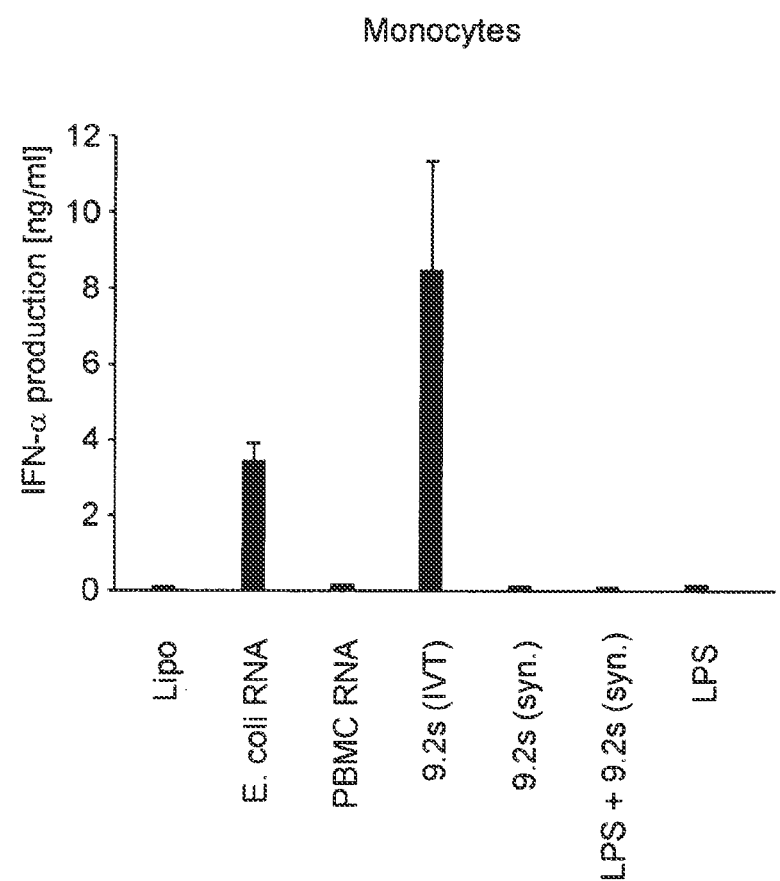

FIG. 9: Prokaryotic RNA, but not eukaryotic RNA induces IFN-α production in monocytes Total RNA was isolated from *E. coli* bacteria strain DH10B and human PBMC. Subsequently monocytes were transfected with *E. coli* RNA, PBMC RNA, synthetic 9.2s RNA or in vitro transcribed 9.2s (all 200 ng). In addition LPS (100 ng/ml) was added either exogenously or combined with cationic lipid complexed synthetic 9.2s RNA to stimulate monocytes. IFN-α production was analyzed 24 hours after stimulation. Data from two independent donors were summarized and are depicted as mean values±SEM.

Figure 10:
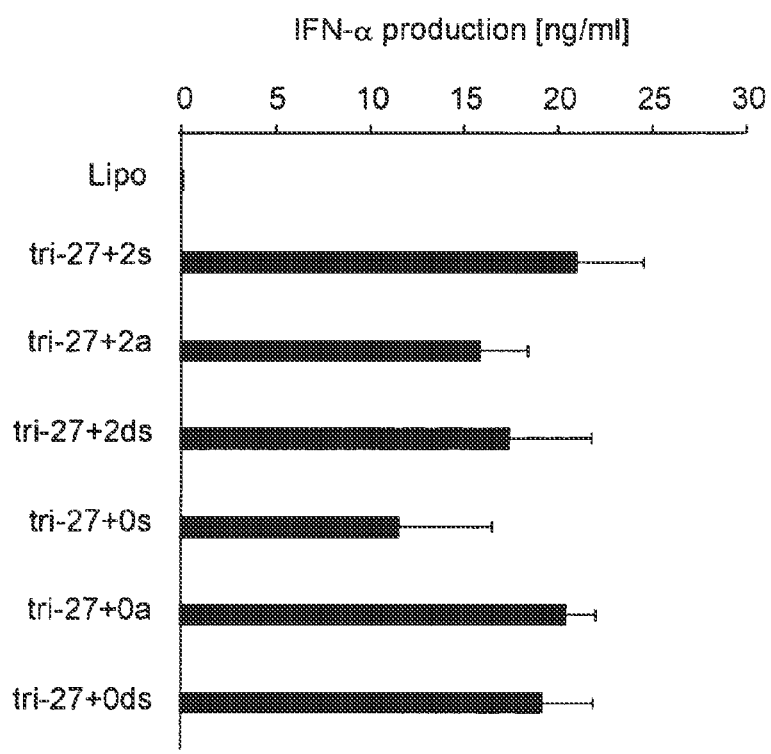

FIG. 10: 3' overhangs of double stranded triphosphate RNA oligonucleotides do not impact on the immunostimulatory activity Purified monocytes were transfected with either tri-27+2s, tri-27+2a, tri-27+0s, tri-27+0a or the respective double stranded oligonucleotides (all 200 ng). IFN-α production was analyzed 24 hours after stimulation. Data from three independent donors were summarized and are depicted as mean values±SEM.

Sequences shown are:

```
tri-27 + 2s:
                                    (SEQ ID NO: 355)
5'-pppGCUGACCCUGAAGUUCAUCUGCACCACUU-3';

tri-27 + 2a:
                                    (SEQ ID NO: 356)
5'-pppGUGGUGCAGAUGAACUUCAGGGUCAGCUU-3';

tri-27 + 2ds: upper strand is
                                    (SEQ ID NO: 355)
5'-pppGCUGACCCUGAAGUUCAUCUGCACCACUU-3'
and lower strand is
                                    (SEQ ID NO: 356)
5'-pppGUGGUGCAGAUGAACUUCAGGGUCAGCUU-3';

tri-27 + 0s:
                                    (SEQ ID NO: 357)
5'-pppAAGCUGACCCUGAAGUUCAUCUGCACC-3';

tri-27 + 0a:
                                    (SEQ ID NO: 358)
5'-pppGGUGCAGAUGAACUUCAGGGUCAGCUU-3';
and tri-27 + 2ds: upper strand is
                                    (SEQ ID NO: 357)
5'-pppAAGCUGACCCUGAAGUUCAUCUGCACC-3'
and lower strand is
                                    (SEQ ID NO: 358)
5'-pppGGUGCAGAUGAACUUCAGGGUCAGCUU-3'.
```

Figure 11:
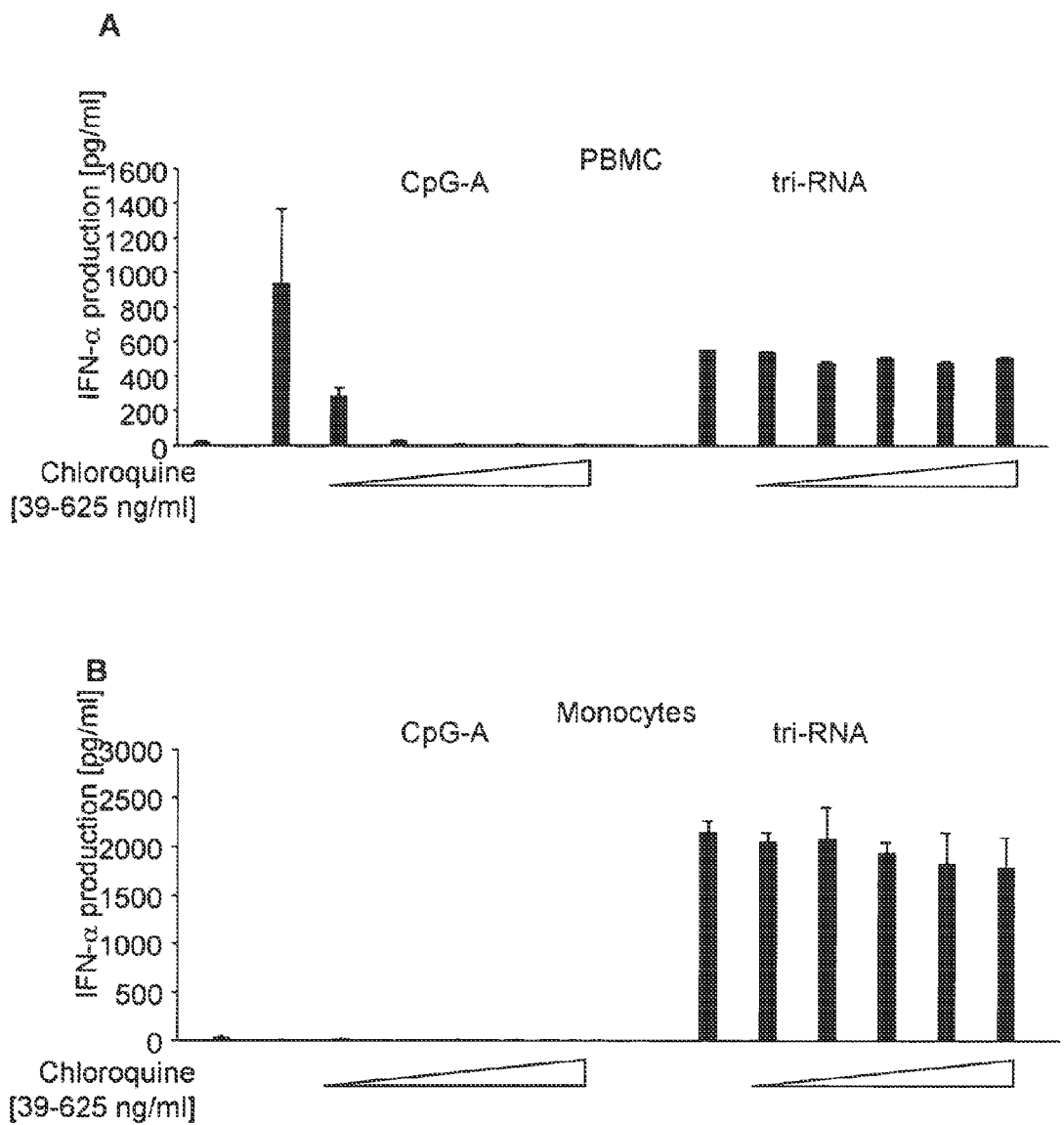
Figure 11:
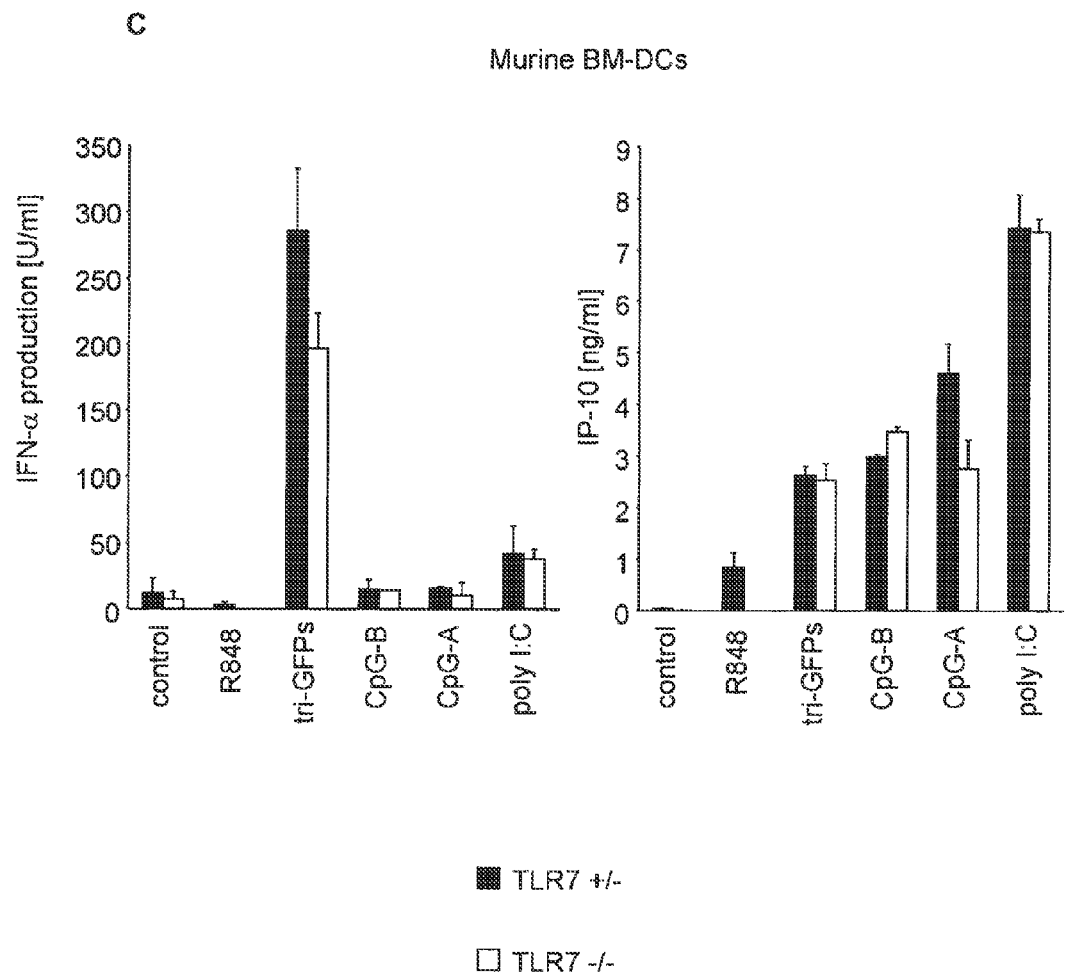

FIG. 11: Triphosphate RNA-mediated IFN-α induction is independent of endosomal maturation and of TLR7

(A) & (B) Purified PDCs (A) and monocytes (B) were pre-incubated with two-fold ascending doses of chloroquine (39-625 ng/ml) and subsequently cells were either stimulated with CpG-A (3 µg/ml) or transfected with 200 ng tri-GFPa. 24 hours after incubation supernatants were collected and IFN-α production was assessed via ELISA. Data from two independent donors were summarized as mean values±SEM.

(C) Murine MDC were generated from bone marrow cells from either TLR7 knock out mice (TLR7 −/−) or respective control animals (TLR7 +/−). Subsequently BM-MDC were transfected with 200 ng tri-GFPs or stimulated with either R848 (10 µM), CpG-B (3 µg/ml), CpG-A (3 µg/ml) or poly I:C (25 µ/ml). 24 hours after incubation supernatants were analyzed for IFN-α and IP-10 production. One representative experiment (mean of duplicates±SEM) out of three is depicted.

Figure 12:
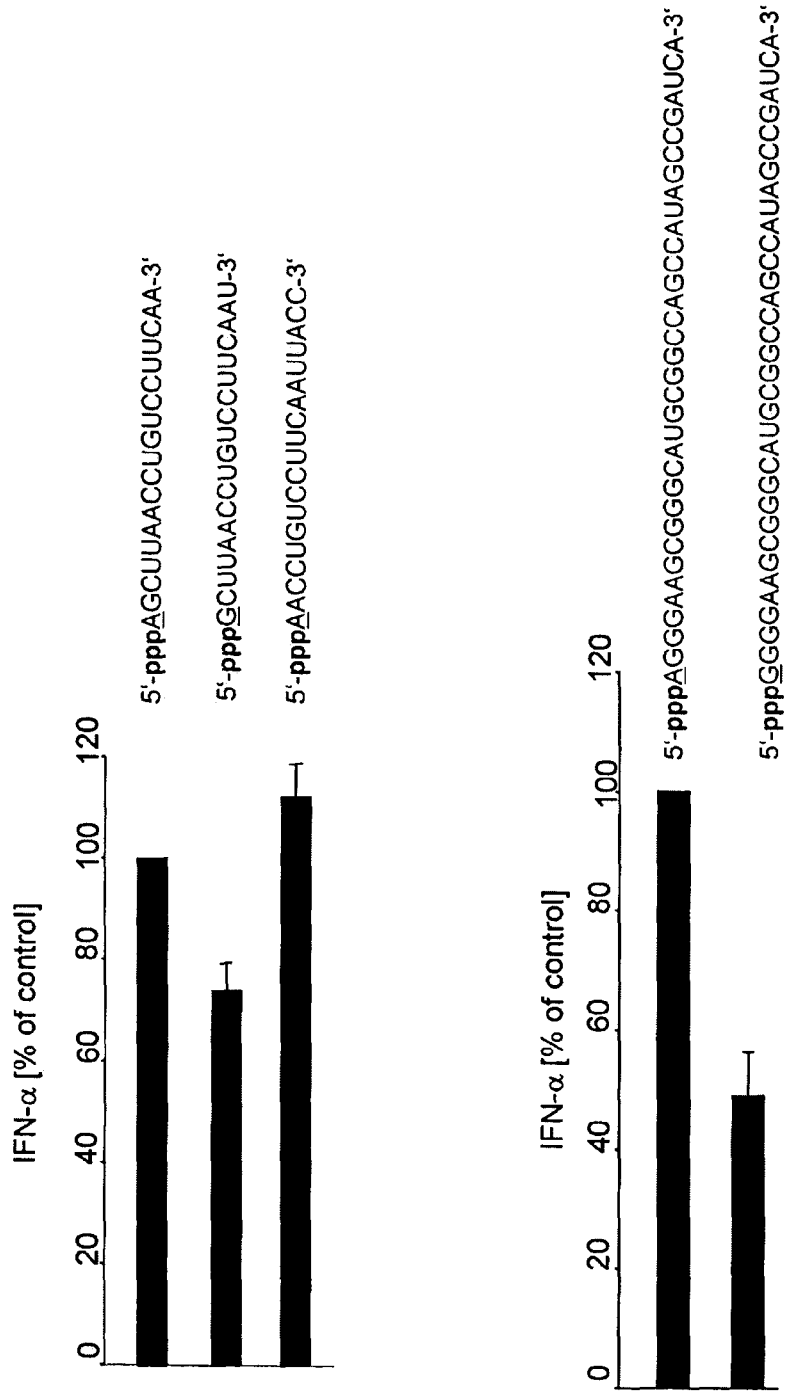

FIG. 12: 5' adenosine-initiated triphosphate transcripts are superior to 5' guanosine initiated transcripts in terms of IFN-α induction Left panel: Purified monocytes were transfected with either RNA9.2-0A, RNA9.2s-1G or RNA9.2s-5A (all 200 ng) and IFN-α production was analyzed 24 hours after stimulation. Data from two independent donors were summarized and are depicted as mean values±SEM.

Sequences shown are:

```
                                    (SEQ ID NO: 359)
    5'-pppAGCUUAACCUGUCCUUCAA-3';

(SEQ ID NO: 360)
    5'-pppGCUUAACCUGUCCUUCAAU-3';
    and (SEQ ID NO: 361)
    5'-pppAACCUGUCCUUCAAUUACC-3'.
```

Right panel: RNA transcripts derived from either the Aφ6.5-35 n or the Gφ6.5-35 n template were transfected into purified monocytes and IFN-α induction was assessed 24 hours after transfection. Data from three independent donors were summarized and are depicted as mean values±SEM.

Sequences shown are:

```
                                          (SEQ ID NO: 362)
5'-pppAGGGAAGCGGGCAUGCGGCCAGCCAUAGCCGAUCA-3'
and (SEQ ID NO: 363)
5'-pppGGGGAAGCGGGCAUGCGGCCAGCCAUAGCCGAUCA-3'.
```

Figure 13:
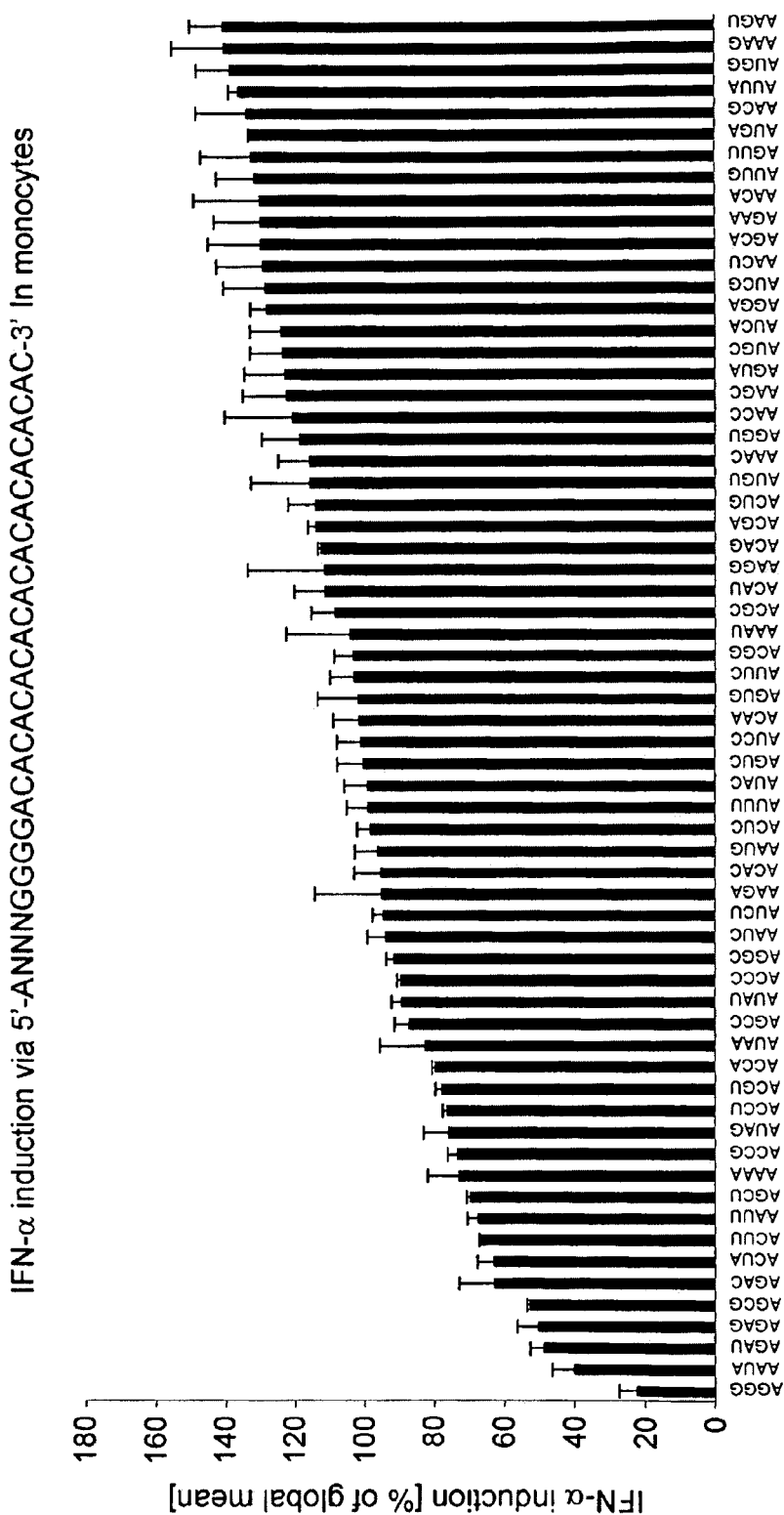

FIG. 13: 5' sequence of adenosine-initiated 5'-triphosphate RNA oligonucleotides dictates IFN-α inducing activity.

Adenosine-initiated triphosphate RNA oligonucleotides with all possible base permutations (A, C, G and U) of the 2nd, 3rd and 4th position of the sequence (5'→3') were generated via in vitro transcription (see Table 2). Subsequently monocytes from three independent donors were isolated and transfected with the respective RNA oligonucleotides. 36 hours after transfection, supernatants were analyzed for IFN-α production. The obtained IFN-α induction levels of all oligonucleotides were normalized to the mean induction level of all oligonucleotides (=100%). The obtained normalized induction levels of all three donors were summarized as mean values±SEM.

Sequences shown are:

```
                                          (SEQ ID NO: 332)
5'-ANNNGGGGAC ACACACACAC ACACACACAC-3';

AAGU;                                     (SEQ ID NO: 205)

AAAG;                                     (SEQ ID NO: 206)

AUGG;                                     (SEQ ID NO: 207)

AUUA;                                     (SEQ ID NO: 208)

AACG;                                     (SEQ ID NO: 209)

AUGA;                                     (SEQ ID NO: 210)

AGUU;                                     (SEQ ID NO: 211)

AUUG;                                     (SEQ ID NO: 212)

AACA;                                     (SEQ ID NO: 213)

AGAA;                                     (SEQ ID NO: 214)

AGCA;                                     (SEQ ID NO: 215)

AACU;                                     (SEQ ID NO: 216)

AUCG;                                     (SEQ ID NO: 217)

AGGA;                                     (SEQ ID NO: 218)

AUCA;                                     (SEQ ID NO: 219)

AUGC;                                     (SEQ ID NO: 220)

AGUA;                                     (SEQ ID NO: 221)

AAGC;                                     (SEQ ID NO: 222)

AACC;                                     (SEQ ID NO: 223)

AGGU;                                     (SEQ ID NO: 224)

AAAC;                                     (SEQ ID NO: 225)

AUGU;                                     (SEQ ID NO: 226)

ACUG;                                     (SEQ ID NO: 227)

ACGA;                                     (SEQ ID NO: 228)

ACAG;                                     (SEQ ID NO: 229)

AAGG;                                     (SEQ ID NO: 230)

ACAU;                                     (SEQ ID NO: 231)

ACGC;                                     (SEQ ID NO: 232)

AAAU;                                     (SEQ ID NO: 233)

ACGG;                                     (SEQ ID NO: 234)

AUUC;                                     (SEQ ID NO: 235)

AGUG;                                     (SEQ ID NO: 236)

ACAA;                                     (SEQ ID NO: 237)

AUCC;                                     (SEQ ID NO: 238)
and

AGUC.                                     (SEQ ID NO: 239)
```

Figure 14:
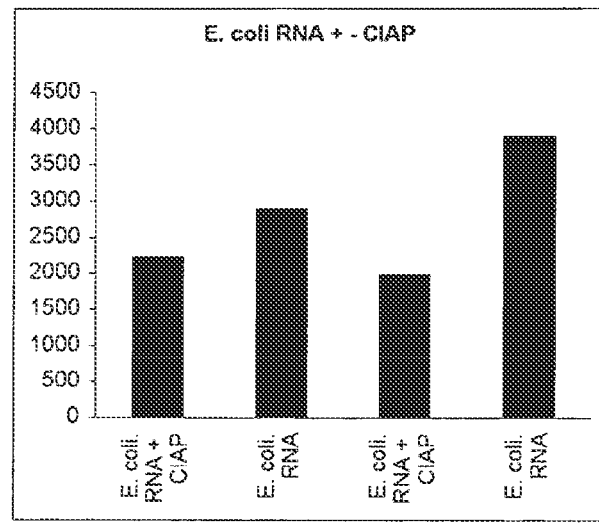
Figure 14:
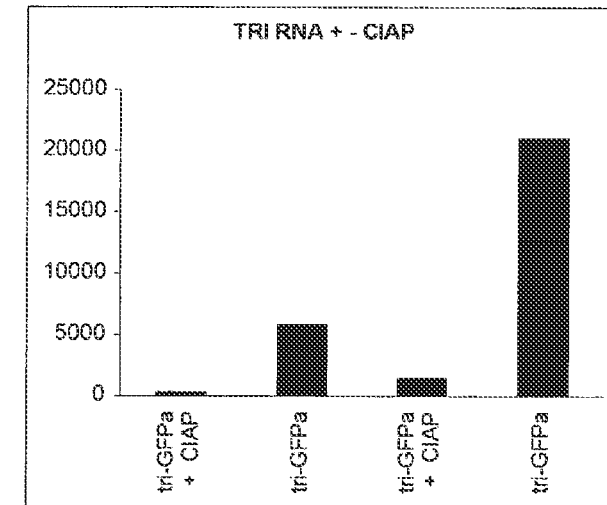

FIG. 14: Prokaryotic RNA, but not in vitro transcribed RNA induces IFN-□ in human monocytes after 5' dephosphorylation.

Tri-GFPa was prepared via in vitro transcription (A), and in addition total RNA was isolated from *E. coli* bacteria strain DH10B (B). Subsequently the respective RNA preparations were treated with CIAP to dephosphorylate the 5' end and transfected into purified monocytes (200 ng of RNA). IFN-α production was analyzed 24 hours after stimulation. Data from two independent donors are depicted.

Figure 15:
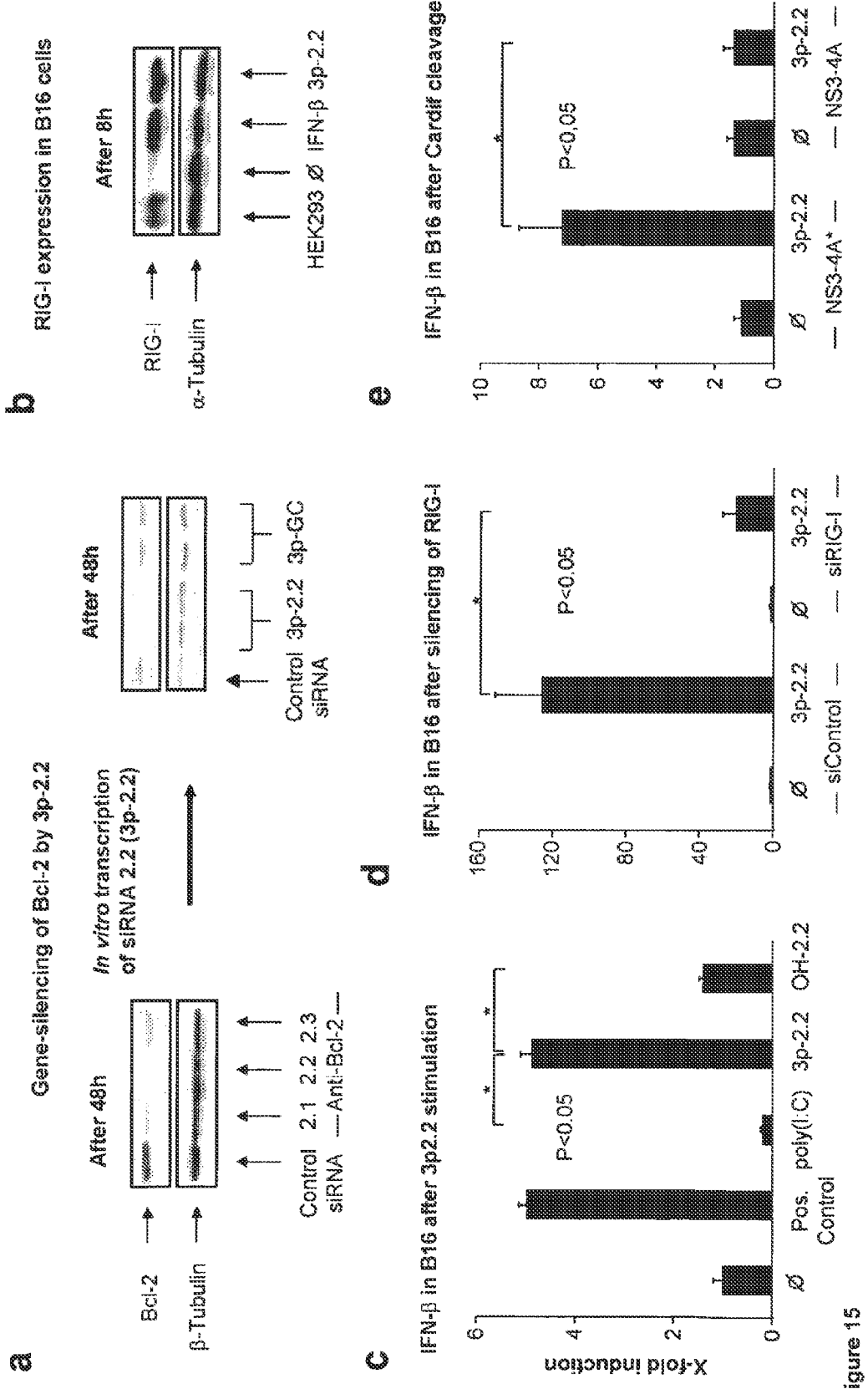

FIG. 15: Combining potent immunostimulatory functions with efficient gene-silencing activity in one RNA-molecule (a) B16 cells were seeded in 24-well plates. At a confluency of 50%, B16 cells were transfected with the selected chemically synthesized siRNAs (anti-Bcl-2 2.1, anti-Bcl-2 2.2 and anti-Bcl-2 2.3) at 1.2 µg/well (100 pmol) using Lipofectamine 2000 (2.0 µl). 48 hours after transfection protein expression of murine Bcl-2 was analyzed by Western-Blot.

Subsequently, the siRNA anti-Bcl-2 2.2 (OH-2.2) was in vitro transcribed (termed 3p-2.2) and tested for its ability to induce gene-silencing. Control siRNA and 3p-GC, a non-specific double-stranded 3p-RNA, served as negative control. One representative experiment of four is shown.

(b) To determine the endogenous expression of RIG-I, B16 cells were stimulated with 3p-2.2 (1.2 μg/well) and murine IFN-β (1000 U/ml). After 6 hours cells were lysed and analyzed for endogenous expression of RIG-I by Western Blot. HEK293 cells overexpressing full-length RIG-I served as positive control. One representative experiment of two is shown.

(c) For monitoring transient IFN-β activation in tumor cells, B16 cells were seeded in 24-well plates and transfected with the indicated expression plasmids using high molecular weight PEI or Lipofectamine 2000. 24 cells were stimulated with poly(I:C) (200 ng/well), 3p-2.2 (200 ng/well) and OH-2.2 (200 ng/well). IRF3-5D served as positive control. 16 h after transfection cells were analyzed for luciferase activity with a microplate luminometer (LUMIstar, BMGLabtechnologies). Data are shown as means±SEM of three independent experiments (*P<0.05 between 3p-2.2, OH-2.2 and poly (I:C); t-test).

(d) B16 cells were seeded in 24-well plates and co-transfected with synthetic siRNAs (10 pmol) and the indicated expression plasmids (200 ng) as described. 24 hours after transfection the cells were stimulated with 3p-2.2 for 16 hours. Data are shown as means±SEM of three independent experiments (*P<0.05 between control siRNA (siCO)+3p-2.2 versus RIG-I siRNA (siRIG-I)+3p-2.2; t-test).

(e) B16 cells were transfected with the indicated expression plasmids for 24 hours and stimulated with 3p-2.2 for 16 hours. Data are shown as means±SEM of two independent experiments (*P<0.05, NS3-4A*+3p-2.2 versus NS3-4A+3p-2.2; t-test).

Figure 16:
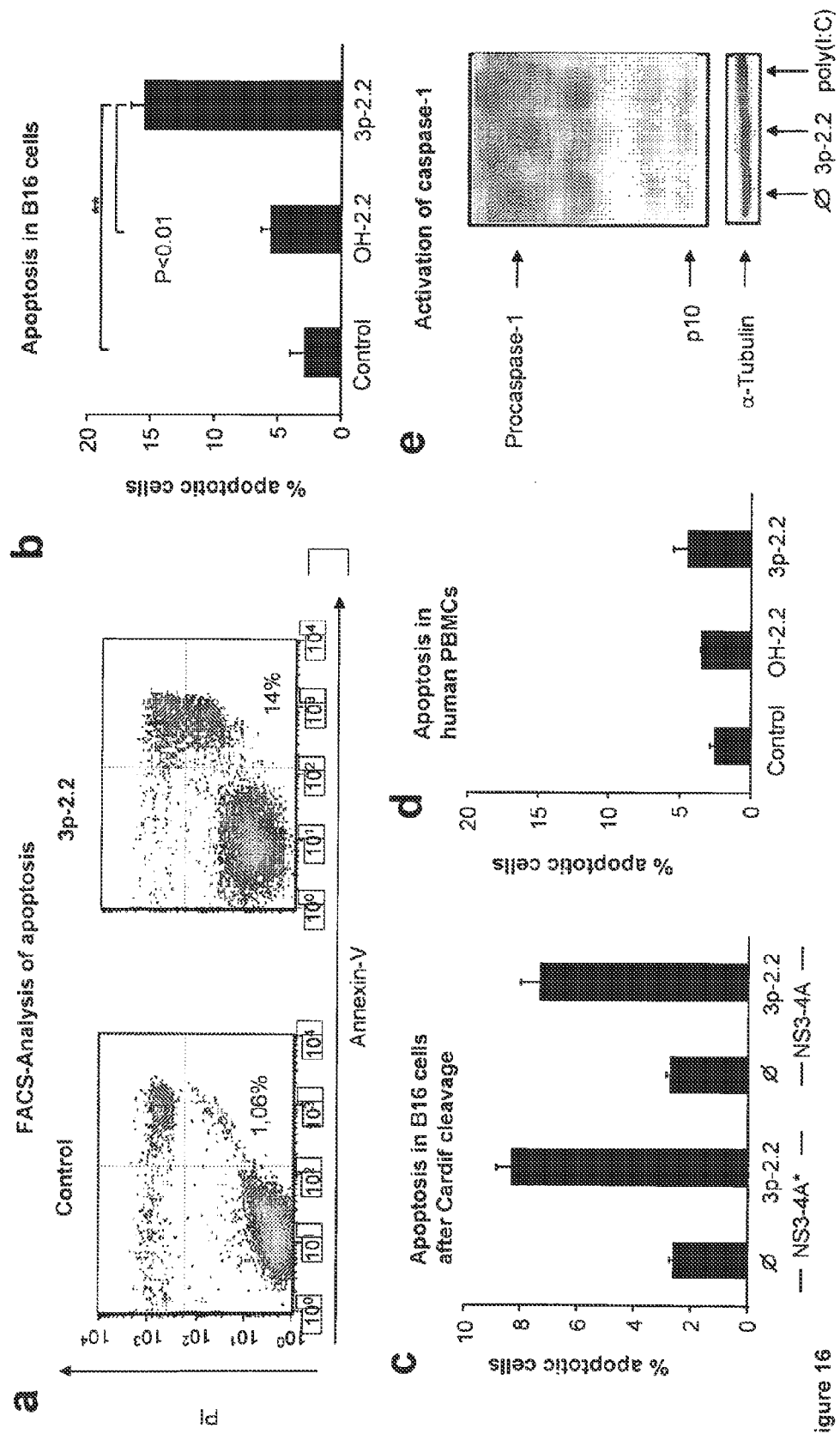

FIG. 16: Transfection of 3p-2.2 directly triggers Cardif-independent apoptosis in tumor cells, but not in primary cells Murine B16 cells were seeded in 24-well plates and transfected with 3p-2.2 (1.2 μg/well), OH-2.2 (1.2 μg/well) and Control-siRNA (1.2 μg/well) using Lipofectamine (2.0 μl). 24 hours after transfection cells were analyzed by flow cytometry for apoptosis by gating on Annexin-V positive cells. Annexin-V positive and PI-positive cells (late apoptotic or dead cells) were excluded.

(a) One representative FACS-Analysis of four independent experiments is shown.

(b) Results of apoptosis of B16 cells are shown as means±SEM of four independent experiments (P**<0.01 3p-2.2 versus OH-2.2 and control siRNA; t-test).

(c) Murine B16 cells were seeded in 24-well plates and transfected with pNS3-4A and pNS3-4A* for 24 h. Then cells were washed and stimulated for 24 hours with 3p-2.2 and the number of apoptotic cells was determined by FACS-analysis. Data are shown as means±SEM of two independent experiments.

(d) Results of apoptosis in human PBMCs are shown as means±SEM of two independent experiments.

(e) B16 cells were incubated with control siRNA, 3p-2.2 and poly(I:C) for 24 hours and assessed for caspase-1 activity via immunoblotting. α-Tublin served as loading control. One representative experiment of three is shown.

Figure 17:
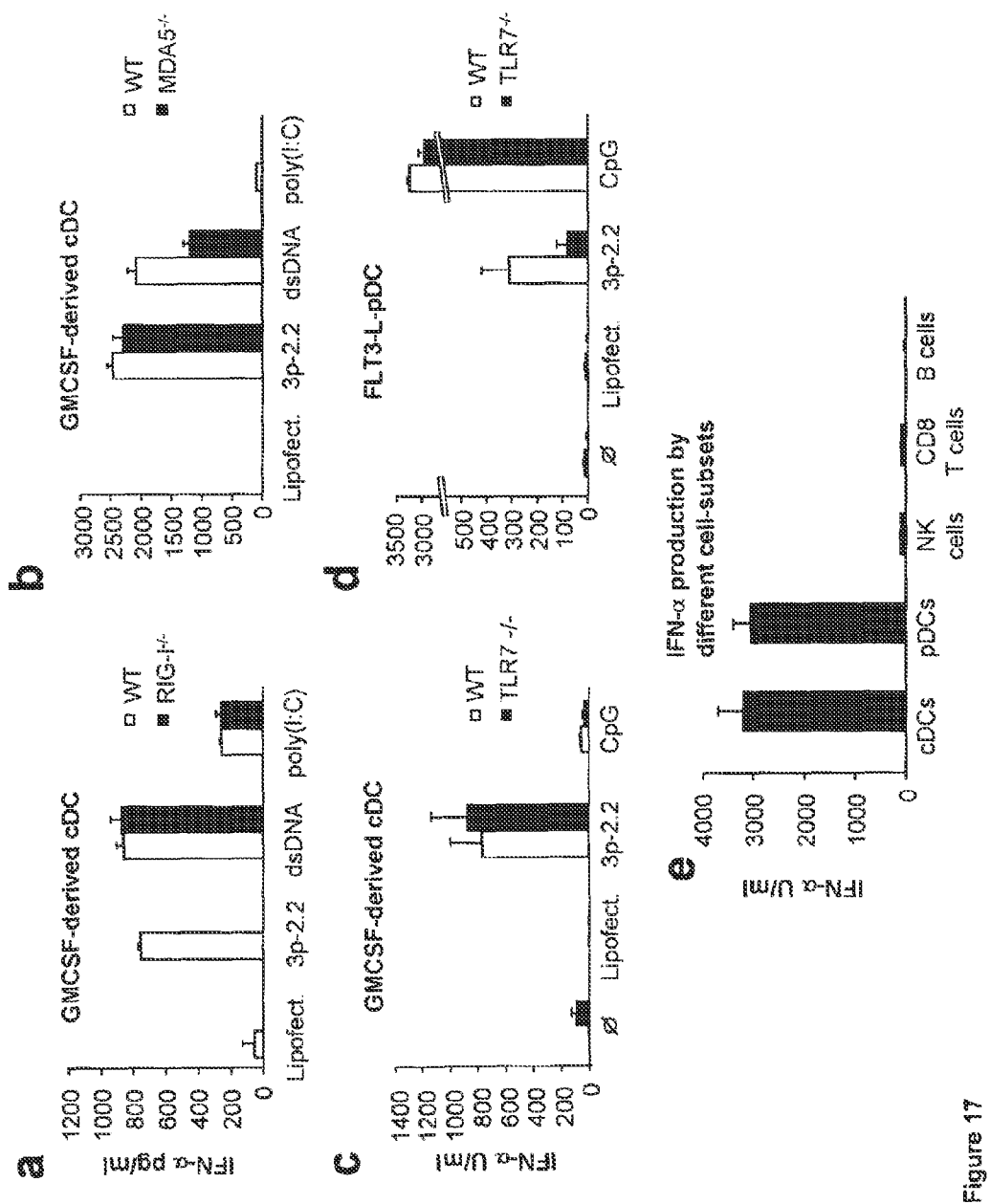

FIG. 17: IFN-α Production by 3p-2.2 requires TLR7 in pDCs and RIG-I in cDCs and is limited to certain immune cell subsets GMCSF-derived cDCs of Wild-type, RIG-I-deficient (a), MDA5-deficient (b) and TLR7-deficient (c) mice and Flt3-L-derived pDCs of TLR7-deficient mice (d) were transfected with 200 ng of 3p-2.2, dsDNA (Sigma; dAdT), poly(I:C) (Sigma) complexed to Lipofectamine 2000 and CpG-A 2216 (3 μg/ml) in 96 well plates. After 24 h, IFN-α was measured in the supernatants by ELISA. Data are expressed as the mean±SEM of two independent experiments.

(e) B cells, NK cells and CD 8 T cells were purified from spleens of wild-type mice using magnetic cell sorting and stimulated with 200 ng of 3p-2.2. Sorted pDCs from Flt3-L induced bone marrow cultures and GMCSF-derived cDCs stimulated with 3p-2.2 served as positive control. Data are expressed as the mean±SEM of two independent experiments.

Figure 18:
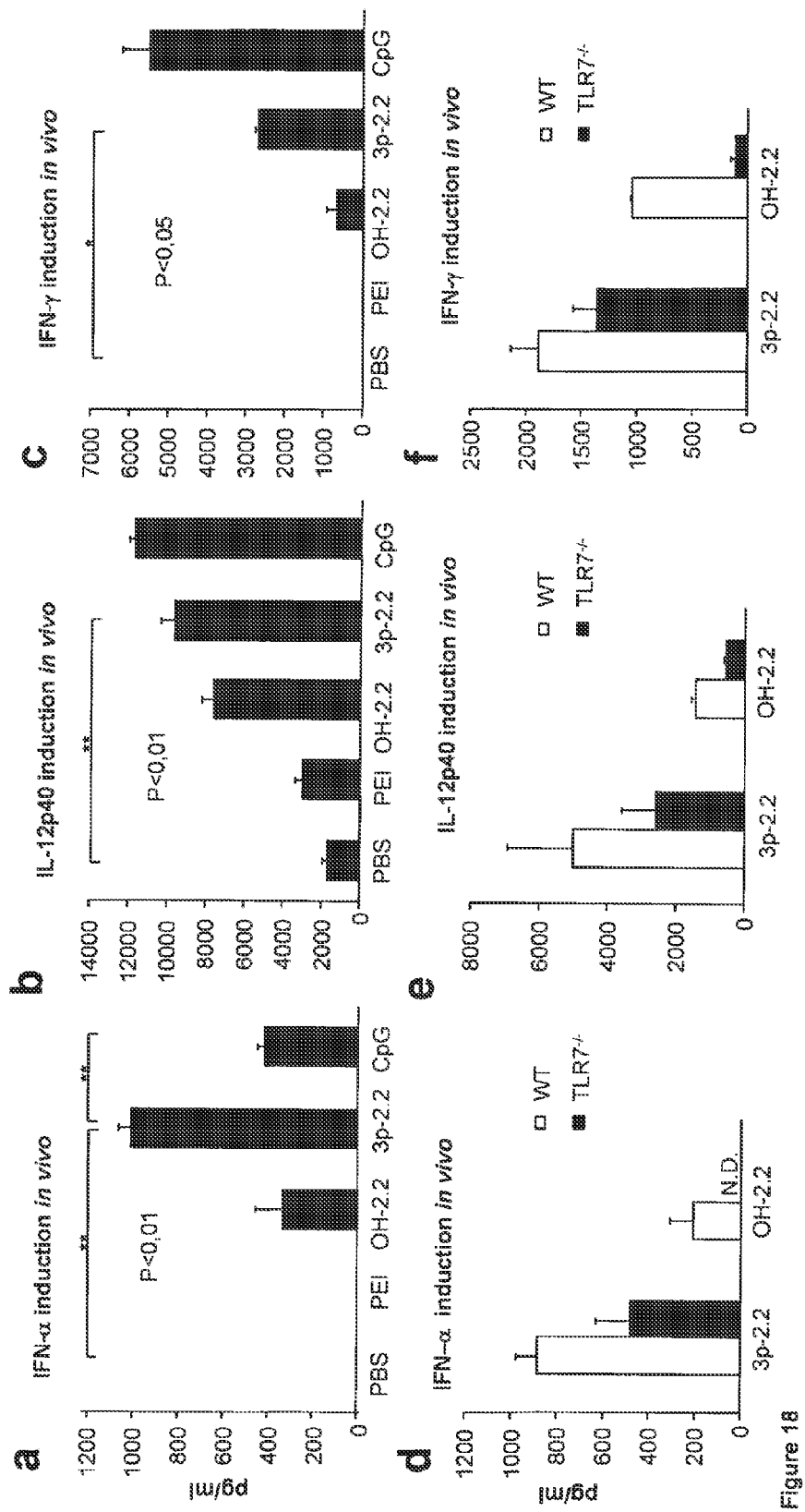

FIG. 18: Encapsulated 3p-2.2 leads to systemic immune activation in vivo

C57BL/6 mice were injected with 200 μl containing 3p-2.2 or OH-2.2 (50 μg/Mouse) complexed with jetPEI™. Subsequently, the complexes were injected in the retro-orbital vein. Serum was collected after 6 hours unless indicated otherwise. Whole blood was obtained by tail clipping at the indicated time points. Cytokine levels of IFN-α (a), IL-12p40 (b) and IFN-γ

(c) were determined by ELISA. CpG1826 served as a positive control. Data are shown as means±SEM of 6 independent experiments; P**<0.01 or P*<0.05.

(d-e) C57BL/6 and TLR7-/- mice were injected intravenously with 3p-2.2 and OH-2.2 (50 μg) complexed to jetPEI™ (Biomol). After 6 hours, mice were sacrificed and serum was analyzed for IFN-α (d), IL-12p40 (e) and IFN-γ (f) production by ELISA. Data are shown as means±SEM of 2 independent experiments.

Figure 19:
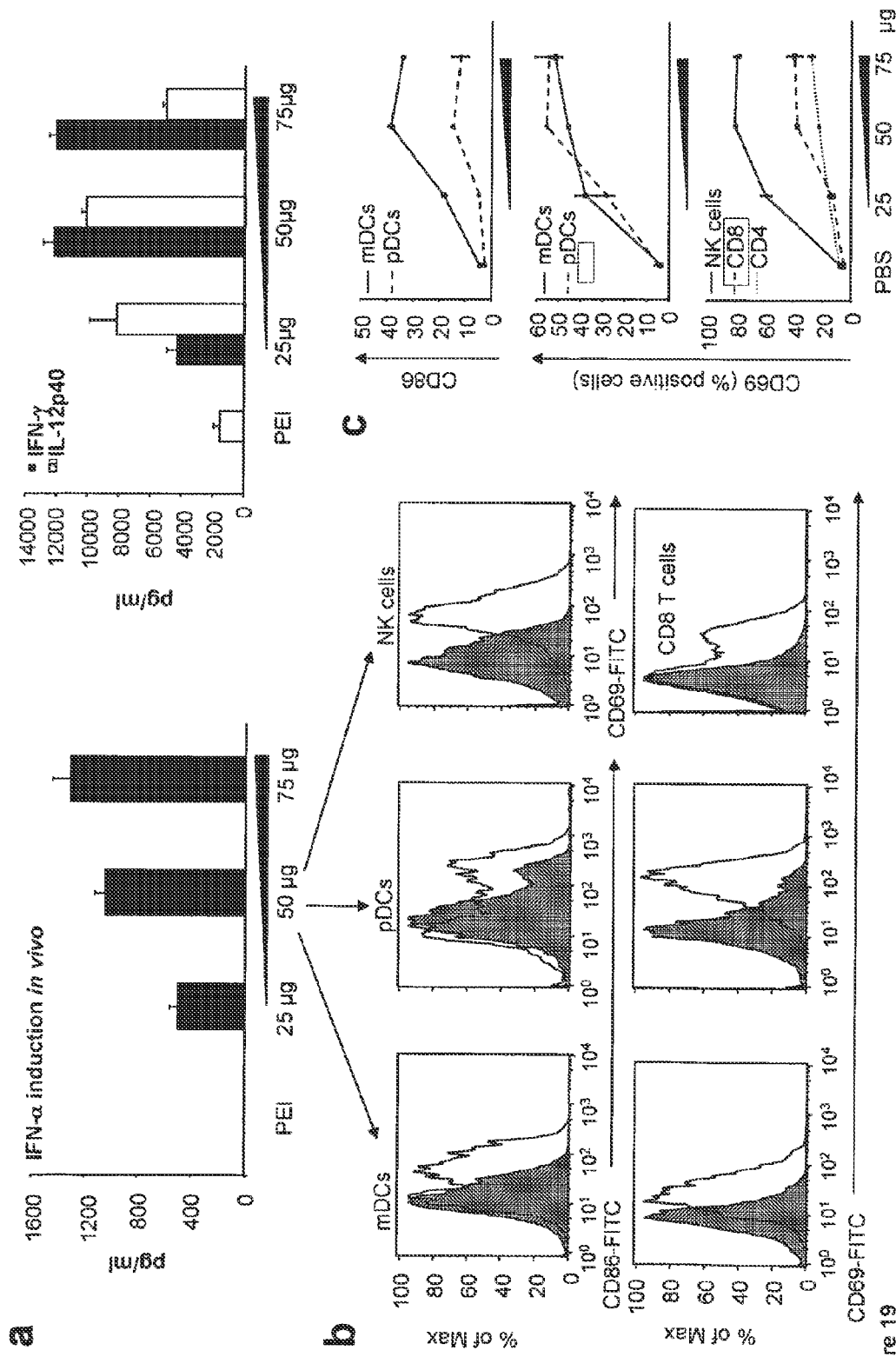

FIG. 19: Dose-dependent activation of immune cell subsets by 3p-2.2 in vivo

C57BL/6 mice were injected with 200 μl of 3p-2.2 (25-, 50- or 75 μg/mouse) complexed with jetPEI™ into the retro-orbital vein. Serum was collected after 6 h unless indicated otherwise.

(a) Serum cytokine levels of IFN-α, IL-12p40 and IFN-γ were determined by ELISA. Data are shown as means±SEM of 5 independent experiments.

(b-c) C57BL/6 mice were injected with 200 μl of nucleic acid (25-, 50- or 75 μg/mouse) complexed with jetPEI™. Spleen cells were isolated 48 hours after injection and CD86 or CD69 expression was analyzed on pDCs, mDCs, NK cells, CD4 T cells and CD8 T cells by flow cytometry. Surface antigen staining was performed as described previously. (b) Histograms of one representative experiment after stimulation with 50 μg 3p-2.2 (grey bar, unstimulated control mice). (c) The dose-dependent activation by 3p-2.2 of different immune cell subsets. Data are shown as means±SEM of 2 independent experiments.

Figure 20:
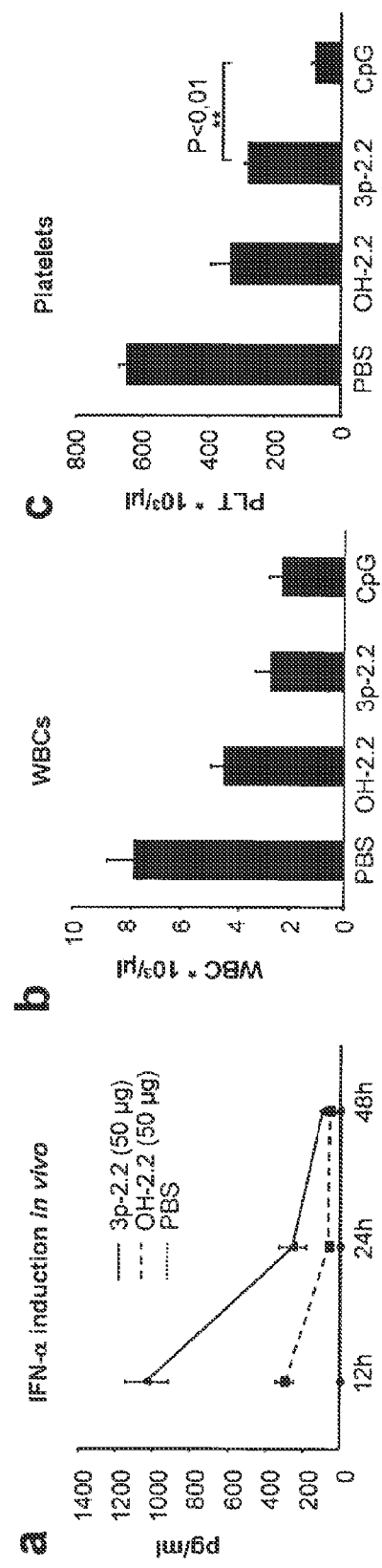

FIG. 20: 3p-2.2 stimulation leads to increased IFN-α serum-levels for less than two days and induces moderate thrombocytopenia and leukopenia in vivo.

(a) C57BL/6 mice were injected with 50 μg 3p-2.2 or OH-2.2 complexed with jetPEI™. Serum was collected 12 h, 24 h, and 48 h after injection unless indicated otherwise. Serum levels of IFN-α were determined by ELISA. Data are shown as means±SEM of 2 independent experiments.

(b & c) C57BL/6 mice were injected with 50 μg 3p-2.2 complexed with jetPEI™. Blood was collected after 48 h and processed as EDTA plasma for measurement of leucocytes (WBC) and platelets. Blood cell counts were performed at the Central Laboratory of the Department of Internal Medicine, University of Munich at the indicated time point (P**<0.01 between the platelet count of 3p-2.2 and CpG). Data are shown as means±SEM of 2 independent experiments.

Figure 21:
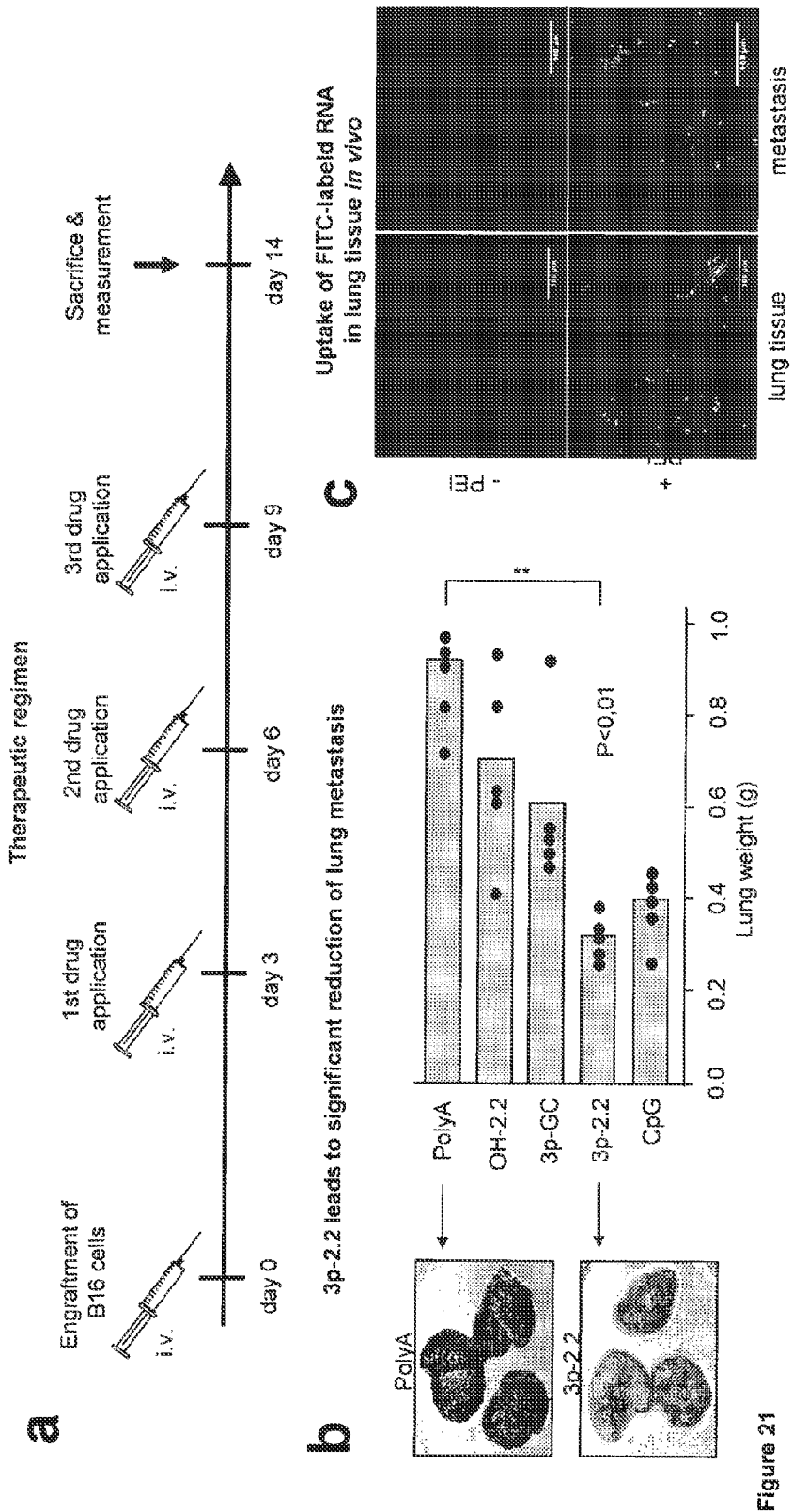

FIG. 21: Delivery of encapsulated 3p-2.2 results in reduction of experimentally induced B16 melanoma lung metastases (a) Therapeutic regimen: Mice were challenged with $4\times10^5$ B16 melanoma cells intravenously to experimentally induce lung metastases on day 0. Mice were treated intravenously with the indicated nucleic acid complexed to jetPEI™ on day 3, 6 and 9 as indicated. 14 days after challenge, the number of macroscopically visible melanoma metastases on the surface of the lungs was counted with the help of a dissecting microscope or the lung weight was calculated.

(b) Groups of five C57BL/6 mice were challenged with $4\times10^5$ B16 and treated as described. Mice were treated intravenously on day 3, 6 and 9 with 50 μg of OH-2.2, 50 μg 3p-2.2, 50 μg 3p-GC (a nonspecific double-stranded 3p-RNA) or 50 μg CpG oligonucleotide ligand, each complexed with jetPEI™. Control groups received 100 μl of Glucose 5% or 50 μg of PolyA complexed with jetPEI™. Tumor growth was assessed after 14 days by measuring the weight of the lungs. Shown are lung weights of five individual mice. The mean lung weight is indicated by a column. The lung weight of healthy mice ranges between 0.2 and 0.24 g ($P** < 0.01$ between 3p-2.2 and PolyA, OH-2.2 and 3p-GC; n=5; generalized Mann-Whitney test).

(c) A single dose of complexed or non-complexed FITC-labeled siRNA (100 μg) was injected intravenously in healthy mice or in tumor-bearing mice. After 6 h, the mice were sacrificed and various tissues including lungs were excised and analyzed for uptake of the RNA complexes. Tissues were then analyzed using a Zeiss LSM510 confocal microscope (Carl Zeiss, Germany) equipped with 488 nm-Argon and 633 nm-Helium-Neon lasers. One representative experiment after injection with 100 μg FITC-labeled siRNA is shown.

Figure 22:
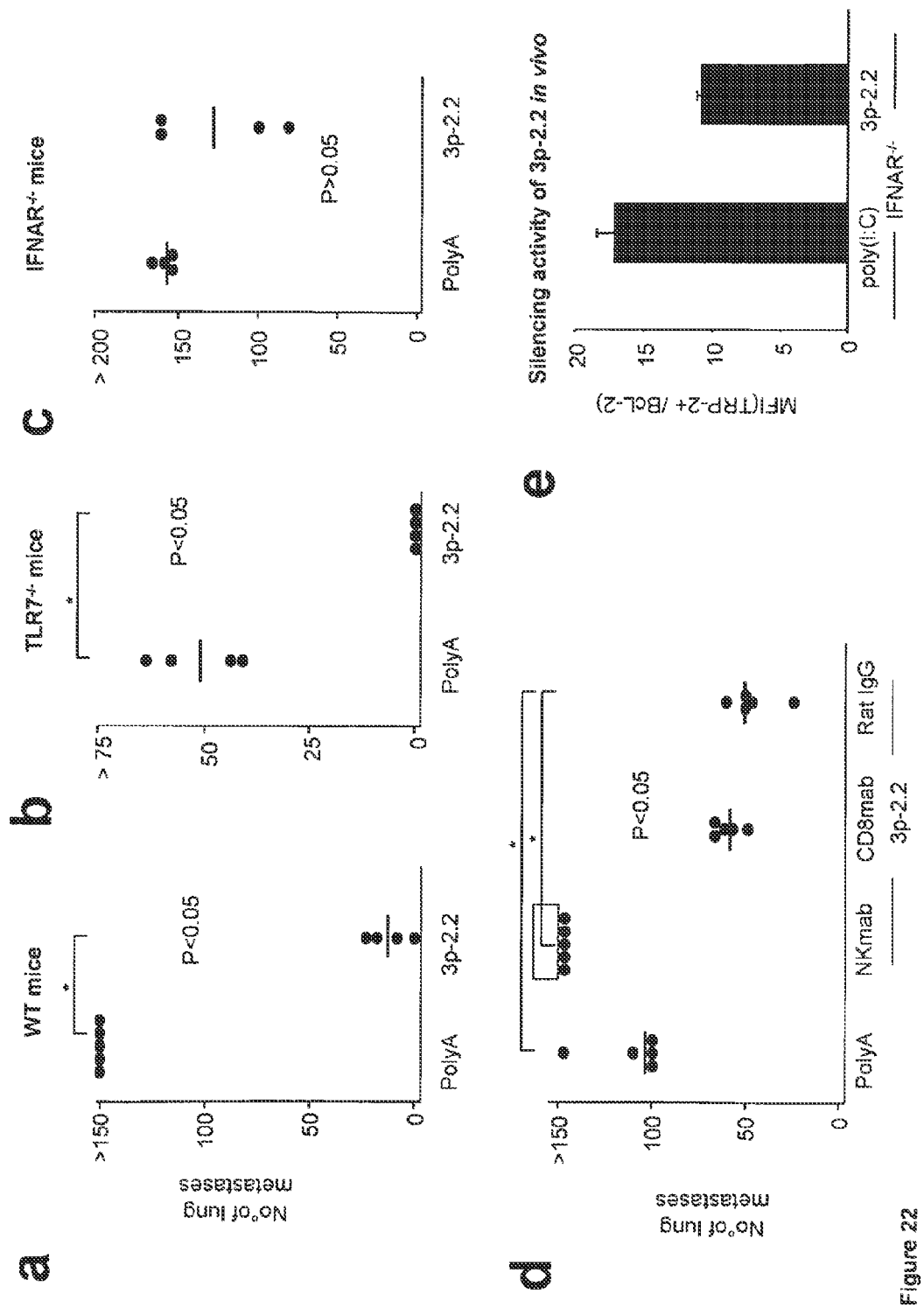

FIG. 22: Mechanisms of tumor reduction by 3p-2.2

(a) Groups of 4 C57BL/6 mice were injected intravenously with $4\times10^5$ B16 melanoma cells to experimentally induce lung metastases. Mice were treated intravenously on day 3, 6 and 9 with 50 μg of 3p-2.2 and 50 μg of poly(I:C), respectively. PolyA-treated animals served as the control group. Tumor growth was assessed on day 14 by counting the number of macroscopically visible melanoma metastases on the lung surfaces. Shown are the number of metastases in individual C57BL/6 mice. The mean number of metastases is indicated by the horizontal line ($P*<0.05$ between 3p-2.2 and PolyA treated mice; n=4; generalized Mann-Whitney test).

(b) Effect of 3p-2.2 complexed with jetPEI™ on tumor growth in TLR7−/− mice ($P*<0.05$ between 3p-2.2 and PolyA treated mice; n=4; generalized Mann-Whitney test).

(c) Effect of 3p-2.2 complexed with jetPEI™ on tumor growth in IFNAR$^{-/-}$ mice ($P*>0.05$ between 3p-2.2 and PolyA treated mice; n=4; generalized Mann-Whitney test).

(d) Effect of antibody-mediated depletion of CD8+ T cells and NK cells on the therapeutic anti-tumor efficacy of 3p-2.2 complexed with jetPEI™ in C57BL/6 wild-type mice.

(e) Bcl-2 expression in metastatic lungs of IFNAR$^{-/-}$ mice treated with 3p-2.2 and poly(I:C) were analyzed by flow cytometry. Results are presented as means±SEM from two individual experiments.

Figure 23:
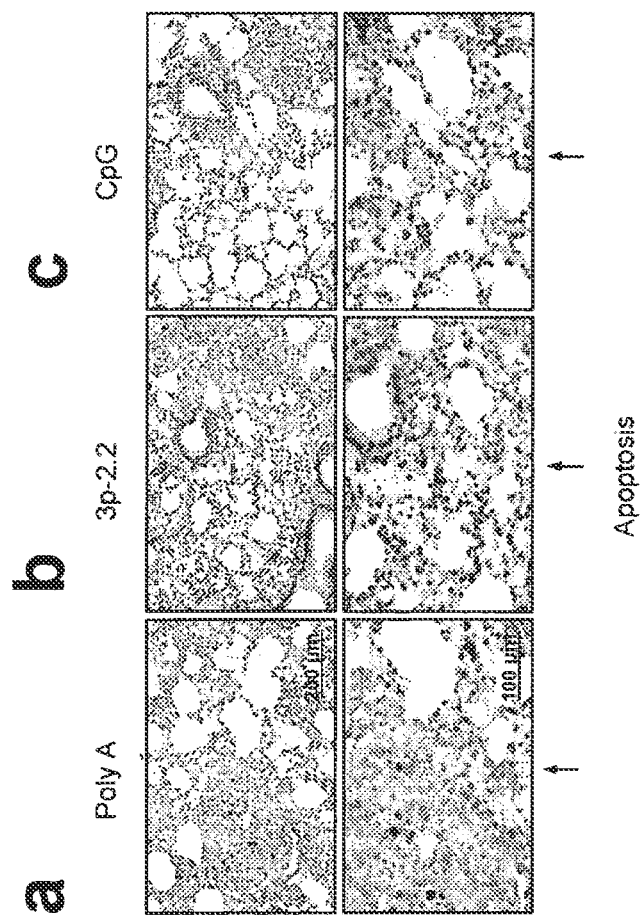

FIG. 23: Induction of apoptosis in lung metastases by 3p-2.2 in vivo

Groups of 5 C57BL/6 mice were injected intravenously with $4\times10^5$ B16 melanoma cells to experimentally induce lung metastases. Mice were treated intravenously on day 3, 6 and 9 with 50 μg of PolyA (a), 50 μg of 3p-2.2 (b) or 50 μg of CpG1826 (c). PolyA-treated animals served as the control group. On day 14, samples of lungs were obtained when mice were sacrificed. Tissue specimens were fixed in absolute ethanol and embedded in paraffin. Apoptosis was detected by the transferase-mediated dUTP nick end-labeling (TUNEL) method according to the manufacturer's instructions. One representative experiment of 5 is shown.

Figure 24:
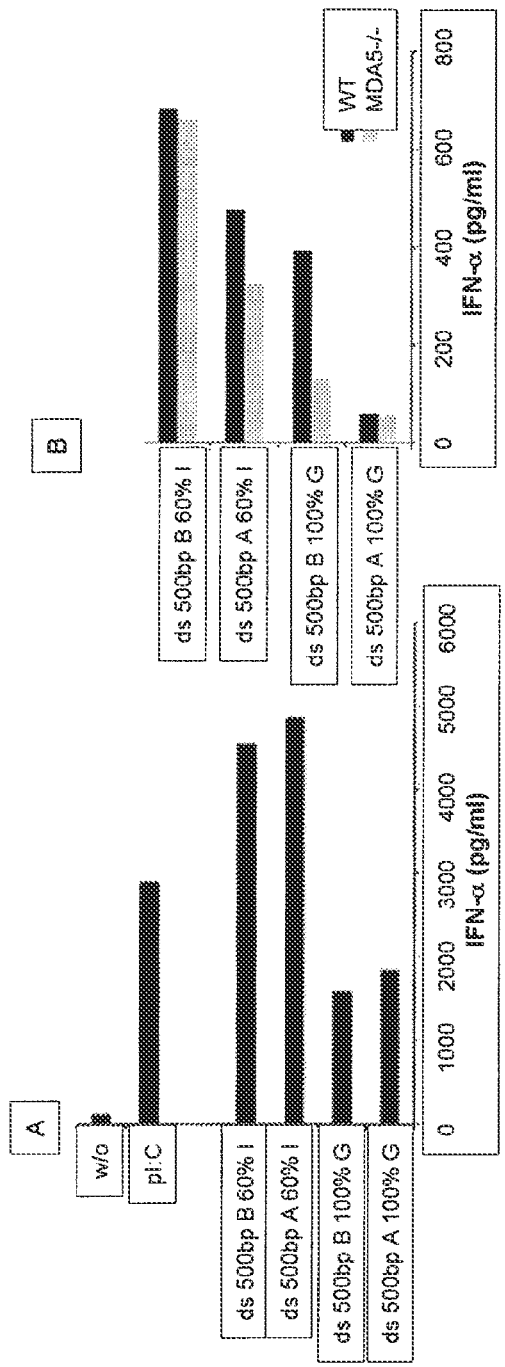

FIG. 24: Inosine content increases the IFN-α inducing activity of 3pRNA.

(A) Monocytes were prepared from human PBMC and transfected with RNA. $4\times10^5$ cells were cultured for 18 hours, and IFN-α was measured by ELISA.

(B) Mouse dendritic cells were prepared by incubating murine bone marrow from wild type and MDA-5−/− mice with GMCSF. Murine dendritic cells ($2\times10^5$ cells per well) were transfected with 400 ng RNA. After 18 h, IFN-α was measured in the supernatants by ELISA.

FIG. 25: IFN-α-inducing activity of synthetic single-stranded 5' triphosphate RNA.

PBMC were transfected with chemically synthesized single-strand oligonucleotides alone or together with their complementary antisense strand (AS) by using Lipofectamine and incubated in the presence or absence of chloroquine (Chl). CpG2331 was used as a positive and chloroquine-sensitive control for IFN-α induction in PBMC.

DETAILED DESCRIPTION OF THE INVENTION

Detection of viral infection is vital for higher organisms to safeguard the integrity of their genome. TLRs contribute to recognition of viral nucleic acids, but their proper function seems largely dispensable for effective antiviral defense (A. Krug et al., *Immunity* 21, 107 (July 2004); K. Tabeta et al., *Proc Natl Acad Sci USA* 101, 3516 (Mar. 9, 2004); T. Delale et al., *J Immunol* 175, 6723 (Nov. 15, 2005); K. Yang et al., *Immunity* 23, 465 (November, 2005)). It was not until recently that it became clear that the two cytoplasmic helicases, MDA-5 and RIG-I (M. Yoneyama et al., *Nat Immunol* 5, 730 (July 2004)), are essential for controlling viral infection.

The present inventors identified RNA with a triphosphate group at the 5' end and an optimal minimal length of 19 nucleotides as a specific ligand for RIG-I. Both exogenous 5' triphosphate RNA transfected into a cell and endogenously formed 5' triphosphate RNA activated RIG-I. Genomic RNA prepared from a negative strand RNA virus and RNA prepared from virus-infected cells, but not RNA from non-infected cells, triggered a potent IFN-α response in a 5' triphosphate-dependent manner. Binding studies of RIG-I and 5' triphosphate RNA revealed a direct molecular interaction.

Uncapped, unmodified 5' triphosphate RNA is the first well-defined molecular structure of viral nucleic acids that is detected by eukaryotic cells. Since viruses due to their life-cycle are composed of the same molecular constituents as their host cells, namely protein and nucleic acid, such defined molecular structures that allow discrimination of viral and self RNA are expected to be rare and the presence of such has been questioned. In this regard, viruses are different from bacteria that contain a variety of molecules such as endotoxin which are absent in eukaryotes and which are easily recognized with high confidence by TLRs such as TLR4 located in the cytoplasmic membrane.

Until now, localization of viral nucleic acids in the endosome rather than a specific molecular feature of viral nucleic acids was thought to be the major factor allowing the detection of viruses. Although TLR-mediated recognition of single-stranded RNA (by TLR7 and TLR8) and of short double-stranded RNA (by TLR7) in the endosome was found to be sequence dependent, the frequency of such sequence motifs in viruses and vertebrates is similar (unpublished observation by the present inventors). This applies even to CpG motifs, which are suppressed in both vertebrate and viral but not bacterial DNA (A. M. Krieg, *Annu Rev Immunol* 20, 709 (2002)). This view is supported by a recent study demonstrating that endosomal localization of TLR9 prevents recognition of self DNA and facilitates detection of viral DNA (G. M. Barton, J. C. Kagan, R. Medzhitov, *Nat Immunol* 7, 49 (January, 2006)). CpG motif independent recognition of DNA by TLR9 has been described by others (J. Vollmer et al., *Antisense Nucleic Acid Drug Dev* 12, 165 (June 2002)).

Given the fact that all primer-independent RNA transcripts are initially generated as 5' triphosphate RNAs, the question arises how eukaryotic RNA evades the recognition of RIG-I. In the cytosol of eukaryotic cells, most if not all self RNA species do not carry a free 5' triphosphate end. Before self RNA leaves the nucleus and reaches the cytosol, RNA is further processed. This holds true for RNA transcripts of all three RNA polymerases in eukaryotes.

Polymerase I transcribes a large polycistronic precursor ribosomal RNA (rRNA) which contains the sequences for the mature rRNAs (18, 5.8S, 25-28S rRNA), two external transcribed spacers and two internal transcribed spacers. This primary transcript is subjected to many endo- and exonucleolytic-processing steps to produce the mature rRNAs. The net result of this maturing process is a monophosphate group at the 5' end of all polymerase I transcribed rRNAs (M. Fromont-Racine et al., *Gene* 313, 17 (Aug. 14, 2003)).

Messenger RNAs (mRNAs) and small nuclear RNAs (snRNAs), which are transcribed by polymerase II, receive a 7' methyl guanosine group that is attached to the 5' triphosphate of the nascent RNA by a process called capping (A. J. Shatkin, J. L. Manley, *Nat Struct Biol* 7, 838 (October 2000)). Thus, upon export into the cytoplasm, no free triphosphate groups are found in polymerase II transcripts.

Polymerase III synthesizes transfer RNAs (tRNAs) and rRNA 5S that are both exported in to the cytoplasm, and other small RNAs including U6 RNA. Prior to the export into the cytoplasm, tRNAs are further matured in the nucleus, including the removal of various nucleotides from the 5' end by ribonuclease P. Therefore all mature tRNAs that can be found in the cytoplasm have been processed at the 5' end resulting in a 5' monophosphate (S. Xiao et al. *Annual review of biochemistry* 71, 165 (2002)). The phosphorylation status of the 5' end of the ribosomal RNA 5S has not been studied and at present is unknown. U6 RNA receives a γ-monomethylphosphate (mpppG) cap structure following transcription (R. Singh, R. Reddy, *PNAS* 86, 8280 (November 1989)).

In addition to the lack of free 5' triphosphate residues, eukaryotic RNA posttranscriptionally undergoes significant modification of its nucleosides and its ribose backbone. Among all nucleoside modifications, pseudouridinylation is one of the most common posttranscriptional modifications of RNA that appears to be universal among rRNAs and small stable RNAs such as splicing small nuclear RNAs (snRNAs), tRNAs, and small nucleolar RNAs (snoRNAs). However, the frequency and location of pseudouridinilated nucleotides vary phylogenetically. Intriguingly, eukaryotes contain far more nucleoside modifications within their RNA species than prokaryotes. Human ribosomal RNA for example, the major constituent of cellular RNA, contains ten times more pseudouridine (ψ) and 25 times more 2'-O-methylated nucleosides than *E. coli* rRNA (J. Rozenski et al. *Nucleic acids research* 27, 196 (Jan. 1, 1999)). The same applies for eukaryotic tRNAs, the most heavily modified subgroup of RNA with up to 25% of modified nucleosides. The host machinery that carries out nucleoside modifications and 2'-O-methylation of the ribose backbone is located in the nucleolus and consists of RNA-protein complexes containing snoRNAs and several associated proteins (i.e., snoRNPs) (W. A. Decatur, M. J. Fournier, *J. Biol. Chem.* 278, 695 (Jan. 3, 2003)).

Information on nucleolus specific nucleoside modifications or ribose 2'-O-methylation of viral RNA genomes is limited. Since most RNA viruses do not replicate in the nucleus and modification is tightly confined to the sequence and structure of their target, extensive modification of viral RNA seems unlikely.

Altogether, post-transcriptional modifications of eukaryotic RNA such as 5' processing or capping as well as nucleoside modifications or ribose backbone methylation provide the molecular basis for the distinction of self RNA generated in the nucleus from viral RNA of cytoplasmic origin.

The mRNAs of viruses infecting eukaryotic cells also commonly contain 7-methyl guanosine cap-structures at their 5' ends and poly(A) tails at their 3' ends (Y. Furuichi, A. J. Shatkin, *Adv Virus Res* 55, 135 (2000)). Some viruses make use of the host transcription machinery to acquire caps and poly(A) tails. RNA viruses that do not rely on the host transcriptional machinery produce their own capping enzymes or utilize other mechanisms such as snatching the 5'-terminal regions of host mRNAs. Despite these adaptations of viruses to the host transcriptional system, viral RNA synthesis leads to transient cytoplasmic RNA intermediates with an uncapped 5'triphosphate end.

With notable exceptions such as the Picornavirus family (see below), viral RNA-dependent RNA polymerases (RdRp) initiate polymerase activity de novo without a specific primer (C. C. Kao, et al., *Virology* 287, 251 (Sep. 1, 2001)). As a consequence, these RdRp-dependent transcripts start with an uncapped 5' triphosphate. This has been studied in great detail for the replication of positive strand RNA viruses of the family of Flaviviridae (including Hepatitis C Virus, Yellow Fever Virus, Japanese Encephilitis Virus and Dengue Virus); all of these viruses were reported to be recognized via RIG-I (H. Kato et al., *Nature* 441, 101 (Apr. 9, 2006); R. Sumpter, Jr. et al., *J. Virol.* 79, 2689 (Mar. 1, 2005, 2005); T.-H. Chang et al., *Microbes and Infection* 8, 157 (2006)). Segmented negative strand RNA virus (NSV) rely on a cap-snatched primer for mRNA transcription, yet initiate genomic and the complementary antigenomic RNA replication by a primer independent de novo mechanism resulting in a 5' triphosphate initiated transcript (A. Honda, et al., *Virus Res* 55, 199 (June 1998); G. Neumann, et al., *Current topics in microbiology and immunology* 283, 121 (2004)). NSV with a nonsegmented genome (Order Mononegavirales), including the Paramyxoviruses and Rhabdoviruses, initiate both replication and transcription de novo leading to 5' triphosphate RNA in the cytosol. Both the full length replication products, vRNA and cRNA, and a short leader RNA which is abundantly synthesized during initiation of transcription, maintain their 5' triphosphate (R. J. Colonno, A. K. Banerjee, *Cell* 15, 93 (1978)), while the virus-encoded mRNA transcripts are further modified at their 5' ends by capping and cap methylation. Consequently, genomic RNA from NSVs per se is expected to trigger an IFN-response without the need for replication and presumed dsRNA formation. Consistent with this notion, not only live virus but also RNA purified from NSV virions, in this case, VSV, has been shown to trigger strong type I interferon responses depending on RIG-I (H. Kato et al., *Nature* 441, 101 (Apr. 9, 2006)).

The present inventors confirmed and extended these observations by demonstrating that dephosphorylation of the viral RNA isolates completely abolished the IFN response, thereby indicating that the 5' triphosphate moiety is required for recognition. In case of RV-infected cells, full length RNAs are permanently enclosed within nucleoprotein (N) to form a linear, helical nucleoprotein-RNA complex (RNP) in which the RNA is not accessible to even small cellular molecules such as RNases. Similarly, leader RNA has been reported to be encapsulated by N (Blumberg D M & Kolakofsky D, *J Virol.* 1981 November; 40(2):568-76; Blumberg B M et al. *Cell* 1981 March; 23(3):837-45). The effective recognition of live NSV by RIG-I may suggest that the terminal triphosphates of the linear N-RNA complex are not completely protected by N protein or that in the initial phase of viral transcription, the levels of newly synthesized N protein are insufficient for complete protection. In this respect, it is interesting to note that NSV stocks that contain defective interfering (DI) particle RNAs are potent inducers of IFN (Strahle L. et al. 2006, Virology 351(1):101-11). DIs only contain the terminal promoters for replication and provide plentiful 5' triphosphate ends under conditions of reduced expression of helper virus proteins.

On the other hand, all viruses in the Picornavirus-like supergroup (picorna-, poty-, como-, calici- and other viruses) use a RdRp which exclusively employs a protein as a primer for both positive and negative strand RNA production: this protein primer is part of the precursor RdRp and is cleaved off as elongation of the initial complex occurs, to become a 5'-genome-linked protein, usually known as viral genome-linked protein (VPg) (Y. F. Lee, et al., *Proc Natl Acad Sci USA* 74, 59 (January 1977)). Thus during the lifecycle of Picornaviruses, uncapped, triphosphorylated 5' ends are absent. Consequently, RIG-I is expected to be involved in the detection of Flaviviridae and NSV but not picornaviruses, which was confirmed in a recent study (H. Kato et al., *Nature* 441, 101 (Apr. 9, 2006)).

Prior to the present invention, long double-stranded RNA was believed to be the only defined nucleic acid structure that occurs during viral infection but is absent in normal cells. The notion that the long double-stranded RNA mimic poly(I:C) induces type I IFNs dates back to the early days of type I IFN research (M. Absher, W. R. Stinebring, *Nature* 223, 715 (Aug. 16, 1969)). Double-stranded RNA-dependent protein kinase (PKR) was thought to be involved in IFN-α induction (S. D. Der, A. S. Lau, *Proc Natl Acad Sci USA* 92, 8841 (Sep. 12, 1995)) but Weissmann's group demonstrated that poly(I:C)-induced type I IFN is not impaired in PKR deficient mice (Y. L. Yang et al., *Embo J* 14, 6095 (Dec. 15, 1995)). Others found that poly(I:C)-induced type I IFN was partially dependent on PKR but independent of TLR3 (S. S. Diebold et al., *Nature* 424, 324 (Jul. 17, 2003)). On the other hand, TLR3 was the first receptor proven to specifically bind long dsRNA and to induce type I IFN upon binding (L. Alexopoulou, et al., *Nature* 413, 732 (Oct. 18, 2001)). TLR3 was found to be activated during viral infection (in the case of CMV) (K. Tabeta et al., *Proc Natl Acad Sci USA* 101, 3516 (Mar. 9, 2004)), but was not required for viral clearance (in the case of RSV) (B. D. Rudd et al., *J Immunol* 176, 1937 (Feb. 1, 2006)).

A number of studies suggested that the helicases MDA-5 and RIG-I recognize dsRNA (M. Yoneyama et al., *Nat Immunol* 5, 730 (July 2004); S. Rothenfusser et al., *J Immunol* 175, 5260 (Oct. 15, 2005); J. Andrejeva et al., *Proc Natl Acad Sci USA* 101, 17264 (Dec. 7, 2004)). However, the present inventor found that double-strand formation of RNA is not required for RIG-I-RNA interaction and that dsRNA is not sufficient for RIG-I activation. The present inventors further found that MDA-5 is not involved in 5' triphosphate RNA recognition. Although there is convincing evidence that MDA-5 is activated by the long dsRNA mimic poly(I:C), activation of MDA-5 by natural long dsRNA is still controversial (H. Kato et al., *Nature* 441, 101 (Apr. 9, 2006)). Taken together, TLR3 so far is the only receptor that leads to the production of type I IFN upon binding of the natural long dsRNA molecule, but the contribution of TLR3 to type I IFN induction and viral clearance in vivo seems to be weak.

It is widely assumed that replication of both DNA and RNA viruses is associated with the formation of intermediate dsRNA in the cytoplasm. A recent study confirms the formation of intermediate dsRNA for positive strand RNA viruses, dsRNA viruses and DNA viruses but not NSV (F. Weber, et al., *J Virol* 80, 5059 (May, 2006)). However, formation of endogenous dsRNA occurs physiologically in eukaryotic cells. In healthy eukaryotic cells, dsRNA is present in the form of micro RNAs (miRNA) and precursor-miRNAs. Precursor-miRNA are 70-nucleotide dsRNA stem-loop structures that are constantly exported from the nucleus into the cytosol to be further processed into 22 nucleotides miRNAs which posttranscriptionally regulate a large number of target genes (B. R. Cullen, *Mol Cell* 16, 861 (Dec. 22, 2004)). Therefore, dsRNA is present in normal healthy eukaryotic cells without inducing an type I IFN response. Therefore, dsRNA in the cytoplasm per se is not virus-specific.

There is good evidence that short dsRNA such as siRNA generated by Dicer-mediated cleavage of long dsRNA does not elicit a type I IFN response in non-immune cells (V. Hornung et al., *Nat Med* 11, 263 (March 2005); D. H. Kim et al., *Nat Biotechnol* 22, 321 (March 2004); S. M. Elbashir et al., *Nature* 411, 494 (May 24, 2001)). A recent study suggests that the two nucleotides overhang at the 3' end of dicer cleavage products are essential for the lack of immunorecognition of short dsRNA (J. T. Marques et al., *Nat Biotechnol* 24, 559 (May, 2006)). In the same study, it was proposed that synthetic blunt end short dsRNA is recognized via RIG-I. The conclusion that RIG-I is the receptor for blunt end short dsRNA is based on experiments using RIG-I overexpressing cells and using RIG-I specific siRNA (short dsRNA with two nucleotides 3' overhangs) on top of stimulation with blunt end short dsRNA. RIG-I deficient cells were not examined in this study.

It is well known that 5' triphosphate independent recognition of short dsRNA as well as ssRNA occurs in the endosomal compartment of a highly specialized subset of immune cells, the plasmacytoid dendritic cell (PDC). PDC carry only two functional TLRs, TLR7 for the detection of RNA, and TLR9 for the detection of DNA. In humans, TLR-induced IFN-α induction is largely confined to PDC. It has been reported that PDC are responsible for the early induction of IFN-α during viral infection (A. Krug et al., *Immunity* 21, 107 (July 2004)). However, depleting PDC has no major impact on host survival after viral infection (T. Delale et al., *J Immunol* 175, 6723 (Nov. 15, 2005)). Based on these data, a concept is evolving that PDC contribute to early antiviral immune responses, while the major antiviral activity is based on cytoplasmic recognition of the virus via RIG-I and/or MDA-5. In situations where the virus escapes recognition of RIG-I and/or MDA-5, PDC and TLR-mediated virus recognition may play a more critical role. Thus, PDC serve as sentinels for viral particles before it comes to viral replication in virus-infected cells, and may serve as a backup strategy if the virus escapes RIG-I and/or MDA-5 recognition.

The potency of the 5' triphosphate RNA specific antiviral response is illustrated by the finding of the present inventors that human primary monocytes produce large amounts of IFN-α upon stimulation with 5' triphosphate RNA. Unlike in mice (S. S. Diebold et al., *Nature* 424, 324 (Jul. 17, 2003)), human myeloid cells have not been shown previously to produce considerable amounts of IFN-α upon stimulation with nucleic acids. With 5' triphosphate RNA, now for the first time a molecule is available which is a real mimic of viral infection of cells and consequently is capable of inducing IFN-α in any cell type including immune cells that normally do not make IFN-α, non-immune cells and tumor cells.

Prior to the present invention, the only way to induce a similar type of response was to use attenuated replicating viruses. However, attenuated viruses may cause viral infection and disease in immunosuppressed patients and mutations could eventually revert viruses to become more pathogenic. 5' triphosphate RNA has the potential to mimic attenuated replicating viruses with respect to their potent stimulation of immunity. In this respect, 5' triphosphate RNA seems to be the perfect biologically dead molecule which can be used in the development of vaccines, therapeutic vaccines, or immunotherapies for the prevention and/or treatment of established diseases such as chronic viral infection and tumors.

In addition, the present inventors found that 5' triphosphate RNA induces not only type I IFN production in tumor cells, but also apoptosis of tumor cells. Tumor cells are more susceptible than non-tumor cells to apoptosis induced by 5' triphosphate RNA. Therefore, 5' triphosphate RNA is an ideal candidate for tumor therapy.

In the prior art, 5' triphosphate RNAs, whether single-stranded or double stranded, were routinely generated by in vitro transcription using bacteriophage RNA polymerases, such as T7, T3, and SP6, which inevitably start the transcripts with a 5' G (Maitra U et al. (1980) PNAS 77(7):3908-3911; Stump W T & Hall K B (1993) Nucleic Acids Research 21(23):5480-5484). In contrast to the established practice in the art, the present inventors found that 5' triphosphate RNAs which start with a 5' A are more potent at inducing a type I IFN response.

Furthermore, the present inventors found that the 5' sequence of the 5' triphosphate RNA affects its potency. In contrast, the 3'sequence of a 5' triphosphate RNA had little impact as short 5' triphosphate RNA oligonucleotides with poly A, poly U, poly C or poly G at the 3'end had similar activity.

Moreover, the present inventors found that the type I IFN-inducing activity of a 5' triphosphate RNA increases with an increasing inosine content.

In addition, in contrast to short oligonucleotides, long 5' triphosphate RNA showed different levels of activity. This may be explained by secondary structure formation of long RNA molecules that could affect accessibility of the 5' triphosphate end for RIG-I.

It was later discovered by the present inventors that not only free, uncapped 5' triphosphate group was capable of inducing type I IFN production, so were free, uncapped 5' monophosphate and diphosphate groups. Therefore, the present invention provides the use, in particular, therapeutic use of an oligonucleotide/polynucleotide bearing at least one free, uncapped phosphate group at the 5' end (i.e, a 5' phosphate olignucleotide/polynucleotide).

Even though Kim D H et al. (2004, Nature Biotech. 22(3): 321-325) and US 2006/0178334 teach that in vitro-transcribed single-stranded 5' triphosphate RNA and single-stranded viral RNA induced type I IFN production in selected cell lines and type I IFN-inducing single-stranded 5' triphosphate RNA may also be obtained from chemical synthesis, surprisingly, the present inventors found that chemically synthesized 5' triphosphate RNA did not have any type I IFN-inducing activity on its own. Rather, the formation of a double-stranded structure was required. The in vitro transcribed single-stranded RNA and single-stranded viral RNA are likely to contain double-stranded structure due to the looping back of the 3' end or other intra- or inter-molecular double-strand formation, which accounts for their ability to induce type I IFN in the absence of an antisense (i.e., complementary) strand.

This surprising finding opens up the possibility of inducing type I IFN in a sequence- and cell-specific manner. In this approach, a single-stranded 5' phosphate RNA, in particular, a 5' triphosphate RNA, whose sequence is complementary to a tissue- or cell-specific RNA can be chemically synthesized and introduced into cells, tissues, organs or whole organisms in vitro, in vivo or ex vivo.

One example of a tissue- or cell-specific RNA is an mRNA of a disease/disorder-related gene. When introduced into healthy cells which do not express the disease/disorder-related gene or do not express the disease/disorder-related gene to any significant degree, the single-stranded 5' phosphate RNA remains single-stranded and is incapable of being recognized by RIG-I or inducing type I IFN. In contrast, when introduced into diseased cells expressing the disease/disorder-related gene or expressing the disease/disorder-related gene at an elevated level, the single-stranded 5' phosphate RNA binds the mRNA of the disease/disorder-related gene, forms a double-stranded structure which is recognized by RIG-I, leading to type I IFN production.

Another example of a tissue- or cell-specific RNA is a microRNA (miRNA). MicroRNAs (miRNAs) are single-stranded molecules about 21-23 nucleotides in length having a hairpin or stem-loop structure; they are partially complementary to mRNAs of genes and regulate the expression of said genes. miRNAs are expressed in a tissue-, cell- and/or developmental stage-specific manner and are known to be associated with certain diseases/disorders such as cancer and heart disease.

This way, type I IFN response, which is normally cytotoxic to cells, is only induced in diseased cells but not in healthy bystander cells, leading to the effective eradication of diseased cells without harming any healthy bystander cells.

The single-stranded 5' phosphate RNA useful in the present invention can possesses gene silencing activity. However, the single-stranded 5' triphosphate RNA useful in the present invention does not need to possess any gene silencing activity. So long as the single-stranded 5' phosphate RNA is capable of binding the target endogenous RNA, i.e., has sequence complementarity to the target endogenous RNA, it is useful in inducing type I IFN in a target cell-specific manner. Under certain circumstances, it may be desirable to use a single-stranded 5' phosphate RNA with gene silencing activity. For example, it may be desirable to use an antisense RNA against an oncogene in tumor cells to induce type I IFN production and to reduce the proliferative potential of the tumor cells at the same time. Under other circumstances, it may be desirable to use a single-stranded 5' phosphate RNA without gene silencing activity. It is conceivable that single-stranded 5' phosphate RNA lacking gene silencing activity does not get effectively recognized and degraded by the cellular machinery upon binding to its target mRNA. As a result, the single-stranded 5' phosphate RNA lacking gene silencing activity may have a prolonged intracelluar half life.

Furthermore, 5' triphosphate RNA is found to be capable of inducing IL-18 and IL-1β production. Without being bound to any theory, it is believed that 5' triphosphate is recognized by the inflammasome, leading to the production of IL-18 and IL-1β. Therefore, 5' triphosphate RNA may be useful in the treatment of diseases and/or conditions which may be alleviated by the induction of these respective cytokines. The diseases and/or conditions include, but are not limited to, allergies, malignant and benign tumors, viral infections, bacterial infections (in particular, intracellular bacterial infections), immunodeficiencies and Immunosuppression (including bone marrow suppression by cytotoxic chemotherapy).

Since certain structural features are required for a 5' triphosphate oligonucleotide to be an effective ligand for RIG-I and thus effective in inducing type I IFN, IL-18 and/or IL-1β, it is possible to inhibit RIG-I activation and the induction of type I IFN, IL-18 and/or IL-1β by using, for example, chemically modified 5' triphosphate RNA, high concentrations of 5' triphosphate RNA which is too short for optimal signaling, high concentrations of 5' triphosphate RNA in which the double-stranded section is too short for optimal signaling, high concentration of single-stranded 5' triphosphate RNA which lacks sequence complementarity to any cellular mRNA in a target cell. Such oligonucleotides has inhibitory effect on the induction of type I IFN, IL-18 and/or IL-1β either by binding RIG-I without initiating signaling or by diluting out 5' triphosphate RNA which is capable of inducing said cytokines.

Such inhibitory 5' triphosphate oligonucleotides may be useful in the treatment of diseases or conditions which are associated with elevated levels of type I IFN, IL-18 and/or IL-1. The diseases include, but are not limited to, autoimmune diseases, such as rheumatoid arthritis and gout, and inflammatory diseases.

Another surprising finding of the present inventors is that, in addition to in vitro transcribed RNA, chemically synthesized RNA bearing free 5' phosphate group and viral RNA, bacterial RNA is very potent in inducing a type I IFN response. Similar to in vitro transcribed RNA and viral RNA, bacterial RNA contains a 5' triphosphate and lacks the eukaryotic cell-specific modifications. Even more surprisingly, it was found that the IFN-inducing activity of bacterial RNA is not entirely attributable to the presence of the 5' triphosphate, as is the case with in vitro transcribed RNA. Therefore, in addition to 5' triphosphate, bacterial RNA contains further molecular features which are responsible for its ability to be recognized by eukaryotic cells and to induce type I IFN production.

This surprising finding of the present inventors opens up a new venue in the development of pharmaceutical compositions which are capable of inducing an anti-viral response and/or an anti-bacterial response and are useful for the treatment of diseases such as viral infections, bacterial infections, (in particular, intracellular bacterial infections), tumors, allergy, autoimmune diseases and immunodeficiencies.

Bacterial RNA is advantageous over attenuated virus and viral RNA as a therapeutic agent because of its safety profile. Whereas attenuated virus may cause viral infection and disease and viral RNA may integrate into the eukaryotic genome causing unwanted genetic alteration, bacterial RNA is inert and does not cause any undesirable diseases or conditions.

In addition, bacterial RNA can be produced in large quantities at very low cost. Therefore, it is a lot more economical to use bacterial RNA as a therapeutic agent than attenuated virus, viral RNA, or in vitro transcribed RNA.

DEFINITIONS

As used herein, "a" and "an" refers to not only a single individual, but also a group or species of entities.
Oligonucleotide As used herein, the term "oligonucleotide" refers to a polynucleotide formed from a plurality of linked nucleoside units; "oligonucleotide" and "polynucleotide" are used synonymously. Such oligonucleotides can be obtained from existing nucleic acid sources, including genomic or cDNA, but are preferably produced by synthetic methods including chemical synthesis, in vitro and in vivo transcription. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, pyrophosphate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_p)$- or $(S_p)$-phosphorothioate, alkylphosphonate, or phosphotriester linkages).

The oligonucleotides of the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside. In some embodiments, the modified nucleoside is a 2'-substituted ribonucleoside, an arabinonucleoside or a 2'-deoxy-2'-substituted-arabinoside.

As used herein, the term "2'-substituted ribonucleoside" or "2'-substituted arabinoside" includes ribonucleosides or arabinonucleoside in which the hydroxyl group at the 2' position of the pentose moiety is substituted to produce a 2'-substituted or 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of 2'-O-substituted ribonucleosides or 2'-O-substituted-arabinosides include, without limitation, 2'-O-methylribonucleosides or 2'-O-methylarabinosides and 2'-O-methoxyethylribonucleosides or 2'-O-methoxyethylarabinosides.

The term "2'-substituted ribonucleoside" or "2'-substituted arabinoside" also includes ribonucleosides or arabinonucleosides in which the 2'-hydroxyl group is replaced with a lower alkyl group containing 1-6 saturated or unsaturated carbon atoms, or with an amino or halo group. Examples of such 2'-substituted ribonucleosides or 2'-substituted arabinosides include, without limitation, 2'-amino, 2'-fluoro, 2'-allyl, and 2'-propargyl ribonucleosides or arabinosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., U.S. Pat. Nos. 5,652,355, 6,346,614 and 6,143,881).

RNA oligonucleotides discussed herein include otherwise unmodified RNA as well as RNA which have been modified (e.g., to improve efficacy), and polymers of nucleoside surrogates.

Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. 1994, *Nucleic Acids Res* 22: 2183-2196. Such rare or unusual RNAs, often termed modified RNAs (apparently because these are typically the result of a post-transcriptional modification) are within the term unmodified RNA, as used herein.

Modified RNA as used herein refers to a molecule in which one or more of the components of the nucleic acid, namely sugars, bases, and phosphate moieties, are different from that which occurs in nature, preferably different from that which occurs in the human body. While they are referred to as modified "RNAs," they will of course, because of the modification, include molecules which are not RNAs.

Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone.

All nucleic acid sequences listed herein are in the 5' to 3' direction unless otherwise indicated.

The RNA oligonucleotide of the invention can be single-stranded (ssRNA), double-stranded (dsRNA), or partially double-stranded (partially dsRNA).

A single-stranded RNA oligonucleotide may contain self-complementary sequences and forms a hairpin. For example, 5'-GACCTAGCCTAAAACTAGGTC-3' (SEQ ID NO: 318). The self-complementary sequence may be a palindromic sequence. For example, 5'AAAGATCCGGATCAAAA-3' (SEQ ID NO: 319).

A double-stranded RNA oligonucleotide may have one- or two-nucleotide overhang at the 5' or 3' end of one or both strands.

A partially double-stranded RNA oligonucleotide may comprise two strands of the same or different length(s), wherein at least one of the strands contains nucleotides outside the complementary sequence. For example,

```
Example 1:
                                           (SEQ ID NO: 320)
5'-AAAAGUUCAAAGCUCAAAA-3'

(SEQ ID NO: 321)
3'-CAAGUUUCGAG-5'

Example 2:
                                           (SEQ ID NO: 322)
5'-UCAAAGUCAAAAGCUCAAAGUUGAAAGUUUAAA-3'

(SEQ ID NO: 323)
3'-GACUUGAAAAUUUCAGUUUUCGAGUUUAAGUUGAAAACUCG-5'

Example 3:
                                           (SEQ ID NO: 324)
5'-UCAAAGUCAAAAGCUCAAAGUUGAAA-3'

(SEQ ID NO: 325)
3'-UUUCAGUUUUCGAGUUUAAGUUGAAAACUCG-5'
```

The length of a single-stranded RNA oligonucleotide is the number of nucleotides contained in the oligonucleotide.

In the case of a double-stranded or partially double-stranded oligonucleotide, the length of the oligonucleotide is the length of the individual strands. In other words, a partially double-stranded oligonucleotide can have two lengths.

Enhanced Nuclease Resistance

For increased nuclease resistance and/or binding affinity to the target, an oligonucleotide can include, for example, 2'-modified ribose units and/or phosphorothioate linkage(s) and/or pyrophosphate linkage(s). For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially dsRNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'-OCH3, 2'-O-allyl, 2'-C-allyl, and 2'-fluoro.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An oligonucleotide agent can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 5'-3'-exonucleases.

Single-stranded RNA oligonucleotides which contain self-complementary sequences and form a hairpin structure have enhanced nuclease resistance compared to single-stranded oligonucleotides which do not.

Tethered Ligands

The RNA oligonucleotides of the present invention also include those with tethered ligands. The properties of a RNA oligonucleotide, including its pharmacological properties, can be influenced and tailored by the introduction of ligands, e.g. tethered ligands.

The ligands may be coupled, covalently or non-covalently, preferably covalently, either directly or indirectly via an intervening tether, to the RNA oligonucleotide. In preferred embodiments, the ligand is attached to the oligonucleotide via an intervening tether.

In preferred embodiments, a ligand alters the distribution, targeting or lifetime of a RNA oligonucleotide into which it is incorporated. In preferred embodiments, a ligand provides an enhanced affinity for a selected target, e.g., molecule, cell or cell type, a cellular or organ compartment, tissue, organ or region of the body.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

A wide variety of ligands may be used. Ligands may include agents that allow for the specific targeting of the oligonucleotide; diagnostic compounds or reporter groups which allow for the monitoring of oligonucletotide distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic poly amino acid. Examples of poly amino acids include, without limitation, poly L-lysine, poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, poly lysine, spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetylglucosamine, multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one embodiment, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In another embodiment, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another embodiment, the ligand is a cell-permeation agent, preferably a helical cell-permeation agent. Preferably, the agent is amphipathic. An exemplary agent is a peptide such as that or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

In a preferred embodiment, the ligand is an antibody or a fragment thereof which is specific for a moiety present in a cell to be targeted. The moiety may be a protein, a carbohydrate structure, a polynucleotide, or a combination thereof. The moiety may be secreted, associated with the plasma membrane (e.g., on the extracellular or intracellular surface), cytosolic, associated with intracellular organelles (e.g., ER, Golgi complex, mitochondria, endosome, lysosome, secretory vesicle) or nuclear. The antibody may be monoclonal or polyclonal. The antibody may be chemeric or humanized. The antibody may be a single chain antibody. The antibody fragment may be a Fab fragment, a F(ab')$_2$ fragment, or any fragments that retain the antigen-binding specificity of the intact antibody.

Immunostimulatory Activity

As used herein, "immunostimulatory activity" refers to the capability of an agent, such as a molecule or a composition, to induce an immune response. In one embodiment, the immunostimulatory activity refers to the type I IFN-inducing activity, in particular, the IFN-α-inducing activity.

As used herein, "inducing an immune response" means initiating or causing an increase in one or more of B-cell activation, T-cell activation, natural killer cell activation, activation of antigen presenting cells (e.g., B cells, dendritic cells, monocytes and macrophages), cytokine production, chemokine production, specific cell surface marker expression, in particular, expression of co-stimulatory molecules. In one aspect, such an immune response involves the production of type I IFN (IFN-α and/or IFN-β), in particular, IFN-α, in cells such as PDC (plasmacytoid dendritic cells) and/or monocytes.

As used herein, "type I IFN inducing activity" includes IFN-α-inducing activity and/or IFN-β inducing activity.

As used herein, "IFN-α-inducing activity" refers to the capability of an agent, such as a molecule or composition, to induce IFN-α production from a cell capable of producing IFN-α. Cells capable of producing IFN-α include, but are not limited to, peripheral blood mononuclear cells (PBMC) (e.g., B cells, dendritic cells (myeloid dendritic cells and plasmacytoid dendritic cells), macrophages, monocytes, natural killer cells, granulocytes), endothelial cells, and cell lines.

As used herein, "IFN-β-inducing activity" refers to the capability of an agent, such as a molecule or composition, to induce IFN-β production from a cell capable of producing IFN-β. Any somatic cells, such as PBMC, myeloid dendritic cells, monocytes, PDC, fibroblasts, are capable of producing IFN-β.

Anti-Viral Response

As used herein, "anti-viral response" refers to the response by a cell, tissue or organism upon infection by a virus with the purpose of eliminating or incapacitating the virus. Typical anti-viral responses include, but are not limited to, type I IFN, MIP1-a, MCP, RANTES, IL-8, IL-6, IP-10, and IFN-γ production.

Anti-Bacterial Response

An anti-bacterial response is the response by a cell, tissue or organism upon infection by a bacterium with the purpose of eliminating or incapacitating the bacterium. Typical anti-bacterial responses include, but are not limited to, T cell or NK cell-mediated elimination of the infected cell by either receptor-mediated apoptosis or cytokine-mediated apoptosis via TNF or TRAIL, macrophage or monocytes phagocytosis.

An anti-bacterial response, in particular, type I and type II IFN production, may be induced in immune cells or non-immune cells. Immune cells include, but are not limited to, peripheral blood mononuclear cells (PBMC), plasmacytoid dendritic cells (PDC), myeloid dendritic cells (MDC), B cells, macrophages, monocytes, natural killer cells, NKT cells, CD4+ T cells, CD8+ T cells, granulocytes. Non-immune cells include, among others, tumor cells, epithelial cells, endothelial cells, and fibroblasts.

Disorder/Disease-Related Gene, RNA and Antigen

As used herein, "disorder/disease-related gene" refers to a gene that is expressed or overexpressed in a disease/disorder and that is not expressed or expressed in reduced amount in normal healthy cells. For example, a mutant CF gene is expressed in cystic fibrosis patient but not in an individual without cystic fibrosis; ErbB2 (or Her2) is overexpressed in breast cancer cells compared to normal breast cells; a viral gene or a virally-induced host gene is expressed in infected cells but not in uninfected cells. The gene product of the disorder/disease-related gene is referred to herein as the "disorder/disease-related antigen". A "disorder/disease-related RNA" refers to an RNA molecule that is present or present in an elevated level in a diseased cell and that is not present or present in reduced level in a normal healthy cell. A disorder/disease-related RNA may be an mRNA, a miRNA, or other non-coding RNA such as rRNA or tRNA.

Mammal

As used herein, the term "mammal" includes, without limitation, rats, mice, cats, dogs, horses, sheep, cattle, cows, pigs, rabbits, non-human primates, and humans.

Oligonucleotide and Precursor Thereof

The present invention provides an oligonucleotide capable of inducing an anti-viral response, in particular, type I IFN production, wherein the oligonucleotide comprises a at least one, preferably at least two, and more preferably at least three phosphate groups at the 5' end, wherein the phosphate group is free of any cap structure or modification, wherein the oligonucleotide comprises at least 1, preferably at least 2, 3, 4, 5, more preferably at least 6, 7, 8, 9, 10, 11, even more preferably at least 12, 13, 14, 15, 16, 17, most preferably at least 18, 19, 20, 21 ribonucleotide(s) at the 5' end, and wherein the oligonucleotide is at least 12, preferably at least 18, more preferably at least 19, even more preferably at least 20, and most preferably at least 21 nucleotides in length.

The oligonucleotide of the invention may be single-stranded, single-stranded containing a self-complementary sequence which can form a hairpin structure, double-stranded, or partially double-stranded.

When the oligonucleotide is single-stranded, single-stranded containing a self-complementary sequence or double-stranded, the length of the oligonucleotide is the length of a single-strand.

When the oligonucleotide is partially double-stranded, the length of the oligonucleotide is the length of the longer strand. Therefore, the oligonucleotide of the present invention include partially double-stranded oligonucleotides wherein at least one of the strands is at least 12, 18, 19, 20 or 21 nucleotides in length.

In the oligonucleotide of the invention, the at least 1 ribonucleotide at the 5' end comprises the at least one 5' phosphate group in the form of a monophosphate, a diphosphate or a triphosphate. In the case of a double-stranded or partially double-stranded oligonucleotide, at least one of the strandes comprises at least one 5' phosphate group. When both strands comprise 5' phosphate groups, the number of phosphate groups may be the same or may be different on the two strands. Therefore, the oligonuculeotide of the invention may comprise 1, 2, 3, 4, 5, or 6 5' phosphate groups in the form of monophosphate, diphosphate and/or triphosphate. In the case of a partially double-stranded oligonucleotide, the at least 1 ribonucleotide at the 5' end which comprises the at least one 5' phosphate can be on either the long or the short strand, wherein at least the long strand is at least 12, 18, 19, 20, or 21 nucleotides in length.

In the oligonucleotide of the invention, the at least 2, 3, 4, 5, 6, 7, 8, 9, 10, 11, 12, 13, 14, 15, 16, 17, 18, 19, 20, 21 ribonucleotides at the 5' end are on the same strand.

In one embodiment, at least one of the 5' phosphate groups is not comprised in a triphosphate. In another embodiment, the oligonucleotide comprises at least one group selected from a monophosphate and a diphosphate at the 5' end, wherein the monophosphate and/or diphophate is free of any cap or modification.

In one embodiment, the first ribonucleotide at the 5' end of the oligonucleotide comprises a ribonucleotide selected from A, U, C and G. In a preferred embodiment, the first ribonucleotide at the 5' end of the oligonucleotide comprise a ribonucleotide selected from A, C and U. In a more preferred embodiment, the first ribonucleotide at the 5' end of the oligonucleotide comprise a ribonucleotide selected from A and C. In a most preferred embodiment, the first ribonucleotide at the 5' end comprises an adenine (A).

In preferred embodiments, the sequence of the first 4 nucleotides at the 5' end of the oligonucleotide is selected from: AAGU (SEQ ID NO: 205), AAAG (SEQ ID NO: 206), AUGG (SEQ ID NO: 207), AUUA (SEQ ID NO: 208), AACG (SEQ ID NO: 209), AUGA (SEQ ID NO: 210), AGUU (SEQ ID NO: 211), AUUG (SEQ ID NO: 212), AACA (SEQ ID NO: 213), AGAA (SEQ ID NO: 214), AGCA (SEQ ID NO: 215), AACU (SEQ ID NO: 216), AUCG (SEQ ID NO: 217), AGGA (SEQ ID NO: 218), AUCA (SEQ ID NO: 219), AUGC (SEQ ID NO: 220), AGUA (SEQ ID NO: 221), AAGC (SEQ ID NO: 222), AACC (SEQ ID NO: 223), AGGU (SEQ ID NO: 224), AAAC (SEQ ID NO: 225), AUGU (SEQ ID NO: 226), ACUG (SEQ ID NO: 227), ACGA (SEQ ID NO: 228), ACAG (SEQ ID NO: 229), AAGG (SEQ ID NO: 230), ACAU (SEQ ID NO: 231), ACGC (SEQ ID NO: 232), AAAU (SEQ ID NO: 233), ACGG (SEQ ID NO: 234), AUUC (SEQ ID NO: 235), AGUG (SEQ ID NO: 236), ACAA (SEQ ID NO: 237), AUCC (SEQ ID NO: 238), AGUC (SEQ ID NO: 239), wherein all sequences are in the 5'→3' direction.

In more preferred embodiments, the sequence of the first 4 nucleotides at the 5' end of the oligonucleotide is selected from: AAGU (SEQ ID NO: 205), AAAG (SEQ ID NO: 206), AUGG (SEQ ID NO: 207), AUUA (SEQ ID NO: 208), AACG (SEQ ID NO: 209), AUGA (SEQ ID NO: 210), AGUU (SEQ ID NO: 211), AUUG (SEQ ID NO: 212), AACA (SEQ ID NO: 213), AGAA (SEQ ID NO: 214), AGCA (SEQ ID NO: 215), AACU (SEQ ID NO: 216), AUCG (SEQ ID NO: 217), AGGA (SEQ ID NO: 218), AUCA (SEQ ID NO: 219), AUGC (SEQ ID NO: 220), AGUA (SEQ ID NO: 221), AAGC (SEQ ID NO: 222), AACC (SEQ ID NO: 223), wherein all sequences are in the 5'→3 direction.

In even more preferred embodiments, the sequence of the first 4 nucleotides at the 5' end of the oligonucleotide is selected from: AAGU (SEQ ID NO: 205), AAAG (SEQ ID NO: 206), AUGG (SEQ ID NO: 207), AUUA (SEQ ID NO: 208), AACG (SEQ ID NO: 209), AUGA (SEQ ID NO: 210), AGUU (SEQ ID NO: 211), AUUG (SEQ ID NO: 212), AACA (SEQ ID NO: 213), wherein all sequences are in the 5'→3' direction.

In most preferred embodiments, the sequence of the first 4 nucleotides at the 5' end of the oligonucleotide is selected from: AAGU (SEQ ID NO: 205), AAAG (SEQ ID NO: 206), AUGG (SEQ ID NO: 207), AUUA (SEQ ID NO: 208), wherein all sequences are in the 5'→3' direction.

In other embodiments, the first nucleotide of the above-listed 5' 4-nucleotide sequences is a U, C or G instead of A.

In a preferred embodiment, the oligonucleotide comprises at least 1, 2, 3, 4, 5, preferably at least 6, 7, 8, 9, 10, more preferably at least 11, 12, 13, 14, 15, even more preferably at least 16, 17, 18, 19, 20, and most preferably at least 21, 22, 23, 24, 25 inosine (I). In one embodiment, at least 1, 2, 3, 4, 5%, preferably at least 10, 15, 20, 25, 30, more preferably at least 35, 40, 45, 50, 55, 60%, even more preferably at least 70, 80, or 90% of the adenosine (A) and/or guanosine (G) in the oligonucleotide is replaced with inosine (I).

The oligonucleotide of the invention may be a RNA oligonucleotide, or a chimeric RNA-DNA oligonucleotide. A chimeric RNA-DNA oligonucleotide comprises both ribonucleotides and deoxyribonucleotides. The ribonucleotides and the deoxyribonucleotides may be on the same strand, or may be on different strands.

In one embodiment, the oligonucleotide (RNA or chimeric RNA-DNA) comprises a phosphorothioate backbone. In preferred embodiments, at least 1, preferably at least 2, more preferably at least 3, even more preferably at least 4 nucleotides are phosphorothioate.

In a preferred embodiment, the oligonucleotide of the invention does not contain any modifications such as pseudouridine, 2-thiouridine, 2'-Fluorine-dNTP, 2'-O-methylated NTP, in particular 2'-fluorine-dCTP, 2'-fluorine-dUTP, 2'-O-methylated CTP, 2'-O-methylated UTP.

In some embodiments, the oligonucleotide has gene silencing activity. In one embodiment, the oligonucleotide is active in RNA interference (RNAi), or is an RNAi molecule. The RNAi molecule may be a siRNA (small interfering RNA, double-stranded), shRNA (small hairpin RNA, single-stranded with a hairpin structure) or miRNA (microRNA, single-stranded with a hairpin structure).

In a preferred embodiment, the RNA oligonucleotide is a single-stranded RNA oligonucleotide which does not contain any sequence which is capable of forming any intramolecular or intermolecular double-stranded structure with itself under physiological condition, in particular, physiological condition inside a cell, and the nucleotide sequence of the ssRNA is complementary to a RNA in a target cell.

In one embodiment, the RNA is expressed in a tissue-, cell- and/or developmental stage-specific manner. In a preferred embodiment, the RNA is a disease/disorder-related RNA. In one embodiment, the disease/disorder-related RNA is an mRNA of a disease/disorder-related gene. In another embodiment, the disease/disorder-related RNA is a miRNA. The disease/disorder-related RNA may be a endogenous cellular RNA, a viral RNA, a RNA from an invading microorganism or organism such as a bacterium, a fungus, or a parasite.

The degree of complementarity is preferably at least 50%, 60%, 70%, more preferably at least 75%, 80%, 85%, 90%, even more preferably at least 95%, 96%, 97%, 98%, 99%, and most preferably 100%. As used in the art, the term "degree of complementarity" between two oligonucleotides/polynucleotides refers to the percentage of complementary bases in the overlapping region of the two oligonucleotides. Two bases are complementary to each other if they can form a base pair via hydrogen bonding. Base pairs include both Waston-Crick base pairs and wobble base pairs. Waston-Crick base pairs include A-T, C-G, A-U; wobble base pairs include G-U, I-U, I-A, I-C. The degree of complementarily can be determined by a skilled person using any known methods in the art, either manually or automatically by various engines such as BLAST. For example, ATCG has 100% complementarity to CGAT and CGATGG, and 75% complementarity to CGTT and CGTTGG. In a preferred embodiment, complementarity between the oligonucleotide of the present invention and the target RNA in the target cell exists over the entire length of the oligonucleotide.

The term "physiological condition" is used herein as commonly understood in the art. Physiological condition inside a cell refers to parameters such as the ionic strength, osmolarity, salt concentration, pH, temperature that are normally found inside a cell, i.e., in the cytosol. The cell may be in vivo, in vitro or ex vivo. The cell may be a healthy or normal cell or a diseased or abnormal cell. A diseased or abnormal cell may be, for example, a cell infected by bacteria or viruses, a tumor cell, an autoimmune cell, a cell having an inflammatory response. Physiological condition refers to the conditions inside or outside a cell in vivo, in vitro or ex vivo. Physiological conditions may be found in an living organism, tissue, or cell or may be obtained artificially in a laboratory. An example of a physiological condition is 150±50 mM NaCl, pH 7.4±0.8, and 20±20° C.

Whether a RNA oligonucleotide contains any double-stranded structure can be readily determined by a skilled person using known methods in the art. For example, a spectrometer may be used to measure double-stranded versus single-stranded absorption spectra while increasing the temperature. In certain embodiments, the number of basepairing within the double-stranded structure is at least 6, 7, 8, 9, preferably at least 10, 11, 12, 13, 14, 15, more preferably at least 16, 17, 18, 19, 20, 21, even more preferably at least 22, 23, 24, 25. Base pairs include both Waston-Crick basepairs and wobble basepairs. Waston-Crick basepairs include A-T, C-G, A-U; wobble basepairs include G-U, I-U, I-A, I-C.

The ssRNA oligonucleotide may be generated by chemical synthesis.

In one embodiment, the ssRNA oligonucleotide does not have any gene-silencing activity.

In another embodiment, the ssRNA oligonucleotide has gene-silencing activity.

The present invention also provides precursors of the oligonucleotide of the invention.

As used herein, the "precursor of the oligonucleotide" of the invention refers to any molecule which can be processed to generate the oligonucleotide of the invention. The precursors of the oligonucleotide of the invention include, but are not limited to, DNA or RNA molecules which can serve as templates for the synthesis of the RNA oligonucleotides of the invention, RNA or RNA-DNA chimeric molecules which can be enzymatically cleaved to produce the oligonucleotides of the invention.

The oligonucleotide or precursor thereof of the invention may also contain motifs or molecular signatures which are recognized by TLRs. For example, long dsRNA (longer than 30 bases) bearing a 5' phosphate can serve as a ligand for both RIG-I and TLR3. A chimeric RNA-DNA oligonucleotide comprising a ssRNA bearing a 5' phosphate and a ssDNA containing CpG can serve as a ligand for both RIG-I and TLR9. ssRNA or dsRNA bearing a 5' phosphate and defined sequence motifs (S. S. Diebold et al., *Science* 303, 1529 (Mar. 5, 2004); F. Heil et al., *Science* 303, 1526 (Mar. 5, 2004); V. Hornung et al., *Nat Med* 11, 263 (March 2005); WO 03/086280; European patent application no. 05020020.3) can serve as a ligand for both RIG-I and TLR7. ssRNA bearing a 5' triphosphate and GU-rich motifs (WO 03/086280, European patent application no. 05 020 019.5) can serve as a ligand for both RIG-I and TLR8.

In one embodiment, the oligonucleotide or precursor thereof of the invention comprises at least one, preferably at least two, more preferably at least three, even more preferably at least four, even more preferably at least five, and most preferably at least six, of the 4-nucleotide (4mer) motifs selected from the group consisting of:

GUUC, (SEQ ID NO: 240)

GUCA, (SEQ ID NO: 241)

GCUC, (SEQ ID NO: 242)

GUUG, (SEQ ID NO: 243)

GUUU, (SEQ ID NO: 244)

GGUU, (SEQ ID NO: 245)

GUGU, (SEQ ID NO: 246)

GGUC, (SEQ ID NO: 247)

GUCU, (SEQ ID NO: 248)

GUCC, (SEQ ID NO: 249)

GCUU, (SEQ ID NO: 250)

UUGU, (SEQ ID NO: 251)

UGUC, (SEQ ID NO: 252)

CUGU, (SEQ ID NO: 253)

CGUC, (SEQ ID NO: 254)

UGUU, (SEQ ID NO: 255)

GUUA, (SEQ ID NO: 256)

UGUA, (SEQ ID NO: 257)

UUUC, (SEQ ID NO: 258)

UGUG, (SEQ ID NO: 259)

GGUA, (SEQ ID NO: 260)

GUCG, (SEQ ID NO: 261)

UUUG, (SEQ ID NO: 262)

UGGU, (SEQ ID NO: 263)

GUGG, (SEQ ID NO: 264)

GUGC, (SEQ ID NO: 265)

GUAC, (SEQ ID NO: 266)

GUAU, (SEQ ID NO: 267)

UAGU, (SEQ ID NO: 268)

GUAG, (SEQ ID NO: 269)

UUCA, (SEQ ID NO: 270)

UUGG, (SEQ ID NO: 271)

-continued

UCUC, (SEQ ID NO: 272)

CAGU, (SEQ ID NO: 273)

UUCG, (SEQ ID NO: 274)

CUUC, (SEQ ID NO: 275)

GAGU, (SEQ ID NO: 276)

GGUG, (SEQ ID NO: 277)

UUGC, (SEQ ID NO: 278)

UUUU, (SEQ ID NO: 279)

CUCA, (SEQ ID NO: 280)

UCGU, (SEQ ID NO: 281)

UUCU, (SEQ ID NO: 282)

UGGC, (SEQ ID NO: 283)

CGUU, (SEQ ID NO: 284)

CUUG, (SEQ ID NO: 285)

UUAC, (SEQ ID NO: 286)

wherein the nucleotide sequences of the motifs are 5'→3', wherein the oligonucleotide or precursor thereof is between 12 and 64, preferably between 12 and 50, more preferably between 14 and 40, even more preferably between 16 and 36, and most preferably between 18 and 25 nucleotides in length.

In one embodiment, the 4mer motifs are selected from the group consisting of SEQ ID NOs: 240-258, SEQ ID NOs: 240-257, SEQ ID NOs: 240-256, SEQ ID NOs: 240-255, preferably, SEQ ID NOs: 240-254, SEQ ID NOs: 240-253, SEQ ID NOs: 240-252, SEQ ID NOs: 240-251, more preferably, SEQ ID NOs: 240-250, SEQ ID NOs: 240-249, SEQ ID NOs: 240-248, SEQ ID NOs: 240-247, SEQ ID NOs: 240-246, even more preferably, SEQ ID NOs: 240-245, SEQ ID NOs: 240-244, SEQ ID NOs: 240-243, SEQ ID NOs: 240-242, most preferably, SEQ ID NO: 240 and SEQ ID NO: 241 of the 4mer motifs.

The oligonucleotide or precursor thereof of the invention may comprise one or more copies of the same 4mer motif, or one or more copies of different 4mer motifs.

In another embodiment, the oligonucleotide or a precursor thereof of the invention comprises at least one, preferably at least two, more preferably at least three, even more preferably at least four, even more preferably at least five, and most preferably at least six, of the 4-nucleotide (4mer) motifs selected from the group consisting of:

UCGU, (SEQ ID NO: 281)

GUUG, (SEQ ID NO: 243)

UGGU, (SEQ ID NO: 263)

UGGC, (SEQ ID NO: 283)

GGUA, (SEQ ID NO: 260)

UGAU, (SEQ ID NO: 287)

UGCU, (SEQ ID NO: 288)

UUGC, (SEQ ID NO: 278)

UUGU, (SEQ ID NO: 251)

UAGU, (SEQ ID NO: 268)

GGUU, (SEQ ID NO: 245)

GUUU, (SEQ ID NO: 244)

UGUG, (SEQ ID NO: 259)

GUGU, (SEQ ID NO: 246)

UGCC, (SEQ ID NO: 289)

GUAU, (SEQ ID NO: 267)

GUGC, (SEQ ID NO: 265)

UGUA, (SEQ ID NO: 257)

UGUC, (SEQ ID NO: 252)

CUGU, (SEQ ID NO: 253)

UGAC, (SEQ ID NO: 290)

UGUU, (SEQ ID NO: 255)

UAAU, (SEQ ID NO: 291)

GUAG, (SEQ ID NO: 269)

UCUU, (SEQ ID NO: 292)

UUGG, (SEQ ID NO: 271)

UUUG, (SEQ ID NO: 262)

-continued

GGAU, (SEQ ID NO: 293)

UUUU, (SEQ ID NO: 279)

CGUU, (SEQ ID NO: 284)

UUAU, (SEQ ID NO: 294)

GUUC, (SEQ ID NO: 240)

GUGG, (SEQ ID NO: 264)

GGUG, (SEQ ID NO: 277)

UAUU, (SEQ ID NO: 295)

UCUG, (SEQ ID NO: 296)

GUAC, (SEQ ID NO: 266)

UAGG, (SEQ ID NO: 297)

UCUC, (SEQ ID NO: 272)

UAGC, (SEQ ID NO: 298)

UAUC, (SEQ ID NO: 299)

CUAU (No. 42), (SEQ ID NO: 300)

UACU, (SEQ ID NO: 301)

CGGU, (SEQ ID NO: 302)

UGCG, (SEQ ID NO: 303)

UUUC, (SEQ ID NO: 258)

UAUG, (SEQ ID NO: 304)

UAAG, (SEQ ID NO: 305)

UACC, (SEQ ID NO: 306)

UUAG, (SEQ ID NO: 307)

GCUU, (SEQ ID NO: 250)

CAGU, (SEQ ID NO: 273)

UGAG, (SEQ ID NO: 308)

GAUU, (SEQ ID NO: 309)

GAGU, (SEQ ID NO: 276)

GUUA, (SEQ ID NO: 256)

UGCA, (SEQ ID NO: 310)

UUCU, (SEQ ID NO: 282)

GCCU, (SEQ ID NO: 311)

GGUC, (SEQ ID NO: 247)

GGCU, (SEQ ID NO: 312)

UUAC, (SEQ ID NO: 286)

UCAU, (SEQ ID NO: 313)

GCGU, (SEQ ID NO: 314)

GCAU, (SEQ ID NO: 315)

GAUG, (SEQ ID NO: 316)

GUCU, (SEQ ID NO: 248)

CGUA, (SEQ ID NO: 317)

CGAU, (SEQ ID NO: 333)

wherein the nucleotide sequences of the motifs are 5'→3', wherein the oligonucleotide or precursor thereof is between 12 and 64, preferably between 12 and 50, more preferably between 14 and 40, even more preferably between 16 and 36, and most preferably between 18 and 30 nucleotides in length.

In one embodiment, the 4mer motifs are selected from the group consisting of SEQ ID NO: 281, SEQ ID NO: 243, SEQ ID NO: 263, SEQ ID NO: 283, SEQ ID NO: 260, SEQ ID NO: 287, SEQ ID NO: 288, SEQ ID NO: 278, SEQ ID NO: 251, SEQ ID NO: 268, and SEQ ID NO: 245, preferably SEQ ID NO: 281, SEQ ID NO: 243, SEQ ID NO: 263, SEQ ID NO: 283, SEQ ID NO: 260, SEQ ID NO: 287, SEQ ID NO: 288, SEQ ID NO: 278, SEQ ID NO: 251, and SEQ ID NO: 268, more preferably SEQ ID NO: 281, SEQ ID NO: 243, SEQ ID NO: 263, SEQ ID NO: 283, SEQ ID NO: 260, SEQ ID NO: 287, SEQ ID NO: 288, even more preferably SEQ ID NO: 281, SEQ ID NO: 243, SEQ ID NO: 263 of the above-listed 4mer motifs, most preferably, the 4mer motif is UCGU (SEQ ID NO: 281).

The oligonucleotide or precursor thereof of the invention may comprise one or more copies of the same 4mer motif, or one or more copies of different 4mer motifs.

The oligonucleotide or the precursor thereof of the invention can be used to generate a large amount of type I IFN, in particular, IFN-α, IL-18 and/or IL-1β in vitro and/or in vivo. Said cytokines can be generated at high quantities from different cellular sources, including both immune and non-immune cells, from different species of vertebrates.

The oligonucleotide and precursor thereof of the invention may be prepared by synthetic methods including, but not limited to, chemical synthesis, in vitro transcription and in vivo transcription. In in vitro transcription, polymerases including, but not limited to, bacteriophage polymerase such as T7 polymerase, T3 polymerase, SP6 polymerase, viral polymerases, and E. coli RNA polymerase may be used. In vivo transcription may be achieved in virally infected cells, or bacteria that are either non-infected or infected with a phage.

Furthermore, the oligonucleotides or precursor thereof, in particular, the RNA oligonucleotides, of the invention may be covalently or non-covalently linked to one or more lipophilic groups which enhance the stability and/or the activity and/or facilitate the delivery of the oligonucleotides or precursor thereof.

As used herein, the term "lipophilic" or "lipophilic group" broadly refers to any compound or chemical moiety having an affinity for lipids. Lipophilic groups encompass compounds of many different types, including those having aromatic, aliphatic or alicyclic characteristics, and combinations thereof.

In specific embodiments, the lipophilic group is an aliphatic, alicyclic, or polyalicyclic substance, such as a steroid (e.g., sterol) or a branched aliphatic hydrocarbon. The lipophilic group generally comprises a hydrocarbon chain, which may be cyclic or acyclic. The hydrocarbon chain may comprise various substituents and/or at least one heteroatom, such as an oxygen atom. Such lipophilic aliphatic moieties include, without limitation, saturated or unsatarated fatty acids, waxes (e.g., monohydric alcohol esters of fatty acids and fatty diamides), terpenes (e.g., the $C_{10}$ terpenes, $C_{15}$ sesquiterpenes, $C_{20}$ diterpenes, $C_{30}$ triterpenes, and $C_{40}$ tetraterpenes), and other polyalicyclic hydrocarbons.

The lipophilic group may be attached by any method known in the art, including via a functional grouping present in or introduced into the RNA oligonucleotide, such as a hydroxy group (e.g., —CO—CH$_2$—OH). Conjugation of the RNA oligonucleotide and the lipophilic group may occur, for example, through formation of an ether or a carboxylic or carbamoyl ester linkage between the hydroxy and an alkyi group R—, an alkanoyl group RCO— or a substituted carbamoyl group KNHCO—. The alkyl group R may be cyclic (e.g., cyclohexyl) or acyclic (e.g., straight-chained or branched; and saturated or unsaturated). Alkyl group R may be a butyl, pentyl, hexyl, heptyl, octyl, nonyl, decyl, undecyl, dodecyl, tridecyl, tetradecyl, pentadecyl, hexadecyl, heptadecyl or octadecyl group, or the like. Preferably, the lipophilic group is conjugated to the 5'-hydroxyl group of the terminal nucleotide. In a preferred embodiment, the liphophilic group is 12-hydroxydodeconoic acid bisdecylamide.

In another embodiment, the lipophilic group is a steroid, such as sterol. Steroids are polycyclic compounds containing a perhydro-1,2-cyclopentanophenanthrene ring system. Steroids include, without limitation, bile acids (e.g., cholic acid, deoxycholic acid and dehydrocholic acid), cortisone, digoxigenin, testosterone, cholesterol and cationic steroids, such as cortisone.

In a preferred embodiment, the lipophilic group is cholesterol or a derivative thereof. A "cholesterol derivative" refers to a compound derived from cholesterol, for example by substitution, addition or removal of substituents. The steroid may be attached to the RNA oligonucleotide by any method known in the art. In a preferred embodiment, the liphophilic group is cholesteryl (6-hydroxyhexyl) carbamate.

In another embodiment, the lipophilic group is an aromatic moiety. In this context, the term "aromatic" refers broadly to mono- and polyaromatic hydrocarbons. Aromatic groups include, without limitation, $C_6$-$C_{14}$ aryl moieties comprising one to three aromatic rings, which may be optionally substituted; "aralkyl" or "arylalkyl" groups comprising an aryl group covalently linked to an alkyl group, either of which may independently be optionally substituted or unsubstituted; and "heteroaryl" groups. As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, between one and about three heteroatoms selected from the group consisting of nitrogen (N), oxygen (O), and sulfur (S).

As used herein, a "substituted" alkyl, cycloalkyl, aryl, heteroaryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyi, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The lipophilic group can be covalently linked directly or indirectly via a linker to the oligonucleotide or precursor thereof. The covalent linkage may or may not comprise a phosphodiester group. And the linker may be of various lengths. The preferred lengths of the linker are known to those skilled in the art and may be determined experimentally.

In one embodiment, the lipophilic group is covalently linked to the 3' end of at least one strand of the oligonucleotide or precursor thereof.

In addition, the oligonucleotide or precursor thereof of the invention may be coupled to a solid support. By "coupled" it is meant that the oligonucleotide or precursor thereof is covalently or non-covalently, directly or indirectly, linked to the solid support. Suitable solid supports include, but are not limited to, silicon wafers, synthetic polymer support such as polystyrene, polypropylene, polyglycidylmethacrylate, substituted polystyrene (e.g., aminated or carboxylated polystyrene, polyacrlamides, polyamides, polyvinylchlorides, etc.), glass, agarose, nitrocellulose, nylon and gelatin nanoparticles. Solid support may enhance the stability and the activity of the oligonucleotide, especially short oligonucleotides less than 16 nucleotides in length.

Oligonucleotide Conjugates

The present invention also provides an oligonucleotide conjugate which is capable of inducing an anti-viral response, in particular, type I IFN production, comprising an oligonucleotide of the invention and an antigen conjugated to the oligonucleotide. In preferred embodiments, the antigen is conjugated to the oligonucleotide at a position other than its 5' end which carries the 5' triphosphate. In some embodiments, the antigen produces a vaccine effect.

The antigen is preferably selected from disease/disorder-related antigens. The disorder may be, for example, a cancer, an immune disorder, a metabolic disorder, or an infection. The antigen may be a protein, a polypeptide, a peptide, a carbohydrate, or a combination thereof.

The oligonucleotide of the invention may be covalently linked to the antigen, or it is otherwise operatively associated with the antigen. As used herein, the term "operatively associated with" refers to any association that maintains the activity of both the oligonucleotide and the antigen. Non-limiting examples of such operative associations include being part of the same liposome or other such delivery vehicle or reagent. In embodiments wherein the oligonucleotide agent is covalently linked to the antigen, such covalent linkage preferably is at any position on the oligonucleotide that does not interfere with the capability of the oligonucleotide to induce an anti-viral response.

Pharmaceutical Composition

The present invention provides a pharmaceutical composition comprising one or more of the oligonucleotide(s) or a precursor thereof described above and a pharmaceutically acceptable carrier.

The present invention also provides a pharmaceutical composition comprising bacterial RNA and a pharmaceutically acceptable carrier.

As used herein, "bacterial RNA" refers to any RNA species isolated from a bacterium, including, but not limited to, total RNA, mRNA, ribosomal RNA, phage RNA, miRNA, structural RNA, and enzymatic RNA. Bacterial RNA may be endogenous to a bacterium, or may be derived from exogenous DNA that has been introduced into the bacterium. Bacterial RNA can be of any length. Bacterial RNA preparations may contain a single RNA species with a single nucleotide sequence, a single RNA species with more than one nucleotide sequences, or multiple RNA species with more than one nucleotide sequences. Bacterial RNA may comprise any type of nucleotides and bases known in the field, including naturally occurring nucleotides and nucleotides converted inside the cell, such as inosine triphosphate and inosine, any known modifications to the backbone and bases, and a monophosphate, a diphosphate, or a triphosphate group at the 5' end. Bacterial RNA may be single-stranded or double-stranded. Bacterial RNA may comprise a heteroduplex of RNA and DNA. Bacterial RNA may be composed of a mixture of RNAs isolated from different types of bacteria.

In a preferred embodiment, the bacterial RNA does not have a nucleotide sequence that is more than 50%, 60%, 70%, 80%, 85%, 90%, 95%, or 99% complementary or that is 100% to a eukaryotic gene coding sequence. In other words, the bacterial RNA preferably does not have any gene-silencing or RNA interference (RNAi) activity.

The term complementary is well understood by those skilled in the art. For example, A is complementary to T, G is complementary to C, 5'-AG-3' is complementary to 5'-CT-3'.

The degree of complementarity between two nucleotide sequences is the percentage of complementary bases in the overlapping region of the two nucleotide sequences. The degree of complementarily can be determined manually or automatically by various engines such as BLAST. For example, ATCG has 100% complementarity to CGAT and CGATGG, and 75% complementarity to CGTT and CGT-TGG. Furthermore, the degree of complementarity between a RNA oligonucleotide or polynucleotide and any sequences present in the public databases (e.g., EMBL, GeneBank) can be determined by the BLAST program.

In a preferred embodiment, the pharmaceutical composition of the invention further comprises an agent which facilitates the delivery of the oligonucleotide or the precursor thereof or the bacterial RNA into a cell, in particular, into the cytosol of the cell.

In one embodiment, the delivery agent is a complexation agent which forms a complex with the oligonucleotide or the precursor thereof and facilitates the delivery of the oligonucleotide or precursor thereof into cells. In one embodiment, the complexation agent is a polymer, preferably a cationic polymer. In a preferred embodiment, the complexation agent is a cationic lipid. In another preferred embodiment, the complexation agent is polyethylenimine (PEI) (K. Wu et al., *Brain Research* 1008(2):284-287 (May 22, 2004); B. Urban-Klein et al. *Gene Therapy* 12(5):461-466 (2005)). Additional examples of complexation agent include, but are not limited to, collagen derivatives (Y. Minakuchi et al. *Nucleic Acids Research* 32(13):e109 (2004)), and biodegradable microspheres such as liposomes (M. Sioud, D. Sorensen, *Biochem Biophys Res Commun* 312(4):1220-1225 (2003); P Y Chien et al. *Cancer Gene Therapy* 12(3):321-328 (2005)), virosomes (J de Jonge et al. *Gene Therapy,* 13:400-411 (2006)), SNALPs (J J Rossi, *Gene Therapy* 13:583-584 (2006)), SICOMATRIX® (CSL Limited) (I. D. Davis et al. *PNAS* 101(29):10697-10702 (Jul. 20, 2004); M J Pearse, D. Drane, *Adv Drug Deliv Rev* 57(3):465-474 (Jan. 10, 2005)), and poly (D,L-lactide-co-glycolide) copolymer (PLGA) microspheres (A. Khan et al. J Drug Target 12(6):393-404 (2004)).

Polyethylenimine (PEI) can be linear or branched. In a preferred embodiment, PEI is in vivo-jetPEI™ which is a linear PEI developed by PolyPlus-transfection for effective and reproducible delivery of anionic oligonucleotides with low toxicity in vivo. The preferred in vivo routes of administration include, but are not limited to, intravenous, intracerebral and intraperitoneal routes.

Virosomes are reconstituted viral envelopes which are prepared from membrane-enveloped viruses, in particular influenza virus, by solubilization of the viral membrane with a suitable detergent, removal of the nucleocapsids by ultracentrifugation and reconstitution of the viral envelope through extraction of the detergent. Typically, virosomes contain viral lipids and viral glycoproteins (such as hemagglutinin (HA) and neuraminidase (NA) in the case of influenza virosomes), resemble the native virus particles in size and morphology and retain the target specificity and the fusogenic activity of the native viral particles.

SNALPs stand for Stable-Nucleic-Acid-Lipid Particles and contain a lipid bilayer comprised of a mixture of cationic and fusogenic lipid coated with diffusible polyethylene glycol (PEG). The SNALPs are in the 120 nanometer diameter size range, protect the enclosed nucleic acid from serum nucleases and allow cellular endosomal uptake and subsequent cytoplasmic release of the nucleic acid.

ISCOMATRIX® is made from saponin, cholesterol and phospholipids under defined conditions and forms cage like structures typically 40 nm in diameter. ISCOMATRIX® has the duel capability of facilitating cargo (e.g., antigen) delivery and stimulating the immune system, both the cellular and humoral immune response.

In another embodiment, the delivery agent is a virus, preferably a replication-deficient virus. In one embodiment, the oligonucleotide described in the invention is contained in a viral capsule. In another embodiment, the precursor of the oligonucleotide described in the invention is comprised in a viral vector which is contained in a viral capsule. In one embodiment, the viral particle contains an enzyme or a nucleic acid encoding the enzyme required for the processing of the precursor into the oligonucleotide described in the invention. In another embodiment, the virus comprising the precursor is administered in conjunction with the enzyme or the nucleic acid encoding the enzyme required for the processing of the precursor into the oligonucleotide described in the invention.

Suitable viruses include, but are not limited to, polymyxoviruses which target upper respiratory tract epithelia and other cells, hepatitis B virus which targets liver cells, influenza virus which targets epithelial cells and other cells, adenoviruses which targets a number of different cell types, papilloma viruses which target epithelial and squamous cells, herpes virus which targets neurons, retroviruses such as HIV which targets CD4[+] T cells and dendritic cells and other cells, and modified Vaccinia Ankara which targets a variety of cells.

Viruses may be selected based on their target specificity.

In one embodiment, the virus is an oncolytic virus. Oncolytic viruses target tumor cells and cause the lysis of the infected tumor cells. Examples of oncolytic viruses include, but are not limited to, naturally occurring wild-type Newcastle disease virus (A. Phuangsab et al. *Cancer Lett* 172:27-36 (2001)), attenuated strains of reovirus (M C Coffey et al. *Science* 282:1332-1334 (1998)) and vesicular stomatitis virus (VSV) (D F Stojdl et al. *Nat Med* 6:821-825 (2000)), genetically engineered mutants of herpes simplex virus type 1 (HSV-1), adenovirus, poxvirus and measles virus (Chiocca E A *Nat Rev Cancer* 2:938-950 (2002); Russell S J Cancer Gene Ther 9:961-966 (2002); H J Zeh, D L Bartlett *Cancer Gene Ther* 9:1001-1012 (2002)).

In addition to being delivered by a delivery agent, the oligonucleotide or precursor thereof described in the invention or bacterial RNA can be delivered into cells via physical means such as electroporation, shock wave administration (Tschoep K et al., *J Mol Med* 2001; 79:306-13), ultrasound triggered transfection, and gene gun delivery with gold particles.

The pharmaceutical composition of the invention may further comprises another agent such as an agent that stabilizes the oligonucleotide or precursor thereof or bacterial RNA, in particular, RNA oligonucleotide, e.g., a protein that complexes with the oligonucleotide agent to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

A formulated composition can assume a variety of states. In some examples, the composition is at least partially crystalline, uniformly crystalline, and/or anhydrous (e.g., less than 80, 50, 30, 20, or 10% water). In another example, the oligonucleotide agent is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the oligonucleotide composition is formulated in a manner that is compatible with the intended method of administration.

The pharmaceutical compositions encompassed by the invention may be administered by any means known in the art including, but not limited to, oral or parenteral routes, including intravenous, intramuscular, intraperitoneal, subcutaneous, transdermal, airway (aerosol), ocular, rectal, vaginal, and topical (including buccal and sublingual) administration. In preferred embodiments, the pharmaceutical compositits are administered by intravenous or intraparenteral infusion or injection. The pharmaceutical compositions can also be administered intraparenchymally, intrathecally, and/or by stereotactic injection.

For oral administration, the oligonucleotide or the precursor thereof described in the invention or bacterial RNA will generally be provided in the form of tablets or capsules, as a powder or granules, or as an aqueous solution or suspension.

Tablets for oral use may include the active ingredients mixed with pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions can also include encapsulated formulations to protect the oligonucleotide or precursor thereof or bacterial RNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075.

In general, a suitable dose of an oligonucleotide or precursor thereof or bacterial RNA will be in the range of 0.001 to 500 milligrams per kilogram body weight of the recipient per day (e.g., about 1 microgram per kilogram to about 500 milligrams per kilogram, about 100 micrograms per kilogram to about 100 milligrams per kilogram, about 1 milligrams per kilogram to about 75 milligrams per kilogram, about 10 micrograms per kilogram to about 50 milligrams per kilogram, or about 1 microgram per kilogram to about 50 micrograms per kilogram). The pharmaceutical composition may be administered once per day, or the oligonucleotide or precursor thereof or bacterial RNA may be administered as two, three, four, five, six or more sub-doses at appropriate intervals throughout the day. In that case, the oligonucleotide or precursor thereof or bacterial RNA contained in each sub-dose must be correspondingly smaller in order to achieve the total daily dosage. The dosage unit can also be compounded for delivery over several days, e.g., using a conventional sustained release formulation which provides sustained release of the oligonucleotide agent or bacterial RNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the infection or disease/disorder, previous treatments, the general health and/or age of the subject, and other diseases/disorders present. Moreover, treatment of a subject with a therapeutically effective amount of a composition can include a single treatment or a series of treatments. Estimates of effective dosages and in vivo half-lives for the individual oligonucleotide or precursor thereof described in the invention or bacterial RNA can be made using conventional methodologies or on the basis of in vivo testing using an appropriate animal model.

Toxicity and therapeutic efficacy of the oligonucleotide or precursor thereof or bacterial RNA and the pharmaceutical composition of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Oligonucleotide agents or bacterial RNA that exhibit high therapeutic indices are preferred.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any oligonucleotide agent or bacterial RNA used in the method of the invention, the therapeutically effective dose can be estimated initially from cell culture assays. A dose may be formulated in animal models to achieve a circulating plasma concentration range of the oligonucleotide agent or bacterial RNA that includes the IC50 (i.e., the concentration of the test oligonucleotide agent which achieves a half-maximal inhibition of symptoms) as determined in cell culture. Such information can be used to more accurately determine useful doses in humans. Levels in plasma may be measured, for example, by high performance liquid chromatography.

The administering physician can adjust the amount and timing of the administration of the pharmaceutical composition of the invention on the basis of results observed using standard measures of efficacy known in the art or described herein.

The pharmaceutical composition of the invention can be used to generate a large amount of type I IFN, in particular, IFN-α, IL-18 and/or IL-1β, in vitro and/or in vivo. The type I IFN, in particular, IFN-α, IL-18 and/or IL-1β, can be generated at high quantities from different cellular sources, including both immune and non-immune cells, from different species of vertebrates.

The pharmaceutical composition of the invention can be used for preventing and/or treating a disease and/or disorder in a vertebrate animal, in particular, a mammal, in medical and/or veterinary practice. The disease and/or disorder include, but are not limited to infections, tumor, allergy, multiple sclerosis, and immune disorders.

Combined Preparation

The present invention provides a combined preparation comprising an oligonucleotide or a precursor thereof described in the invention or a bacterial RNA and a pharmaceutically active agent, wherein the oligonucleotide or a precursor thereof or the bacterial RNA and the agent are for simultaneous, separate or sequential administration.

The pharmaceutically active agents include, but are not limited to, immunostimulatory RNA oligonucleotides, immunostimulatory DNA oligonucleotides, cytokines, chemokines, growth factors, antibiotics, anti-angiogenic factors, chemotherapeutic agents, anti-viral agents, anti-bacterial agents, anti-fungal agents, anti-parasitic agents, antibodies and gene silencing agents.

The combined preparation of the invention may comprise one or more pharmaceutically active agent(s). The more than one pharmaceutically active agents maybe of the same or different category as exemplified above.

In one embodiment, the combined preparation comprises an oligonucleotide or a precursor thereof described in the invention or a bacterial RNA and an immunostimulatory agent, wherein the oligonucleotide or a precursor thereof or the bacterial RNA and the agent are for simultaneous, separate or sequential administration. In one embodiment, the combined preparation further comprises an anti-viral and/or anti-tumor agent.

In another embodiment, the combined preparation comprises an oligonucleotide or a precursor thereof described in the invention or a bacterial RNA and an anti-viral and/or anti-bacterial and/or anti-tumor agent, wherein the oligonucleotide or a precursor thereof or the bacterial RNA and the agent are for simultaneous, separate or sequential administration. In one embodiment, the combined preparation further comprises an immunostimulatory agent.

The oligonucleotide or a precursor thereof described in the invention or the bacterial RNA and the pharmaceutically active agent may be comprised in the same or in separate compositions. The separate compositions may be administered simultaneously or sequentially.

The combined preparation of the present invention may further comprise retinoic acid and/or type I IFN. Retinoic acid and/or type I IFN are known to upregulate RIG-I expression in most cell types, including for example endothelial cells, epithelial cells, fibroblasts, immune cells and tumor cells.

An immunostimulatory agent is an agent, such as a molecule or a composition, which is capable of inducing an immune response. Immunostimulatory agents include, but are not limited to, immunostimulatory RNA oligonucleotides such as those capable of inducing IFN-α or IL-12 (Heil F et al. 2004, $Science$ 303: 1526-1529; Sioud M et al. 2005, $J Mol Biol$ 348: 1079-1090; Hornung V et al. 2005, $Nat Med$ 11: 263-270; Judge A D et al. 2005, $Nat Biotechnol$ 2005. 23: 457-462; Sugiyama et al. 2005, $J Immunol$ 174:2273-2279; Gitlin L et al. 2006, $PNAS$ 103(22):8459-8464; European patent application nos. 05020020.3 and 05020019.5) (e.g., poly(I:C) and immunostimulatory DNA oligonucleotides such as a CpG-containing or non-CpG-containing DNA oligonucleotide capable of inducing IFN-α (see e.g., WO 01/22990, WO 03/101375), cytokines such as type I IFN and IL-12, chemokines such as IP-10, MIP1-α, MCP, RANTES, IL-8, and growth factors such as IL-3, GMCSF, GSCF, MCSF.

In one embodiment, the immunostimulatory agent is capable of inducing an anti-viral response, such as type I IFN, MIP1-a, MCP, RANTES, IL-8, and IL-6 production.

An anti-viral agent is an agent that is useful in the prevention and the treatment of a viral infection. Anti-viral agents include, but are not limited to nucleoside analogs (such as aciclovir, ganciclovir, ribavirin, lamivudin, etc.), protease inhibitors (such as ritonavir etc), cytotoxic agents (such as taxols, carboplatins, cyclophosphamide, methotrexat, azathiprin, 5-fluoruracil, etc.)

In another embodiment, the immunostimulatory agent is capable of inducing an anti-bacterial response, such as type I and/or type II IFN production.

An anti-bacterial agent is an agent that is useful in the prevention and the treatment of a bacterial infection, in particular, intracellular bacterial infection. Anti-bacterial agents include, but are not limited to, Aminoglycosides, Carbapenems, Cephalosporins, Glycopeptides, Macrolides, Monobactam, Penicillins, Polypeptides, Quinolones, Sulfonamides, Tetracyclines.

An anti-tumor agent is an agent that is useful in the prevention and the treatment of tumor or cancer. Anti-tumor agents include, but are not limited to chemotherapeutic agents (such as cisplatin, doxorubicin, taxols, carboplatins, cyclophosphamide, methotrexat, azathiprin, 5-fluoruracil, etc.), anti-angiogenic factors (such as vasostatin and anti-VEGF antibody), and other anti-cancer agents such as Herceptin®, Rituxan®, Gleevec®, and Iressa®.

A gene silencing agent is an agent that is capable of down-regulating the expression of a gene. The gene may encode a protein, a rRNA, a tRNA, or a miRNA. Examples of a gene siclencing agent include, but are not limited to, an antisense RNA, a RNAi molecule (such as siRNA, shRNA, miRNA), and an antagomir (which is a cholesterol-conjugated ssRNA that is complementary to an miRNA).

In a preferred embodiment, the combined preparation of the invention further comprises an oligonucleotide delivery agent as described previously. In other preferred embodiments, the oligonucleotide or precursor thereof or the bacterial RNA may be delivered by physical means as described previously.

Pharmaceutical Package

The present invention provides a pharmaceutical package comprising the pharmaceutical composition or the combined preparation of the invention and an instruction for use.

Use of the Oligonucleotide or Precursor Thereof or Bacterial RNA for Inducing an Anti-Viral Response The present application provides the use of the oligonucleotide or precursor thereof described in the invention or a bacterial RNA for the preparation of a pharmaceutical composition for inducing an anti-viral response, in particular, type I IFN production, IL-18 production, and/or IL-1β production, in a vertebrate animal, in particular, a mammal.

An anti-viral response is the response by a cell, tissue or organism upon infection by a virus with the purpose of eliminating or incapacitating the virus. Typical anti-viral responses include, but are not limited to, type I IFN, MIP1-a, MCP, RANTES, IL-8, IL-6, IP-10, and IFN-γ production.

An anti-viral response, in particular, type I IFN, IL-18, and/or IL-1β production, may be induced in immune cells or non-immune cells. Immune cells include, but are not limited to, peripheral blood mononuclear cells (PBMC), plasmacytoid dendritric cells (PDC), myeloid dendritic cells (MDC), B cells, CD4+ T cells, CD8+ T cells, macrophages, monocytes, natural killer cells, NKT cells, granulocytes. Non-immune cells include, but are not limited to, fibroblasts, endothelial cells, epithelial cells and tumor cells.

The induction of an anti-viral response, in particular, type I IFN, IL-18, and/or IL-1β production, may aid the prevention and treatment of various disorders and/or diseases such as tumor, infections, and immune disorders.

In a preferred embodiment, the RNA oligonucleotide is a single-stranded RNA oligonucleotide which does not contain any sequence which is capable of forming any intramolecular or intermolecular double-stranded structure with itself under physiological condition, in particular, physiological condition inside a cell, and the nucleotide sequence of the ssRNA is complementary to a viral RNA or a cellular RNA induced by the virus in a virally infected cell.

The degree of complementarity is preferably at least 50%, 60%, 70%, more preferably at least 75%, 80%, 85%, 90%, even more preferably at least 95%, 96%, 97%, 98%, 99%, and most preferably 100%.

In one embodiment, the ssRNA olignucleotide has gene silencing activity. In another embodiment, the ssRNA oligonucleotide lacks gene silencing activity.

In one embodiment, the ssRNA oligonucleotide and its complementary strand are delivered separately into cells, preferably in a target cell-specific manner.

In another embodiment, a single-stranded RNA oligonucleotide comprising one or more modifications selected from pseudouridine, 2-thiouridine, 2'-Fluorine-dNTP, 2'-O-methylated NTP, in particular 2'-fluorine-dCTP, 2'-fluorine-dUTP, 2'-O-methylated CTP, 2'-O-methylated UTP and having a nucleotide sequence which is complementary to a RNA oligonucleotide described in the present invention may be used to inactivate the RNA oligonucleotide and to halt the anti-viral response.

In one embodiment, the pharmaceutical composition further comprises a delivery agent as described previously. The oligonucleotide or precursor thereof or bacterial RNA may also be delivered by physical means as described previously. In another embodiment, the pharmaceutical composition further comprises another agent such as an agent that stabilizes the oligonucleotide or precursor thereof or bacterial RNA as described previously.

In one embodiment, the oligonucleotide or precursor thereof described in the invention or the bacterial RNA is used in combination with at least one agent selected from an immunostimulatory agent which is capable of inducing an anti-viral response, an anti-viral agent and a gene silencing agent. In a further embodiment, the oligonucleotide or precursor thereof described in the invention or the bacterial RNA is used in combination with retinoic acid and/or type I IFN.

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

Use of the Oligonucleotide or Precursor Thereof or Bacterial RNA for Inducing an Anti-Bacterial Response The present application provides the use of the oligonucleotide or precursor thereof described in the invention or a bacterial RNA for the preparation of a pharmaceutical composition for inducing an anti-bacterial response, in particular, a response against intracellular bacteria, in a vertebrate animal, in particular, a mammal.

Intracellular bacteria include, but are not limited to, mycobacteria (tuberculosis), chlamydia, mycoplasma, listeria, and facultative intracellular bacteria such as staphylococcus aureus.

An anti-bacterial response is the response by a cell, tissue or organism upon infection by a bacterium with the purpose of eliminating or incapacitating the bacterium. Typical anti-bacterial responses include, but are not limited to, T cell or NK cell-mediated elimination of the infected cell by either receptor-mediated apoptosis or cytokine-mediated apoptosis via TNF or TRAIL, macorphage or monocytes phagocytosis.

In one embodiment, the anti-bacterial response comprises type I IFN, type II IFN, IL-18 and/or IL-1β production.

An anti-bacterial response, in particular, type I IFN, type II IFN, IL-18, and/or IL-1β production, may be induced in immune cells or non-immune cells. Immune cells include, but are not limited to, peripheral blood mononuclear cells (PBMC), plasmacytoid dendritric cells (PDC), myeloid dendritic cells (MDC), B cells, macrophages, monocytes, natural killer cells, NKT cells, CD4+ T cells, CD8+ T cells, granulocytes. Non-immune cells include, among others, tumor cells, epithelial cells, endothelial cells, and fibroblasts.

The induction of an anti-bacterial response, in particular, type I IFN, type II IFN, IL-18 and/or IL-1β production, may aid the prevention and treatment of various disorders and/or diseases such as tumor, infections, and immune disorders.

In a preferred embodiment, the RNA oligonucleotide is a single-stranded RNA oligonucleotide which does not contain any sequence which is capable of forming any intramolecular or intermolecular double-stranded structure with itself under physiological condition, in particular, physiological condition inside a cell, and the nucleotide sequence of the ssRNA is complementary to a bacterial RNA or a cellular RNA induced by the bacteria in a bacteria-infected cell.

The degree of complementarity is preferably at least 50%, 60%, 70%, more preferably at least 75%, 80%, 85%, 90%, even more preferably at least 95%, 96%, 97%, 98%, 99%, and most preferably 100%.

In one embodiment, the ssRNA olignucleotide has gene silencing activity. In another embodiment, the ssRNA oligonucleotide lacks gene silencing activity.

In one embodiment, the ssRNA oligonucleotide and its complementary strand are delivered separately into cells, preferably in a target cell-specific manner.

In another embodiment, a single-stranded RNA oligonucleotide comprising one or more modifications selected from pseudouridine, 2-thiouridine, 2'-Fluorine-dNTP, 2'-O-methylated NTP, in particular 2'-fluorine-dCTP, 2'-fluorine-dUTP, 2'-O-methylated CTP, 2'-O-methylated UTP and having a nucleotide sequence which is complementary to a RNA oligonucleotide described in the present invention may be used to inactivate the RNA oligonucleotide and to halt the anti-bacterial response.

In one embodiment, the pharmaceutical composition further comprises a delivery agent as described previously. The oligonucleotide or precursor thereof or bacterial RNA may also be delivered by physical means as described previously. In another embodiment, the pharmaceutical composition further comprises another agent such as an agent that stabilizes the oligonucleotide or precursor thereof or bacterial RNA as described previously.

In one embodiment, the oligonucleotide or precursor thereof described in the invention or the bacterial RNA is used in combination with at least one agent selected from an immunostimulatory agent which is capable of inducing an anti-bacterial response, an anti-bacterial agent and a gene silencing agent. In a further embodiment, the oligonucleotide or precursor thereof described in the invention or the bacterial RNA is used in combination with retinoic acid and/or type I IFN.

Vertebrate animals include, but are not limited to, fish, amphibians, birds, and mammals.

Mammals include, but are not limited to, rats, mice, cats, dogs, horses, sheep, cattle, cows, pigs, rabbits, non-human primates, and humans. In a preferred embodiment, the mammal is human.

Use of the Oligonucleotide or Precursor Thereof or Bacterial RNA for Inducing Apoptosis The present application provides the use of the oligonucleotide or precursor thereof described in the invention or a bacterial RNA for the preparation of a pharmaceutical composition for inducing apoptosis in vitro and in vivo, in particular, in a vertebrate animal, in particular, in a mammal.

In a preferred embodiment, the apoptosis is induced in tumor cells.

The induction of apoptosis may be therapeutically beneficial to individuals having diseases/disorders caused by over-proliferation and/or compromised apoptosis of cells, for example, tumor.

Use of the Oligonucleotide or Precursor Thereof or Bacterial RNA for Inducing An Anti-Tumor Response The present application provides the use of the oligonucleotide or precursor thereof described in the invention or a bacterial RNA for the preparation of a pharmaceutical composition for inducing an anti-tumor response in a vertebrate animal, in particular, a mammal.

The tumor may be benign or malignant.

The anti-tumor response comprises type I IFN induction and/or tumor cell apoptosis.

In a preferred embodiment, the RNA oligonucleotide is a single-stranded RNA oligonucleotide which does not contain any sequence which is capable of forming any intramolecular or intermolecular double-stranded structure with itself under physiological condition, in particular, physiological condition inside a cell, and the nucleotide sequence of the ssRNA is complementary to a tumor-specific RNA.

The tumor-specific RNA may be an mRNA of a tumor-specific antigen. The tumor-specific RNA may be an miRNA.

The degree of complementarity is preferably at least 50%, 60%, 70%, more preferably at least 75%, 80%, 85%, 90%, even more preferably at least 95%, 96%, 97%, 98%, 99%, and most preferably 100%.

In one embodiment, the ssRNA olignucleotide has gene silencing activity. In another embodiment, the ssRNA oligonucleotide lacks gene silencing activity.

In one embodiment, the ssRNA oligonucleotide and its complementary strand are delivered separately into cells, preferably in a target cell-specific manner.

In another embodiment, a single-stranded RNA oligonucleotide comprising one or more modifications selected from pseudouridine, 2-thiouridine, 2'-Fluorine-dNTP, 2'-O-methylated NTP, in particular 2'-fluorine-dCTP, 2'-fluorine-dUTP, 2'-O-methylated CTP, 2'-O-methylated UTP and having a nucleotide sequence which is complementary to a RNA oligonucleotide described in the present invention may be used to inactivate the RNA oligonucleotide and to halt the anti-tumor response.

Use of the Oligonucleotide or Precursor Thereof or Bacterial RNA for Treating Diseases/Disorders The present invention provides the use of the oligonucleotide or precursor thereof described in the invention or a bacterial RNA for the preparation of a pharmaceutical composition for preventing and/or treating a disease and/or disorder in a vertebrate animal, in particular, a mammal, in medical and/or veterinary practice.

The disease and/or disorder include, but are not limited to infections, tumor, allergy, multiple sclerosis, and immune disorders.

Infections include, but are not limited to, viral infections, bacterial infections, anthrax, parasitic infections, fungal infections and prion infection.

Viral infections include, but are not limited to, infection by hepatitis C, hepatitis B, herpes simplex virus (HSV), HIV-AIDS, poliovirus, encephalomyocarditis virus (EMCV) and smallpox virus. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus).

In certain embodiments, the viral infections are selected from chronic hepatitis B, chronic hepatitis C, HIV infection, RSV infection, HSV infection, VSV infection, CMV infection, and influenza infection.

In one embodiment, the infection to be prevented and/or treated is upper respiratory tract infections caused by viruses and/or bacteria. In another embodiment, the infection to be prevented and/or treated is bird flu.

Bacterial infections include, but are not limited to, *streptococci, staphylococci, E. coli, pseudomonas*.

In one embodiment, bacterial infection is intracellular bacterial infection. Intracellular bacterial infection refers to infection by intracellular bacteria such as mycobacteria (tuberculosis), chlamydia, mycoplasma, listeria, and facultative intracellular bacteria such as staphylococcus aureus.

Parasitic infections include, but are not limited to, worm infections, in particular, intestinal worm infection.

Tumors include both benign and malignant tumors (i.e., cancer).

Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, cancers are selected from hairy cell leukemia, chronic myelogenous leukemia, cutaneous T-cell leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basaliom, colon carcinoma, cervical dysplasia, and Kaposi's sarcoma (AIDS-related and non-AIDS related).

Allergies include, but are not limited to, respiratory allergies, contact allergies and food allergies.

Immune disorders include, but are not limited to, autoimmune diseases, immunodeficiency, and immunosuppression.

Autoimmune diseases include, but are not limited to, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, automimmune thyroiditis, dermatitis (including atopic dermatitis and eczematous dermatitis), psoriasis, Sjogren's Syndrome, Crohn's disease, apht-hous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency (such as that induced by immunosuppressants used in transplantation and chemotherapeutic agents used for treating cancer), immunosuppression caused by chronic hemodialysis, trauma or surgical procedures.

Immunosuppression includes, but is not limited to, bone marrow suppression by cytotoxic chemotherapy.

In one embodiment, the pharmaceutical composition is a tumor vaccine. The oligonucleotide or precursor thereof described in the invention or the bacterial RNA may induce tumor cell apoptosis through binding to RIG-I, induce type I IFN, IL-18 and/or IL-1β production by the tumor cells, directly and/or indirectly activate effector cells of innate immunity such as NK cells, NKT cells, and γδ cells, and/or directly and/or indirectly inactivate suppressor T cells, thereby leading to tumor cell growth inhibition and/or destruction.

Tumor cells which have been stimulated with an RIG-I ligand, such as the oligonucleotide or precursor thereof described in the present invention or a bacterial RNA, may also be used as a tumor vaccine.

In a preferred embodiment, the RNA oligonucleotide is a single-stranded RNA oligonucleotide which does not contain any sequence which is capable of forming any intramolecular or intermolecular double-stranded structure with itself under physiological condition, in particular, physiological condition inside a cell, and the nucleotide sequence of the ssRNA is complementary to a disease/disorder-related RNA.

In one embodiment, the disease/disorder-related RNA is an mRNA of a disease/disorder-related gene. In another embodiment, the disease/disorder-related RNA is a miRNA. The disease/disorder-related RNA may be a endogenous cellular RNA, a viral RNA, a RNA from an invading microorganism or organism such as a bacterium, a fungus, or a parasite.

The degree of complementarity is preferably at least 50%, 60%, 70%, more preferably at least 75%, 80%, 85%, 90%, even more preferably at least 95%, 96%, 97%, 98%, 99%, and most preferably 100%.

In one embodiment, the ssRNA olignucleotide has gene silencing activity. In another embodiment, the ssRNA oligonucleotide lacks gene silencing activity.

In one embodiment, a single-stranded RNA oligonucleotide comprising one or more modifications selected from pseudouridine, 2-thiouridine, 2'-Fluorine-d NTP, 2'-O-methylated NTP, in particular 2'-fluorine-dCTP, 2'-fluorine-dUTP, 2'-O-methylated CTP, 2'-O-methylated UTP and having a nucleotide sequence which is complementary to ssRNA oligonucleotide may be used to inactivate the ssRNA oligonucleotide and to halt type I IFN induction.

In certain embodiments, the oligonucleotide or precursor thereof described in the invention or the bacterial RNA is used in combination with one or more pharmaceutically active agents such as immunostimulatory agents, anti-viral agents, antibiotics, anti-fungal agents, anti-parasitic agents, anti-tumor agents, cytokines, chemokines, growth factors, anti-angiogenic factors, chemotherapeutic agents, antibodies and gene silencing agents. The more than one pharmaceutically active agents may be of the same or different category.

In preferred embodiments, the oligonucleotide or precursor thereof described in the invention or the bacterial RNA is used in combination with an anti-viral vaccine or an anti-bacterial vaccine or an anti-tumor vaccine, wherein the vaccine can be prophylactic and/or therapeutic.

In other embodiments, the pharmaceutical composition is for use in combination with one or more prophylactic or therapeutic treatments of diseases and/or disorders such as infection, tumor, multiple sclerosis, and immunodeficiency. For example, treatments of cancer include, but are not limited to, surgery, chemotherapy, radiation therapy, neoadjuvant therapy, thermoablation, and cryoablation.

In a further embodiment, the oligonucleotide or precursor thereof described in the present invention or a bacterial RNA is used in combination with retinoic acid and/or type I IFN. Retinoic acid and/or type I IFN are known to upregulate RIG-I expression in most cell types, including for example endothelial cells, epithelial cells, fibroblasts, immune cells and tumor cells.

In one embodiment, the pharmaceutical composition further comprises a delivery agent as described previously. The oligonucleotide or precursor thereof or bacterial RNA may also be delivered by physical means as described previously. In another embodiment, the pharmaceutical composition further comprises another agent such as an agent that stabilizes the oligonucleotide or precursor thereof or bacterial RNA as described previously.

The pharmaceutical composition may be formulated for oral, nasal, ocular, parenteral (including intraveneous, intradermal, intramuscular, intraperitoneal, and subcutaneous), rectal, vaginal or topical (including buccal and sublingual) administration.

In preferred embodiment, the pharmaceutical composition is for prophylactic local (e.g., mucosa, skin) or systemic use. For example, a spray (i.e., aerosol) preparation may be used to strengthen the antiviral capability of the nasal and the pulmonary mucosa.

Vertebrate animals include, but are not limited to, fish, amphibians, birds, and mammals.

Mammals include, but are not limited to, rats, mice, cats, dogs, horses, sheep, cattle, cows, pigs, rabbits, non-human primates, and humans. In a preferred embodiment, the mammal is human.

Use of the Oligonucleotide or Precursor Thereof or Bacterial RNA as an Adjuvant

The prevent invention provides the use of the oligonucleotide or precursor thereof described in the invention or a bacterial RNA in combination with at least one antigen for the preparation of a vaccine for inducing an immune response against the at least one antigen in a vertebrate animal, in particular, a mammal.

The at least one antigen may be a protein, a polypeptide, a peptide, a carbohydrate, a nucleic acid, or a combination thereof.

The at least one antigen is preferably a disease/disorder-associated antigen, against which the generation of an immune response is beneficial for the prevention and/or treatment of the disease/disorder.

The oligonucleotide or precursor thereof or the bacterial RNA may be covalently linked to or non-covalently complexed with the at least one antigen. In one embodiment, the oligonucleotide or precursor thereof or the bacterial RNA is covalently linked to the at least one antigen. In another embodiment, both the oligonucleotide or precursor thereof or the bacterial RNA which is anionic and the protein or peptide antigen which is rendered anionic by N- or C-terminal extension of glutamic acid residues are complexed with cationic polymers. In yet another embodiment, phosphothioates which are incorporated into the oligonucleotide or precursor thereof or the bacterial RNA to increase nuclease resistance complexes with cysteine residues added to the N-terminal of antigenic protein or peptide. In a further embodiment, the at least one antigen can be encoded by a vector, in particular, a viral vector, which also comprises the oligonucleotide or precursor thereof. In yet a further embodiment, the at least one antigen can be a part of a virosome which encapsulates the oligonucleotide or precursor thereof or the bacterial RNA.

The oligonucleotide or precursor thereof or the bacterial RNA and the at least one antigen may also be comprised in separate compositions which are administered simultaneously.

In one embodiment, the vaccine further comprises a delivery agent as described previously. The oligonucleotide or precursor thereof or the bacterial RNA may also be delivered by physical means as described previously. In another embodiment, the pharmaceutical composition further comprises another agent such as an agent that stabilizes the oligonucleotide or precursor thereof or the bacterial RNA as described previously.

Vertebrate animals include, but are not limited to, fish, amphibians, birds, and mammals.

Mammals include, but are not limited to, rats, mice, cats, dogs, horses, sheep, cattle, cows, pigs, rabbits, non-human primates, and humans. In a preferred embodiment, the mammal is human.

In Vitro Method for Stimulating an Anti-Viral and/or Anti-bacterial Response

The present invention provides an in vitro method for stimulating an anti-viral response and/or an anti-bacterial response in a cell, comprising the steps of:
(a) mixing an oligonucleotide or precursor described in the invention or a bacterial RNA with a complexation agent; and
(b) contacting a cell with the mixture of (a), wherein the cell expresses RIG-I and/or components of the inflammasome.

In a preferred embodiment, the anti-viral response or the anti-bacterial response comprises type I IFN, in particular, IFN-α production, type II IFN production, IL-18 production, and/or IL-1β production.

The cells include, but are not limited to, primary immune cells, primary non-immune cells, and cell lines. Immune cells include, but are not limited to, peripheral blood mononuclear cells (PBMC), plasmacytoid dendritic cells (PDC), myeloid dendritic cells (MDC), B cells, macrophages, monocytes, natural killer cells, granulocytes, CD4+ T cells, CD8+ T cells, NKT cells. Non-immune cells include, but are not limited to, fibroblasts, endothelial cells, and epithelial cells. Cell lines include those that endogenously express RIG-I and/or components of the inflammasome and those containing exogenous DNA which directs the expression of RIG-I and/or components of the inflammasome.

In Vitro Method for Stimulating Th1 Cytokine Production

The present invention provides an in vitro method for stimulating the production of a Th1 cytokine in a cell, comprising the steps of:
(a) mixing an oligonucleotide or precursor described in the invention or a bacterial RNA with a complexation agent; and
(b) contacting a cell with the mixture of (a), wherein the cell is capable of producing the Th1 cytokine.

In one embodiment, the cell expresses RIG-I and/or components of the inflammasome.

In a preferred embodiment, the Th1 cytokine is IL-18 or IL-1β.

The cells include, but are not limited to, immune cells and non-immune cells. Immune cells include, but are not limited to, peripheral blood mononuclear cells (PBMC), plasmacytoid dendritric cells (PDC), myeloid dendritic cells (MDC), B cells, macrophages, monocytes, natural killer cells, granulocytes, CD4+ T cells, CD8+ T cells, NKT cells. In a preferred embodiment, the cell is a macrophage. Non-immune cells include, but are not limited to fibroblasts, endothelial cells, and epithelial cells.

Method for Preparing an Oligonucleotide Capable of Inducing an Anti-Viral and/or Anti-Bacterial and/or Anti-Tumor Response The present invention provides a method for preparing an oligonucleotide capable of inducing an anti-viral and/or anti-bacterial response, comprising the steps of:
(a) introducing at least one uncapped 5' phosphate group into an oligonucleotide; and
(b) introducing a nucleotide sequence capable of forming double-stranded structure inside a cell into the oligonucleotide.

The oligonucleotide may be single-stranded, single-stranded comprising a sequence capable of forming a double-stranded structure, or double-stranded. The double-stranded structure may be formed inside a cell by the oligonucleotide itself either intramolecularly or intramolecularly or between a single-stranded oligonucleotide and a RNA molecule of the cell, such as a mRNA or miRNA, which comprises a sequence complementary to the oligonucleotide. The degree of complementarity is preferably at least 50%, 60%, 70%, more preferably at least 75%, 80%, 85%, 90%, even more preferably at least 95%, 96%, 97%, 98%, 99%, and most preferably 100%. The degree of complementarity can be determined by a skilled person using known methods in the art, such as BLAST. In certain embodiments, the number of basepairing within the double-stranded structure is at least 6, 7, 8, 9, preferably at least 10, 11, 12, 13, 14, 15, more preferably at least 16, 17, 18, 19, 20, 21, even more preferably at least 22, 23, 24, 25. Basepairs include both Waston-Crick basepairs and wobble basepairs. Waston-Crick basepairs include A-T, C-G, A-U; wobble basepairs include G-U, I-U, I-A, I-C.

One or more of the following steps may be incorporated into the method for preparing an oligonucleotide capable of inducing an anti-viral and/or anti-bacterial response of the present invention to further enhance the anti-viral and/or anti-bacterial response-inducing activity of the oligonucleotide:
(c) preparing an oligonucletide having adenosine (A) at the 5' end;
(d) preparing an olignucleotide having a sequence selected from AAGU (SEQ ID NO: 205), AAAG (SEQ ID NO: 206), AUGG (SEQ ID NO: 207), AUUA (SEQ ID NO: 208), AACG (SEQ ID NO: 209), AUGA (SEQ ID NO: 210), AGUU (SEQ ID NO: 211), AUUG (SEQ ID NO: 212), AACA (SEQ ID NO: 213), AGAA (SEQ ID NO: 214), AGCA (SEQ ID NO: 215), AACU (SEQ ID NO: 216), AUCG (SEQ ID NO: 217), AGGA (SEQ ID NO: 218), AUCA (SEQ ID NO: 219), AUGC (SEQ ID NO: 220), AGUA (SEQ ID NO: 221), AAGC (SEQ ID NO: 222), AACC (SEQ ID NO: 223), AGGU (SEQ ID NO: 224), AAAC (SEQ ID NO: 225), AUGU (SEQ ID NO: 226), ACUG (SEQ ID NO: 227), ACGA (SEQ ID NO: 228), ACAG (SEQ ID NO: 229), AAGG (SEQ ID NO: 230), ACAU (SEQ ID NO: 231), ACGC (SEQ ID NO: 232), AAAU (SEQ ID NO: 233), ACGG (SEQ ID NO: 234), AUUC (SEQ ID NO: 235), AGUG (SEQ ID NO: 236), ACAA (SEQ ID NO: 237), AUCC (SEQ ID NO: 238), AGUC (SEQ ID NO: 239) at the 5' end; and
(e) incorporating inosine (I) into the oligonucleotide.

In a preferred embodiment, the anti-viral response or the anti-bacterial response comprises type I IFN, in particular, IFN-α production, type II IFN production, IL-18 production, and/or IL-1β production.

Method for Preparing an Oligonucleotide Free of Anti-Viral Response-Inducing Activity and Anti-Bacterial Response-Inducing Activity The present invention also provides a method for preparing an oligonucleotide free of any anti-viral response-inducing activity and anti-bacterial response-inducing activity, comprising one or more of the following steps:
(a) eliminating all 5' phosphate groups from the oligonucleotide;
(b) capping all 5' monophosphate, diphosphate or triphosphate of the oligonucleotide;
(c) eliminating any nucleotide sequence capable of forming double-stranded structure inside a cell from the oligonucleotide; and
(d) incorporating modified nucleotides such as pseudouridine, 2-thiouridine, 2'-Fluorine-dNTPs-2'-O-methylated NTPs, preferably 2'-fluorine-dCTP, 2'-fluorine-dUTP, 2'-O-methylated CTP, 2'-O-methylated UTP, into the oligonucleotide.

Nucleotide sequence capable of forming double-stranded structure inside a cell includes those which allow the formation of a double-stranded structure within the same oligonucleotide (i.e., intramolecular), between two of the same olignucleotides (i.e., intermolecular), or between an oligonucleotide and a RNA (e.g., mRNA, miRNA) in a target cell.

In a preferred embodiment, the anti-viral response or the anti-bacterial response comprises type I IFN, in particular, IFN-α production, type II IFN production, IL-18 production, and/or IL-1β production.

Method for Preparing RNA for Gene Therapy

The present invention provides a method for preparing an RNA for use in gene therapy, comprising the step of eliminating 5' monophosphate, diphosphate or triphosphate from an RNA and/or incorporating modified nucleotides such as pseudouridine, 2-thiouridine, 2'-Fluorine-dNTPs-2'-O-methylated NTPs, preferably 2'-fluorine-dCTP, 2'-fluorine-dUTP, 2'-O-methylated CTP, 2'-O-methylated UTP, into the RNA. The RNA prepared according to the method of the invention lacks immunostimulatory activity and/or capability of inducing an anti-viral response and is therefore suitable for gene transfer in vertebrate cells.

RNA useful in gene therapy include those that upregulate or downregulate the expression/translation of a gene of interest. In the former case, the RNA encodes a protein of interest, the expression of which is of therapeutic value (e.g., a tumor suppressor; the cystic fibrosis protein). In the latter case, the RNA interferes with the expression of a protein of interest, the downregulation of which is of therapeutic value (e.g., an oncogene). In the latter case, the RNA may be an antisense RNA, an siRNA, an shRNA or a miRNA.

The utility of the oligonucleotide or precursor thereof described in the present invention or the bacterial RNA may be extended to other RIG-I ligands.

The present invention is illustrated by the following examples.

EXAMPLES

Material and Methods

Examples 1-10

Cell Culture

Human PBMC were prepared from whole blood donated by young healthy donors by Ficoll-Hypaque density gradient centrifugation (Biochrom, Berlin, Germany). PDC were isolated by MACS using the blood dendritic cell Ag (BCDA)-4 dendritic cell isolation kit from Miltenyi Biotec (Bergisch-Gladbach, Germany). Briefly, PDC were labelled with anti-BDCA-4 Ab coupled to colloidal paramagnetic microbeads and passed through a magnetic separation column twice (LS column, then MS column; Miltenyi Biotec). The purity of isolated PDC (lineage-negative, MHC-II-positive and CD123-positive cells) was above 95%. Before isolation of monocytes, PDC were depleted by MACS (LD column; Miltenyi Biotec) and then monocytes were isolated using the monocyte isolation kit II (Miltenyi Biotec). Murine bone marrow-derived conventional dendritic cells were generated by incubating pooled bone marrow cells in the presence of murine GM-CSF (10 ng/ml; R&D Systems, Minneapolis, Minn.). After 7 days, these cultures typically contained more than 90% cDC (CD11c+, CD11b+, B220−). Viability was above 95%, as determined by trypan blue exclusion. All cells, except PDC (2.5*10$^6$ cells/ml), were cultured at a density of 2*10$^6$ cells/ml in RPMI 1640 culture medium (Biochrom, Berlin, Germany) supplemented with 10% (v/v) FCS (Biochrom), 1.5 mM L-glutamine, 100 U/ml penicillin, and 100 µg/ml streptomycin (all from Sigma-Aldrich, Munich, Germany). PDC cultures were additionally supplemented with 10 ng/ml IL-3 (R&D Systems). HEK 293 cells (human embryonic kidney) were maintained in RPMI 1640 culture medium (Biochrom) supplemented with 10% (v/v) FCS (Biochrom), 1.5 mM L-glutamine, 100 U/ml penicillin, and 100 µg/ml streptomycin (all from Sigma-Aldrich). Vero (African green monkey kidney) and HEK 293T (human embryonic kidney) cells were maintained in Dulbecco's modified Eagle's medium supplemented with antibiotics and 5% or 10% foetal calf serum, respectively. BSR cells were propagated in Glasgow minimal essential medium supplemented with 10% newborn calf serum, phosphate broth, amino acids and antibiotics.

Mice

TLR7, RIG-I and MDA5 deficient mice have been previously described (Hemmi H et al. Nat. Immunol. 3:196, February 2002; Kato H et al., Immunity 23:19, July 2005; Kato H et al. Nature 441(7089):101-105, Apr. 9, 2006). Female wild-type C57BL/6 mice were purchased from Harlan-Winkelmann (Borchen, Germany). Mice were 6-12 weeks of age at the onset of experiments. Animal studies were approved by the local regulatory agency (Regierung von Oberbayern, Munich, Germany).

ELISA

Human IFN-α was assessed in cell culture supernatants using the IFN-α module set (Bender MedSystems, Graz, Austria). The murine IP-10 ELISA was from Biosource (Solingen, Germany), the murine IFN-☐ ELISA was from PBL Biomedical Laboratories (Piscataway, USA). All ELISA procedures were performed, according to manufacturers' recommendations. Murine IFN-α was measured according to the following protocol: monoclonal rat anti-mouse IFN-α (clone RMMA-1) was used as the capture Ab, and polyclonal rabbit anti-mouse IFN-α serum for detection (both PBL Biomedical Laboratories) together with HRP-conjugated donkey anti-rabbit IgG as the secondary reagent (Jackson ImmunoResearch Laboratories). Mouse rIFN-A (PBL Biomedical Laboratories) was used as the standard (IFN-α concentration in IU/ml).

RNAs

Chemically synthesized RNA oligonucleotides were purchased from Eurogentec (Leiden, Belgium). In vitro transcribed RNAs were synthesized using the Silencer siRNA construction Kit (Ambion, Huntingdon, UK) or according to the following protocol: Using partially overlapping single stranded DNA oligonucleotides, a double-stranded DNA template was constructed using Exo$^-$ Klenow (Fermentas). The 2500 nucleotides transcript (FIG. 1) was generated using the control template of the Opti mRNA Kit (Curevac, Tübingen, Germany). Templates larger than 40 by were constructed via PCR using the pBluescript KS as a template (for a detailed list of all in vitro transcription templates see table 1). The obtained templates contained a T7 RNA polymerase consensus promoter followed by the sequence of interest to be transcribed. 20 pmol of the DNA template were incubated with 30 U T7 RNA polymerase, 40 U RNase inhibitor, 0.3 U yeast inorganic pyrophosphatase in a buffer containing 40 mM Tris-HCl pH 8.0, 10 mM DTT, 2 mM spermidine-HCl (Sigma) and 20 mM MgCl$_2$. Capped RNA was transcribed using the Opti mRNA Kit (Curevac). To transcribe nucleoside modified RNAs, uridine-5'-triphosphate was replaced by either pseudouridine-5'-triphosphate or 2-thiouridine-5'-triphosphate (both TriLink, San Diego, USA) during the in vitro transcription reaction. For the incorporation of 2'-O-methylated UTP (Trilink), T7 R&DNA™ Polymerase (Eipcentre, Madison, USA) was used. This polymerase has single-base active-site mutations that allow the incorporation of NTPs with 2'-substituents such as 2'-O-methyl. In vitro transcription was carried out overnight at 37° C. The DNA template was digested using DNase I (Fermentas) and subsequently RNAs were purified using the Roche high pure RNA isolation kit (Roche Applied Science, Mannheim, Germany) with the following modifications: Binding buffer was 2.0 M guanidine thiocyanate in 70% ethanol and wash buffer was substituted by 100 mM NaCl, 4.5 mM EDTA, 10 mM Tris HCl in 70% ethanol. After elution, excess salts and NTPs were removed by passing the RNAs through a Mini Quick Spin™ Oligo Column (Roche). Size and integrity of RNAs was checked via gel electrophoresis.

TABLE 1

A: DNA oligonucleotides for the generation of in vitro transcription templates:

| SEQ ID No. | Name | Sequence | Corr. strand |
|---|---|---|---|
| 84 | AF6.5-35n | CAGTAATACGACTCACTATTAGGGAAGCGGGCA-3' | 1 |
| 82 | GF6.5-35n | 5'-CAGTAATACGACTCACTATAGGGGAAGCGGGCA-3' | 1 |
| 101 | RNA9.2s-0A | 5'-TTGAAGGACAGGTTAAGCTAATAGTGAGTCG-3' | 2 |
| 80 | RNA9.2s-1G | 5'-ATTGAAGGACAGGTTAAGCTATAGTGAGTCGTA-3' | 3 |
| 97 | RNA9.2s-5A | 5'-GGTAATTGAAGGACAGGTTAATAGTGAGTCG-3' | 2 |
| 92 | tri-09-mer | 5'-GGGATCCCCTATAGTGAGTCGTA-3' | 3 |

TABLE 1-continued

A: DNA oligonucleotides for the generation of in vitro transcription templates:

| SEQ ID No. | Name | Sequence | Corr. strand |
|---|---|---|---|
| 96 | tri-12-mer | 5'-GGGTTCATCCCCTATAGTGAGTCGTA-3' | 3 |
| 90 | tri-15-mer | 5'-GGGAAGTTCATCCCCTATAGTGAGTCGTA-3' | 3 |
| 93 | tri-18-mer | 5'-GGGCTGAAGTTCATCCCCTATAGTGAGTCGTA-3' | 3 |
| 91 | tri-21-mer | 5'-GGGACCCTGAAGTTCATCCCCTATAGTGAGTCGTA-3' | 3 |
| 94 | tri-24-mer | 5'-GGGCTGACCCTGAAGTTCATCCCCTATAGTGAGTCGTA-3' | 3 |
| 89 | tri-27-mer | 5'-GGGAAGCTGACCCTGAAGTTCATCCCCTATAGTGAGTCGTA-3' | 3 |
| 73 | tri-G-AC-U-Bio | 5'-AAATGTGTGTGTGTGTGTGCCTGTCTC-3' | 5 |
| 74 | tri-GFPa | 5'-AAGATGAACTTCAGGGTCAGCCCCTATAGTGAGTCGTA-3' | 3 |
| 75 | tri-GFPs | 5'-AAGCTGACCCTGAAGTTCATCCCCTATAGTGAGTCGTA-3' | 3 |
| 102 | tri-Poly A | 5'-TTTTTTTTTTTTTTTTTTTTCCTGTCTC-3' | 5 |
| 95 | tri-Poly C | 5'-GGGGGGGGGGGGGGGGGGGGCCTGTCTC-3' | 5 |
| 85 | tri-Poly G | 5'-CCCCCCCCCCCCCCCCCCCCCCTGTCTC-3' | 5 |
| 71 | tri-Poly T | 5'-AAAAAAAAAAAAAAAAAAAACCTGTCTC-3' | 5 |
| 72 | tri-singleG-24 mer | 5'-AAAGTGTGTGTGTGTGTGTGTCTATAGTGAGTCGTA-3' | 3 |
| 78 | tri-27 + 2s | 5'-AAGTGGTGCAGATGAACTTCAGGGTCAGCTATAGTGAGTCGTA-3' | 3 |
| 76 | tri-27 + 2a | 5'-AAGCTGACCCTGAAGTTCATCTGCACCACTATAGTGAGTCGTA-3' | 2 |
| 98 | tri-27 + 0s | 5'-G GTGCAGATGAACTTCAGGGTCAGCTTAATAGTGAGTCG-3' | 3 |
| 77 | tri-27 + 0a | 5'-AAGCTGACCCTGAAGTTCATCTGCACCTATAGTGAGTCGTA-3' | 3 |
| 202 | RV leader RNA | 5'-ACATTTTTGCTTTGCAATTGACAATGTCTGTTTTTTCTTTGATCTGGTTGTTAAGCGTTATAGTGAGTCGTATTACGCG-3' | 4 |

Corresponding Strands:

| SEQ ID No. | Name | Sequence |
|---|---|---|
| 100 | 1 | 5'-TGATCGGCTATGGCTGGCCGCATGCCCGCTTCC-3' |
| 83 | 2 | 5'-CAGTAATACGACTCACTATTA-3' |
| 99 | 3 | 5'-TAATACGACTCACTATA-3' |
| 203 | 4 | 5'-AATTCGCGTAATACGACTCACTATA-3' |
| — | 5 | Ambion T7 Promoter Primer |

B: PCR primer for the generation of in vitro transcription templates using pBKS as the PCR template Forward Primer:

| SEQ ID No. | Name | Sequence |
|---|---|---|
| 204 | pBKS T7 prom. | 5'-GGATCCTAATACGACTCACTATAGGGCGA-3' |

Backward Primer:

| SEQ ID No. | Name | Sequence |
|---|---|---|
| 81 | pBKS 27-mer | 5'-CACCGCGGTGGAGCTCCAATTCGCCCTAT-3' |
| 88 | pBKS 57-mer | 5'-CGGGGGATCCACTAGTTCT-3' |
| 86 | pBKS 105-mer | 5'-CCTCGAGGTCGACGGTATC-3' |
| 87 | pBKS 204-mer | 5'-CGGATAACAATTTCACACAGGA-3' |
| 79 | pBKS 302-mer | 5'-AGTGAGCGCAACGCAATTA-3' |

RNA Isolation

RNA from *E. coli* strain DH10B and human PBMC was isolated using Trizol® reagent (Invitrogen, Karlsruhe, Germany) according to the manufacturer's protocol. CIAP treatment was performed the following way: 10 µg in vitro transcribed RNA, 15 µg cellular RNA or 1.5 µg viral RNA was treated with 30 U of calf intestine alkaline phosphatase (CIAP) (Stratagene, La Jolla, USA) for 3 hours at 37° C. in a buffer containing 50 mM Tris-HCl, 0.1 mM EDTA in the presence of 10U of RNase inhibitor (RNAguard™; Amersham-Biosciences). Following CIAP treatment, the RNA was cleaned up using the RNeasy Mini kit.

Cell Extracts

Cell lysates were prepared according to Meister et al. (G. Meister et al., *Mol Cell* 15, 185 (Jul. 23, 2004)) with minor modifications. HEK 293 cells were transfected using high molecular weight (25 kDa) polyethylenimine (PEI; Sigma, 40.872-7). At a confluency of 80-90%, cells were transfected with a PEI:DNA ratio of 1.5:1. 24-36 hours after transfection cells were harvested and the cell pellet was resuspended in five pellet volumes of 10 mM KCl, 1.5 mM MgCl2, 0.5 mM dithiothreitol, 10 mM HEPES-NaOH (pH 7.9), 0.5 mM PMSF and incubated for ten minutes on ice. Subsequently cells were washed and the cell pellet was resuspended in two pellet volumes of the buffer described above and homogenized by douncing. The cell nuclei were removed from the cell lysate by centrifugation at 2.000 g for ten minutes. The supernatant was transferred into microcentrifuge tubes and cleared further by centrifugation at 2.000 g for ten minutes and further centrifugation for 30 minutes at 20.000 g to obtain the cytoplasmic extract. The concentration of KCl of the extract was subsequently raised to 100 mM by addition of 2 M KCl and glycerol was added to a percentage of 10%. For purification of FLAG-tagged RIG-IC complexes, cytoplasmic extracts were incubated in FLAG M2 agarose beads (Sigma). FLAG M2 agarose beads were washed once with 0.1 M glycine (pH 3.5) and equilibrated by washing with 1 M Tris-HCl (pH 8.0). The beads were then resuspended in buffer C (0.1 M KCl, 5 mM MgCl2, 10% glycerol, 10% Tween20, 10 mM β-mercaptoethanol, 0.2 mM PMSF, and 20 mM Tris-HCl [pH 8.0]) and incubated with cytoplasmic extracts for four hours at 4° C. with rotation. The beads were collected and washed twice in wash buffer (300 mM NaCl, 5 mM MgCl2, 50 mM Tris-HCl [pH 7.5]) supplemented with 0.1% NP40. Affinity-bound complexes were then eluted by shaking the beads in 0.2 µg/ml 3×FLAG peptide (Sigma) in wash buffer for two hours at 10° C. and after centrifugation the eluate was collected.

Ligand Binding Studies

Whole cell lysate or 25 µl RIG-IC eluate was incubated with 0.375 µg biotinylated RNA in the presence of 40U RNase inhibitor (Fermentas), 0.5 mM PMSF in a final volume of 100 µl in wash buffer for two hours at 4° C. with rotation. 50 µl streptavidin-coated beads (Pierce, Rockford, USA; 20347) were added to the lysate for another hour at room temperature with rotation. Beads were then washed four times with wash buffer supplemented with 0.1% NP40. Supernatant and beads were lysed in Laemli buffer for further immunoblot analysis.

Western Blotting

For Western blotting, samples were separated by SDS-PAGE and transferred to a nitrocellulose membrane (Amersham-Biosciences, UK) by semi-dry electroblotting. As primary antibody, monoclonal anti-Flag antibody (Sigma) was used. As secondary antibody, peroxidase-conjugated anti-mouse antibody (Amersham-Biosciences) was used. Bound antibodies were visualized by enhanced chemiluminescence system (ECL) according to the manufacturer's protocol (Amersham-Biosciences).

Reporter Assays 12-16 hours prior to transfection, HEK 293 cells were seeded in 48-well plates. At a confluency of 80%, HEK 293 cells were transfected using PEI with 300 ng of a reporter plasmid (pIFNβ-luc), 500 ng of a normalisation plasmid (expressing Rous sarcoma virus β-galactosidase) and the indicated expression plasmids giving a total of 1.5 µg DNA/well. 24 hours after transfection culture medium was aspirated and the cells washed once in 0.5 ml PBS containing 10 mM EDTA. Then cells were lysed in 50 µl luciferase lysis buffer (10% glycerol, 1% Triton-X, 2 mM EDTA, 25 mM TrisHCl [pH 7.8], 2 mM DTT). 20 µl of each sample were mixed with 20 µl of Luciferase Detection Reagent (Promega) and analyzed for luciferase activity with a microplate luminometer (LUMIstar, BMGLabtechnologies). To measure beta-galactosidase activity, 10 µl lysate was incubated with 100 µl of solution 1 (1% Galacton-Plus [TROPIX], 0.1% 0.1 M MgCl$_2$, 20% 0.5 M phosphate [pH 8], 78.9% H$_2$O for 20 minutes and then 50 µl of solution 2 was added (20% 1 M NaOH, 10% Emerald [TROPIX] 70% H$_2$O). Luciferase activity values were normalized against beta-galactosidase activity of the same extract. Reporter assays for experiments involving viral infection (FIG. 5) were performed the following way: 12 to 18 hours prior to transfection, HEK 293T or Vero cells were seeded in 24-well plates. At a confluency of 80%, the cells were transfected using Lipofectamine 2000 (Invitrogen) with 400 ng of a reporter plasmid encoding firefly luciferase (p125-Luc) and 2 ng of a plasmid encoding CMV-controlled renilla luciferase (pRL-CMV, Promega) for normalization along with 400 ng of empty vector of RIG-expressing plasmids when indicated. 6 hours after DNA transfection the cells were either infected or transfected with the indicated amounts of RNA using PEI. 48 hours after DNA transfection the cell extracts were prepared and assayed in the Dual Luciferase Reporter System (Promega). Luciferase activity was measured in a Luminometer (Berthold) according to the supplier's instructions.

Plasmids pIFN-beta-Luc was kindly provided by T. Maniatis. RIG-I CARD2 was kindly provided by S. Rothenfusser. p125-Luc, RIG-I full, RIG-IC, RIG-I K270A and the empty control vector were kindly provided by T. Fujita (M. Yoneyama et al., Nat Immunol 5, 730 (July 2004)). RIG-I ΔHelicase_C (AS 655-734) was constructed from RIG-I full via loop out PCR using the following PCR primer pair: 5'-ACTGAGTTTAG-GATTTCCTTCAATCC-3' (SEQ ID NO: 326), 5'-GGTAG-CAAGTGCTTCCTTCTGA-3' (SEQ ID NO: 327). pSC6-T7-NEO was kindly provided by M. Billeter F. (Radecke et al., Embo J 14, 5773 (Dec. 1, 1995)). T7 D812N was constructed from pSC6-T7-NEO via site directed mutagenesis using the following PCR primer pair: 5'-GCACTGAT-TCACGCCTCCTTCGGTACC-3' (SEQ ID NO: 328), 5'-GGTACCGAAGGAGGCGTGAATCAGTGC-3' (SEQ ID NO: 329). RIG-I ΔHelicase_C and T7 RNA D812N were confirmed by sequencing.

Virus Stocks

Recombinant RV SAD L16 (Schnell M J et al., 1994, EMBO J. 13(18):4195-4203) was used as wt RV. Cloning of cDNA, recovery of recombinant SAD ΔPLP virus, which encodes P from the most promoter-distal gene position, and virus propagation, was described previously (K. Brzozka, et al. Journal of virology 79, 7673 (June 2005)).

For isolation of total RNA from non-infected cells or from cells infected with RV at MOI of 1 for 2 days, the RNeasy minikit (QIAGEN, Hilden, Germany) was used according to manufacturer's instructions. For isolation of RV particle RNA, virions were pelleted from cell-free supernatants by ultracentrifugation in SW32Ti for 2 h at 4° C. and 27,000 rpm. RNA was isolated from pellets with the RNeasy minikit.

Examples 11-16

Media and Reagents

RPMI 1640 (Biochrom) supplemented with 10% (v/v) heat-inactivated FCS (Invitrogen Life Technologies), 3 mM L-glutamine, 0.01 M HEPES, 100 U/ml penicillin, and 100 µg/ml streptomycin (all from Sigma-Aldrich) and Dulbecco's modified Eagle's medium (PAN, Aidenbach, Germany) supplemented with 10% fetal calf serum (FCS), 3 mM L-glutamine, 100 U/ml penicillin and 100 µg/ml streptomycin was used. CpG ODNs (Coley Pharmaceutical Group) show small letters, phosphorothioate (PT) linkage and capital letters, phosphodiester (PD) linkage 3' of the base; CpG-A-ODN 2216 (5'-ggGGGACGATCGTCggggG-3') (SEQ ID NO: 330), CpG-B ODN 1826 (5'-TCCATGACGTTCCT-GACGTT-3') (SEQ ID NO: 331). Polyinosinic:polycytidylic acid (poly(I:C)) was purchased from Sigma-Aldrich. For depletion of NK cells and CD8 T cells, the IL-2 receptor-1 chain-specific mAb TMβ1 and mAb RmCD8-2 were used as described (kind gift of Ralph Mocikat, GSF-Institut für Molekulare Immunologie, Munich, Germany). Recombinant murine IFNβ was purchased at Europa Bioproducts LTD. In vivo-jetPEI™ (#201-50) was purchased at Biomol GmbH (Hamburg, Germany).

RNAs

Chemically synthesized RNA oligonucleotides were purchased from Eurogentec (Leiden, Belgium) or MWG-BIO-TECH AG (Ebersberg, Germany) (for a detailed list of all chemically synthesized RNA oligonucleotides see Table 3). In vitro transcribed RNAs were synthesized according to the manufacturers instruction's using the megashort script kit (Ambion, Huntingdon, UK) (for a detailed list of all in vitro transcription templates see Table 4). The obtained templates contained a T7 RNA Polymerase consensus promoter followed by the sequence of interest to be transcribed. For generation of in vitro transcribed double-stranded RNA the DNA templates of the sense and anti-sense strands were transcribed for 6 hours in separate reactions. An extra G was added to both the sense and the anti-sense strands in order to transcribe with T7 RNA polymerase. The reactions were then mixed and the combined reaction was incubated overnight at 37° C. The DNA template was digested using DNAse-I (Ambion) and subsequently RNAs were purified using phenol:chloroform extraction and alcohol precipitation. After elution, excess salts and NTPs were removed by passing the RNAs through a Mini Quick Spin™ Oligo Column (Roche). Integrity of RNAs was checked via gel electrophoresis.

Cells

Flt3-Ligand (Flt3-L) induced mixed cultures of murine myeloid and plasmacytoid dendritic cells were grown as described (3). Plasmacytoid DC from FLT-3 ligand induced bone marrow cultures were sorted with B220 microbeads (Miltenyi Biotec). Conventional dendritic cells (cDCs) were generated by incubating pooled bone marrow cells in the presence of murine GM-CSF (10 ng/ml; R&D Systems, Minneapolis, Minn.). After 7 days, these cultures typically contained more than 80% cDC (CD11c+, CD11b+, B220−). For some experiments B cells were isolated from spleens of wild-type mice by MACS using the mouse B cell isolation kit and CD19 microbeads (Milteny Biotec). Untouched NK cells and CD 8 T cells were sorted from spleens using the NK cell isolation and the CD8 T Cell Isolation Kit (Mileny Biotec). Viability of all cells was above 95%, as determined by trypan blue exclusion and purity was >90% as analyzed by FACS. Murine primary cells were cultivated in RPMI (PAN, Aidenbach, Germany) supplemented with 10% fetal calf serum (FCS), 4 mM L-glutamine and 10-5 M mercaptoethanol. Murine B16 cells (H-2b) were a kind gift of Thomas Tüting and cultivated in Dulbecco's modified Eagle's medium (PAN, Aidenbach, Germany) supplemented with 10% fetal calf serum (FCS), 2 mM L-glutamine, 100 U/ml penicillin and 100 µg/ml streptomycin.

Cell Culture

All cells were cultured at a density of $2*10^6$ cells/ml and seeded in 24-well flat-bottom plates, respectively. If not indicated otherwise, cells were incubated for 24 hours with 3 µg/ml CpG-B-DN 1826 and/or CpG-ODN 2216, 1 µM R848. RNAs were transfected with Lipofectamine 2000 according to the manufacturer's protocol (Invitrogen). If not indicated otherwise, we transfected 200 ng of nucleic acid with 0.5 µl of Lipofectamine. After 24 h the supernatants were collected for analysis of cytokine secretion by enzyme-linked immunosorbent assay (ELISA), and cells were harvested for flow cytometric analysis.

Cytokine Measurement

Concentrations of murine IFN-γ and IL-12p40 in the culture supernatants and sera were determined by ELISA according to the manufacture's instructions (BD PharMingen, San Diego, Calif.). Murine IFN-α was analysed using the mouse IFN-α ELISA kit (PBL Biomedical Laboratories, PBL #42100-2, New Brunswick, N.J.). For some experiments, murine IFN-α was measured according to the following protocol: monoclonal rat anti-mouse IFN-α (clone RMMA-1) was used as the capture Ab, and polyclonal rabbit anti-mouse IFN-α serum for detection (both PBL Biomedical Laboratories) together with HRP-conjugated donkey anti-rabbit IgG as the secondary reagent (Jackson ImmunoResearch Laboratories). Mouse rIFN-α (PBL Biomedical Laboratories) was used as the standard (IFN-α concentration in IU/ml).

Transfection and Reporter Assay

For monitoring transient IFN-β activation by 5'triphosphate siRNA murine B16 cells were seeded in 24-well plates. At a confluency of 70%, B16 cells were transfected using PEI with 200 ng of a reporter plasmid (pIFNβ-luc DAM/DCM), 200 ng of a normalisation plasmid (expressing Renilla-Luc) and the indicated expression plasmids giving a total of 1.5 µg DNA/well. B16 cells were transfected using high molecular weight (25 kDa) polyethylenimine (PEI; Sigma, 40.872-7) with a PEI:DNA ratio of 1.5:1. In some experiments we used Lipofectamine 2000 (Invitrogen) for cotransfection of synthetic siRNAs with the indicated expression plasmids according to the manufacturer's protocol. 16 hours after transfection culture medium was aspirated, the cells were washed once in 0.5 ml PBS and then stimulated with different ligands for the indicated time points. The supernatant was collected and the cells were washed again in 0.5 ml PBS containing 10 mM EDTA. Then cells were lysed in 100 µl of Promega lysis buffer (Promega, #1531). 20 µl of each sample were mixed with 20 µl of Luciferase Detection Reagent (Luciferase Assay Kit, Biozym Scientific GmbH, Oldendorf, Germany) and analyzed for luciferase activity with a microplate luminometer (LUMIstar, BMGLabtechnologies). To measure Renilla luciferase activity, 20 µl lysate was incubated with 20 µl of Renilla substrate (Coelenterazine (Promega, #2001). Luciferase activity values were normalized against Renilla activity of the same extract.

Plasmids

IFN-β-Luc reporter plasmids, wild-type pPME-myc NS3-4A (NS3-4A), pPME-myc MutNS3-4A (NS3-4A*; containing an inactivating Serin 139 to Ala mutation) were kindly provided by T. Maniatis and J. Chen. RIG-I full, RIG-IC, RIG-I K270A and the empty control vector were kindly provided by T. Fujita (Yoneyama M et al. (2004) Nat. Immunol. 5(7):730-737). The renilla-luciferase transfection efficiency vector (phRLTK) was purchased from Promega.

Western Blotting

For Western blotting, samples were separated by SDS-PAGE and transferred to a nitrocellulose membrane (Amersham-Biosciences, UK) by semi-dry electroblotting. As primary antibody polyclonal rat anti-RIG-I (kind gift of Dr. Kremer), polyclonal rabbit anti-Bcl-2 (Santa Cruz, sc-7382) and rabbit anti-caspase-1 (Santa Cruz, sc-7148) antibody were used. As secondary antibody, peroxidase-conjugated anti-mouse or anti-rabbit antibody (Amersham-Biosciences) were used. Bound antibodies were visualized by enhanced chemiluminescence system (ECL) according to the manufacturer's protocol (Amersham-Biosciences).

Flow Cytometry

At the time points indicated, surface antigen staining was performed as described previously. Fluorescence-labelled monoclonal antibodies (mAbs) against B220, CD11c, NK1.1, CD4, CD8, CD69, CD86 and appropriate isotype control antibodies were purchased from BD Pharmingen (Heidelberg, Germany). Flow cytometric data were acquired on a Becton Dickinson FACSCalibur equipped with 2 lasers (excitation at 488- and 635-nm wavelength). Data were analyzed using Cellquest software (Becton Dickinson, Heidelberg, Germany). To determine Bcl-2 Expression of B16 melanoma cells in metastatic lungs single cell suspensions were prepared from lung metastases of IFNAR-deficient mice. Cells were fixed and permabilized using 2% PFA and Saponin and incubated with a specific unconjugated rabbit-TRP-1 Ab (kind gift of Thomas Tüting) for 20 min on ice. Then cells were washed and incubated with goat anti-rabbit FITC Ab (Santa Cruz; sc-2012) for 20 min. Again cells were washed and PE-conjugated Bcl-2-Ab (Santa Cruz, sc-7382-PE) was added to the cells. After 20 min of incubation cells were analysed by flow cytometry.

Quantification of Apoptotic and Dead Cells

Adherent and supernatant cells were analyzed by staining with FITC-labelled Annexin-V (Roche) and propidium iodide (BD Biosciences). Annexin-V staining was performed according to the manufacturer's instructions. Propidium iodide was added to a final concentration of 0.5 mg/ml and cells were analyzed by flow cytometry and CellQuest software (Becton Dickinson, Heidelberg, Germany).

Confocal Microscopy

C57BL/6 mice were injected intravenously with FITC labelled RNA (100 µg) complexed to jetPEI (Biomol). After 6 h mice were sacrificed and the desired organs were analysed for uptake of the RNA complexes. Briefly, sections of metastatic lungs or non-diseased lungs were transferred on microscope slides and fixed in acetone for 10 min. Nuclear counterstaining was performed using TOPRO-3 (Molecular Probes). Washing steps were done in Tris-buffered saline and cells were mounted in Vectarshield Mounting Medium (Vector Laboratories). Cells were then analysed using a Zeiss LSM510 confocal mircroscope (Carl Zeiss, Germany) equipped with 488 nm-Argon and 633 nm-Helium-Neon lasers.

Mice

RIG-I-, MDA-5-, TLR7-deficient mice were established as described (Kato et al. (2006) Nature 441:101; Akira S et al. (2004) C R Biol. 327(6):581-9). IFNAR-deficient mice were a kind gift of Ulrich Kalinke. Female C57BL/6 mice were purchased from Harlan-Winkelmann (Borchen, Germany). Mice were 6-12 weeks of age at the onset of experiments. Animal studies were approved by the local regulatory agency (Regierung von Oberbayern, Munich, Germany).

Mouse Studies

For in vivo studies, we injected C57BL/6 mice with 200 µl containing nucleic acids with prior jetPEI-complexation according to the manufacturer's protocol. Briefly, 10 µl of in vivo jetPEI was mixed with 50 µg of nucleic acids at a N:P ration of 10/1 in 5% Glucose solution and incubated for 15 min. Subsequently, the complexes were injected in the retro-orbital vein. Serum was collected after 6 h unless indicated otherwise. Whole blood was obtained by tail clipping at the indicated time points. Serum was prepared from whole blood by coagulation for 30 min at 37° C. and subsequent centrifugation and stored at −20° C. Cytokine levels were determined by ELISA.

Engraftment of B16 Melanoma in the Lungs and Depletion of CD8 T Cells and NK Cells In Vivo For the induction of lung metastases we injected $4 \times 10^5$ B16 melanoma cells into the tail vein of the indicated mice. On day 3, 6 and 9 we injected the mice with 200 µl containing nucleic acids (50 µg each) with prior jetPEI-complexation as described. Subsequently, the complexes were injected in the retro-orbital vein. 14 days after challenge the number of macroscopically visible melanoma metastases on the surface of the lungs was counted with the help of a dissecting microscope or, in case of massive tumor load, lung weight was determined. Depletion of NK cells and CD8 T cells was performed as described {Adam, 2005 #49; Mocikat, 2003 #50}. Briefly, TMβ1 mAb was given intraperitoneally 4 days (1 mg) before and 2 (0.2 mg) and 14 (0.1 mg) days after tumor challenge. To neutralize CD8 T cells, the mAb RmCD8-2 was injected intraperitoneally one (0.5 mg) and four days (0.1 mg)

before and 4 (0.1 mg) and 14 (0.1 mg) days after tumor inoculation. Experiments were done in groups of four to five mice and repeated two to four times.

Histopatholoqic Analyses

Samples of lungs were obtained when mice were sacrificed. Tissue specimens were fixed in absolute ethanol and embedded in paraffin. Apoptosis was detected by the transferase-mediated dUTP nick end-labeling (TUNEL) method according to the manufacturer's instructions (Boehringer Roche, Mannheim, Germany). Briefly, deparaffinized and rehydrated sections were incubated for 1 h at 37° C. with tailing mix containing 1× tailing buffer, 1 mM CoCl_2, 1 μl of 10×DIG DNA labeling mix and 200 units of terminal transferase (double dist. water added to a total volume of 50 μl). After washing in trisbuffered saline, sections were incubated for 1 h at room temperature with an alkaline phosphatase-conjugated antidigoxigenin antibody (diluted 1:250 in 10% fetal calf serum). The reaction was visualized with nitro blue tetrazolium/5-bromo-4-chloro-3-indolyl phosphate.

Example 1

In Vitro Transcribed RNA Stimulates IFN-α Production in Human Primary Monocytes

Figure 1:
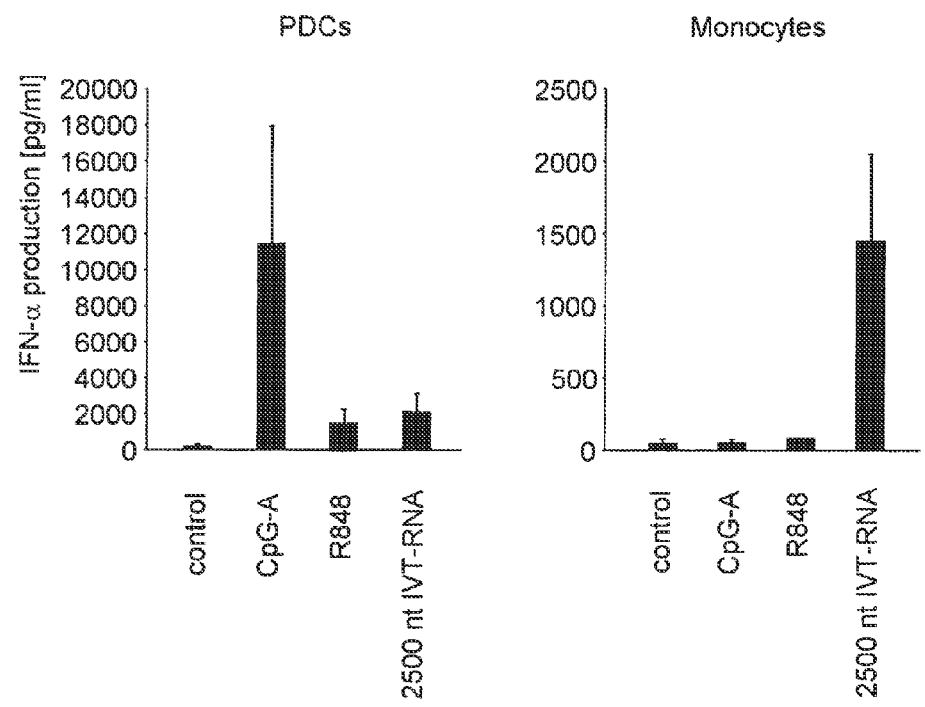
FIG. 1: In vitro transcribed RNA induces a potent IFN-α response in human monocytes (A) PDC and monocytes were plated in 96-well plates and transfected with 200 ng in vitro transcribed RNA (2500 nucleotides). CpG-A (3 µg/ml) and R848 (10 µM) were used as control stimuli for TLR9- or TLR7-mediated IFN-α induction in PDC. Supernatant was harvested 24 hours after stimulation and IFN-α production was assessed via ELISA. Data of two independent donors were summarized and are depicted as mean values±SEM.
Figure 1:
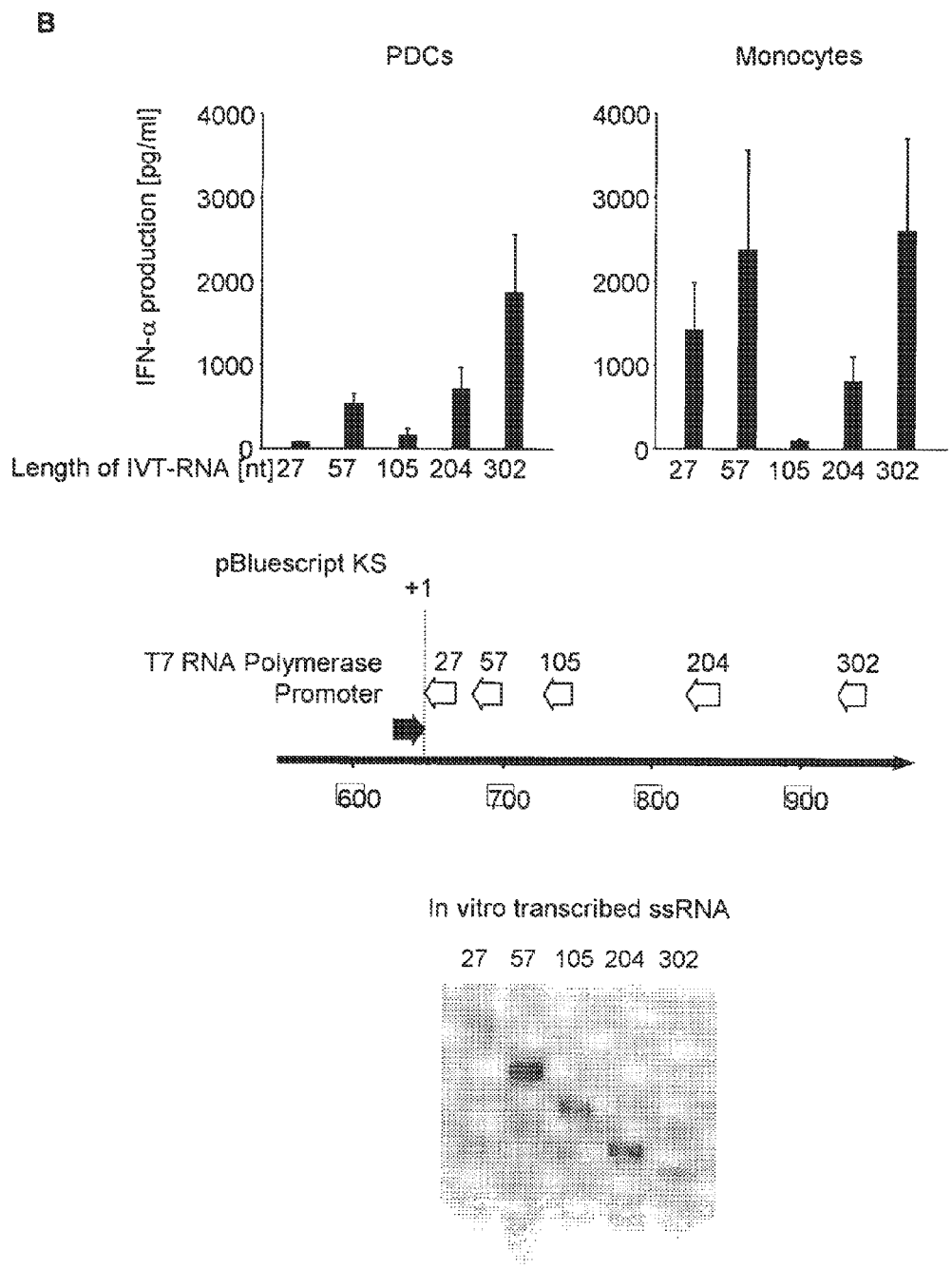
Figure 1:
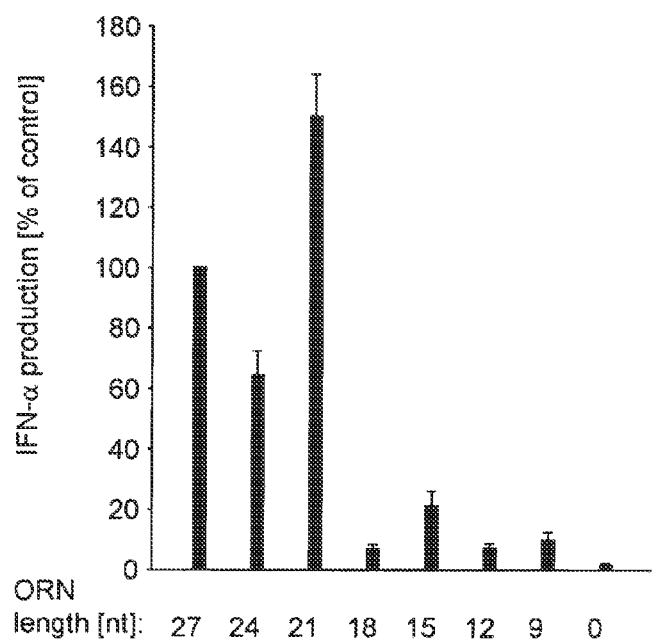
Figure 1:
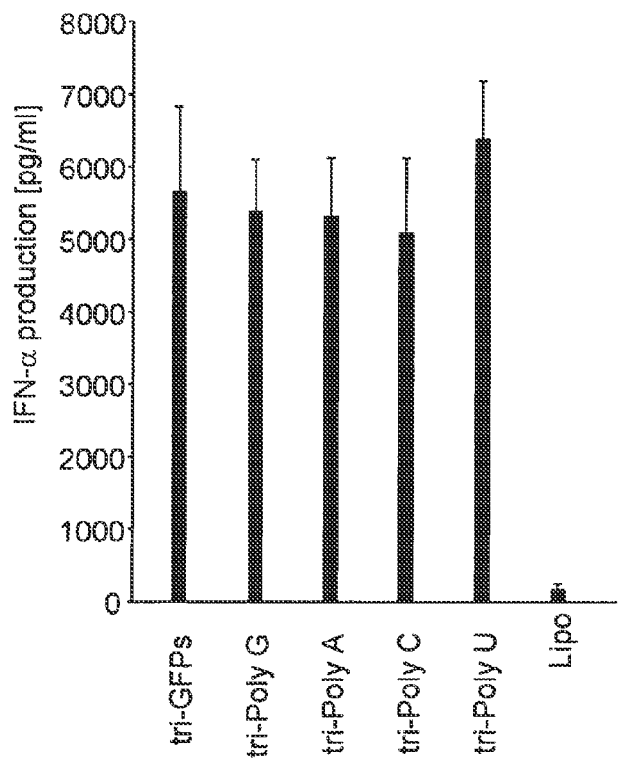

IFN-α production in the human immune system is thought to be largely confined to PDC. IFN-α production in human primary monocytes has not been reported so far. As demonstrated in previous studies (V. Hornung et al., *J Immunol* 168, 4531 (May 1, 2002); I. B. Bekeredjian-Ding et al., *J Immunol* 174, 4043 (Apr. 1, 2005)), monocytes express TLR2, TLR4, TLR6 and TLR8 but no TLR3, TLR7 or TLR9, and produce IL-6 in response to TLR2/6- TLR4- and TLR8-ligands but not to TLR3-, TLR7- or TLR9-ligands (I. B. Bekeredjian-Ding et al., *J Immunol* 174, 4043 (Apr. 1, 2005)). Monocytes failed to produce IFN-α upon stimulation with all TLR ligands tested including CpG-A ODN 2216 (A. Krug et al., *Eur J Immunol* 31, 2154 (July 2001)) and R848, both of which induce IFN-α in PDC (FIG. 1 and data not shown). We hypothesized that motif patterns or sequences in RNA may exist in long RNA molecules that induce IFN-α in monocytes.

In vitro transcription was used to generate long ssRNA molecules as chemical synthesis is impracticable to generate ssRNA larger than 100 nucleotides. RNA transcripts were transfected in monocytes and PDC and IFN-α production was assessed by ELISA.

The present inventors found that a 2500-nucleotide long RNA molecule, but not the TLR9 ligand CpG-A ODN 2216 or the TLR7/8 ligand R848, stimulated a strong IFN-α response in primary human monocytes (FIG. 1A).

The templates that were used to generate the set of ssRNA molecules of different lengths (27-302 nucleotides) were identical at the 5' end, whereas the 3' end was gradually shortened. As a consequence, this set of ssRNA molecules was identical in sequence at the 5' end. IFN-a induction in monocytes was also seen when in vitro transcribed RNA molecules of different length (from 27 nucleotides to 302 nucleotides) were used (FIG. 1B).

Next, whether the length of the 3' sequence impacts on the IFN-α-inducing activity of 5' phosphate RNA was tested. 5' triphosphate RNA oligonucleotides ranging from 27 to 9 nucleotides were generated by the gradual shortening (in steps of three nucleotides) of a 27-mer oligonucleotide from the 3' end. Whereas RNA oligonucleoties 27, 24 and 21 nucleotides in length were potent inducers of IFN-α in monocytes, a sharp drop of activity was observed for shorter sequences (FIG. 1C). This suggested that in vitro transcribed RNA had to have a minimal length of 21 bases to induce IFN-α in monocytes.

Since the results presented in FIG. 1B may be interpreted to suggest that the 3' sequence may influence the IFN-α inducing activity of 5' triphosphate RNA, 31-mer (i.e., 31-nucleotide long) 5' triphosphate RNA oligonucleotides were generated in which the 3' sequence (21 nucleotides) was either a poly G (tri-poly G), a poly A (tri-poly A), a poly C (tri-poly C) or a poly U (tri-poly U) homopolymer. The ten bases at the 5' end were identical for these oligonucleotides. All four RNA oligonucleotides turned out to be equally potent in terms of IFN-α induction in monocytes (FIG. 1D).

These results indicated that a minimal length is required for the 5' triphosphate RNA to be recognized. Although these results suggested that the 3' sequence of in vitro transcribed RNA oligonucleotides had no strong impact on the IFN-α-inducing activity, data with larger RNA molecules (FIG. 1B) pointed to a possible influence of secondary structure formation.

Furthermore, these results indicated that a molecular characteristic shared by all in vitro transcribed RNA molecules rather than a specific sequence motif is responsible for IFN-α induction in monocytes.

Example 2

The 5' Triphosphate Moiety of In Vitro Transcribed RNA is Required for IFN-α Induction in Human Primary Monocytes In general, for in vitro transcription of RNA, the bacteriophage T7 DNA-dependent RNA polymerase is used. Unlike synthetic RNA or eukaryotic mRNA, RNA generated by T7 RNA polymerase contains an uncapped triphosphate group at the 5' end of the RNA molecule.

To study the sequence-independent contribution of the 5' triphosphate, IFN-α induction by a synthetic and an in vitro transcribed version of an immunostimulatory ssRNA oligonucleotide 9.2s (isRNA9.2s, 19 nucleotides) was compared. isRNA9.2s was identified as a potent stimulus for IFN-α production in PDC in previous studies (V. Hornung et al., *Nat Med* 11, 263 (March 2005)).

Only the in vitro transcribed version of isRNA9.2s, but not synthetic isRNA9.2s, strongly induced IFN-α production in monocytes (FIG. 2A upper panel). This difference in IFN-α inducing activity was not due to different transfection efficiency (FIG. 7). In contrast to monocytes, PDC produced IFN-α in response to both in vitro transcribed and synthetic isRNA9.2s (FIG. 2A lower panel).

Next, in vitro transcription was used to generate a dsRNA oligonucleotide with an overhang of one nucleotide at the 5' position. The two single-stranded oligonucleotides (tri-GFPs, tri-GFPa) and the double-stranded oligonucleotide (tri-GFPds) induced comparable levels of IFN-α in monocytes (FIG. 2B). Cleavage of the 5' overhang (including the 5'triphosphate) of the dsRNA (tri-GFPds) by RNAse T1, an endoribonuclease that specifically degrades single-stranded RNA at G residues, completely abolished the IFN-α inducing activity (FIG. 2B). Moreover, when calf intestine alkaline phosphatase (CIAP) was used to dephosphorylate the 5' end of the in vitro transcribed single-stranded RNA oligonucleotides, a complete abrogation of the IFN-α response was observed in monocytes (FIG. 2C). In contrast, PDCs, which are known to detect single-stranded RNA oligonucleotides via TLR7, showed no decrease in IFN-α production when oligonucleotides were dephosphorylated (FIG. 2C).

Unlike the oligonucleotide with a guanosine-5'-triphosphate, in vitro transcribed RNA generated to contain a guanosine-5'-diphosphate, a guanosine-5'-monophosphate or a guanosine-5'-hydroxyl did not induce IFN-α in monocytes (FIG. 8).

Together, these data indicated that the 5'triphosphate is responsible for the IFN-α inducing activity of in vitro transcribed RNA in monocytes, and that a 5' triphosphate confers IFN-α-inducing activity to both ssRNA and dsRNA.

Example 3

7-methyl-guanosine Capping and Eukaryote-Specific Base Modifications Abolish IFN-α Induction Via 5' Triphosphate RNA In eukaryotic cells, 7'methyl-guanosine is attached to the 5' triphosphate of a nascent mRNA transcript by a process called capping. Capping improves the stability of eukaryotic RNA against nucleases and enhances binding of ribosomal proteins to mRNA.

The influence of capping on the IFN-α inducing activity of 5' triphosphate RNA was examined. Capped RNA can be generated via in vitro transcription by including a synthetic cap analog, N-7 methyl GpppG, in the in vitro transcription reaction. Since both N-7 methyl GpppG and GTP (typically in a 4:1 mixture of N-7 methyl GpppG:GTP) need to be present during in vitro transcription and both are incorporated by T7 RNA polymerase, approximately 80% of all transcripts are capped after in vitro transcription. It was found that RNA of different lengths transcribed in the presence of the synthetic cap analog, which contained approximately 20% uncapped and 80% capped RNA, was much less active at inducing IFN-α production in monocytes when compared to uncapped in vitro transcribed RNA (100% uncapped) (FIG. 3A).

Besides 5' capping, eukaryotic RNA undergoes several other posttranscriptional maturation steps including the modification of various nucleosides of the RNA transcript and the methylation of the backbone ribose at the 2'-hydroxyl position. In this respect, it has been previously shown that the incorporation of nucleoside modifications that are abundant in matured eukaryotic, but not in prokaryotic or viral RNA can lead to the complete abrogation of a RNA-triggered inflammatory response mediated via the TLR-system (K. Kariko, et al. Immunity 23, 165 (August 2005). To test whether this phenomenon holds also true for 5' triphosphate RNA triggered IFN-α response, RNA oligonucleotides were generated via in vitro transcription with various NTPs substituted with the respective nucleoside- or ribose-modified NTPs.

A significant decrease in IFN-α production was seen when either pseudouridine (ψ) or 2-thiouridine (s2U) substituted for uridine (U) (FIG. 3B). Analogous results were obtained when 2'-O-methylated UTP was incorporated into the 5' triphosphate RNA oligonucleotides instead of UTP (FIG. 3C). In accordance with these results, transfection of prokaryotic RNA that lacks 5' caps and is low in the respective nucleoside and ribose modifications resulted in a strong IFN-α response in monocytes, whereas eukaryotic RNA was completely inactive in terms of IFN-α induction (FIG. 9).

Lipopolysaccharide (LPS) alone or in combination with synthetic RNA did not contribute to IFN-α production in monocytes (FIG. 9).

Structural features like the presence of a two-nucleotide 3' overhang in a 5' triphosphate RNA duplex, as it occurs in natural cleavage products of the endonuclease dicer, did not interfere with the immunostimulatory activity of the 5' triphosphate RNA oligonucleotides (FIG. 10).

Altogether, these results indicated that posttranscriptional modifications commonly found in mature eukaryotic RNA species suppress the immunostimulatory activity of 5' triphosphate RNA oligonucleotides, thereby providing molecular structures that can be employed for the distinction of self and non-self RNA.

Example 4

IFN-α Induction by 5"Triphosphate RNA Oligonucleotides is Independent of Endosomal maturation Among the family of TLRs, TLR3, TLR7, TLR8 and TLR9 are known to detect nucleic acids. A number of studies suggest that single-stranded RNA is recognized via TLR7 and TLR8, both located in the endosomal membrane. Similar to CpG-DNA, recognition of single-stranded RNA by TLR7/8 can be blocked by chloroquine, which inhibits endosomal maturation. The present inventors found that in PBMC, increasing concentrations of chloroquine inhibited IFN-α induction by CpG-A but not by 5'triphosphate RNA (FIG. 12A); furthermore, chloroquine did not affect 5' triphosphate RNA induced IFN-α production in isolated monocytes (FIG. 12B). CpG-A is inactive in monocytes with and without chloroquine due to the lack of TLR9 (FIG. 12B).

In analogy to the human system, murine bone marrow cells and myeloid dendritic cells produced vast amounts of IFN-α upon transfection with 5'triphosphate RNA. IFN-α and IP-10 induction in bone marrow-derived myeloid dendritic cells from TLR7−/− mice (FIG. 12C) or LPS2 −/− mice (data not shown) was comparable to the level of IFN-α induction in wild type mice.

Altogether these data suggested that the recognition of 5'triphosphate RNA does not require endosomal maturation, and that TLR3, TLR7/8 or TLR9 are not involved.

Example 5

Type I IFN Induction by Exogenous and Endogenous 5' Triphosphate RNA Requires RIG-I But Not MDA5

In previous studies we found that TLR7-mediated recognition of synthetic immunostimulatory RNA requires complexation with a cationic polymer which enables endosomal delivery and confers protection against nuclease degradation, but not transfection of RNA into the cytosol. In contrast to synthetic isRNA, 5' triphosphate RNA induced IFN-α in monocytes only when transfected into the cytosol by cationic lipids, whereas complexation with cationic peptides was not sufficient (data not shown). Consistent with these observations, 5' triphosphate RNA mediated IFN-α induction required neither endosomal maturation nor TLR7 (FIG. 11) or TLR3 (data not shown). These results indicated that the receptor for 5' triphosphate RNA is located in the cytosol and not in the endosomal compartment.

RIG-I and MDA-5 are cytoplasmic proteins involved in the recognition of RNA viruses (H. Kato et al., Nature 441, 101 (Apr. 9, 2006)); both RIG-I and MDA-5 are thought to be involved in dsRNA recognition. Although 5' triphosphate RNA in the present invention was active as ssRNA, it remained to be determined whether RIG-I or MDA-5 are involved in 5' triphosphate recognition.

In order to address the effect of dominant negative mutants of RIG-I, HEK 293 cells expressing the reporter luciferase under the control of the IFN-β promoter were used instead of monocytes. As expected, HEK 293 cells transiently transfected with RIG-I did not respond to poly(I:C) or synthetic isRNA (RNA9.2s) (FIG. 4A). However, unexpectedly, single-stranded 5' triphosphate RNA (tri-GFPs and tri-GFPa) strongly activated reporter expression in RIG-I expressing HEK 293 cells. Only HEK 293 cells expressing full length RIG-I responded to 5'triphosphate RNA; HEK293 cells expressing truncated RIG-I which lacked the N terminal CARD domain or RIG-I 270KA mutant devoid of the ATPase activity did not.

To confirm that RIG-I was required for the recognition of 5' triphosphate RNA, the activity of 5' triphosphate RNA in RIG-I-/- MEFs was tested. Whereas wild type MEFs produced large amounts of IFN-β (FIG. 4B) and IL-6 (data not shown) in response to 5' triphosphate RNA stimulation, no response was detected in RIG-I-- MEFs (FIG. 4B). The response to 5' triphosphate RNA in MDA-5 -/- MEFs was similar to wild type MEFs.

Together, these data provided evidence that RIG-I, but not MDA-5, is required for the recognition of 5' triphosphate RNA and that the recognition of 5' triphosphate RNA is not confined to immune cells such as primary monocytes.

It is hypothesized that since 5' triphosphate RNA is recognized via RIG-I, the formation of endogenous 5' triphosphate RNA via cytoplasmic overexpression of T7 RNA polymerase should trigger the type I IFN pathway. To test this hypothesis, a system, which has been extensively used to generate recombinant negative strand RNA viruses (NSV) from in vivo transcribed cDNA in the context of reverse genetics approaches (F. Radecke et al., *Embo J* 14, 5773 (Dec. 1, 1995)), was employed. This system allows template-dependent direct transcription of RNA inside a cell via cytosolically expressed T7 RNA polymerase.

Indeed, coexpression of wild type RIG-I and wild type T7 RNA polymerase, in the absence of exogenously added 5' triphosphate RNA, strongly induced a type I IFN response (FIG. 4C). No type I IFN response was detected when a combination of wild type RIG-I and a mutated form of T7 RNA polymerase (T7 D812N) or a combination of mutant RIG-I (RIG-IC) and wild type T7 RNA polymerase was expressed.

At high levels of expression, a template-independent, T7 RNA polymerase-mediated type I IFN induction was seen (FIG. 4C: no template and X8dT); the presence of a T7 RNA polymerase promoter-containing template was able to enhance the transcription dependent type I IFN induction (FIG. 4C: pBKS). When T7 RNA polymerase was expressed at lower levels, a complete template-dependent type I IFN induction could be seen (FIG. 4D; 100 ng T7 RNA polymerase).

These results demonstrated that not only exogenously added but also endogenously generated 5' triphosphate RNA is recognized via RIG-I, and confirmed that contaminants in the exogenously added 5' triphosphate RNA preparations are not involved in the induction of type I IFN.

Example 6

RIG-I Directly Detects Genomic Triphosphate RNA from a Mammalian Negative Strand RNA Virus Characteristically, all NSV initiate viral RNA replication in a primer-independent manner, resulting in the presence of a triphosphate moiety at the 5' end of the viral genome (vRNA) or antigenome (cRNA). Moreover, in case of NSV with a nonsegmented genome (Order Mononegavirales), including for example the Paramyxoviruses and Rhabdoviruses, RNA transcription yields abundant amounts of short (approximately 60 nt) 5' triphosphate RNAs, known as leader RNAs, which are templated by the 3' end of vRNA (S. P. Whelan, et al. *Current topics in microbiology and immunology* 283, 61 (2004)). To assess the importance of NSV 5' triphosphate RNAs in the recognition of virus infection by RIG-I, rabies virus (RV), a prototype Rhabdovirus, was used.

Wildtype RV (SAD L16) encodes a potent antagonist of IFN induction, the phosphoprotein P, and therefore does not induce considerable IFN expression upon infection of epithelial cells.

In contrast, a RV mutant genetically engineered to express little P (SAD ΔPLP) is an efficient inducer of IFN (K. Brzozka, et al. *Journal of virology* 79, 7673 (June 2005); K. Brzozka, et al. *Journal of virology* 80, 2675 (March 2006)). To confirm that RIG-I is involved in the recognition of RV infection, Vero cells were infected with the IFN-inducing RV, SAD ΔPLP, in the absence or presence of transfected RIG-I or RIG-IC (a dominant negative truncation mutant of RIG-I). SAD ΔPLP infection triggered a potent IFN-response which could be further enhanced by the overexpression of RIG-I and strongly suppressed by RIG-IC (FIG. 5A).

These results indicated that RIG-I is required for the initiation of an IFN-response upon RV infection, as has been observed for other NSV, VSV and Flu (H. Kato et al., *Nature* 441, 101 (Apr. 9, 2006)).

To address whether RV RNA itself or viral replication is recognized via RIG-I, RNA was isolated from RV infected BSR cells and subsequently transfected into HEK 293T cells. RNA from RV-infected cells, but not RNA from non-infected cells, induced a potent IFN-β response (FIG. 5B). Moreover, the observed IFN-β production was completely abrogated the isolated RNA was dephosphorylated by CIAP prior to transfection (FIG. 5B), indicating that the 5' triphosphate group was required for recognition.

The RNA of NSV and of NSV-infected cells is not considered infectious and does not allow the initiation of a replicative cycle. The fact that RNA from RV SAD L16-infected cells was equally potent in terms of IFN-β induction as RNA from RV SAD ΔPLP-infected cells indicated that little or no productive translation and replication was initiated via the transfection of the respective RNA isolates.

Nevertheless, to completely rule out that replication of RV was required to trigger a type I IFN response, full-length RNA from virions was isolated and assessed for its capability of inducing type I IFN expression. Transfection of 200 ng of purified RV RNA effectively stimulated type I IFN induction in HEK 293T cells and dephosphorylation of the genomic RV RNA completely abrogated the IFN response. An in vitro transcribed ssRNA corresponding to the 58-nucleotide long RV leader RNA confirmed recognition of and potent type I IFN induction by viral ssRNA.

Altogether, these results demonstrated that RIG-I directly recognizes genomic RNA from RV independent of replication and that this recognition is abolished if the 5' end of the RNA is dephosphorylated.

Example 7

5' Triphosphate RNA Directly Binds to RIG-I

The fact that RIG-I is required for the recognition of 5' triphosphate RNA provides no evidence that RIG-I is the receptor for 5' triphosphate RNA. To identify the receptor for 5' triphosphate RNA, in vitro binding assays was carried out to test the ability of 5' triphosphate RNA to pull down RIG-I or RIG-IC, the RNA binding domain of RIG-I.

RNA oligonucleotides with 3' terminal biotin tags were generated and incubated with whole cell lysate from HEK 293 cells overexpressing full length RIG-I, RIG-I CARD2 (the second CARD of RIG-I) or RIG-I Δ Helicase_C (RIG-I devoid of the predicted helicase superfamily c-terminal domain). Subsequently streptavidin beads were used to pull down the biotin tags on the 5' triphosphate RNA oligonucleotides.

Whereas the biotinylated 5' triphosphate oligonucleotide (tri-G-AC-U-Bio) was able to immunoprecipitate full length RIG-I (FIG. 6A, third panel, middle part), it was not very effective at pulling down truncated versions of RIG-I, CARD2 and RIG-I Δ Helicase_C (FIG. 6A, third panel left an right part). Unbiotinylated control RNA oligonucleotide (tri-G-AC-U) did not immunoprecipitate RIG-I. Purified RIG-IC was also efficiently pulled down by 5' triphosphate RNA oligonucleotides (FIG. 6B, second lane). If the initial 5' triphosphate group of the RNA oligonucleotide was enzymatically removed prior to incubation with RIG-I, no co-precipitation was seen (FIG. 6B, fourth lane).

These results indicated that 5'triphosphate RNA directly binds to full length RIG-I or RIG-IC, i.e., RIG-I is the direct receptor responsible for the recognition of 5' triphosphate RNA.

Example 8

5' Adenosine Triphosphate RNA Oligonucleotides are Superior to 5' Guanosine Triphosphate RNA Oligonucleotides in Inducing IFN-α production The classical in vitro transcription system makes use of the T7 RNA polymerase consensus promoter (J. J. Dunn, F. W. Studier, *J Mol Biol* 166, 477 (Jun. 5, 1983)). Transcription under this promoter is initiated by GTP and usually requires two or more consecutive guanosines at the 5' end of RNA for efficient transcription. Nevertheless, it is possible to use a promoter system for T7 RNA polymerase which initiates with a 5' ATP (F. Huang et al. *Biochemistry* 39, 15548 (Dec. 19, 2000)). Using this system, the role of the initial 5' guanosine in the type I-IFN inducing activity of 5' triphosphate RNA oligonucleotides was assessed. RNA9.2s (RNA9.2s-0A) was used as a reference oligonucleotide since it starts with a 5' adenosine.

Comparing RNA9.2s-0A (5' ATP) with RNA9.2s-1G (5' GTP), which is shifted one base downstream of the corresponding human TLR9 mRNA, the latter showed a reduction of approximately 25% in IFN-α induction (FIG. 12, upper panel). Four bases further downstream of the human TLR9 mRNA, another 19-mer oligonucleotide could be transcribed which initiated with a 5' adenosine (RNA9.2s-5A). RNA9.2s-5A paralleled RNA9.2-0A in terms of IFN-α induction.

A second set of experiments corroborated these findings: comparison of the in vitro transcribed 35-mer RNA oligonucleotide AΦ6.5-35 n (5' ATP) with GΦ6.5-35 n (5' GTP) revealed a clear superiority of the transcript initiated with an adenosine in inducing type I IFN, even though these oligonucleotides share more than 97% homology in sequence (FIG. 12, lower panel).

Together, these findings indicated that RNA transcripts initiated with a 5' adenosine are more potent in terms of IFN-α induction than those initiated with a 5' guanosine. Further data demonstrate that of all four possible bases at the 5' end, the highest IFN-α-inducing activity was seen when A was at the 5' end, followed by C, U and G (FIG. 25).

Example 9

The IFN-α-Inducing Activity of Adenosine-Initiated 5'-triphosphate RNA Oligonucleotide Depends On Its 5' Nucleotide Sequence Adenosine-initiated triphosphate RNA oligonucleotides with all possible base permutations (A, C, G and U) of the 2nd, 3rd and 4th position of the sequence (5'→3') (Table 2) were generated via in vitro transcription. Subsequently monocytes from three independent donors were isolated and transfected with the respective RNA oligonucleotides. 36 hours after transfection, supernatants were analyzed for IFN-α production. The obtained IFN-α induction levels of all oligonucleotides were normalized to the mean induction level of all oligonucleotides (=100%). The obtained normalized induction levels of all three donors were summarized as mean values±SEM (FIG. 13).

It is clear from FIG. 13 that adenosine-initiated, in vitro transcribed RNA oligonucleotides having identical 3' sequence but different nucleotides at the 2nd, 3rd and 4th positions have different levels of IFN-α-inducing activity. The 5' 4-nucleotide sequences which confer the highest IFN-α-inducing activity include AAGU (SEQ ID NO: 205), AAAG (SEQ ID NO: 206), AUGG (SEQ ID NO: 207), AUUA (SEQ ID NO: 208), AACG (SEQ ID NO: 209), AUGA (SEQ ID NO: 210), AGUU (SEQ ID NO: 211), AUUG (SEQ ID NO: 212), AACA (SEQ ID NO: 213), AGAA (SEQ ID NO: 214), AGCA (SEQ ID NO: 215), AACU (SEQ ID NO: 216), AUCG (SEQ ID NO: 217), AGGA (SEQ ID NO: 218), AUCA (SEQ ID NO: 219), AUGC (SEQ ID NO: 220), AGUA (SEQ ID NO: 221), AAGC (SEQ ID NO: 222), AACC (SEQ ID NO: 223), AGGU (SEQ ID NO: 224), AAAC (SEQ ID NO: 225), AUGU (SEQ ID NO: 226), ACUG (SEQ ID NO: 227), ACGA (SEQ ID NO: 228), ACAG (SEQ ID NO: 229), AAGG (SEQ ID NO: 230), ACAU (SEQ ID NO: 231), ACGC (SEQ ID NO: 232), AAAU (SEQ ID NO: 233), ACGG (SEQ ID NO: 234), AUUC (SEQ ID NO: 235), AGUG (SEQ ID NO: 236), ACAA (SEQ ID NO: 237), AUCC (SEQ ID NO: 238), AGUC (SEQ ID NO: 239).

TABLE 2

All Oligos share the same sequence except the 2nd, 3rd and 4th position(5'- ANNNGGGGACACACACACACACACACACAC-3') (SEQ ID NO: 332)

| SEQ ID No. | Sequence of First Four Nucleotides | IFN-α induction (*100%) mean | SEM |
|---|---|---|---|
| 111 | AGGG | 0.22 | 0.05 |
| 112 | AAUA | 0.40 | 0.07 |
| 113 | AGAU | 0.48 | 0.04 |
| 114 | AGAG | 0.50 | 0.06 |
| 115 | AGCG | 0.52 | 0.01 |
| 116 | AGAC | 0.62 | 0.10 |
| 117 | ACUA | 0.62 | 0.05 |
| 118 | ACUU | 0.66 | 0.01 |

TABLE 2-continued

All Oligos share the same sequence except the 2nd, 3rd and 4th position(5'-ANNNGGGGACACACACACACACACACAC-3') (SEQ ID NO: 332)

| SEQ ID No. | Sequence of First Four Nucleotides | IFN-α induction (*100%) mean | SEM |
|---|---|---|---|
| 119 | AAUU | 0.67 | 0.03 |
| 120 | AGCU | 0.69 | 0.01 |
| 121 | AAAA | 0.73 | 0.09 |
| 122 | ACCG | 0.73 | 0.03 |
| 123 | AUAG | 0.76 | 0.07 |
| 124 | ACCU | 0.76 | 0.01 |
| 125 | ACGU | 0.77 | 0.02 |
| 126 | ACCA | 0.79 | 0.01 |
| 127 | AUAA | 0.82 | 0.13 |
| 128 | AGCC | 0.87 | 0.04 |
| 129 | AUAU | 0.89 | 0.03 |
| 130 | ACCC | 0.89 | 0.01 |
| 131 | AGGC | 0.91 | 0.02 |
| 132 | AAUC | 0.94 | 0.05 |
| 133 | AUCU | 0.94 | 0.03 |
| 134 | AAGA | 0.95 | 0.19 |
| 135 | ACAC | 0.95 | 0.08 |
| 136 | AAUG | 0.96 | 0.07 |
| 137 | ACUC | 0.98 | 0.04 |
| 138 | AUUU | 0.99 | 0.06 |
| 139 | AUAC | 0.99 | 0.07 |
| 140 | AGUC | 1.00 | 0.08 |
| 141 | AUCC | 1.01 | 0.07 |
| 142 | ACAA | 1.01 | 0.08 |
| 143 | AGUG | 1.01 | 0.12 |
| 144 | AUUC | 1.03 | 0.07 |
| 145 | ACGG | 1.03 | 0.05 |
| 146 | AAAU | 1.04 | 0.19 |
| 147 | ACGC | 1.08 | 0.07 |
| 148 | ACAU | 1.11 | 0.09 |
| 149 | AAGG | 1.11 | 0.22 |
| 150 | ACAG | 1.12 | 0.01 |
| 151 | ACGA | 1.14 | 0.02 |
| 152 | ACUG | 1.14 | 0.08 |
| 153 | AUGU | 1.15 | 0.17 |
| 154 | AAAC | 1.15 | 0.09 |
| 155 | AGGU | 1.18 | 0.11 |
| 156 | AACC | 1.20 | 0.19 |
| 157 | AAGC | 1.22 | 0.13 |
| 158 | AGUA | 1.22 | 0.12 |
| 159 | AUGC | 1.23 | 0.10 |
| 160 | AUCA | 1.24 | 0.09 |
| 161 | AGGA | 1.27 | 0.05 |
| 162 | AUCG | 1.28 | 0.12 |
| 163 | AACU | 1.29 | 0.13 |
| 164 | AGCA | 1.29 | 0.15 |
| 165 | AGAA | 1.29 | 0.14 |
| 166 | AACA | 1.30 | 0.19 |
| 167 | AUUG | 1.31 | 0.11 |
| 168 | AGUU | 1.32 | 0.15 |
| 169 | AUGA | 1.32 | 0.01 |
| 170 | AACG | 1.34 | 0.15 |
| 171 | AUUA | 1.36 | 0.03 |
| 172 | AUGG | 1.38 | 0.10 |
| 173 | AAAG | 1.40 | 0.15 |
| 174 | AAGU | 1.40 | 0.10 |

Example 10

The IFN-α-Inducing Activity of Bacterial RNA is Only Partially Dependent on the Presence of 5' Triphosphate As shown in FIG. 9, total bacterial RNA is capable of inducing IFN-α production from monocytes.

To determine whether the IFN-α-inducing activity of bacterial RNA is due to the presence of the 5' triphosphate, total RNA was isolated from *E. coli* bacteria strain DH10B, either treated or not treated with CIAP to dephosphorylate the 5' end, and subsequently transfected into purified monocytes (200 ng of RNA). IFN-α production was analyzed 24 hours after stimulation.

As controls, Tri-GFPa was prepared via in vitro transcription, either treated or not treated with CIAP to dephosphorylate the 5' end, and subsequently transfected into purified monocytes (200 ng of RNA). IFN-α production was analyzed 24 hours after stimulation.

As previously shown in Example 2 and FIG. 2C, the removal of 5' triphosphate from in vitro transcribed RNA oligonucleotides almost completely abolish the ability of the oligonucleotides to induce IFN-α from monocytes (FIG. 14B). In contrast, the removal of 5' triphosphate from total bacterial RNA reduced the amount of IFN-α induced from monocytes by less than 30% (FIG. 14A).

Therefore, 5' triphosphate is only one of the molecular features which are responsible for the ability of bacterial RNA to induce IFN-α.

Example 11

Combining Potent Immunostimulatory Functions with Efficient Gene-Silencing Activity in One RNA Molecule We identified several sequences targeting murine Bcl-2 and subsequently generated three synthetic siRNAs (anti-Bcl-2.1, anti-Bcl-2.2, anti-Bcl-2.3) targeting different portions of murine Bcl-2 mRNA (for a detailed list of all chemically synthesized RNA oligonucleotides see Table 3).

TABLE 3

Chemically synthesized RNA Sequences

| SEQ ID No. | Name | Type | Sequence 5'->3 |
|---|---|---|---|
| 103 | Murine Bcl-2 2.1 sense | RNA | AUGCCUUUGUGGAACUAUA |
| 104 | Murine Bcl-2 2.1 antisense | RNA | UAUAGUUCCACAAAGGCAU |
| 105 | Murine Bcl-2 2.2 sense | RNA | GCAUGCGACCUCUGUUUGA |
| 106 | Murine Bcl-2 2.2 Anti-sense | RNA | UCAAACAGAGGUCGCAUGC |
| 107 | Murine Bcl-2 2.3 sense | RNA | GGAUGACUGAGUACCUGAA |
| 108 | Murine Bcl-2 2.3 Anti-sense | RNA | UUCAGGUACUCAGUCAUCC |
| 109 | Poly-A | RNA | AAAAAAAAAAAAAAAAAA |
| 175 | Murine RIG-I Sense | RNA | GAAGCGUCUUCUAAUAAUU |
| 176 | Murine RIG-I Anti-sense | RNA | AAUUAUUAGAAGACGCUUC |
| 177 | Control Sense | RNA | UUCUCCGAACGUGUCACGU |
| 178 | Control Antisense | RNA | ACGUGACACGUUCGGAGAA |

After transfection of the different anti-Bcl-2-siRNAs and a control siRNA in B16 melanoma cells, we determined downregulation of Bcl-2 by western blotting of the cell lysates (FIG. 15a, upper panel). Different siRNAs displayed different efficiencies in target downregulation. Treatment of B16 melanoma cells with a single dose of anti-Bcl-2.2 (now termed OH-2.2) resulted in an efficient downregulation of Bcl-2 expression 48 h after transfection compared to the control siRNA (FIG. 15a, upper panel). This specific reduction of Bcl-2 was already observed after 18 h, lasted for at least 72 h and was confirmed by FACS analysis of intracellular Bcl-2 (data not shown).

Subsequently, anti-Bcl-2.2 was in vitro transcribed thus bearing 5' triphosphates (now termed 3p-2.2; for a detailed list of all in vitro transcription templates see Table 4).

TABLE 4

DNA templates for in vitro transcription

| SEQ ID No. | Name | Type | Sequence 5'->3 |
|---|---|---|---|
| 68 | Murine Bcl-2 2.2 sense | DNA | TCAAACAGAGGTCGCATGCCTATAGTGAGTCG |
| 69 | Murine Bcl-2 2.2 Anti-sense | DNA | GCATGCGACCTCTGTTTGACTATAGTGAGTCG |
| 70 | GA | DNA | TTTTTTTTTTTTCCCCCCCCCCCTATAGTGAGTCG |
| 179 | GC sense | DNA | GGCGCCCCGCCGCGCCCCGCTATAGTGAGTCG |
| 180 | GC Anti-sense | DNA | GCGGGGCGCGGCGGGGCGCCTATAGTGAGTCG |

3p-2.2 was tested for its ability to reduce Bcl-2 expression (FIG. 15a). Transfection of B16 cells with 3p-2.2 siRNA also resulted in an efficient downregulation of Bcl-2. Importantly, this specific reduction of Bcl-2 was not observed with a nonspecific 3p-siRNA (3p-GC) or a synthetic control siRNA.

Using an anti-RIG-I antibody, we next determined the expression of endogenous RIG-I in B16 cells before and after stimulation by western blot (FIG. 15b). Interestingly, RIG-I-expression in B16 cells was strongly upregulated by exogenous IFN-β (1000 U/ml), and to a similar extend by 3p-2.2 siRNA.

To investigate the immunostimulatory potential of transfected 3p-2.2 in B16 cells, we monitored IFN-β promoter activation (FIG. 15c). Surprisingly, stimulation of B16 cells with 3p-2.2, but not poly(I:C) or OH-2.2, significantly enhanced the induction of a reporter gene (Renilla luciferase) driven by the IFN-β promoter (pIFNβ-luc; *$P<0.05$ between 3p-2.2, OH-2.2 and poly(I:C)).

This prompted us to further evaluate the contribution of RIG-I and its CARD-containing adaptor protein, Cardif (Kawai T et al. (2005) Nat. Immunol. 6(10): 981-988; Meylan E et al (2005) Nature 437(7062): 1167-72; Seth R et al. (2005) Cell 122(5): 669-82; Xu L et al. (2005) Mol Cell 19(6): 727-40) in B16 cells.

A synthetic siRNA targeting mouse RIG-I (see Table 3) significantly reduced the 3p-2.2-dependent IFN-β promoter activation (FIG. 15d; *$P<0.05$ between control siRNA (siCO)+3p-2.2 and RIG-I siRNA (siRIG-I)+3p-2.2), demonstrating a clear role for RIG-I in 3p-2.2-induced signaling.

NS3-4A is a multifunctional serine protease of hepatitis C virus (HCV) which is capable of specifically cleaving and thereby inactivating Cardif (Chen Z et al. (2007) J Virol. 81(2):964-76; Meylan E et al (2005) Nature 437(7062):1167-72). Expression of NS3-4A in B16 cells greatly reduced IFN-β promoter activation by 3p-2.2, whereas expression of the inactive form NS3-4A* had no effect on IFN-β promoter activation (FIG. 15e; *$P<0.05$, NS3-4A*+3p-2.2 versus NS3-4A+3p-2.2).

Taken together, these results indicate that B16 cells upregulate RIG-I upon stimulation with 3p-2.2 and that RIG-I and Cardif are essential for 3p-2.2-induced immunostimulation in B16 melanoma cells. Additionally, we demonstrate that 3p-2.2 induces efficient gene-silencing of Bcl-2 in murine melanoma cells.

Example 12

Transfection of 3p-2.2 Directly Triggers Cardif-Independent Apoptosis in Tumor Cells, But Not in Primary Cells After extended exposure to 3p-RNA, microscopic evaluation of B16 cells revealed reduced cell numbers compared to B16 cells which were transfected with control siRNA or OH-2.2. We hypothesized that an increased cell death by transfection of 3p-2.2 contributed to the reduction of viable B16 cells.

To delineate the mechanisms responsible for the observed cell death, B16 cells were analyzed for an apoptotic phenotype by Annexin-V and propidium iodide staining. 24 h after transfection, a significant increase in the number of apoptotic cells was observed with 3p-2.2 (14%) compared to the control siRNA (1.06%) (FIG. 16a). In all experiments performed, approximately 15% (15.62%±1.01; mean %±SEM) of B16 cells treated with 3p-2.2 were positive for Annexin-V; the number of apoptotic cells was approximately 4-fold lower in cells treated with control siRNAs (FIG. 16b; 2.93%±1.12). Treatment with OH-2.2 also increased the number of apoptotic cells (5.63%±0.66), however to a significantly less extent than 3p-2.2 (FIG. 16b).

Similar experiments were carried out using non-target-specific 3p-RNA in B16 as well as other melanoma cell lines and similar results were obtained, indicating that 3p-RNA induces cell death independently of siRNA-mediated gene-silencing (data not shown).

To identify intracellular pathways relevant for the observed cell death, we first expressed NS3-4A and the inactive form NS3-4A* in B16 cells and analyzed for apoptosis by Annexin-V and propidium iodide staining (FIG. 16c). In these experiments, no change in apoptosis was observed after additional transfection of 3p-2.2 (8.3%±0.5 with the inactive form and 7.3%±0.67 with the active form), indicating that 3p-RNA induced apoptosis is Cardif-independent.

Recent studies further reported that RIG-I-dependent viruses and in vitro transcribed RNAs activate Caspase-1, an important component of the inflammasome (Kanneganti T D e t al. (2006) Nature 440(7081):233-6.). Caspase-1 has also been suggested to be involved in apoptotic processes (Cuesta N (2007) J Immunol. 178(6):3602-11; Henry T et al. 2007 J Exp Med 204(5):987-94). We therefore analysed Caspase-1 activation in B16 cells using western blot. In these experiments, an increased cleavage of procaspase-1 to active subunit p10 was observed when cells were transfected with 3p-2.2 and poly(I:C) (FIG. 16d). However, using two functional siRNAs targeting Caspase-1. we were not able to detect any change in apoptosis (data not shown), suggesting that Caspase-1 is not involved in 3p-2.2-mediated apoptosis.

We then addressed the question whether 3p-2.2-mediated cell death is restricted to tumor cells. Human primary cells, PBMCs, were analyzed for apoptosis by Annexin-V and propidium iodid staining after stimulation with 3p-2.2, control siRNA and OH-2.2. Interestingly, no induction of apoptosis by 3p-2.2 was observed in human PBMCs (FIG. 16d). Furthermore, staining of human fibroblasts and human keratinocytes with Annexin-V revealed no increase in cell death after transfection with 3p-2.2 (data not shown). Taken together, these results indicate that 3p-2.2 induces apoptosis in melanoma cells and but not in primary cells.

Example 13

IFN-α Production by 3p-2.2 Requires TLR7 in pDCs and RIG-I in cDCs

Recent studies demonstrated that the induction of both IFN-α and IFN-β in conventional DCs (cDCs) upon exposure to several RNA viruses, including Newcastle disease virus (NDV), Sendai virus (SeV) and vesicular stomatitis virus (VSV), is regulated by RIG-I (Kato H et al. (2005) Immunity 23(1): 19-28). In contrast, plasmacytoid DCs (pDCs) preferentially use TLR7, but not RIG-I, for the recognition of viruses such as NDV, leading to the induction of Type I IFNs.

We examined the IFN response of wild-type, RIG-I-, TLR7-, and MDA5-deficient cDCs after stimulation with 3p-2.2 by ELISA (FIG. 17a, b, c). As expected, IFN-α production by 3p-2.2-stimulated cDCs from RIG-I-deficient mice was completely abrogated (FIG. 17a). IFN-α production by 3p-2.2-stimulated cDCs from MDA5-deficient (FIG. 17b; Wild-type versus MDA5$^{-/-}$: 2509±96 versus 2333±178; μg/ml±SEM) and TLR7-deficient (FIG. 17c; Wild-type versus TLR7$^{-/-}$; 771±324 versus 881±355; U/ml±SEM) mice was largely normal. These results indicate that the induction of IFN-α by 3p-2.2 is regulated by RIG-I in cDCs.

We then purified pDCs from Flt3-L-induced BM-derived DCs (Flt3-L-DCs) of wild-type and TLR7-deficient mice using magnetic beads and tested for IFN-α secretion. Wild-type pDCs produced IFN-α in response to 3p-2.2 (FIG. 17d). In contrast, TLR7-deficient pDCs showed impaired IFN-α production in response to 3p-2.2 (FIG. 17d).

We also observed IFN-α induction in peritoneal macrophages (data not shown).

Next, we examined the sensitivity of different purified immune cell subsets to 3p-2.2. Compared to cDCs and pDCs, B cells, NK cells and CD8 T cells responded weakly to stimulation with 3p-2.2 by low IFN-α-production (cDCs 2357±437; pDCs 3036±354; NK cells 94±2.07, B cells and CD8 T cells 0; U/ml±SEM).

These observations indicate that cDCs and pDCs mainly exploit RIG-I and the TLR system to recognize 3p-2.2. However, cells of the adaptive immune system do not respond to 3p-RNA in any significant degree by IFN-α production.

Example 14

Complexed 3p-2.2 Leads to Systemic Immune Activation In Vivo

To gain insights into the biological relevance of 3p-2.2-mediated responses in vivo, we challenged mice with 3p-2.2 comlexed to jetPEI™ and measured serum cytokines including IFN-α, IL-12p40 and IFN-γ (FIG. 18a, b, c). After 6 h, 3p-2.2 induced significantly higher levels of IFN-α than CpG 1826 or OH-2.2 (FIG. 18a; P<0.01 between 3p-2.2 and OH-2.2, CpG 1826, jetPEI™ and PBS). Both 3p-2.2 and OH-2.2 induced significant IL-12p40 production (FIG. 18b; P<0.01 between 3p-2.2 and jetPEI™ and PBS). Furthermore, 3p-2.2 induced high level of IFN-γ production in vivo (FIG. 18c; P**<0.01 between 3p-2.2 and OH-2.2; P*<0.05 between 3p-2.2 and jetPEI™ and PBS).

We next examined serum cytokine levels in TLR7-deficient mice after administration of 3p-2.2. Production of IFN-α (FIG. 18d), IL-12p40 (FIG. 18e), and IFN-γ (FIG. 18f) was only partly decreased in TLR7-deficient mice after transfection with 3p-2.2 in comparison to wild-type mice (IFN-α: Wild-type versus TLR7$^{-/-}$, 885±89 versus 406±181; IL-12p40: 5635±1662 versus 2609±973; IFN-γ: 1881±259 versus 1599±259). In contrast, production of IFN-α, IL-12p40 and IFN-γ was severely impaired in TLR7-deficient mice after stimulation with OH-2.2 (IFN-α: Wild-type versus TLR7$^{-/-}$, 207±100 versus 0; IL-12p40: 1444±19 versus 553±147; IFN-γ: 926±30 versus 107±35). Additionally, intravenous administration of 3p-2.2 in wild-type mice enhanced production of serum cytokines in a dose-dependent way (FIG. 19a).

To further characterize the immunostimulatory potential of 3p-2.2 in vivo, we sacrificed wild-type mice 48 h after injection of 3p-2.2, isolated the spleen cells and analyzed surface expression of costimulatory molecules on distinct immune cell subsets by flow cytometry. As shown in FIGS. 19b and 19c, 3p-2.2 not only activated myeloid and plasmacytoid dendritic cells as reflected by increased CD69 and CD86 expression in a dose-dependent manner, but also upregulated CD69 expression on NK cells, CD4+ and CD8+ T cells in vivo.

We then examined the time-course of IFN-α production induced by 3p-2.2 and OH-2.2 in vivo. Consistent with our previous in vivo data, 3p-2.2 induced higher amounts of IFN-α than its synthetic counterpart OH-2.2. 48 hours after stimulation, the cytokine profiles after administration of 3p-2.2 or OH-2.2 reflected moderate leukopenia (FIG. 20b) and thrombocytopenia (FIG. 20c). Thrombocytopenia was more apparent in CpG-treated mice than in mice treated with 3p-2.2 (P**<0.01 between the platelet count of 3p-2.2 and CpG).

Collectively, these observations indicate that 3p-2.2 potently activates distinct immune cell subsets and enhances the production of serum cytokines in a dose-dependent and TLR7-independent manner in vivo.

Example 15

Delivery of Encapsulated 3p-2.2 Results in Reduction of Experimentally Induced B16 Melanoma Lung Metastases We evaluated the anti-tumor activity of 3p-2.2 against B16 melanoma lung metastases in vivo. Groups of five mice were first challenged intravenously with B16 melanoma cells and subsequently treated with PolyA, OH-2.2, 3p-GC or 3p-2.2 according to the schedule depicted in FIG. 21a. PolyA (a nonstimulatory 19-mer RNA molecule; Table 3) complexed to jetPEI™ served as the negative control. CpG 1826 complexed to jetPEI™ served as the positive control. On day 14, mice were sacrificed, and lungs were excised. Then lung meatstases were counted using a dissecting microscope or, in case of massive tumor burden, weighed to determine tumor mass.

Mice treated with OH-2.2 showed a non-significant reduction of lung metastases compared with the PolyA-treated control group (FIG. 21b). Importantly, treatment with 3p-2.2 led to reduction of lung metastases in a significant percentage of mice compared to the OH-2.2- and PolyA-treated groups (P<0.01 between 3p-2.2 and PolyA, OH-2.2). As expected, CpG 1826 was able to promote a significant reduction of lung metastases, but to a lesser extent than 3p-2.2. Interestingly, the administration of 3p-GC, a non-specific double-stranded 5'-triphosphate RNA not containing any uridines (see Table 4), also reduced lung metastasis, but to a significantly lower extent than 3p-2.2 (P<0.01 between 3p-2.2 and 3p-GC).

These data suggested that besides immunostimulation, 3p-2.2 mediates direct anti-tumor activity in vivo.

Recently, it has been shown that intraperitoneal application of PEI-complexed siRNAs leads to favored uptake in tumor cells which have been implanted away from the site of injection (Aigner A et al. (2006) J Biomed Biotechnol 2006(4): 71659; Grzelinski M et al. (2006) Hum Gene Ther. 17(7):751-66; Urban-Klein B et al. (2005) Gene Ther. 2005 March; 12(5):461-6)

We sought to examine the cellular uptake of jetPEI™-complexed siRNA after intravenous administration by confocal microscopy. B16 cells were intravenously injected into C57BL/6 mice and 14 days after tumor inoculation, a single dose of FITC-labeled siRNA (100 µg) was injected retroorbitally. After 6 h, the mice were sacrificed and various tissues including lungs were excised. As expected, in the case of noncomplexed siRNAs, no uptake was observed in lungs of healthy mice or in mice with lung metastases, indicating rapid and complete degradation of the FITC-labeled siRNA (FIG. 21c, upper panel, -PEI). In contrast, upon PEI complexation, intact siRNA was detected in high amounts in several tissues including liver and spleen (data not shown). Considerable amounts of FITC-labeled siRNA were detected in lungs of healthy mice, but to a lower extent in lung metastases of diseased mice (FIG. 21c, lower panel, +PEI).

Taken together, B16 melanoma metastases were significantly reduced in all mice receiving 3p-2.2, but not in OH-2.2-treated mice. Furthermore, direct uptake of FITC-labeled siRNA in the tumor cells in vivo points to direct anti-tumor effects of 3p-2.2 aside from immunostimulation.

Example 16

Mechanisms Responsible for Reduction of B16 Melanoma Metastasis by 3p-2.2

To further investigate the mechanisms responsible for reduction of B16 melanoma metastases in vivo, we challenged wild-type, TLR7- and IFNAR (type I IFN receptor)-deficient mice intravenously with B16 cells and treated these mice with PolyA, 3p-2.2 or poly(I:C). Reduction of B16 melanoma metastases by 3p-2.2 was observed in TLR7-deficient mice to an extend comparable to the control wild-type mice (FIG. 22a, b). In contrast, the anti-tumor activity of 3p-2.2 was diminished in IFNAR-deficient mice (FIG. 22c), suggesting a significant involvement of Type I-IFNs in 3p-2.2-mediated anti-tumor response.

Next, we examined the role of NK cells and CD8 T cells in 3p-2.2-induced anti-tumor response. 3p-2.2-mediated reduction of metastases was abrogated when NK cells were depleted using TMR1-mAb (FIG. 22d). Thus, 3p-2.2-mediated tumor suppression largely relies on the effector NK cells. In contrast, number of lung metastases was not significantly changed by the treatment of mice with anti-CD8 mAb (RmCD8-2 mAb), suggesting that CD8+ T cell-mediated tumor suppression is minimal in this model.

To assess direct anti-tumor activity of 3p-2.2 in vivo, we analyzed Bcl-2 expression in lung metastases of IFNAR-deficient mice by FACS analysis and performed TUNEL stains in lungs of mice that have been treated with 3p-2.2, CpG and PolyA. As seen in FIG. 22e, treatment with 3p-2.2, but not poly(I:C), resulted in a non-significant downregulation of Bcl-2 expression in B16 melanoma metastases. In addition, 3p-2.2, but not PolyA, and to a lesser extent CpG, led to considerable amount of apoptosis among tumor cells (FIG. 23).

Taken together, these observations indicate that 3p-2.2 reduces lung metastases in a NK cell-dependent and IFNAR-dependent manner. Furthermore, the 3p-2.2-induced down-regulation of Bcl-2 and the increase of apoptotic tumor cells in lung metastases also point to direct anti-tumor effects of 3p-2.2 in vivo.

Example 17

Inhibition of HBV Replication by RIG-I Stimulation with 5'-triphosphated RNAs In Vitro and In Vivo Here we show that 3p-siRNAs of 24 nucleotides in length (Table 5) induced an anti-viral IFN-α response via recognition by RIG-I, which leads to a reduction of HBV specific replication markers in vitro and in vivo.

TABLE 5

| SEQ ID No | Name | Position | Sequence |
|---|---|---|---|
| 181 | HBV 1.1 | 3103-3125 | sense 5'-UUUCACCUCUGCCUAAUCA UU-3' |
| 182 | | (conserved) | antisense 3'-UU AAAGUGGAGACGGAUUAGU-5' |
| 183 | | | cDNA TT TTTCACCTCTGCCTAATCA TC |
| 184 | HBV 1.2 | 2971-2993 | sense 5'-CGACCUUGAGGCAUACUUC UU-3' |
| 185 | | (not conserved) | antisense 3'-UU GCUGGAACUCCGUAUGAAG-5' |
| 186 | | | cDNA AC CGACCTTGAGGCATACTTC AA |
| 187 | HBV 1.3 | 2239-2261 | sense 5'-CUAUUAACAGGCCUAUUGA UU-3' |
| 188 | | (not conserved) | antisense 3'-UU GAUAAUUGUCCGGAUAACU |
| 189 | | | cDNA TC CTATTAACAGGCCTATTGA TG |
| 190 | | 2326-2348 | sense 5'-CUGCGUUGAUGCCUUUGUA UU-3' |
| 191 | | (not conserved) | antisense 3'-UU GACGCAACUACGGAAACAU-5' |
| 192 | | | cDNA TC CTGCGTTGATGCCTTTGTA TG |
| 193 | HCV | | Sense 5'-CUGAUAGGGUGCUUGCGAGUUC-3' |
| 194 | control | | antisense 3'-GACUAUCCCACGAACGCUCAAG-5' |

120 nM of the 3p-siRNAs were transfected into HepG2-H1.3 cells and primary human hepatocytes which allow for the replication of HBV 3 days post HBV infection at a MOI of 100. The effects of 3p-siRNAs on HBV replication markers were analyzed on day 3 and 6 post-transfection in comparison to untreated cells.

In infected HepG2-H1.3 cells, type I IFN and 2'-5'-oligoadenylate synthetase (2'-5'-OAS) expression was induced at day 3 post-transfection. HBV progeny decreased by >95% at day 6 post-transfection. HBeAg levels were reduced by about 40%, HBsAg levels by about 50%. The same results were obtained with HBV-infected human hepatocytes.

When 3p-siRNA was injected intravenously into HBV1.3 transgenic mice (provided by H Schaller, Heidelberg, Germany), alanin aminotransferase (ALT) levels remained in the normal range, reflecting the absence of cytoxicity of the RIG-I-ligands. INF-α and 2'-5'-OAS were strongly induced after 3 h, which highly likely accounted for a 60% reduction of HBV RNA at d6 in comparison to mock-treated mice. HBV viremia and HBeAg levels were about 50%, and HBsAg levels about 15% reduced at d6.

Taken together, triggering the RNA helicase RIG-I with RNA olignucleotides bearing 5' triphosphate has profound antiviral effects on HBV. Preferably, siRNA, shRNA or antisense RNA may be designed to target the region of the HBV genome spanning nucleotides 2656-3182 to be used as an anti-viral agent. Alternatively, nucleotides 1272-3183 of the HBV genome may be targeted.

Example 18

Inosin Content Increases the Activity of 5' Triphosphate RNA

Inosin is a nucleoside, which is composed of hypoxanthin and ribose. Under certain circumstances, inosin is present in RNA instead of adenosin. ADAR (adenosine deaminase acting on RNA) desaminates adenosin to inosin (Palladino M J et al. (2000) Cell 102(4): 437-49). An important function of ADAR is the posttranscriptional modification of mRNA (Gerber A P and Keller W (2001) Trends Biochem Sci 26(6): 376-84). Furthermore in the cytoplasm, adenosine in dsRNA is deaminated by ADAR to become inosin (Bass B L and Weintraub H (1988) Cell 55(6): 1089-98). In the case of viral dsRNA, adenins could be replaced by inosin, resulting in I:U and I:C basepairing.

In order to test the contribution of inosin content to the IFN-α-inducing activity of 5' triphosphate RNA, two different dsRNA fragments (A and B, both derived from Taylor virus, plasmid pEL39: fragment A positions 4473 to 5006 and 4499 to 5034; fragment B positions 10953 to 519 and 26 to 548) were prepared by in vitro transcription. For this purpose, 60% of the guanosin content was replaced by inosin during in vitro transcription. Human monocytes produce IFN-α only upon stimulation of cytosolic receptors but not TLRs. Purified human primary monocytes were transfected with dsRNA. After 18 hours, IFN-α was determined in the supernatants by ELISA. We found that the presence of inosin increased the activity of both A and B fragments to induce IFN-α in human monocytes (FIG. 24A). With inosin, the activity of the fragments A and B both were higher than the activity of poly(I:C).

For dsRNA fragments of 500 bp, both RIG-I and MDA-5 are expected to contribute to the biological activity. Therefore we tested the IFN-α-inducing activity of dsRNA fragments in bone marrow dendritic cells from MDA-5−/− mice. In dendritic cells derived from MDA-5 −/− mice, the IFN-α inducing activity was increased by more than 4-fold when 60% of the guanosins were replaced by inosin (FIG. 24B). These data provide clear evidence that the RIG-I-stimulating activity of 5' triphosphate RNA is strongly increased if the RNA contains inosin.

Example 19

Single-Stranded RNA Bearing 5' Triphosphate is Not Capable of Inducing IFN-α Production, double-Strandedness is Required In RNA generated by in vitro transcription, the length and base composition at the 3'end is not chemically defined. In particular, the 3' end may fold back and allow the polymerase to generate partially double-stranded RNA. In order to analyse the contribution of the 3' end and exactly define the contribution of double-strand RNA to the IFN-α-inducing activity of 5' triphosphate RNA, synthetic 5' triphosphate RNAs (Table 6) were prepared as described (Ludwig J (1981) Acta Biochim Biophys Acad Sci Hung. 16:131-3). By using such synthetic 5' triphosphate RNA, uncontrolled elongation of the 3' end resulting in double-strand formation is excluded.

TABLE 6

Chemically synthesized ssRNA oligonucleotides

| | | |
|---|---|---|
| 3P-A: | A(AC)₁₀-UUU | (5'end: only triphosphate) (SEQ ID No. 195) |
| (1-3)P-A: | A(AC)₁₀-UUU | (5'end: predominantly triphosphate) (SEQ ID No. 196) |
| (1-3)P-U: | U(AC)₁₀-UUU | (5'end: predominantly triphosphate) (SEQ ID No. 197) |
| (1-3)P-G: | G(AC)₁₀-UUU | (5'end: predominantly triphosphate) (SEQ ID No. 198) |
| (1-3)P-C: | C(AC)₁₀-UUU | (5'end: predominantly triphosphate) (SEQ ID No. 199) |
| HO-G: | G(AC)₁₀-UUU | (5'end: OH) (SEQ ID No. 200) |
| As: | AAA(GU)₁₀ | (5'end: OH) (SEQ ID No. 364) |

The isRNA9.2 (Hornung V et al. (2005) Nat Med 11(3): 263-70) generated by in vitro transcription was used a positive control (IVT2-3PRNA). CpG2331 is a TLR9 ligand. PBMC (400,000 cells per well) were transfected with oligonucleotides by using Lipofectamin (0.5 µl, 0.2 µg oligonucleotide). Hybridization of complementary strands was performed by heating 4 µg total RNA in 20 µl of buffer (final 50 mM Tris/HCl pH7.5 100 mM NaCl) up to 70° C. followed by cooling down to 40° C. Chloroquine was used to block TLR-mediated nucleic acid recognition (2.5 µg/ml). After 24 hours, IFN-α (hIFN-α) was measured in the supernatants by ELISA.

None of the chemically synthesized ssRNA oligonucleotides, only the in vitro-transcribed control sequence (IVT2-3PRNA), induced IFN-α in PBMC. However, when hybridized with the corresponding antisense strand, all oligonucleotides induced IFN-α (FIG. 25). The strongest IFN-α induction was seen for 3P-A/AS. The same sequence in which most but not all oligonucleotides contained a triphosphate group at the 5'end showed lower activity. Of all four possible bases at the 5' end, the highest IFN-α-inducing activity was seen when an A was at the 5' end, followed by C, U and G (FIG. 25). The control without 5' triphosphate (HO-G/AS) did not induce and IFN-α. The TLR9 ligand CpG2331 also induced IFN-α which was sensitive to chloroquine. The activity of the 5' triphosphate oligonucleotides was not reduced by chloroquine, confirming that IFN-α induction was independent of TLRs.

These results show that the presence of the antisense strand is required for the IFN-α-inducing activity of a 5' triphosphate RNA. When using in vitro transcription for the generation of 5' triphosphate RNA oligonucleotides, the addition of an antisense strand is not required presumably because of the presence of the double-stranded structure in the 3' end. Therefore, an active RIG-I ligand can be generated by in vitro transcription where both "single" and double strand are active, or by using a completely synthetic approach for generating a single-stranded 5' triphosphate RNA, together with the complementary strand which can be synthetic or non-synthetic and which does not need to contain a 5' triphosphate end.

Example 20

Target-Specific Induction of IFN-α by Synthetic Single-Stranded RNA Bearing 5' Triphosphate HepG2-H1.3 cells and primary human hepatocytes are infected with HBV at a MOI of 100 or mock infected. 3 days after infection, chemically synthesized single-stranded RNAs bearing 5' triphosphate and having the nucleotide sequence of the antisense strand of HBV1.1, 1.2, 1.3 and HCV control (Table 5) are transfected into HBV-infected and mock infected cells. The induction of IFN-α is determined by ELISA and the extend of HBV infectinumber of HBV-infected cells, HBeAg levels and HBsAg levels 6 days after transfection. on is determined by the

```
<160> NUMBER OF SEQ ID NOS: 365

<210> SEQ ID NO 1
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 1
cagtaatacg actcactatt aaaaagggga cacac                                35

<210> SEQ ID NO 2
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 2
cagtaatacg actcactatt aaacagggga cacac                                35

<210> SEQ ID NO 3
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 3
cagtaatacg actcactatt aaagagggga cacac                                35

<210> SEQ ID NO 4
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 4
cagtaatacg actcactatt aaatagggga cacac                                35

<210> SEQ ID NO 5
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 5
cagtaatacg actcactatt aacaagggga cacac                                35

<210> SEQ ID NO 6
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 6
cagtaatacg actcactatt aaccagggga cacac                                35
```

<210> SEQ ID NO 7
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 7
cagtaatacg actcactatt aacgagggga cacac                                35

<210> SEQ ID NO 8
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 8
cagtaatacg actcactatt aactagggga cacac                                35

<210> SEQ ID NO 9
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 9
cagtaatacg actcactatt aagaagggga cacac                                35

<210> SEQ ID NO 10
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 10
cagtaatacg actcactatt aagcagggga cacac                                35

<210> SEQ ID NO 11
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 11
cagtaatacg actcactatt aaggagggga cacac                                35

<210> SEQ ID NO 12
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 12
cagtaatacg actcactatt aagtagggga cacac                                35

<210> SEQ ID NO 13
<211> LENGTH: 35
<212> TYPE: DNA
<213> ORGANISM: Artificial Sequence
<220> FEATURE:
<223> OTHER INFORMATION: Synthetic In vitro transcription templates oligonucleotide

<400> SEQUENCE: 13
cagtaatacg actcactatt aataagggga cacac         35

<210> SEQ ID NO 14
<211> LENGTH: 35
<212> TYPE: DNA
<213> ORGANISM: Artificial Sequence
<220> FEATURE:
<223> OTHER INFORMATION: Synthetic In vitro transcription templates oligonucleotide

<400> SEQUENCE: 14
cagtaatacg actcactatt aatcagggga cacac         35

<210> SEQ ID NO 15
<211> LENGTH: 35
<212> TYPE: DNA
<213> ORGANISM: Artificial Sequence
<220> FEATURE:
<223> OTHER INFORMATION: Synthetic In vitro transcription templates oligonucleotide

<400> SEQUENCE: 15
cagtaatacg actcactatt aatgagggga cacac         35

<210> SEQ ID NO 16
<211> LENGTH: 35
<212> TYPE: DNA
<213> ORGANISM: Artificial Sequence
<220> FEATURE:
<223> OTHER INFORMATION: Synthetic In vitro transcription templates oligonucleotide

<400> SEQUENCE: 16
cagtaatacg actcactatt aattagggga cacac         35

<210> SEQ ID NO 17
<211> LENGTH: 35
<212> TYPE: DNA
<213> ORGANISM: Artificial Sequence
<220> FEATURE:
<223> OTHER INFORMATION: Synthetic In vitro transcription templates oligonucleotide

<400> SEQUENCE: 17
cagtaatacg actcactatt acaaagggga cacac         35

<210> SEQ ID NO 18
<211> LENGTH: 35
<212> TYPE: DNA
<213> ORGANISM: Artificial Sequence
<220> FEATURE:
<223> OTHER INFORMATION: Synthetic In vitro transcription templates oligonucleotide

<400> SEQUENCE: 18
cagtaatacg actcactatt acacagggga cacac         35

<210> SEQ ID NO 19

```
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 19
cagtaatacg actcactatt acagagggga cacac                              35

<210> SEQ ID NO 20
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 20
cagtaatacg actcactatt acatagggga cacac                              35

<210> SEQ ID NO 21
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 21
cagtaatacg actcactatt accaagggga cacac                              35

<210> SEQ ID NO 22
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 22
cagtaatacg actcactatt acccagggga cacac                              35

<210> SEQ ID NO 23
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 23
cagtaatacg actcactatt accgagggga cacac                              35

<210> SEQ ID NO 24
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 24
cagtaatacg actcactatt acctagggga cacac                              35

<210> SEQ ID NO 25
<211> LENGTH: 35
```

```
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 25
cagtaatacg actcactatt acgaagggga cacac                           35

<210> SEQ ID NO 26
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 26
cagtaatacg actcactatt acgcagggga cacac                           35

<210> SEQ ID NO 27
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 27
cagtaatacg actcactatt acggagggga cacac                           35

<210> SEQ ID NO 28
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 28
cagtaatacg actcactatt acgtagggga cacac                           35

<210> SEQ ID NO 29
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 29
cagtaatacg actcactatt actaagggga cacac                           35

<210> SEQ ID NO 30
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 30
cagtaatacg actcactatt actcagggga cacac                           35

<210> SEQ ID NO 31
<211> LENGTH: 35
<212> TYPE: DNA
```

<213> ORGANISM: Artificial Sequence
<220> FEATURE:
<223> OTHER INFORMATION: Synthetic In vitro transcription templates
      oligonucleotide

<400> SEQUENCE: 31
cagtaatacg actcactatt actgagggga cacac                              35

<210> SEQ ID NO 32
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 32
cagtaatacg actcactatt acttagggga cacac                              35

<210> SEQ ID NO 33
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 33
cagtaatacg actcactatt agaaagggga cacac                              35

<210> SEQ ID NO 34
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 34
cagtaatacg actcactatt agacagggga cacac                              35

<210> SEQ ID NO 35
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 35
cagtaatacg actcactatt agagagggga cacac                              35

<210> SEQ ID NO 36
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 36
cagtaatacg actcactatt agatagggga cacac                              35

<210> SEQ ID NO 37
<211> LENGTH: 35
<212> TYPE: DNA
<213> ORGANISM: Artificial Sequence

```
<220> FEATURE:
<223> OTHER INFORMATION: Synthetic In vitro transcription templates
      oligonucleotide

<400> SEQUENCE: 37
cagtaatacg actcactatt agcaagggga cacac                               35

<210> SEQ ID NO 38
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 38
cagtaatacg actcactatt agccagggga cacac                               35

<210> SEQ ID NO 39
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 39
cagtaatacg actcactatt agcgagggga cacac                               35

<210> SEQ ID NO 40
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 40
cagtaatacg actcactatt agctagggga cacac                               35

<210> SEQ ID NO 41
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 41
cagtaatacg actcactatt aggaagggga cacac                               35

<210> SEQ ID NO 42
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 42
cagtaatacg actcactatt aggcagggga cacac                               35

<210> SEQ ID NO 43
<211> LENGTH: 35
<212> TYPE: DNA
<213> ORGANISM: Artificial Sequence
<220> FEATURE:
```

```
<223> OTHER INFORMATION: Synthetic In vitro transcription templates
      oligonucleotide

<400> SEQUENCE: 43
cagtaatacg actcactatt agggagggga cacac                              35

<210> SEQ ID NO 44
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 44
cagtaatacg actcactatt aggtagggga cacac                              35

<210> SEQ ID NO 45
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 45
cagtaatacg actcactatt agtaagggga cacac                              35

<210> SEQ ID NO 46
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 46
cagtaatacg actcactatt agtcagggga cacac                              35

<210> SEQ ID NO 47
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 47
cagtaatacg actcactatt agtgagggga cacac                              35

<210> SEQ ID NO 48
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 48
cagtaatacg actcactatt agttagggga cacac                              35

<210> SEQ ID NO 49
<211> LENGTH: 35
<212> TYPE: DNA
<213> ORGANISM: Artificial Sequence
<220> FEATURE:
<223> OTHER INFORMATION: Synthetic In vitro transcription templates
``` oligonucleotide

<400> SEQUENCE: 49
cagtaatacg actcactatt ataaggggga cacac                         35

<210> SEQ ID NO 50
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 50
cagtaatacg actcactatt atacagggga cacac                         35

<210> SEQ ID NO 51
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 51
cagtaatacg actcactatt atagagggga cacac                         35

<210> SEQ ID NO 52
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 52
cagtaatacg actcactatt atatagggga cacac                         35

<210> SEQ ID NO 53
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 53
cagtaatacg actcactatt atcaagggga cacac                         35

<210> SEQ ID NO 54
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 54
cagtaatacg actcactatt atccagggga cacac                         35

<210> SEQ ID NO 55
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 55
cagtaatacg actcactatt atcgagggga cacac        35

<210> SEQ ID NO 56
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 56
cagtaatacg actcactatt atctagggga cacac        35

<210> SEQ ID NO 57
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 57
cagtaatacg actcactatt atgaagggga cacac        35

<210> SEQ ID NO 58
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 58
cagtaatacg actcactatt atgcagggga cacac        35

<210> SEQ ID NO 59
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 59
cagtaatacg actcactatt atggagggga cacac        35

<210> SEQ ID NO 60
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 60
cagtaatacg actcactatt atgtagggga cacac        35

<210> SEQ ID NO 61
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 61
cagtaatacg actcactatt attaagggga cacac					35

<210> SEQ ID NO 62
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 62
cagtaatacg actcactatt attcagggga cacac					35

<210> SEQ ID NO 63
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 63
cagtaatacg actcactatt attgagggga cacac					35

<210> SEQ ID NO 64
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 64
cagtaatacg actcactatt atttagggga cacac					35

<210> SEQ ID NO 65
<211> LENGTH: 26
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 65
gtgtgtgtgt gtgtgtgtgt gtcccc						26

<210> SEQ ID NO 66
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 66
tatagttcca caaaggcatc tatagtgagt cg					32

<210> SEQ ID NO 67
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 67

```
atgcctttgt ggaactatac tatagtgagt cg                                    32
```

<210> SEQ ID NO 68
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 68

```
tcaaacagag gtcgcatgcc tatagtgagt cg                                    32
```

<210> SEQ ID NO 69
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 69

```
gcatgcgacc tctgtttgac tatagtgagt cg                                    32
```

<210> SEQ ID NO 70
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 70

```
ttttttttt ttccccccccc ccctatagtg agtcg                                 35
```

<210> SEQ ID NO 71
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 71

```
aaaaaaaaaa aaaaaaaaaa acctgtctc                                        29
```

<210> SEQ ID NO 72
<211> LENGTH: 38
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 72

```
aaagtgtgtg tgtgtgtgtg tgtctatagt gagtcgta                              38
```

<210> SEQ ID NO 73
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 73

```
aaatgtgtgt gtgtgtgtgt gcctgtctc                              29
```

<210> SEQ ID NO 74
<211> LENGTH: 38
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 74

```
aagatgaact tcagggtcag ccctatagt gagtcgta                     38
```

<210> SEQ ID NO 75
<211> LENGTH: 38
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 75

```
aagctgaccc tgaagttcat ccctatagt gagtcgta                     38
```

<210> SEQ ID NO 76
<211> LENGTH: 43
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 76

```
aagctgaccc tgaagttcat ctgcaccact atagtgagtc gta              43
```

<210> SEQ ID NO 77
<211> LENGTH: 41
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 77

```
aagctgaccc tgaagttcat ctgcacctat agtgagtcgt a                41
```

<210> SEQ ID NO 78
<211> LENGTH: 43
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 78

```
aagtggtgca gatgaacttc agggtcagct atagtgagtc gta              43
```

<210> SEQ ID NO 79
<211> LENGTH: 19
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 79

```
agtgagcgca acgcaatta                                         19
```

<210> SEQ ID NO 80
<211> LENGTH: 33
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 80
attgaaggac aggttaagct atagtgagtc gta                              33

<210> SEQ ID NO 81
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 81
caccgcggtg gagctccaat tcgccctat                                   29

<210> SEQ ID NO 82
<211> LENGTH: 33
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 82
cagtaatacg actcactata ggggaagcgg gca                              33

<210> SEQ ID NO 83
<211> LENGTH: 21
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 83
cagtaatacg actcactatt a                                           21

<210> SEQ ID NO 84
<211> LENGTH: 33
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 84
cagtaatacg actcactatt agggaagcgg gca                              33

<210> SEQ ID NO 85
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 85
cccccccccc cccccccccc ccctgtctc                                   29

<210> SEQ ID NO 86
<211> LENGTH: 19
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 86
cctcgaggtc gacggtatc                                                19

<210> SEQ ID NO 87
<211> LENGTH: 22
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 87
cggataacaa tttcacacag ga                                            22

<210> SEQ ID NO 88
<211> LENGTH: 19
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 88
cgggggatcc actagttct                                                19

<210> SEQ ID NO 89
<211> LENGTH: 41
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 89
gggaagctga ccctgaagtt catccccta t agtgagtcgt a                      41

<210> SEQ ID NO 90
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 90
gggaagttca tccccta tag tgagtcgta                                    29

<210> SEQ ID NO 91
<211> LENGTH: 35
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 91
gggaccctga agttcatccc ctatagtgag tcgta                              35

```
<210> SEQ ID NO 92
<211> LENGTH: 23
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 92
gggatcccct atagtgagtc gta                                           23

<210> SEQ ID NO 93
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 93
gggctgaagt tcatccccta tagtgagtcg ta                                 32

<210> SEQ ID NO 94
<211> LENGTH: 38
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 94
gggctgaccc tgaagttcat cccctatagt gagtcgta                           38

<210> SEQ ID NO 95
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 95
gggggggggg gggggggggg gcctgtctc                                     29

<210> SEQ ID NO 96
<211> LENGTH: 26
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 96
gggttcatcc cctatagtga gtcgta                                        26

<210> SEQ ID NO 97
<211> LENGTH: 31
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 97
ggtaattgaa ggacaggtta atagtgagtc g                                  31

<210> SEQ ID NO 98
```

```
<211> LENGTH: 39
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 98
ggtgcagatg aacttcaggg tcagcttaat agtgagtcg                              39

<210> SEQ ID NO 99
<211> LENGTH: 17
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 99
taatacgact cactata                                                      17

<210> SEQ ID NO 100
<211> LENGTH: 33
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 100
tgatcggcta tggctggccg catgcccgct tcc                                    33

<210> SEQ ID NO 101
<211> LENGTH: 31
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 101
ttgaaggaca ggttaagcta atagtgagtc g                                      31

<210> SEQ ID NO 102
<211> LENGTH: 29
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 102
tttttttttt tttttttttt tcctgtctc                                         29

<210> SEQ ID NO 103
<211> LENGTH: 19
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 103
augccuuugu ggaacuaua                                                    19

<210> SEQ ID NO 104
<211> LENGTH: 19
```

```
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 104
uauaguucca caaaggcau                                                       19

<210> SEQ ID NO 105
<211> LENGTH: 19
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 105
gcaugcgacc ucuguuuga                                                       19

<210> SEQ ID NO 106
<211> LENGTH: 19
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 106
ucaaacagag gucgcaugc                                                       19

<210> SEQ ID NO 107
<211> LENGTH: 19
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 107
ggaugacuga guaccugaa                                                       19

<210> SEQ ID NO 108
<211> LENGTH: 19
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 108
uucagguacu cagucaucc                                                       19

<210> SEQ ID NO 109
<211> LENGTH: 19
<212> TYPE: RNA
<213> ORGANISM: Artificial Sequence
<220> FEATURE:
<223> OTHER INFORMATION: Synthetic In vitro transcription templates
      oligonucleotide

<400> SEQUENCE: 109
aaaaaaaaaa aaaaaaaaa                                                       19

<210> SEQ ID NO 110
<211> LENGTH: 19
<212> TYPE: RNA
```

```
<213> ORGANISM: Artificial Sequence
<220> FEATURE:
<223> OTHER INFORMATION: Synthetic In vitro transcription templates
      oligonucleotide

<400> SEQUENCE: 110
agcuuaaccu guccuucaa                                                      19

<210> SEQ ID NO 111
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 111 aggggggac acacacacac acacacacac                                           30

<210> SEQ ID NO 112
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 112
aauaggggac acacacacac acacacacac                                          30

<210> SEQ ID NO 113
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 113 agaugggac acacacacac acacacacac                                           30

<210> SEQ ID NO 114
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 114 agagggac acacacacac acacacacac                                            30

<210> SEQ ID NO 115
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 115 agcgggac acacacacac acacacacac                                            30

<210> SEQ ID NO 116
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 116
```

```
agacgggac acacacacac acacacacac                              30

<210> SEQ ID NO 117
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 117
acuaggggac acacacacac acacacacac                             30

<210> SEQ ID NO 118
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 118
acuuggggac acacacacac acacacacac                             30

<210> SEQ ID NO 119
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 119
aauuggggac acacacacac acacacacac                             30

<210> SEQ ID NO 120
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 120
agcuggggac acacacacac acacacacac                             30

<210> SEQ ID NO 121
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 121
aaaaggggac acacacacac acacacacac                             30

<210> SEQ ID NO 122
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 122 accggggac acacacacac acacacacac                              30

<210> SEQ ID NO 123
<211> LENGTH: 30
<212> TYPE: RNA
<213> ORGANISM: Artificial Sequence
```

```
<220> FEATURE:
<223> OTHER INFORMATION: Synthetic oligonucleotide

<400> SEQUENCE: 123 auaggggac acacacacac acacacacac                                    30

<210> SEQ ID NO 124
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 124
accuggggac acacacacac acacacacac                                   30

<210> SEQ ID NO 125
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 125
acguggggac acacacacac acacacacac                                   30

<210> SEQ ID NO 126
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 126
accaggggac acacacacac acacacacac                                   30

<210> SEQ ID NO 127
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 127
auaaggggac acacacacac acacacacac                                   30

<210> SEQ ID NO 128
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 128
agccggggac acacacacac acacacacac                                   30

<210> SEQ ID NO 129
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 129
auauggggac acacacacac acacacacac                                   30
```

<210> SEQ ID NO 130
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 130
acccggggac acacacacac acacacacac           30

<210> SEQ ID NO 131
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 131
aggcggggac acacacacac acacacacac           30

<210> SEQ ID NO 132
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 132
aaucggggac acacacacac acacacacac           30

<210> SEQ ID NO 133
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 133 aucggggac acacacacac acacacacac            30

<210> SEQ ID NO 134
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 134 aagagggac acacacacac acacacacac            30

<210> SEQ ID NO 135
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 135
acacggggac acacacacac acacacacac           30

<210> SEQ ID NO 136
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 136 aauggggac acacacacac acacacacac					30

<210> SEQ ID NO 137
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 137
acucggggac acacacacac acacacacac					30

<210> SEQ ID NO 138
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 138
auuuggggac acacacacac acacacacac					30

<210> SEQ ID NO 139
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 139
auacggggac acacacacac acacacacac					30

<210> SEQ ID NO 140
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 140
agucggggac acacacacac acacacacac					30

<210> SEQ ID NO 141
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 141
auccggggac acacacacac acacacacac					30

<210> SEQ ID NO 142
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 142
acaaggggac acacacacac acacacacac					30

<210> SEQ ID NO 143

```
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 143 aguggggac acacacacac acacacacac                               30

<210> SEQ ID NO 144
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 144
auucggggac acacacacac acacacacac                              30

<210> SEQ ID NO 145
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 145
acggggggac acacacacac acacacacac                              30

<210> SEQ ID NO 146
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 146
aaauggggac acacacacac acacacacac                              30

<210> SEQ ID NO 147
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 147
acgcggggac acacacacac acacacacac                              30

<210> SEQ ID NO 148
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 148 acaugggggac acacacacac acacacacac                             30

<210> SEQ ID NO 149
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 149
``` aagggggac acacacacac acacacacac                30

<210> SEQ ID NO 150
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 150 acaggggac acacacacac acacacacac                30

<210> SEQ ID NO 151
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 151
acgaggggac acacacacac acacacacac                30

<210> SEQ ID NO 152
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 152 acuggggac acacacacac acacacacac                30

<210> SEQ ID NO 153
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 153
auguggggac acacacacac acacacacac                30

<210> SEQ ID NO 154
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 154
aaacggggac acacacacac acacacacac                30

<210> SEQ ID NO 155
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 155 aggugggac acacacacac acacacacac                30

<210> SEQ ID NO 156
<211> LENGTH: 30
<212> TYPE: RNA

```
<213> ORGANISM: Artificial Sequence
<220> FEATURE:
<223> OTHER INFORMATION: Synthetic oligonucleotide

<400> SEQUENCE: 156
aaccggggac acacacacac acacacacac                                          30

<210> SEQ ID NO 157
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 157
aagcggggac acacacacac acacacacac                                          30

<210> SEQ ID NO 158
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 158 aguagggac acacacacac acacacacac                                           30

<210> SEQ ID NO 159
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 159
augcggggac acacacacac acacacacac                                          30

<210> SEQ ID NO 160
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 160
aucaggggac acacacacac acacacacac                                          30

<210> SEQ ID NO 161
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 161
aggaggggac acacacacac acacacacac                                          30

<210> SEQ ID NO 162
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 162 aucggggac acacacacac acacacacac                                           30
```

<210> SEQ ID NO 163
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 163
aacuggggac acacacacac acacacacac                                   30

<210> SEQ ID NO 164
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 164
agcaggggac acacacacac acacacacac                                   30

<210> SEQ ID NO 165
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 165
agaaggggac acacacacac acacacacac                                   30

<210> SEQ ID NO 166
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 166
aacaggggac acacacacac acacacacac                                   30

<210> SEQ ID NO 167
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 167 auuggggac acacacacac acacacacac                                    30

<210> SEQ ID NO 168
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 168
aguuggggac acacacacac acacacacac                                   30

<210> SEQ ID NO 169
<211> LENGTH: 30
<212> TYPE: RNA
<213> ORGANISM: Artificial Sequence
<220> FEATURE:

```
<223> OTHER INFORMATION: Synthetic oligonucleotide

<400> SEQUENCE: 169
augaggggac acacacacac acacacacac                                      30

<210> SEQ ID NO 170
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 170 aacggggac acacacacac acacacacac                                       30

<210> SEQ ID NO 171
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 171
auuaggggac acacacacac acacacacac                                      30

<210> SEQ ID NO 172
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 172 auggggac acacacacac acacacacac                                        30

<210> SEQ ID NO 173
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 173 aaaggggac acacacacac acacacacac                                       30

<210> SEQ ID NO 174
<211> LENGTH: 30
<212> TYPE: RNA
<213> ORGANISM: Artificial Sequence
<220> FEATURE:
<223> OTHER INFORMATION: Synthetic oligonucleotide

<400> SEQUENCE: 174 aagugggac acacacacac acacacacac                                       30

<210> SEQ ID NO 175
<211> LENGTH: 19
<212> TYPE: RNA
<213> ORGANISM: Artificial Sequence
<220> FEATURE:
<223> OTHER INFORMATION: Synthetic SiRNA oligonucleotide

<400> SEQUENCE: 175
gaagcgucuu cuaauaauu                                                  19
```

```
<210> SEQ ID NO 176
<211> LENGTH: 19
<212> TYPE: RNA
<213> ORGANISM: Artificial Sequence
<220> FEATURE:
<223> OTHER INFORMATION: Synthetic SiRNA oligonucleotide

<400> SEQUENCE: 176
aauuauuaga agacgcuuc                                               19

<210> SEQ ID NO 177
<211> LENGTH: 19
<212> TYPE: RNA
<213> ORGANISM: Artificial Sequence
<220> FEATURE:
<223> OTHER INFORMATION: Synthetic SiRNA oligonucleotide

<400> SEQUENCE: 177
uucuccgaac gugucacgu                                               19

<210> SEQ ID NO 178
<211> LENGTH: 19
<212> TYPE: RNA
<213> ORGANISM: Artificial Sequence
<220> FEATURE:
<223> OTHER INFORMATION: Synthetic SiRNA oligonucleotide

<400> SEQUENCE: 178
acgugacacg uucggagaa                                               19

<210> SEQ ID NO 179
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 179
ggcgccccgc cgcgccccgc tatagtgagt cg                                32

<210> SEQ ID NO 180
<211> LENGTH: 32
<212> TYPE: DNA
<213> ORGANISM: Artificial Sequence
<220> FEATURE:
<223> OTHER INFORMATION: Synthetic In vitro transcription templates
      oligonucleotide

<400> SEQUENCE: 180
gcggggcgcg gcggggcgcc tatagtgagt cg                                32

<210> SEQ ID NO 181
<211> LENGTH: 21
<212> TYPE: RNA
<213> ORGANISM: Artificial Sequence
<220> FEATURE:
<223> OTHER INFORMATION: Synthetic HBV 1.1 sense oligonucleotide

<400> SEQUENCE: 181
uuucaccucu gccuaaucau u                                            21

<210> SEQ ID NO 182
<211> LENGTH: 21
<212> TYPE: RNA
<213> ORGANISM: Artificial Sequence
<220> FEATURE:
```

<223> OTHER INFORMATION: Synthetic HBV 1.1 sense oligonucleotide

<400> SEQUENCE: 182
uuaaagugga gacggauuag u 21

<210> SEQ ID NO 183
<211> LENGTH: 23
<212> TYPE: DNA
<213> ORGANISM: Hepatitis B virus

<400> SEQUENCE: 183
tttttcacct ctgcctaatc atc 23

<210> SEQ ID NO 184
<211> LENGTH: 21
<212> TYPE: RNA
<213> ORGANISM: Artificial Sequence
<220> FEATURE:
<223> OTHER INFORMATION: Synthetic HBV 1.2 sense oligonucleotide

<400> SEQUENCE: 184
cgaccuugag gcauacuucu u 21

<210> SEQ ID NO 185
<211> LENGTH: 21
<212> TYPE: RNA
<213> ORGANISM: Artificial Sequence
<220> FEATURE:
<223> OTHER INFORMATION: Synthetic HBV 1.2 antisense oligonucleotide

<400> SEQUENCE: 185
uugcuggaac uccguaugaa g 21

<210> SEQ ID NO 186
<211> LENGTH: 23
<212> TYPE: DNA
<213> ORGANISM: Hepatitis B virus

<400> SEQUENCE: 186
accgaccttg aggcatactt caa 23

<210> SEQ ID NO 187
<211> LENGTH: 21
<212> TYPE: RNA
<213> ORGANISM: Artificial Sequence
<220> FEATURE:
<223> OTHER INFORMATION: Synthetic HBV 1.3 sense oligonucleotide

<400> SEQUENCE: 187
cuauuaacag gccuauugau u 21

<210> SEQ ID NO 188
<211> LENGTH: 21
<212> TYPE: RNA
<213> ORGANISM: Artificial Sequence
<220> FEATURE:
<223> OTHER INFORMATION: Synthetic HBV 1.3 antisense oligonucleotide

<400> SEQUENCE: 188
uugauaauug uccggauaac u 21

<210> SEQ ID NO 189
<211> LENGTH: 23
<212> TYPE: DNA
<213> ORGANISM: Hepatitis B virus

```
<400> SEQUENCE: 189
tcctattaac aggcctattg atg                                                23

<210> SEQ ID NO 190
<211> LENGTH: 21
<212> TYPE: RNA
<213> ORGANISM: Artificial Sequence
<220> FEATURE:
<223> OTHER INFORMATION: Synthetic sense strand oligonucleotide

<400> SEQUENCE: 190
cugcguugau gccuuuguau u                                                  21

<210> SEQ ID NO 191
<211> LENGTH: 21
<212> TYPE: RNA
<213> ORGANISM: Artificial Sequence
<220> FEATURE:
<223> OTHER INFORMATION: Synthetic antisense strand oligonucleotide

<400> SEQUENCE: 191
uugacgcaac uacggaaaca u                                                  21

<210> SEQ ID NO 192
<211> LENGTH: 23
<212> TYPE: DNA
<213> ORGANISM: Hepatitis B virus

<400> SEQUENCE: 192
tcctgcgttg atgcctttgt atg                                                23

<210> SEQ ID NO 193
<211> LENGTH: 22
<212> TYPE: RNA
<213> ORGANISM: Hepatitis C virus

<400> SEQUENCE: 193
cugauagggu gcuugcgagu uc                                                 22

<210> SEQ ID NO 194
<211> LENGTH: 22
<212> TYPE: RNA
<213> ORGANISM: Hepatitis C virus

<400> SEQUENCE: 194
gacuauccca cgaacgcuca ag                                                 22

<210> SEQ ID NO 195
<211> LENGTH: 24
<212> TYPE: RNA
<213> ORGANISM: Artificial Sequence
<220> FEATURE:
<223> OTHER INFORMATION: Synthetic ssRNA oligonucleotide

<400> SEQUENCE: 195
aacacacaca cacacacaca cuuu                                               24

<210> SEQ ID NO 196
<211> LENGTH: 24
<212> TYPE: RNA
<213> ORGANISM: Artificial Sequence
<220> FEATURE:
<223> OTHER INFORMATION: Synthetic ssRNA oligonucleotide
```

```
<400> SEQUENCE: 196
aacacacaca cacacacaca cuuu                                          24

<210> SEQ ID NO 197
<211> LENGTH: 24
<212> TYPE: RNA
<213> ORGANISM: Artificial Sequence
<220> FEATURE:
<223> OTHER INFORMATION: Synthetic ssRNA oligonucleotide

<400> SEQUENCE: 197
uacacacaca cacacacaca cuuu                                          24

<210> SEQ ID NO 198
<211> LENGTH: 24
<212> TYPE: RNA
<213> ORGANISM: Artificial Sequence
<220> FEATURE:
<223> OTHER INFORMATION: Synthetic ssRNA oligonucleotide

<400> SEQUENCE: 198
gacacacaca cacacacaca cuuu                                          24

<210> SEQ ID NO 199
<211> LENGTH: 24
<212> TYPE: RNA
<213> ORGANISM: Artificial Sequence
<220> FEATURE:
<223> OTHER INFORMATION: Synthetic ssRNA oligonucleotide

<400> SEQUENCE: 199
cacacacaca cacacacaca cuuu                                          24

<210> SEQ ID NO 200
<211> LENGTH: 24
<212> TYPE: RNA
<213> ORGANISM: Artificial Sequence
<220> FEATURE:
<223> OTHER INFORMATION: Synthetic ssRNA oligonucleotide

<400> SEQUENCE: 200
gacacacaca cacacacaca cuuu                                          24

<210> SEQ ID NO 201
<211> LENGTH: 23
<212> TYPE: RNA
<213> ORGANISM: Artificial Sequence
<220> FEATURE:
<223> OTHER INFORMATION: Synthetic ssRNA oligonucleotide

<400> SEQUENCE: 201
aaaacacaca cacacacaca cac                                           23

<210> SEQ ID NO 202
<211> LENGTH: 79
<212> TYPE: DNA
<213> ORGANISM: Artificial Sequence
<220> FEATURE:
<223> OTHER INFORMATION: Synthetic In vitro transcription template

<400> SEQUENCE: 202 acattttgc tttgcaattg acaatgtctg ttttttcttt gatctggttg ttaagcgtta    60
tagtgagtcg tattacgcg                                                79
```

```
<210> SEQ ID NO 203
<211> LENGTH: 25
<212> TYPE: DNA
<213> ORGANISM: Artificial Sequence
<220> FEATURE:
<223> OTHER INFORMATION: Synthetic In vitro transcription template
      oligonucleotide; corresponding strand

<400> SEQUENCE: 203
aattcgcgta atacgactca ctata                                          25

<210> SEQ ID NO 204
<211> LENGTH: 29
<212> TYPE: DNA
<213> ORGANISM: Artificial Sequence
<220> FEATURE:
<223> OTHER INFORMATION: Synthetic forward primer

<400> SEQUENCE: 204
ggatcctaat acgactcact atagggcga                                      29

<210> SEQ ID NO 205
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 205 aagu                                                                 4

<210> SEQ ID NO 206
<211> LENGTH: 4
<212> TYPE: RNA
<213> ORGANISM: artificial Sequence
<220> FEATURE:
<223> OTHER INFORMATION: Synthetic Oligonucleotide

<400> SEQUENCE: 206 aaag                                                                 4

<210> SEQ ID NO 207
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 207 augg                                                                 4

<210> SEQ ID NO 208
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 208 auua                                                                 4

<210> SEQ ID NO 209
<211> LENGTH: 4
<212> TYPE: RNA
<213> ORGANISM: Artificial Sequence
<220> FEATURE:
<223> OTHER INFORMATION: Synthetic Oligonucleotide
```

```
<400> SEQUENCE: 209 aacg                                                                        4

<210> SEQ ID NO 210
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 210 auga                                                                        4

<210> SEQ ID NO 211
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 211 aguu                                                                        4

<210> SEQ ID NO 212
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 212 auug                                                                        4

<210> SEQ ID NO 213
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 213 aaca                                                                        4

<210> SEQ ID NO 214
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 214 agaa                                                                        4

<210> SEQ ID NO 215
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 215 agca                                                                        4

<210> SEQ ID NO 216
```

```
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 216 aacu                                                                       4

<210> SEQ ID NO 217
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 217 aucg                                                                       4

<210> SEQ ID NO 218
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 218 agga                                                                       4

<210> SEQ ID NO 219
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 219 auca                                                                       4

<210> SEQ ID NO 220
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 220 augc                                                                       4

<210> SEQ ID NO 221
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 221 agua                                                                       4

<210> SEQ ID NO 222
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 222
```

```
aagc                                                                    4

<210> SEQ ID NO 223
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 223 aacc                                                                    4

<210> SEQ ID NO 224
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 224 aggu                                                                    4

<210> SEQ ID NO 225
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 225 aaac                                                                    4

<210> SEQ ID NO 226
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 226 augu                                                                    4

<210> SEQ ID NO 227
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 227 acug                                                                    4

<210> SEQ ID NO 228
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 228 acga                                                                    4

<210> SEQ ID NO 229
<211> LENGTH: 4
<212> TYPE: RNA
```

```
<213> ORGANISM: Artificial Sequence
<220> FEATURE:
<223> OTHER INFORMATION: Synthetic Oligonucleotide

<400> SEQUENCE: 229 acag                                                                    4

<210> SEQ ID NO 230
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 230 aagg                                                                    4

<210> SEQ ID NO 231
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 231 acau                                                                    4

<210> SEQ ID NO 232
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 232 acgc                                                                    4

<210> SEQ ID NO 233
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 233 aaau                                                                    4

<210> SEQ ID NO 234
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 234 acgg                                                                    4

<210> SEQ ID NO 235
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 235 auuc                                                                    4
```

```
<210> SEQ ID NO 236
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 236 agug                                                                       4

<210> SEQ ID NO 237
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 237 acaa                                                                       4

<210> SEQ ID NO 238
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 238 aucc                                                                       4

<210> SEQ ID NO 239
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 239 aguc                                                                       4

<210> SEQ ID NO 240
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 240 guuc                                                                       4

<210> SEQ ID NO 241
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 241 guca                                                                       4

<210> SEQ ID NO 242
<211> LENGTH: 4
<212> TYPE: RNA
<213> ORGANISM: Artificial Sequence
<220> FEATURE:
```

```
<223> OTHER INFORMATION: Synthetic Oligonucleotide

<400> SEQUENCE: 242 gcuc                                                                    4

<210> SEQ ID NO 243
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 243 guug                                                                    4

<210> SEQ ID NO 244
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 244 guuu                                                                    4

<210> SEQ ID NO 245
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 245 gguu                                                                    4

<210> SEQ ID NO 246
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 246 gugu                                                                    4

<210> SEQ ID NO 247
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 247 gguc                                                                    4

<210> SEQ ID NO 248
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 248 gucu                                                                    4
```

```
<210> SEQ ID NO 249
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 249 gucc                                                                    4

<210> SEQ ID NO 250
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 250 gcuu                                                                    4

<210> SEQ ID NO 251
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 251 uugu                                                                    4

<210> SEQ ID NO 252
<211> LENGTH: 4
<212> TYPE: RNA
<213> ORGANISM: Artificial Sequence
<220> FEATURE:
<223> OTHER INFORMATION: Synthetic

<400> SEQUENCE: 252 uguc                                                                    4

<210> SEQ ID NO 253
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 253 cugu                                                                    4

<210> SEQ ID NO 254
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 254 cguc                                                                    4

<210> SEQ ID NO 255
<211> LENGTH: 4
<212> TYPE: RNA
<213> ORGANISM: Artificial Sequence
<220> FEATURE:
<223> OTHER INFORMATION: Synthetic Oligonucleotide
```

```
<400> SEQUENCE: 255 uguu                                                                    4

<210> SEQ ID NO 256
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 256 guua                                                                    4

<210> SEQ ID NO 257
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 257 ugua                                                                    4

<210> SEQ ID NO 258
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 258 uuuc                                                                    4

<210> SEQ ID NO 259
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 259 ugug                                                                    4

<210> SEQ ID NO 260
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 260 ggua                                                                    4

<210> SEQ ID NO 261
<211> LENGTH: 4
<212> TYPE: RNA
<213> ORGANISM: Artificial Sequence
<220> FEATURE:
<223> OTHER INFORMATION: Synthetic

<400> SEQUENCE: 261 gucg                                                                    4

<210> SEQ ID NO 262
<211> LENGTH: 4
```

```
<212> TYPE: RNA
<213> ORGANISM: Artificial Sequence
<220> FEATURE:
<223> OTHER INFORMATION: Synthetic Oligonucleotide

<400> SEQUENCE: 262 uuug                                                                      4

<210> SEQ ID NO 263
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 263 uggu                                                                      4

<210> SEQ ID NO 264
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 264 gugg                                                                      4

<210> SEQ ID NO 265
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 265 gugc                                                                      4

<210> SEQ ID NO 266
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 266 guac                                                                      4

<210> SEQ ID NO 267
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 267 guau                                                                      4

<210> SEQ ID NO 268
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 268
``` uagu                                                            4

<210> SEQ ID NO 269
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 269 guag                                                            4

<210> SEQ ID NO 270
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 270 uuca                                                            4

<210> SEQ ID NO 271
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 271 uugg                                                            4

<210> SEQ ID NO 272
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 272 ucuc                                                            4

<210> SEQ ID NO 273
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 273 cagu                                                            4

<210> SEQ ID NO 274
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 274 uucg                                                            4

<210> SEQ ID NO 275
<211> LENGTH: 4
<212> TYPE: RNA
<213> ORGANISM: Artificial Sequence

```
<220> FEATURE:
<223> OTHER INFORMATION: Synthetic Oligonucleotide

<400> SEQUENCE: 275 cuuc                                                                  4

<210> SEQ ID NO 276
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 276 gagu                                                                  4

<210> SEQ ID NO 277
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 277 ggug                                                                  4

<210> SEQ ID NO 278
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 278 uugc                                                                  4

<210> SEQ ID NO 279
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 279 uuuu                                                                  4

<210> SEQ ID NO 280
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 280 cuca                                                                  4

<210> SEQ ID NO 281
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 281 ucgu                                                                  4
```

```
<210> SEQ ID NO 282
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 282 uucu                                                                     4

<210> SEQ ID NO 283
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 283 uggc                                                                     4

<210> SEQ ID NO 284
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 284 cguu                                                                     4

<210> SEQ ID NO 285
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 285 cuug                                                                     4

<210> SEQ ID NO 286
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 286 uuac                                                                     4

<210> SEQ ID NO 287
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 287 ugau                                                                     4

<210> SEQ ID NO 288
<211> LENGTH: 4
<212> TYPE: RNA
<213> ORGANISM: Artificial Sequence
<220> FEATURE:
<223> OTHER INFORMATION: Synthetic Oligonucleotide
```

```
<400> SEQUENCE: 288 ugcu                                                                    4

<210> SEQ ID NO 289
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 289 ugcc                                                                    4

<210> SEQ ID NO 290
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 290 ugac                                                                    4

<210> SEQ ID NO 291
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 291 uaau                                                                    4

<210> SEQ ID NO 292
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 292 ucuu                                                                    4

<210> SEQ ID NO 293
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 293 ggau                                                                    4

<210> SEQ ID NO 294
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 294 uuau                                                                    4

<210> SEQ ID NO 295
```

```
<210> SEQ ID NO 295
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 295 uauu                                                                      4

<210> SEQ ID NO 296
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 296 ucug                                                                      4

<210> SEQ ID NO 297
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 297 uagg                                                                      4

<210> SEQ ID NO 298
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 298 uagc                                                                      4

<210> SEQ ID NO 299
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 299 uauc                                                                      4

<210> SEQ ID NO 300
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 300 cuau                                                                      4

<210> SEQ ID NO 301
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 301
``` uacu 4

<210> SEQ ID NO 302
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 302 cggu 4

<210> SEQ ID NO 303
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 303 ugcg 4

<210> SEQ ID NO 304
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 304 uaug 4

<210> SEQ ID NO 305
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 305 uaag 4

<210> SEQ ID NO 306
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 306 uacc 4

<210> SEQ ID NO 307
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 307 uuag 4

<210> SEQ ID NO 308
<211> LENGTH: 4
<212> TYPE: RNA

```
<213> ORGANISM: Artificial Sequence
<220> FEATURE:
<223> OTHER INFORMATION: Synthetic Oligonucleotide

<400> SEQUENCE: 308 ugag                                                                       4

<210> SEQ ID NO 309
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 309 gauu                                                                       4

<210> SEQ ID NO 310
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 310 ugca                                                                       4

<210> SEQ ID NO 311
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 311 gccu                                                                       4

<210> SEQ ID NO 312
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 312 ggcu                                                                       4

<210> SEQ ID NO 313
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 313 ucau                                                                       4

<210> SEQ ID NO 314
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 314 gcgu                                                                       4
```

<210> SEQ ID NO 315
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 315 gcau                                                                    4

<210> SEQ ID NO 316
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 316 gaug                                                                    4

<210> SEQ ID NO 317
<211> LENGTH: 4
<212> TYPE: RNA
<213> ORGANISM: Artificial Sequence
<220> FEATURE:
<223> OTHER INFORMATION: Synthetic Oligonucleotide

<400> SEQUENCE: 317 cgua                                                                    4

<210> SEQ ID NO 318
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 318
gacctagcct aaaactaggt c                                                21

<210> SEQ ID NO 319
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 319
aaagatccgg atcaaaa                                                     17

<210> SEQ ID NO 320
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 320
aaaaguucaa agcucaaaa                                                   19

<210> SEQ ID NO 321
<211> LENGTH: 11
<212> TYPE: RNA
<213> ORGANISM: Artificial Sequence
<220> FEATURE:

<223> OTHER INFORMATION: Synthetic Oligonucleotide

<400> SEQUENCE: 321
caaguuucga g                                                              11

<210> SEQ ID NO 322
<211> LENGTH: 33
<212> TYPE: RNA
<213> ORGANISM: Artificial Sequence
<220> FEATURE:
<223> OTHER INFORMATION: Synthetic Oligonucleotide

<400> SEQUENCE: 322
ucaaagucaa aagcucaaag uugaaaguuu aaa                                      33

<210> SEQ ID NO 323
<211> LENGTH: 41
<212> TYPE: RNA
<213> ORGANISM: Artificial Sequence
<220> FEATURE:
<223> OTHER INFORMATION: Synthetic Oligonucleotide

<400> SEQUENCE: 323
gacuugaaaa uuucaguuuu cgaguuuaag uugaaaacuc g                             41

<210> SEQ ID NO 324
<211> LENGTH: 26
<212> TYPE: RNA
<213> ORGANISM: Artificial Sequence
<220> FEATURE:
<223> OTHER INFORMATION: Synthetic Oligonucleotide

<400> SEQUENCE: 324
ucaaagucaa aagcucaaag uugaaa                                              26

<210> SEQ ID NO 325
<211> LENGTH: 31
<212> TYPE: RNA
<213> ORGANISM: Artificial Sequence
<220> FEATURE:
<223> OTHER INFORMATION: Synthetic Oligonucleotide

<400> SEQUENCE: 325
uuucaguuuu cgaguuuaag uugaaaacuc g                                        31

<210> SEQ ID NO 326
<211> LENGTH: 26
<212> TYPE: DNA
<213> ORGANISM: Artificial Sequence
<220> FEATURE:
<223> OTHER INFORMATION: Synthetic primer

<400> SEQUENCE: 326
actgagttta ggatttcctt caatcc                                              26

<210> SEQ ID NO 327
<211> LENGTH: 22
<212> TYPE: DNA
<213> ORGANISM: Artificial Sequence
<220> FEATURE:
<223> OTHER INFORMATION: Synthetic primer

<400> SEQUENCE: 327
ggtagcaagt gcttccttct ga                                                  22

<210> SEQ ID NO 328
<211> LENGTH: 27
<212> TYPE: DNA
<213> ORGANISM: Artificial Sequence
<220> FEATURE:
<223> OTHER INFORMATION: Synthetic primer

<400> SEQUENCE: 328
gcactgattc acgcctcctt cggtacc                                        27

<210> SEQ ID NO 329
<211> LENGTH: 27
<212> TYPE: DNA
<213> ORGANISM: Artificial Sequence
<220> FEATURE:
<223> OTHER INFORMATION: Synthetic primer

<400> SEQUENCE: 329
ggtaccgaag gaggcgtgaa tcagtgc                                        27

<210> SEQ ID NO 330
<211> LENGTH: 20
<212> TYPE: DNA
<213> ORGANISM: Artificial Sequence
<220> FEATURE:
<223> OTHER INFORMATION: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (15)..(20)
<223> OTHER INFORMATION: Phosphorothioate linkage

<400> SEQUENCE: 330
gggggacgat cgtcggggggg                                               20

<210> SEQ ID NO 331
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 331
tccatgacgt tcctgacgtt                                                20

<210> SEQ ID NO 332
<211> LENGTH: 30
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (2)..(4)
<223> OTHER INFORMATION: a, c, g, or u

<400> SEQUENCE: 332 annngggggac acacacacac acacacacac                                    30

<210> SEQ ID NO 333
<211> LENGTH: 4
<212> TYPE: RNA
<213> ORGANISM: Artificial Sequence
<220> FEATURE:
<223> OTHER INFORMATION: Synthetic Oligonucleotide

```
<400> SEQUENCE: 333 cgau                                                                    4

<210> SEQ ID NO 334
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 334
ggggcugacc cugaaguuca ucuuccc                                          27

<210> SEQ ID NO 335
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 335
ggggcugacc cugaaguuca uccc                                             24

<210> SEQ ID NO 336
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 336
ggggcugacc cugaaguucc c                                                21

<210> SEQ ID NO 337
<211> LENGTH: 18
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 337
ggggcugacc cugaaccc                                                    18

<210> SEQ ID NO 338
<211> LENGTH: 15
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 338
ggggcugacc cuccc                                                       15

<210> SEQ ID NO 339
<211> LENGTH: 12
<212> TYPE: RNA
```

```
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 339
ggggcugacc cc                                                          12

<210> SEQ ID NO 340
<211> LENGTH: 9
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 340 ggggcuccc                                                               9

<210> SEQ ID NO 341
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 341
ggggcugacc cugaaguuca ucuu                                              24

<210> SEQ ID NO 342
<211> LENGTH: 31
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 342
gggagacagg gggggggggg gggggggggg g                                      31

<210> SEQ ID NO 343
<211> LENGTH: 31
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 343
gggagacagg aaaaaaaaaa aaaaaaaaaa a                                      31

<210> SEQ ID NO 344
<211> LENGTH: 31
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 344
gggagacagg cccccccccc cccccccccc c                                      31
```

-continued

<210> SEQ ID NO 345
<211> LENGTH: 31
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 345
gggagacagg uuuuuuuuuu uuuuuuuuuu u                              31

<210> SEQ ID NO 346
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-OH

<400> SEQUENCE: 346
agcuuaaccu guccuucaa                                            19

<210> SEQ ID NO 347
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 347
agcuuaaccu guccuucaa                                            19

<210> SEQ ID NO 348
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 348
ggggaugaac uucaggguca gcuu                                      24

<210> SEQ ID NO 349
<211> LENGTH: 31
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group
<220> FEATURE:
<221> NAME/KEY: modified_base
<222> LOCATION: (29)..(31)
<223> OTHER INFORMATION: Biotinylated U

<400> SEQUENCE: 349
gggagacagg caccacacac acacacacuu u                              31

<210> SEQ ID NO 350
<211> LENGTH: 31
<212> TYPE: RNA

```
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 350
gggagacagg caccacacac acacacacuu u                              31

<210> SEQ ID NO 351
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-OH

<400> SEQUENCE: 351
gacacacaca cacacacaca cuuu                                      24

<210> SEQ ID NO 352
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-phosphate group

<400> SEQUENCE: 352
gacacacaca cacacacaca cuuu                                      24

<210> SEQ ID NO 353
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-diphosphate group

<400> SEQUENCE: 353
gacacacaca cacacacaca cuuu                                      24

<210> SEQ ID NO 354
<211> LENGTH: 24
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 354
gacacacaca cacacacaca cuuu                                      24

<210> SEQ ID NO 355
<211> LENGTH: 29
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 355
gcugacccug aaguucaucu gcaccacuu                                 29
```

```
<210> SEQ ID NO 356
<211> LENGTH: 29
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 356
guggugcaga ugaacuucag ggucagcuu                                              29

<210> SEQ ID NO 357
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 357
aagcugaccc ugaaguucau cugcacc                                                27

<210> SEQ ID NO 358
<211> LENGTH: 27
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 358
ggugcagaug aacuucaggg ucagcuu                                                27

<210> SEQ ID NO 359
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 359
agcuuaaccu guccuucaa                                                         19

<210> SEQ ID NO 360
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 360
gcuuaaccug uccuucaau                                                         19

<210> SEQ ID NO 361
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
```

-continued

```
<223> OTHER INFORMATION: 5'-triphosphate group

<400> SEQUENCE: 361
aaccuguccu ucaauuacc                                              19

<210> SEQ ID NO 362
<211> LENGTH: 35
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 362
agggaagcgg gcaugcggcc agccauagcc gauca                            35

<210> SEQ ID NO 363
<211> LENGTH: 35
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-triphosphate group

<400> SEQUENCE: 363
ggggaagcgg gcaugcggcc agccauagcc gauca                            35

<210> SEQ ID NO 364
<211> LENGTH: 23
<212> TYPE: RNA
<213> ORGANISM: Artificial Sequence
<220> FEATURE:
<223> OTHER INFORMATION: Synthetic oligonucleotide
<220> FEATURE:
<223> OTHER INFORMATION: 5'-OH

<400> SEQUENCE: 364
aaagugugug ugugugugug ugu                                         23

<210> SEQ ID NO 365
<211> LENGTH: 4
<212> TYPE: PRT
<213> ORGANISM: Unknown
<220> FEATURE:
<223> OTHER INFORMATION: "DEAD" box motif peptide

<400> SEQUENCE: 365

Asp Glu Ala Asp
1
```

The invention claimed is:

1. An oligonucleotide wherein the oligonucleotide
    (a) is 12 to 64 nucleotides in length;
    (b) comprises a 5' triphosphate;
    (c) comprises at least 1 ribonucleotide at the 5' end, wherein the first ribonucleotide at the 5' end comprises an A or G; and
    (d) comprises a 2'-methyl-dNTP and/or 2'-fluorine-dNTP modification.

2. The oligonucleotide of claim 1, wherein the oligonucleotide is covalently linked to at least one antigen.

3. A composition comprising the oligonucleotide of claim 1 or a viral vector encoding the oligonucleotide of claim 1, and a pharmaceutically acceptable carrier or diluent.

4. The composition of claim 3, further comprising one or more of a complexation agent, an antiviral agent, an antibacterial agent, an anti-tumor agent, an immunostimulatory agent, retinoic acid, type I IFN, and an antigen.

* * * * *